(12) United States Patent
Van Eyk et al.

(10) Patent No.: US 9,039,994 B2
(45) Date of Patent: *May 26, 2015

(54) BIOMARKERS FOR MYOCARDIAL ISCHEMIA

(71) Applicant: The Johns Hopkins University, Baltimore, MD (US)

(72) Inventors: Jennifer Van Eyk, Baltimore, MD (US); Simon Sheng, Baltimore, MD (US); Qin Fu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/953,226

(22) Filed: Jul. 29, 2013

(65) Prior Publication Data

US 2014/0186852 A1 Jul. 3, 2014

Related U.S. Application Data

(63) Continuation of application No. 12/994,034, filed as application No. PCT/US2009/045168 on May 26, 2009, now Pat. No. 8,497,078.

(60) Provisional application No. 61/128,688, filed on May 23, 2008.

(51) Int. Cl.
*G01N 31/00* (2006.01)
*G01N 33/53* (2006.01)
*G01N 33/68* (2006.01)
*G01N 33/573* (2006.01)

(52) U.S. Cl.
CPC ........ *G01N 33/5308* (2013.01); *G01N 33/6893* (2013.01); *G01N 2400/40* (2013.01); *G01N 2800/324* (2013.01); *G01N 33/573* (2013.01)

(58) Field of Classification Search
CPC .............. G01N 33/566; G01N 33/582; G01N 33/6893; A61K 38/00; C07K 14/705; C07K 16/18; B01L 3/502; B01L 9/54
See application file for complete search history.

*Primary Examiner* — Lisa Cook
(74) *Attorney, Agent, or Firm* — Johns Hopkins Technology Transfer

(57) ABSTRACT

This invention relates, e.g., to a method for determining if a subject has myocardial ischemia, comprising (a) providing a blood sample obtained from a subject suspected of having myocardial ischemia; (b) determining in the sample the amount of one or more of the following proteins: (i) Lumican and/or (ii) Extracellular matrix protein 1 and/or (iii) Carboxypeptidase N; and (c) comparing the amount(s) of the protein(s) to a baseline value that is indicative of the amount of the protein in a subject that does not have myocardial ischemia, wherein a statistically significantly increased amount of the protein(s) compared to the baseline value is indicative of myocardial ischemia. Other proteins indicative of myocardial ischemia are also described, as are methods for treating a subject based on a diagnostic procedure of the invention, and kits for carrying out a method of the invention.

2 Claims, 6 Drawing Sheets

SEQUENCE LISTING

```
<160> NUMBER OF SEQ ID NOS: 44

<210> SEQ ID NO 1
<211> LENGTH: 474
<212> TYPE: PRT
<213> ORGANISM: Homo sapiens

<400> SEQUENCE: 1

Met Lys Arg Val Leu Val Leu Leu Leu Ala Val Ala Phe Gly His Ala
1               5                   10                  15
```

```
Leu Glu Arg Gly Arg Asp Tyr Glu Lys Asn Lys Val Cys Lys Glu Phe
             20                  25                  30

Ser His Leu Gly Lys Glu Asp Phe Thr Ser Leu Ser Leu Val Leu Tyr
         35                  40                  45

Ser Arg Lys Phe Pro Ser Gly Thr Phe Glu Gln Val Ser Gln Leu Val
50                  55                  60

Lys Glu Val Val Ser Leu Thr Glu Ala Cys Cys Ala Glu Gly Ala Asp
65                  70                  75                  80

Pro Asp Cys Tyr Asp Thr Arg Thr Ser Ala Leu Ser Ala Lys Ser Cys
                 85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Gly Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285

Leu Ser Thr Lys Asn Ser Lys Phe Glu Asp Cys Cys Gln Glu Lys Thr
290                 295                 300

Ala Met Asp Val Phe Val Cys Thr Tyr Phe Met Pro Ala Ala Gln Leu
305                 310                 315                 320

Pro Glu Leu Pro Asp Val Glu Leu Pro Thr Asn Lys Asp Val Cys Asp
                325                 330                 335

Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
        355                 360                 365

Leu Lys Ser Leu Gly Glu Cys Cys Asp Val Glu Asp Ser Thr Thr Cys
370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr
                405                 410                 415

Glu Tyr Lys Lys Lys Leu Ala Glu Arg Leu Lys Ala Lys Leu Pro Asp
            420                 425                 430
```

```
Ala Thr Pro Lys Glu Leu Ala Lys Leu Val Asn Lys Arg Ser Asp Phe
            435                 440                 445

Ala Ser Asn Cys Cys Ser Ile Asn Ser Pro Pro Leu Tyr Cys Asp Ser
    450                 455                 460

Glu Ile Asp Ala Glu Leu Lys Asn Ile Leu
465                 470

<210> SEQ ID NO 2
<211> LENGTH: 415
<212> TYPE: PRT
<213> ORGANISM: Homo sapiens

<400> SEQUENCE: 2

Met Ser Pro Phe Leu Tyr Leu Val Leu Val Leu Gly Leu His Ala
1               5                   10                  15

Thr Ile His Cys Ala Ser Pro Glu Gly Lys Val Thr Ala Cys His Ser
                20                  25                  30

Ser Gln Pro Asn Ala Thr Leu Tyr Lys Met Ser Ser Ile Asn Ala Asp
            35                  40                  45

Phe Ala Phe Asn Leu Tyr Arg Arg Phe Thr Val Glu Thr Pro Asp Lys
    50                  55                  60

Asn Ile Phe Phe Ser Pro Val Ser Ile Ser Ala Ala Leu Val Met Leu
65                  70                  75                  80

Ser Phe Gly Ala Cys Cys Ser Thr Gln Thr Glu Ile Val Glu Thr Leu
                85                  90                  95

Gly Phe Asn Leu Thr Asp Thr Pro Met Val Glu Ile Gln His Gly Phe
            100                 105                 110

Gln His Leu Ile Cys Ser Leu Asn Phe Pro Lys Lys Glu Leu Glu Leu
        115                 120                 125

Gln Ile Gly Asn Ala Leu Phe Ile Gly Lys His Leu Lys Pro Leu Ala
    130                 135                 140

Lys Phe Leu Asn Asp Val Lys Thr Leu Tyr Glu Thr Glu Val Phe Ser
145                 150                 155                 160

Thr Asp Phe Ser Asn Ile Ser Ala Ala Lys Gln Glu Ile Asn Ser His
                165                 170                 175

Val Glu Met Gln Thr Lys Gly Lys Val Val Gly Leu Ile Gln Asp Leu
            180                 185                 190

Lys Pro Asn Thr Ile Met Val Leu Val Asn Tyr Ile His Phe Lys Ala
        195                 200                 205

Gln Trp Ala Asn Pro Phe Asp Pro Ser Lys Thr Glu Asp Ser Ser Ser
    210                 215                 220

Phe Leu Ile Asp Lys Thr Thr Thr Val Gln Val Pro Met Met His Gln
225                 230                 235                 240

Met Glu Gln Tyr Tyr His Leu Val Asp Met Glu Leu Asn Cys Thr Val
                245                 250                 255

Leu Gln Met Asp Tyr Ser Lys Asn Ala Leu Ala Leu Phe Val Leu Pro
            260                 265                 270

Lys Glu Gly Gln Met Glu Ser Val Glu Ala Ala Met Ser Ser Lys Thr
        275                 280                 285

Leu Lys Lys Trp Asn Arg Leu Leu Gln Lys Gly Trp Val Asp Leu Phe
    290                 295                 300

Val Pro Lys Phe Ser Ile Ser Ala Thr Tyr Asp Leu Gly Ala Thr Leu
305                 310                 315                 320

Leu Lys Met Gly Ile Gln His Ala Tyr Ser Glu Asn Ala Asp Phe Ser
                325                 330                 335
```

Gly Leu Thr Glu Asp Asn Gly Leu Lys Leu Ser Asn Ala Ala His Lys
                340                 345                 350

Ala Val Leu His Ile Gly Glu Lys Gly Thr Glu Ala Ala Ala Val Pro
                355                 360                 365

Glu Val Glu Leu Ser Asp Gln Pro Glu Asn Thr Phe Leu His Pro Ile
            370                 375                 380

Ile Gln Ile Asp Arg Ser Phe Met Leu Leu Ile Leu Glu Arg Ser Thr
385                 390                 395                 400

Arg Ser Ile Leu Phe Leu Gly Lys Val Val Asn Pro Thr Glu Ala
                405                 410                 415

<210> SEQ ID NO 3
<211> LENGTH: 338
<212> TYPE: PRT
<213> ORGANISM: Homo sapiens

<400> SEQUENCE: 3

Met Ser Leu Ser Ala Phe Thr Leu Phe Leu Ala Leu Ile Gly Gly Thr
1               5                   10                  15

Ser Gly Gln Tyr Tyr Asp Tyr Asp Phe Pro Leu Ser Ile Tyr Gly Gln
                20                  25                  30

Ser Ser Pro Asn Cys Ala Pro Glu Cys Asn Cys Pro Glu Ser Tyr Pro
            35                  40                  45

Ser Ala Met Tyr Cys Asp Glu Leu Lys Leu Lys Ser Val Pro Met Val
        50                  55                  60

Pro Pro Gly Ile Lys Tyr Leu Tyr Leu Arg Asn Asn Gln Ile Asp His
65                  70                  75                  80

Ile Asp Glu Lys Ala Phe Glu Asn Val Thr Asp Leu Gln Trp Leu Ile
                85                  90                  95

Leu Asp His Asn Leu Leu Glu Asn Ser Lys Ile Lys Gly Arg Val Phe
                100                 105                 110

Ser Lys Leu Lys Gln Leu Lys Lys Leu His Ile Asn His Asn Asn Leu
            115                 120                 125

Thr Glu Ser Val Gly Pro Leu Pro Lys Ser Leu Glu Asp Leu Gln Leu
        130                 135                 140

Thr His Asn Lys Ile Thr Lys Leu Gly Ser Phe Glu Gly Leu Val Asn
145                 150                 155                 160

Leu Thr Phe Ile His Leu Gln His Asn Arg Leu Lys Glu Asp Ala Val
                165                 170                 175

Ser Ala Ala Phe Lys Gly Leu Lys Ser Leu Glu Tyr Leu Asp Leu Ser
            180                 185                 190

Phe Asn Gln Ile Ala Arg Leu Pro Ser Gly Leu Pro Val Ser Leu Leu
        195                 200                 205

Thr Leu Tyr Leu Asp Asn Asn Lys Ile Ser Asn Ile Pro Asp Glu Tyr
    210                 215                 220

Phe Lys Arg Phe Asn Ala Leu Gln Tyr Leu Arg Leu Ser His Asn Glu
225                 230                 235                 240

Leu Ala Asp Ser Gly Ile Pro Gly Asn Ser Phe Asn Val Ser Ser Leu
                245                 250                 255

Val Glu Leu Asp Leu Ser Tyr Asn Lys Leu Lys Asn Ile Pro Thr Val
            260                 265                 270

Asn Glu Asn Leu Glu Asn Tyr Tyr Leu Glu Val Asn Gln Leu Glu Lys
        275                 280                 285

Phe Asp Ile Lys Ser Phe Cys Lys Ile Leu Gly Pro Leu Ser Tyr Ser

```
                    290                 295                 300
Lys Ile Lys His Leu Arg Leu Asp Gly Asn Arg Ile Ser Glu Thr Ser
305                 310                 315                 320

Leu Pro Pro Asp Met Tyr Glu Cys Leu Arg Val Ala Asn Glu Val Thr
                325                 330                 335

Leu Asn

<210> SEQ ID NO 4
<211> LENGTH: 136
<212> TYPE: PRT
<213> ORGANISM: Homo sapiens

<400> SEQUENCE: 4

Met Ser Asn Val Pro His Lys Ser Ser Leu Pro Glu Gly Ile Arg Pro
1               5                   10                  15

Gly Thr Val Leu Arg Ile Arg Gly Leu Val Pro Pro Asn Ala Ser Arg
                20                  25                  30

Phe His Val Asn Leu Leu Cys Gly Glu Glu Gln Gly Ser Asp Ala Ala
            35                  40                  45

Leu His Phe Asn Pro Arg Leu Asp Thr Ser Glu Val Val Phe Asn Ser
        50                  55                  60

Lys Glu Gln Gly Ser Trp Gly Arg Glu Glu Arg Gly Pro Gly Val Pro
65                  70                  75                  80

Phe Gln Arg Gly Gln Pro Phe Glu Val Leu Ile Ile Ala Ser Asp Asp
                85                  90                  95

Gly Phe Lys Ala Val Val Gly Asp Ala Gln Tyr His His Phe Arg His
            100                 105                 110

Arg Leu Pro Leu Ala Arg Val Arg Leu Val Glu Val Gly Gly Asp Val
        115                 120                 125

Gln Leu Asp Ser Val Arg Ile Phe
    130                 135

<210> SEQ ID NO 5
<211> LENGTH: 567
<212> TYPE: PRT
<213> ORGANISM: Homo sapiens

<400> SEQUENCE: 5

Met Gly Thr Thr Ala Arg Ala Ala Leu Val Leu Thr Tyr Leu Ala Val
1               5                   10                  15

Ala Ser Ala Ala Ser Glu Gly Gly Phe Thr Ala Thr Gly Gln Arg Gln
                20                  25                  30

Leu Arg Pro Glu His Phe Gln Glu Val Gly Tyr Ala Ala Pro Pro Ser
            35                  40                  45

Pro Pro Leu Ser Arg Ser Leu Pro Met Asp His Pro Asp Ser Ser Gln
        50                  55                  60

His Gly Pro Pro Phe Glu Gly Gln Ser Gly Lys Glu Gly Arg Gly Pro
65                  70                  75                  80

Arg Pro His Ser Gln Pro Trp Leu Gly Glu Arg Val Gly Cys Ser His
                85                  90                  95

Ile Pro Pro Ser Ile Val Gln Pro Pro Ser Gln Glu Ala Thr Pro
            100                 105                 110

Leu Gln Gln Glu Lys Leu Leu Pro Ala Gln Leu Pro Ala Glu Lys Glu
        115                 120                 125

Val Gly Pro Pro Leu Pro Gln Glu Ala Val Pro Leu Gln Lys Glu Leu
    130                 135                 140
```

```
Pro Ser Leu Gln His Pro Asn Glu Gln Lys Glu Gly Thr Ala Pro
145                 150                 155                 160

Phe Gly Asp Gln Ser His Pro Glu Pro Glu Ser Trp Asn Ala Ala Gln
                165                 170                 175

His Cys Gln Gln Asp Arg Ser Gln Gly Gly Trp Gly His Arg Leu Asp
            180                 185                 190

Gly Phe Pro Pro Gly Arg Pro Ser Pro Asp Asn Leu Asn Gln Ile Cys
        195                 200                 205

Leu Pro Asn Arg Gln His Val Val Tyr Gly Pro Trp Asn Leu Pro Gln
    210                 215                 220

Ser Ser Tyr Ser His Leu Thr Arg Gln Gly Glu Thr Leu Asn Phe Leu
225                 230                 235                 240

Glu Ile Gly Tyr Ser Arg Cys Cys His Cys Arg Ser His Thr Asn Arg
                245                 250                 255

Leu Glu Cys Ala Lys Leu Val Trp Glu Glu Ala Met Ser Arg Phe Cys
            260                 265                 270

Glu Ala Glu Phe Ser Val Lys Thr Arg Pro His Trp Cys Cys Thr Arg
        275                 280                 285

Gln Gly Glu Ala Arg Phe Ser Cys Phe Gln Glu Ala Pro Gln Pro
    290                 295                 300

His Tyr Gln Leu Arg Ala Cys Pro Ser His Gln Pro Asp Ile Ser Ser
305                 310                 315                 320

Gly Leu Glu Leu Pro Phe Pro Pro Gly Val Pro Thr Leu Asp Asn Ile
                325                 330                 335

Lys Asn Ile Cys His Leu Arg Arg Phe Arg Ser Val Pro Arg Asn Leu
            340                 345                 350

Pro Ala Thr Asp Pro Leu Gln Arg Glu Leu Leu Ala Leu Ile Gln Leu
        355                 360                 365

Glu Arg Glu Phe Gln Arg Cys Cys Arg Gln Gly Asn Asn His Thr Cys
    370                 375                 380

Thr Trp Lys Ala Trp Glu Asp Thr Leu Asp Lys Tyr Cys Asp Arg Glu
385                 390                 395                 400

Tyr Ala Val Lys Thr His His Leu Cys Cys Arg His Pro Pro Ser
                405                 410                 415

Pro Thr Arg Asp Glu Cys Phe Ala Arg Arg Ala Pro Tyr Pro Asn Tyr
            420                 425                 430

Asp Arg Asp Ile Leu Thr Ile Asp Ile Gly Arg Val Thr Pro Asn Leu
        435                 440                 445

Met Gly His Leu Cys Gly Asn Gln Arg Val Leu Thr Lys His Lys His
    450                 455                 460

Ile Pro Gly Leu Ile His Asn Met Thr Ala Arg Cys Cys Asp Leu Pro
465                 470                 475                 480

Phe Pro Glu Gln Ala Cys Cys Ala Glu Glu Lys Leu Thr Phe Ile
                485                 490                 495

Asn Asp Leu Cys Gly Pro Arg Arg Asn Ile Trp Arg Asp Pro Ala Leu
            500                 505                 510

Cys Cys Tyr Leu Ser Pro Gly Asp Glu Gln Val Asn Cys Phe Asn Ile
        515                 520                 525

Asn Tyr Leu Arg Asn Val Ala Leu Val Ser Gly Asp Thr Glu Asn Ala
    530                 535                 540

Lys Gly Gln Gly Glu Gln Gly Ser Thr Gly Gly Thr Asn Ile Ser Ser
545                 550                 555                 560
```

```
Thr Ser Glu Pro Lys Glu Glu
            565

<210> SEQ ID NO 6
<211> LENGTH: 402
<212> TYPE: PRT
<213> ORGANISM: Homo sapiens

<400> SEQUENCE: 6

Met Lys Pro Asn Ile Ile Phe Val Leu Ser Leu Leu Ile Leu Glu
1               5                   10                  15

Lys Gln Ala Ala Val Met Gly Gln Lys Gly Gly Ser Lys Gly Arg Leu
            20                  25                  30

Pro Ser Glu Phe Ser Gln Phe Pro His Gly Gln Lys Gly Gln His Tyr
            35                  40                  45

Ser Gly Gln Lys Gly Lys Gln Gly Thr Glu Ser Lys Gly Ser Phe Ser
50                      55                  60

Ile Gln Tyr Thr Tyr His Val Asp Ala Asn Asp His Asp Gln Ser Arg
65                  70                  75                  80

Lys Ser Gln Gln Tyr Asp Leu Asn Ala Leu His Lys Thr Thr Lys Ser
                85                  90                  95

Gln Arg His Leu Gly Gly Ser Gln Gln Leu Leu His Asn Lys Gln Glu
            100                 105                 110

Gly Arg Asp His Asp Lys Ser Lys Gly His Phe His Arg Val Val Ile
            115                 120                 125

His His Lys Gly Gly Lys Ala His Arg Gly Thr Gln Asn Pro Ser Gln
130                 135                 140

Asp Gln Gly Asn Ser Pro Ser Gly Lys Gly Ile Ser Ser Gln Tyr Ser
145                 150                 155                 160

Asn Thr Glu Glu Arg Leu Trp Val His Gly Leu Ser Lys Glu Gln Thr
                165                 170                 175

Ser Val Ser Gly Ala Gln Lys Gly Arg Lys Gln Gly Gly Ser Gln Ser
            180                 185                 190

Ser Tyr Val Leu Gln Thr Glu Glu Leu Val Ala Asn Lys Gln Gln Arg
            195                 200                 205

Glu Thr Lys Asn Ser His Gln Asn Lys Gly His Tyr Gln Asn Val Val
210                 215                 220

Glu Val Arg Glu Glu His Ser Ser Lys Val Gln Thr Ser Leu Cys Pro
225                 230                 235                 240

Ala His Gln Asp Lys Leu Gln His Gly Ser Lys Asp Ile Phe Ser Thr
                245                 250                 255

Gln Asp Glu Leu Leu Val Tyr Asn Lys Asn Gln His Gln Thr Lys Asn
            260                 265                 270

Leu Asn Gln Asp Gln Gln His Gly Arg Lys Ala Asn Lys Ile Ser Tyr
            275                 280                 285

Gln Ser Ser Ser Thr Glu Glu Arg Arg Leu His Tyr Gly Glu Asn Gly
290                 295                 300

Val Gln Lys Asp Val Ser Gln Arg Ser Ile Tyr Ser Gln Thr Glu Lys
305                 310                 315                 320

Leu Val Ala Gly Lys Ser Gln Ile Gln Ala Pro Asn Pro Lys Gln Glu
                325                 330                 335

Pro Trp His Gly Glu Asn Ala Lys Gly Glu Ser Gly Gln Ser Thr Asn
            340                 345                 350

Arg Glu Gln Asp Leu Leu Ser His Glu Gln Lys Gly Arg His Gln His
            355                 360                 365
```

```
Gly Ser His Gly Gly Leu Asp Ile Val Ile Glu Gln Glu Asp
        370                 375                 380

Ser Asp Arg His Leu Ala Gln His Leu Asn Asn Asp Arg Asn Pro Leu
385                 390                 395                 400

Phe Thr

<210> SEQ ID NO 7
<211> LENGTH: 484
<212> TYPE: PRT
<213> ORGANISM: Homo sapiens

<400> SEQUENCE: 7

Met Ala Gly Pro Trp Thr Phe Thr Leu Leu Cys Gly Leu Leu Ala Ala
1               5                   10                  15

Thr Leu Ile Gln Ala Thr Leu Ser Pro Thr Ala Val Leu Ile Leu Gly
            20                  25                  30

Pro Lys Val Ile Lys Glu Lys Leu Thr Gln Glu Leu Lys Asp His Asn
        35                  40                  45

Ala Thr Ser Ile Leu Gln Gln Leu Pro Leu Leu Ser Ala Met Arg Glu
    50                  55                  60

Lys Pro Ala Gly Gly Ile Pro Val Leu Gly Ser Leu Val Asn Thr Val
65                  70                  75                  80

Leu Lys His Ile Ile Trp Leu Lys Val Ile Thr Ala Asn Ile Leu Gln
                85                  90                  95

Leu Gln Val Lys Pro Ser Ala Asn Asp Gln Glu Leu Leu Val Lys Ile
            100                 105                 110

Pro Leu Asp Met Val Ala Gly Phe Asn Thr Pro Leu Val Lys Thr Ile
        115                 120                 125

Val Glu Phe His Met Thr Thr Glu Ala Gln Ala Thr Ile Arg Met Asp
    130                 135                 140

Thr Ser Ala Ser Gly Pro Thr Arg Leu Val Leu Ser Asp Cys Ala Thr
145                 150                 155                 160

Ser His Gly Ser Leu Arg Ile Gln Leu Leu His Lys Leu Ser Phe Leu
                165                 170                 175

Val Asn Ala Leu Ala Lys Gln Val Met Asn Leu Leu Val Pro Ser Leu
            180                 185                 190

Pro Asn Leu Val Lys Asn Gln Leu Cys Pro Val Ile Glu Ala Ser Phe
        195                 200                 205

Asn Gly Met Tyr Ala Asp Leu Leu Gln Leu Val Lys Val Pro Ile Ser
    210                 215                 220

Leu Ser Ile Asp Arg Leu Glu Phe Asp Leu Leu Tyr Pro Ala Ile Lys
225                 230                 235                 240

Gly Asp Thr Ile Gln Leu Tyr Leu Gly Ala Lys Leu Leu Asp Ser Gln
                245                 250                 255

Gly Lys Val Thr Lys Trp Phe Asn Asn Ser Ala Ala Ser Leu Thr Met
            260                 265                 270

Pro Thr Leu Asp Asn Ile Pro Phe Ser Leu Ile Val Ser Gln Asp Val
        275                 280                 285

Val Lys Ala Ala Val Ala Val Leu Ser Pro Glu Glu Phe Met Val
    290                 295                 300

Leu Leu Asp Ser Val Leu Pro Glu Ser Ala His Arg Leu Lys Ser Ser
305                 310                 315                 320

Ile Gly Leu Ile Asn Glu Lys Ala Ala Asp Lys Leu Gly Ser Thr Gln
                325                 330                 335
```

```
Ile Val Lys Ile Leu Thr Gln Asp Thr Pro Glu Phe Phe Ile Asp Gln
                340                 345                 350

Gly His Ala Lys Val Ala Gln Leu Ile Val Leu Glu Val Phe Pro Ser
            355                 360                 365

Ser Glu Ala Leu Arg Pro Leu Phe Thr Leu Gly Ile Glu Ala Ser Ser
    370                 375                 380

Glu Ala Gln Phe Tyr Thr Lys Gly Asp Gln Leu Ile Leu Asn Leu Asn
385                 390                 395                 400

Asn Ile Ser Ser Asp Arg Ile Gln Leu Met Asn Ser Gly Ile Gly Trp
                405                 410                 415

Phe Gln Pro Asp Val Leu Lys Asn Ile Ile Thr Glu Ile Ile His Ser
            420                 425                 430

Ile Leu Leu Pro Asn Gln Asn Gly Lys Leu Arg Ser Gly Val Pro Val
                435                 440                 445

Ser Leu Val Lys Ala Leu Gly Phe Glu Ala Ala Glu Ser Ser Leu Thr
            450                 455                 460

Lys Asp Ala Leu Val Leu Thr Pro Ala Ser Leu Trp Lys Pro Ser Ser
465                 470                 475                 480

Pro Val Ser Gln

<210> SEQ ID NO 8
<211> LENGTH: 147
<212> TYPE: PRT
<213> ORGANISM: Homo sapiens

<400> SEQUENCE: 8

Met Val Met Gly Leu Gly Val Leu Leu Leu Val Phe Val Leu Gly Leu
1               5                   10                  15

Gly Leu Thr Pro Pro Thr Leu Ala Gln Asp Asn Ser Arg Tyr Thr His
            20                  25                  30

Phe Leu Thr Gln His Tyr Asp Ala Lys Pro Gln Gly Arg Asp Asp Arg
        35                  40                  45

Tyr Cys Glu Ser Ile Met Arg Arg Arg Gly Leu Thr Ser Pro Cys Lys
    50                  55                  60

Asp Ile Asn Thr Phe Ile His Gly Asn Lys Arg Ser Ile Lys Ala Ile
65                  70                  75                  80

Cys Glu Asn Lys Asn Gly Asn Pro His Arg Glu Asn Leu Arg Ile Ser
                85                  90                  95

Lys Ser Ser Phe Gln Val Thr Thr Cys Lys Leu His Gly Gly Ser Pro
            100                 105                 110

Trp Pro Pro Cys Gln Tyr Arg Ala Thr Ala Gly Phe Arg Asn Val Val
        115                 120                 125

Val Ala Cys Glu Asn Gly Leu Pro Val His Leu Asp Gln Ser Ile Phe
    130                 135                 140

Arg Arg Pro
145

<210> SEQ ID NO 9
<211> LENGTH: 597
<212> TYPE: PRT
<213> ORGANISM: Homo sapiens

<400> SEQUENCE: 9

Met His Pro Pro Lys Thr Pro Ser Gly Ala Leu His Arg Lys Arg Lys
1               5                   10                  15
```

-continued

```
Met Ala Ala Trp Pro Phe Ser Arg Leu Trp Lys Val Ser Asp Pro Ile
             20                  25                  30

Leu Phe Gln Met Thr Leu Ile Ala Ala Leu Leu Pro Ala Val Leu Gly
         35                  40                  45

Asn Cys Gly Pro Pro Pro Thr Leu Ser Phe Ala Ala Pro Met Asp Ile
     50                  55                  60

Thr Leu Thr Glu Thr Arg Phe Lys Thr Gly Thr Thr Leu Lys Tyr Thr
65                  70                  75                  80

Cys Leu Pro Gly Tyr Val Arg Ser His Ser Thr Gln Thr Leu Thr Cys
                 85                  90                  95

Asn Ser Asp Gly Glu Trp Val Tyr Asn Thr Phe Cys Ile Tyr Lys Arg
             100                 105                 110

Cys Arg His Pro Gly Glu Leu Arg Asn Gly Gln Val Glu Ile Lys Thr
         115                 120                 125

Asp Leu Ser Phe Gly Ser Gln Ile Glu Phe Ser Cys Ser Glu Gly Phe
     130                 135                 140

Phe Leu Ile Gly Ser Thr Thr Ser Arg Cys Glu Val Gln Asp Arg Gly
145                 150                 155                 160

Val Gly Trp Ser His Pro Leu Pro Gln Cys Glu Ile Val Lys Cys Lys
                 165                 170                 175

Pro Pro Pro Asp Ile Arg Asn Gly Arg His Ser Gly Glu Glu Asn Phe
             180                 185                 190

Tyr Ala Tyr Gly Phe Ser Val Thr Tyr Ser Cys Asp Pro Arg Phe Ser
         195                 200                 205

Leu Leu Gly His Ala Ser Ile Ser Cys Thr Val Glu Asn Glu Thr Ile
     210                 215                 220

Gly Val Trp Arg Pro Ser Pro Pro Thr Cys Glu Lys Ile Thr Cys Arg
225                 230                 235                 240

Lys Pro Asp Val Ser His Gly Glu Met Val Ser Gly Phe Gly Pro Ile
                 245                 250                 255

Tyr Asn Tyr Lys Asp Thr Ile Val Phe Lys Cys Gln Lys Gly Phe Val
             260                 265                 270

Leu Arg Gly Ser Ser Val Ile His Cys Asp Ala Asp Ser Lys Trp Asn
         275                 280                 285

Pro Ser Pro Pro Ala Cys Glu Pro Asn Ser Cys Ile Asn Leu Pro Asp
     290                 295                 300

Ile Pro His Ala Ser Trp Glu Thr Tyr Pro Arg Pro Thr Lys Glu Asp
305                 310                 315                 320

Val Tyr Val Val Gly Thr Val Leu Arg Tyr Arg Cys His Pro Gly Tyr
                 325                 330                 335

Lys Pro Thr Thr Asp Glu Pro Thr Thr Val Ile Cys Gln Lys Asn Leu
             340                 345                 350

Arg Trp Thr Pro Tyr Gln Gly Cys Glu Ala Leu Cys Cys Pro Glu Pro
         355                 360                 365

Lys Leu Asn Asn Gly Glu Ile Thr Gln His Arg Lys Ser Arg Pro Ala
     370                 375                 380

Asn His Cys Val Tyr Phe Tyr Gly Asp Glu Ile Ser Phe Ser Cys His
385                 390                 395                 400

Glu Thr Ser Arg Phe Ser Ala Ile Cys Gln Gly Asp Gly Thr Trp Ser
                 405                 410                 415

Pro Arg Thr Pro Ser Cys Gly Asp Ile Cys Asn Phe Pro Pro Lys Ile
             420                 425                 430

Ala His Gly His Tyr Lys Gln Ser Ser Ser Tyr Ser Phe Phe Lys Glu
```

```
                        435                 440                 445
Glu Ile Ile Tyr Glu Cys Asp Lys Gly Tyr Ile Leu Val Gly Gln Ala
        450                 455                 460

Lys Leu Ser Cys Ser Tyr Ser His Trp Ser Ala Pro Ala Pro Gln Cys
465                 470                 475                 480

Lys Ala Leu Cys Arg Lys Pro Glu Leu Val Asn Gly Arg Leu Ser Val
                485                 490                 495

Asp Lys Asp Gln Tyr Val Glu Pro Glu Asn Val Thr Ile Gln Cys Asp
                500                 505                 510

Ser Gly Tyr Gly Val Val Gly Pro Gln Ser Ile Thr Cys Ser Gly Asn
        515                 520                 525

Arg Thr Trp Tyr Pro Glu Val Pro Lys Cys Glu Trp Glu Thr Pro Glu
        530                 535                 540

Gly Cys Glu Gln Val Leu Thr Gly Lys Arg Leu Met Gln Cys Leu Pro
545                 550                 555                 560

Asn Pro Glu Asp Val Lys Met Ala Leu Glu Val Tyr Lys Leu Ser Leu
                565                 570                 575

Glu Ile Glu Gln Leu Glu Leu Gln Arg Asp Ser Ala Arg Gln Ser Thr
                580                 585                 590

Leu Asp Lys Glu Leu
                595

<210> SEQ ID NO 10
<211> LENGTH: 458
<212> TYPE: PRT
<213> ORGANISM: Homo sapiens

<400> SEQUENCE: 10

Met Ser Asp Leu Leu Ser Val Phe Leu His Leu Leu Leu Phe Lys
1               5                   10                  15

Leu Val Ala Pro Val Thr Phe Arg His His Arg Tyr Asp Asp Leu Val
                20                  25                  30

Arg Thr Leu Tyr Lys Val Gln Asn Glu Cys Pro Gly Ile Thr Arg Val
            35                  40                  45

Tyr Ser Ile Gly Arg Ser Val Glu Gly Arg His Leu Tyr Val Leu Glu
        50                  55                  60

Phe Ser Asp His Pro Gly Ile His Glu Pro Leu Glu Pro Glu Val Lys
65                  70                  75                  80

Tyr Val Gly Asn Met His Gly Asn Glu Ala Leu Gly Arg Glu Leu Met
                85                  90                  95

Leu Gln Leu Ser Glu Phe Leu Cys Glu Glu Phe Arg Asn Arg Asn Gln
                100                 105                 110

Arg Ile Val Gln Leu Ile Gln Asp Thr Arg Ile His Ile Leu Pro Ser
            115                 120                 125

Met Asn Pro Asp Gly Tyr Glu Val Ala Ala Gln Gly Pro Asn Lys
130                 135                 140

Pro Gly Tyr Leu Val Gly Arg Asn Asn Ala Asn Gly Val Asp Leu Asn
145                 150                 155                 160

Arg Asn Phe Pro Asp Leu Asn Thr Tyr Ile Tyr Tyr Asn Glu Lys Tyr
                165                 170                 175

Gly Gly Pro Asn His His Leu Pro Leu Pro Asp Asn Trp Lys Ser Gln
                180                 185                 190

Val Glu Pro Glu Thr Arg Ala Val Ile Arg Trp Met His Ser Phe Asn
            195                 200                 205
```

Phe Val Leu Ser Ala Asn Leu His Gly Gly Ala Val Ala Asn Tyr
210                 215                 220

Pro Tyr Asp Lys Ser Phe Glu His Arg Val Arg Gly Val Arg Thr
225                 230                 235                 240

Ala Ser Thr Pro Thr Pro Asp Asp Lys Leu Phe Gln Lys Leu Ala Lys
            245                 250                 255

Val Tyr Ser Tyr Ala His Gly Trp Met Phe Gln Gly Trp Asn Cys Gly
            260                 265                 270

Asp Tyr Phe Pro Asp Gly Ile Thr Asn Gly Ala Ser Trp Tyr Ser Leu
            275                 280                 285

Ser Lys Gly Met Gln Asp Phe Asn Tyr Leu His Thr Asn Cys Phe Glu
290                 295                 300

Ile Thr Leu Glu Leu Ser Cys Asp Lys Phe Pro Pro Glu Glu Glu Leu
305                 310                 315                 320

Gln Arg Glu Trp Leu Gly Asn Arg Glu Ala Leu Ile Gln Phe Leu Glu
                325                 330                 335

Gln Val His Gln Gly Ile Lys Gly Met Val Leu Asp Glu Asn Tyr Asn
            340                 345                 350

Asn Leu Ala Asn Ala Val Ile Ser Val Ser Gly Ile Asn His Asp Val
            355                 360                 365

Thr Ser Gly Asp His Gly Asp Tyr Phe Arg Leu Leu Leu Pro Gly Ile
370                 375                 380

Tyr Thr Val Ser Ala Thr Ala Pro Gly Tyr Asp Pro Glu Thr Val Thr
385                 390                 395                 400

Val Thr Val Gly Pro Ala Glu Pro Thr Leu Val Asn Phe His Leu Lys
                405                 410                 415

Arg Ser Ile Pro Gln Val Ser Pro Val Arg Arg Ala Pro Ser Arg Arg
            420                 425                 430

His Gly Val Arg Ala Lys Val Gln Pro Gln Ala Arg Lys Lys Glu Met
            435                 440                 445

Glu Met Arg Gln Leu Gln Arg Gly Pro Ala
    450                 455

<210> SEQ ID NO 11
<211> LENGTH: 1212
<212> TYPE: PRT
<213> ORGANISM: Homo sapiens

<400> SEQUENCE: 11

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Glu Lys Glu Phe Arg Gln Ile Leu Lys Asn Pro
        35                  40                  45

Asp Asp Pro Asp Met Val Asp Val Phe Met Asp His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His Asp Lys His Glu Asp
            100                 105                 110

Asn Lys Gln Glu Glu Asn Lys Glu Asn Arg Lys Arg Pro Ser Ser Leu
        115                 120                 125

```
Glu Arg Arg Asn Asn Arg Lys Gly Asn Lys Gly Arg Ser Lys Ser Pro
    130                 135                 140
Arg Glu Thr Gly Gly Lys Arg His Glu Ser Ser Glu Lys Lys Glu
145                 150                 155                 160
Arg Lys Gly Tyr Ser Pro Thr His Arg Glu Glu Tyr Gly Lys Asn
                165                 170                 175
His His Asn Ser Ser Lys Lys Glu Lys Asn Lys Thr Glu Asn Thr Arg
            180                 185                 190
Leu Gly Asp Asn Arg Lys Arg Leu Ser Glu Arg Leu Glu Glu Lys Glu
        195                 200                 205
Asp Asn Glu Glu Gly Val Tyr Asp Tyr Glu Asn Thr Gly Arg Met Thr
    210                 215                 220
Gln Lys Trp Ile Gln Ser Gly His Ile Ala Thr Tyr Tyr Thr Ile Gln
225                 230                 235                 240
Asp Glu Ala Tyr Asp Thr Thr Asp Ser Leu Leu Glu Glu Asn Lys Ile
                245                 250                 255
Tyr Glu Arg Ser Arg Ser Ser Asp Gly Lys Ser Ser Ser Gln Val Asn
            260                 265                 270
Arg Ser Arg His Glu Asn Thr Ser Gln Val Pro Leu Gln Glu Ser Arg
        275                 280                 285
Thr Arg Lys Arg Arg Gly Ser Arg Val Ser Gln Asp Arg Asp Ser Glu
    290                 295                 300
Gly His Ser Glu Asp Ser Glu Arg His Ser Gly Ser Ala Ser Arg Asn
305                 310                 315                 320
His His Gly Ser Ala Trp Glu Gln Ser Arg Asp Gly Ser Arg His Pro
                325                 330                 335
Arg Ser His Asp Glu Asp Arg Ala Ser His Gly His Ser Ala Asp Ser
            340                 345                 350
Ser Arg Gln Ser Gly Thr Arg His Ala Glu Thr Ser Ser Arg Gly Gln
        355                 360                 365
Thr Ala Ser Ser His Glu Gln Ala Arg Ser Ser Pro Gly Glu Arg His
    370                 375                 380
Gly Ser Gly His Gln Gln Ser Ala Asp Ser Ser Arg His Ser Ala Thr
385                 390                 395                 400
Gly Arg Gly Gln Ala Ser Ser Ala Val Ser Asp Arg Gly His Arg Gly
                405                 410                 415
Ser Ser Gly Ser Gln Ala Ser Asp Ser Glu Gly His Ser Glu Asn Ser
            420                 425                 430
Asp Thr Gln Ser Val Ser Gly His Gly Lys Ala Gly Leu Arg Gln Gln
        435                 440                 445
Ser His Gln Glu Ser Thr Arg Gly Arg Ser Gly Glu Arg Ser Gly Arg
    450                 455                 460
Ser Gly Ser Phe Ile Tyr Gln Val Ser Thr His Glu Gln Ser Glu Ser
465                 470                 475                 480
Ala His Gly Arg Thr Arg Thr Ser Thr Gly Arg Arg Gln Gly Ser His
                485                 490                 495
His Glu Gln Ala Arg Asp Ser Ser Arg His Ser Ala Ser Gln Glu Gly
            500                 505                 510
Gln Asp Thr Ile Arg Ala His Pro Gly Ser Arg Arg Gly Gly Arg Gln
        515                 520                 525
Gly Ser His His Glu Gln Ser Val Asp Arg Ser Gly His Ser Gly Ser
    530                 535                 540
```

-continued

```
His His Ser His Thr Thr Ser Gln Gly Arg Ser Asp Val Ser Arg Gly
545                 550                 555                 560

Gln Ser Gly Ser Arg Ser Val Ser Arg Gln Thr Arg Asn Glu Lys Gln
            565                 570                 575

Ser Gly Asp Gly Ser Arg His Ser Gly Ser Arg His His Glu Ala Ser
        580                 585                 590

Ser Arg Ala Asp Ser Ser Arg His Ser Gln Val Gly Gln Gly Gln Ser
    595                 600                 605

Ser Gly Pro Arg Thr Ser Arg Asn Gln Gly Ser Ser Val Ser Gln Asp
610                 615                 620

Ser Asp Ser Gln Gly His Ser Glu Asp Ser Glu Arg Arg Ser Gly Ser
625                 630                 635                 640

Ala Ser Arg Asn His His Gly Ser Ala Gln Glu Gln Ser Arg Asp Gly
                645                 650                 655

Ser Arg His Pro Arg Ser His His Glu Asp Arg Ala Gly His Gly His
            660                 665                 670

Ser Ala Glu Ser Ser Arg Gln Ser Gly Thr His His Ala Glu Asn Ser
        675                 680                 685

Ser Gly Gly Gln Ala Ala Ser Ser His Glu Gln Ala Arg Ser Ser Ala
    690                 695                 700

Gly Glu Arg His Gly Ser His His Gln Gln Ser Ala Asp Ser Ser Arg
705                 710                 715                 720

His Ser Gly Ile Gly His Gly Gln Ala Ser Ser Ala Val Arg Asp Ser
                725                 730                 735

Gly His Arg Gly Ser Ser Gly Ser Gln Ala Ser Asp Ser Glu Gly His
            740                 745                 750

Ser Glu Asp Ser Asp Thr Gln Ser Val Ser Ala His Gly Gln Ala Gly
        755                 760                 765

Pro His Gln Gln Ser His Gln Glu Ser Thr Arg Gly Arg Ser Ala Gly
    770                 775                 780

Arg Ser Gly Arg Ser Gly Ser Phe Leu Tyr Gln Val Ser Thr His Glu
785                 790                 795                 800

Gln Ser Glu Ser Ala His Gly Arg Thr Arg Thr Ser Thr Gly Arg Arg
                805                 810                 815

Gln Gly Ser His His Glu Gln Ala Arg Asp Ser Ser Arg His Ser Ala
            820                 825                 830

Ser Gln Glu Gly Gln Asp Thr Ile Arg Gly His Pro Gly Ser Ser Arg
        835                 840                 845

Arg Gly Arg Gln Gly Ser His Tyr Glu Gln Ser Val Asp Arg Ser Gly
    850                 855                 860

His Ser Gly Ser His His Ser His Thr Thr Ser Gln Gly Arg Ser Asp
865                 870                 875                 880

Ala Ser Arg Gly Gln Ser Gly Ser Arg Ser Ala Ser Arg Gln Thr Arg
                885                 890                 895

Asn Asp Glu Gln Ser Gly Asp Gly Ser Arg His Ser Trp Ser His His
            900                 905                 910

His Glu Ala Ser Thr Gln Ala Asp Ser Ser Arg His Ser Gln Ser Gly
        915                 920                 925

Gln Gly Gln Ser Ala Gly Pro Arg Thr Ser Arg Asn Gln Gly Ser Ser
    930                 935                 940

Val Ser Gln Asp Ser Asp Ser Gln Gly His Ser Glu Asp Ser Glu Arg
945                 950                 955                 960

Trp Ser Gly Ser Ala Ser Arg Asn His Arg Gly Ser Ala Gln Glu Gln
```

```
                965                 970                 975
Ser Arg Asp Gly Ser Arg His Pro Thr Ser His His Glu Asp Arg Ala
            980                 985                 990
Gly His Gly His Ser Ala Glu Ser  Ser Arg Gln Ser Gly  Thr His His
        995                 1000                1005
Ala Glu  Asn Ser Ser Gly Gly  Gln Ala Ala Ser Ser   His Glu Gln
    1010                1015                1020
Ala Arg  Ser Ser Ala Gly Glu  Arg His Gly Ser His  His Gln Gln
    1025                1030                1035
Ser Ala  Asp Ser Ser Arg His  Ser Gly Ile Gly His  Gly Gln Ala
    1040                1045                1050
Ser Ser  Ala Val Arg Asp Ser  Gly His Arg Gly Ser  Ser Gly Ser
    1055                1060                1065
Gln Ala  Ser Asp Ser Glu Gly  His Ser Glu Asp Ser  Asp Thr Gln
    1070                1075                1080
Ser Val  Ser Ala His Gly Gln  Ala Gly Pro His Gln  Gln Ser His
    1085                1090                1095
Gln Glu  Ser Thr Arg Gly Arg  Ser Ala Gly Arg Ser  Gly Arg Ser
    1100                1105                1110
Gly Ser  Phe Leu Tyr Gln Val  Ser Thr His Glu Gln  Ser Glu Ser
    1115                1120                1125
Ala His  Gly Arg Ala Gly Pro  Ser Thr Gly Gly Arg  Gln Gly Ser
    1130                1135                1140
Arg His  Glu Gln Ala Arg Asp  Ser Ser Arg His Ser  Ala Ser Gln
    1145                1150                1155
Glu Gly  Gln Asp Thr Ile Arg  Gly His Pro Gly Ser  Arg Arg Gly
    1160                1165                1170
Gly Arg  Gln Gly Ser Tyr His  Glu Gln Ser Val Asp  Arg Ser Gly
    1175                1180                1185
His Ser  Gly Ser His His Ser  His Thr Thr Ser Gln  Gly Arg Ser
    1190                1195                1200
Asp Ala  Ser His Gly Gln Ser  Gly Ser
    1205                1210

<210> SEQ ID NO 12
<211> LENGTH: 1404
<212> TYPE: PRT
<213> ORGANISM: Homo sapiens

<400> SEQUENCE: 12

Met Ala Trp Lys Thr Leu Pro Ile Tyr Leu Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110
```

-continued

```
Pro Pro Ser Ser Lys Lys Ala Pro Pro Ser Gly Ala Ser Gln Thr
        115                 120                 125
Ile Lys Ser Thr Thr Lys Arg Ser Pro Lys Pro Asn Lys Lys Lys
130                 135                 140
Thr Lys Lys Val Ile Glu Ser Glu Glu Ile Thr Glu Glu His Ser Val
145                 150                 155                 160
Ser Glu Asn Gln Glu Ser Ser Ser Ser Ser Ser Ser Ser Ser
                165                 170                 175
Ser Thr Ile Arg Lys Ile Lys Ser Ser Lys Asn Ser Ala Ala Asn Arg
            180                 185                 190
Glu Leu Gln Lys Lys Leu Lys Val Lys Asp Asn Lys Lys Asn Arg Thr
        195                 200                 205
Lys Lys Lys Pro Thr Pro Lys Pro Pro Val Val Asp Glu Ala Gly Ser
210                 215                 220
Gly Leu Asp Asn Gly Asp Phe Lys Val Thr Thr Pro Asp Thr Ser Thr
225                 230                 235                 240
Thr Gln His Asn Lys Val Ser Thr Ser Pro Lys Ile Thr Thr Ala Lys
                245                 250                 255
Pro Ile Asn Pro Arg Pro Ser Leu Pro Pro Asn Ser Asp Thr Ser Lys
                260                 265                 270
Glu Thr Ser Leu Thr Val Asn Lys Glu Thr Thr Val Glu Thr Lys Glu
        275                 280                 285
Thr Thr Thr Asn Lys Gln Thr Ser Thr Asp Gly Lys Glu Lys Thr
        290                 295                 300
Thr Ser Ala Lys Glu Thr Gln Ser Ile Glu Lys Thr Ser Ala Lys Asp
305                 310                 315                 320
Leu Ala Pro Thr Ser Lys Val Leu Ala Lys Pro Thr Pro Lys Ala Glu
                325                 330                 335
Thr Thr Thr Lys Gly Pro Ala Leu Thr Thr Pro Lys Glu Pro Thr Pro
                340                 345                 350
Thr Thr Pro Lys Glu Pro Ala Ser Thr Thr Pro Lys Glu Pro Thr Pro
                355                 360                 365
Thr Thr Ile Lys Ser Ala Pro Thr Thr Pro Lys Glu Pro Ala Pro Thr
        370                 375                 380
Thr Thr Lys Ser Ala Pro Thr Thr Pro Lys Glu Pro Ala Pro Thr Thr
385                 390                 395                 400
Thr Lys Glu Pro Ala Pro Thr Thr Pro Lys Glu Pro Ala Pro Thr Thr
                405                 410                 415
Thr Lys Glu Pro Ala Pro Thr Thr Thr Lys Ser Ala Pro Thr Thr Pro
                420                 425                 430
Lys Glu Pro Ala Pro Thr Thr Pro Lys Lys Pro Ala Pro Thr Thr Pro
                435                 440                 445
Lys Glu Pro Ala Pro Thr Thr Pro Lys Glu Pro Thr Pro Thr Thr Pro
        450                 455                 460
Lys Glu Pro Ala Pro Thr Thr Lys Glu Pro Ala Pro Thr Thr Pro Lys
465                 470                 475                 480
Glu Pro Ala Pro Thr Ala Pro Lys Lys Pro Ala Pro Thr Thr Pro Lys
                485                 490                 495
Glu Pro Ala Pro Thr Thr Pro Lys Glu Pro Ala Pro Thr Thr Thr Lys
                500                 505                 510
Glu Pro Ser Pro Thr Thr Pro Lys Glu Pro Ala Pro Thr Thr Thr Lys
                515                 520                 525
Ser Ala Pro Thr Thr Thr Lys Glu Pro Ala Pro Thr Thr Thr Lys Ser
```

-continued

```
            530                 535                 540
Ala Pro Thr Thr Pro Lys Glu Pro Ser Pro Thr Thr Lys Glu Pro
545                 550                 555                 560

Ala Pro Thr Thr Pro Lys Glu Pro Ala Pro Thr Thr Pro Lys Pro
                565                 570                 575

Ala Pro Thr Thr Pro Lys Glu Pro Ala Pro Thr Thr Pro Lys Glu Pro
                    580                 585                 590

Ala Pro Thr Thr Thr Lys Lys Pro Ala Pro Thr Pro Lys Glu Pro
                595                 600                 605

Ala Pro Thr Pro Lys Glu Thr Ala Pro Thr Thr Pro Lys Lys Leu
            610                 615                 620

Thr Pro Thr Thr Pro Glu Lys Leu Ala Pro Thr Thr Pro Glu Lys Pro
625                 630                 635                 640

Ala Pro Thr Thr Pro Glu Glu Leu Ala Pro Thr Thr Pro Glu Glu Pro
                645                 650                 655

Thr Pro Thr Thr Pro Glu Glu Pro Ala Pro Thr Thr Pro Lys Ala Ala
                660                 665                 670

Ala Pro Asn Thr Pro Lys Glu Pro Ala Pro Thr Thr Pro Lys Glu Pro
            675                 680                 685

Ala Pro Thr Thr Pro Lys Glu Pro Ala Pro Thr Thr Pro Lys Glu Thr
            690                 695                 700

Ala Pro Thr Thr Pro Lys Gly Thr Ala Pro Thr Thr Leu Lys Glu Pro
705                 710                 715                 720

Ala Pro Thr Thr Pro Lys Lys Pro Ala Pro Lys Glu Leu Ala Pro Thr
                725                 730                 735

Thr Thr Lys Glu Pro Thr Ser Thr Thr Cys Asp Lys Pro Ala Pro Thr
                740                 745                 750

Thr Pro Lys Gly Thr Ala Pro Thr Thr Pro Lys Glu Pro Ala Pro Thr
                755                 760                 765

Thr Pro Lys Glu Pro Ala Pro Thr Thr Pro Lys Gly Thr Ala Pro Thr
                770                 775                 780

Thr Leu Lys Glu Pro Ala Pro Thr Thr Pro Lys Lys Pro Ala Pro Lys
785                 790                 795                 800

Glu Leu Ala Pro Thr Thr Lys Gly Pro Thr Ser Thr Thr Ser Asp
                805                 810                 815

Lys Pro Ala Pro Thr Thr Pro Lys Glu Thr Ala Pro Thr Thr Pro Lys
                820                 825                 830

Glu Pro Ala Pro Thr Thr Pro Lys Lys Pro Ala Pro Thr Thr Pro Glu
                835                 840                 845

Thr Pro Pro Thr Thr Ser Glu Val Ser Thr Pro Thr Thr Thr Lys
850                 855                 860

Glu Pro Thr Thr Ile His Lys Ser Pro Asp Ser Thr Pro Glu Leu
865                 870                 875                 880

Ser Ala Glu Pro Thr Pro Lys Ala Leu Glu Asn Ser Pro Lys Glu Pro
                885                 890                 895

Gly Val Pro Thr Thr Lys Thr Pro Ala Ala Thr Lys Pro Glu Met Thr
                900                 905                 910

Thr Thr Ala Lys Asp Lys Thr Thr Glu Arg Asp Leu Arg Thr Pro
                915                 920                 925

Glu Thr Thr Thr Ala Ala Pro Lys Met Thr Lys Glu Thr Ala Thr Thr
                930                 935                 940

Thr Glu Lys Thr Thr Glu Ser Lys Ile Thr Ala Thr Thr Gln Val
945                 950                 955                 960
```

```
Thr Ser Thr Thr Thr Gln Asp Thr Thr Pro Phe Lys Ile Thr Thr Leu
            965                 970                 975
Lys Thr Thr Thr Leu Ala Pro Lys Val Thr Thr Thr Lys Lys Thr Ile
            980                 985                 990
Thr Thr Thr Glu Ile Met Asn Lys Pro Glu Glu Thr Ala Lys Pro Lys
            995                1000                1005
Asp Arg Ala Thr Asn Ser Lys Ala Thr Thr Pro Lys Pro Gln Lys
           1010                1015            1020
Pro Thr Lys Ala Pro Lys Lys Pro Thr Ser Thr Lys Lys Pro Lys
           1025                1030            1035
Thr Met Pro Arg Val Arg Lys Pro Lys Thr Thr Pro Thr Pro Arg
           1040                1045            1050
Lys Met Thr Ser Thr Met Pro Glu Leu Asn Pro Thr Ser Arg Ile
           1055                1060            1065
Ala Glu Ala Met Leu Gln Thr Thr Thr Arg Pro Asn Gln Thr Pro
           1070                1075            1080
Asn Ser Lys Leu Val Glu Val Asn Pro Lys Ser Glu Asp Ala Gly
           1085                1090            1095
Gly Ala Glu Gly Glu Thr Pro His Met Leu Leu Arg Pro His Val
           1100                1105            1110
Phe Met Pro Glu Val Thr Pro Asp Met Asp Tyr Leu Pro Arg Val
           1115                1120            1125
Pro Asn Gln Gly Ile Ile Ile Asn Pro Met Leu Ser Asp Glu Thr
           1130                1135            1140
Asn Ile Cys Asn Gly Lys Pro Val Asp Gly Leu Thr Thr Leu Arg
           1145                1150            1155
Asn Gly Thr Leu Val Ala Phe Arg Gly His Tyr Phe Trp Met Leu
           1160                1165            1170
Ser Pro Phe Ser Pro Pro Ser Pro Ala Arg Arg Ile Thr Glu Val
           1175                1180            1185
Trp Gly Ile Pro Ser Pro Ile Asp Thr Val Phe Thr Arg Cys Asn
           1190                1195            1200
Cys Glu Gly Lys Thr Phe Phe Phe Lys Asp Ser Gln Tyr Trp Arg
           1205                1210            1215
Phe Thr Asn Asp Ile Lys Asp Ala Gly Tyr Pro Lys Pro Ile Phe
           1220                1225            1230
Lys Gly Phe Gly Gly Leu Thr Gly Gln Ile Val Ala Ala Leu Ser
           1235                1240            1245
Thr Ala Lys Tyr Lys Asn Trp Pro Glu Ser Val Tyr Phe Phe Lys
           1250                1255            1260
Arg Gly Gly Ser Ile Gln Gln Tyr Ile Tyr Lys Gln Glu Pro Val
           1265                1270            1275
Gln Lys Cys Pro Gly Arg Arg Pro Ala Leu Asn Tyr Pro Val Tyr
           1280                1285            1290
Gly Glu Thr Thr Gln Val Arg Arg Arg Phe Glu Arg Ala Ile
           1295                1300            1305
Gly Pro Ser Gln Thr His Thr Ile Arg Ile Gln Tyr Ser Pro Ala
           1310                1315            1320
Arg Leu Ala Tyr Gln Asp Lys Gly Val Leu His Asn Glu Val Lys
           1325                1330            1335
Val Ser Ile Leu Trp Arg Gly Leu Pro Asn Val Val Thr Ser Ala
           1340                1345            1350
```

```
Ile Ser Leu Pro Asn Ile Arg Lys Pro Asp Gly Tyr Asp Tyr Tyr
    1355                1360                1365

Ala Phe Ser Lys Asp Gln Tyr Tyr Asn Ile Asp Val Pro Ser Arg
    1370                1375                1380

Thr Ala Arg Ala Ile Thr Thr Arg Ser Gly Gln Thr Leu Ser Lys
    1385                1390                1395

Val Trp Tyr Asn Cys Pro
    1400

<210> SEQ ID NO 13
<211> LENGTH: 367
<212> TYPE: PRT
<213> ORGANISM: Homo sapiens

<400> SEQUENCE: 13

Met Lys Ser Leu Val Leu Leu Leu Cys Leu Ala Gln Leu Trp Gly Cys
1               5                   10                  15

His Ser Ala Pro His Gly Pro Gly Leu Ile Tyr Arg Gln Pro Asn Cys
            20                  25                  30

Asp Asp Pro Glu Thr Glu Glu Ala Ala Leu Val Ala Ile Asp Tyr Ile
        35                  40                  45

Asn Gln Asn Leu Pro Trp Gly Tyr Lys His Thr Leu Asn Gln Ile Asp
    50                  55                  60

Glu Val Lys Val Trp Pro Gln Gln Pro Ser Gly Glu Leu Phe Glu Ile
65                  70                  75                  80

Glu Ile Asp Thr Leu Glu Thr Thr Cys His Val Leu Asp Pro Thr Pro
                85                  90                  95

Val Ala Arg Cys Ser Val Arg Gln Leu Lys Glu His Ala Val Glu Gly
            100                 105                 110

Asp Cys Asp Phe Gln Leu Leu Lys Leu Asp Gly Lys Phe Ser Val Val
        115                 120                 125

Tyr Ala Lys Cys Asp Ser Ser Pro Asp Ser Ala Glu Asp Val Arg Lys
    130                 135                 140

Val Cys Gln Asp Cys Pro Leu Leu Ala Pro Leu Asn Asp Thr Arg Val
145                 150                 155                 160

Val His Ala Ala Lys Ala Ala Leu Ala Ala Phe Asn Ala Gln Asn Asn
                165                 170                 175

Gly Ser Asn Phe Gln Leu Glu Glu Ile Ser Arg Ala Gln Leu Val Pro
            180                 185                 190

Leu Pro Pro Ser Thr Tyr Val Glu Phe Thr Val Ser Gly Thr Asp Cys
        195                 200                 205

Val Ala Lys Glu Ala Thr Glu Ala Ala Lys Cys Asn Leu Leu Ala Glu
    210                 215                 220

Lys Gln Tyr Gly Phe Cys Lys Ala Thr Leu Ser Glu Lys Leu Gly Gly
225                 230                 235                 240

Ala Glu Val Ala Val Thr Cys Thr Val Phe Gln Thr Gln Pro Val Thr
                245                 250                 255

Ser Gln Pro Gln Pro Glu Gly Ala Asn Glu Ala Val Pro Thr Pro Val
            260                 265                 270

Val Asp Pro Asp Ala Pro Pro Ser Pro Pro Leu Gly Ala Pro Gly Leu
        275                 280                 285

Pro Pro Ala Gly Ser Pro Asp Ser His Val Leu Leu Ala Ala Pro
    290                 295                 300

Pro Gly His Gln Leu His Arg Ala His Tyr Asp Leu Arg His Thr Phe
305                 310                 315                 320
```

```
Met Gly Val Val Ser Leu Gly Ser Pro Ser Glu Val Ser His Pro
            325                 330                 335

Arg Lys Thr Arg Thr Val Val Gln Pro Ser Val Gly Ala Ala Gly
            340                 345                 350

Pro Val Val Pro Pro Cys Pro Gly Arg Ile Arg His Phe Lys Val
            355                 360                 365

<210> SEQ ID NO 14
<211> LENGTH: 249
<212> TYPE: PRT
<213> ORGANISM: Homo sapiens

<400> SEQUENCE: 14

Met Asn Pro Phe Leu Ile Leu Ala Phe Val Gly Ala Ala Gly Glu Val
1               5                   10                  15

Ala Val Pro Phe Asp Asp Asp Lys Ile Val Gly Gly Tyr Thr Cys
            20                  25                  30

Glu Glu Asn Ser Leu Pro Tyr Gln Val Ser Leu Asn Ser Gly Ser His
            35                  40                  45

Phe Cys Gly Gly Ser Leu Ile Ser Glu Gln Trp Val Val Ser Ala Ala
50                  55                  60

His Cys Tyr Lys Thr Arg Ile Gln Val Arg Leu Gly Glu His Asn Ile
65                  70                  75                  80

Lys Val Leu Glu Gly Asn Glu Gln Phe Ile Asn Ala Ala Lys Ile Ile
                85                  90                  95

Arg His Pro Lys Tyr Asn Arg Asp Thr Leu Asp Asn Asp Ile Met Leu
            100                 105                 110

Ile Lys Leu Ser Ser Pro Ala Val Ile Asn Ala Arg Val Ser Thr Ile
            115                 120                 125

Ser Leu Pro Thr Thr Pro Pro Ala Ala Gly Thr Glu Cys Leu Ile Ser
            130                 135                 140

Gly Trp Gly Asn Thr Leu Ser Phe Gly Ala Asp Tyr Pro Asp Glu Leu
145                 150                 155                 160

Lys Cys Leu Asp Ala Pro Val Leu Thr Gln Ala Glu Cys Lys Ala Ser
                165                 170                 175

Tyr Pro Gly Lys Ile Thr Asn Ser Met Phe Cys Val Gly Phe Leu Glu
            180                 185                 190

Gly Gly Lys Asp Ser Cys Gln Arg Asp Ser Gly Gly Pro Val Val Cys
            195                 200                 205

Asn Gly Gln Leu Gln Gly Val Val Ser Trp Gly His Gly Cys Ala Trp
            210                 215                 220

Lys Asn Arg Pro Gly Val Tyr Thr Lys Val Tyr Asn Tyr Val Asp Trp
225                 230                 235                 240

Ile Lys Asp Thr Ile Ala Ala Asn Ser
                245

<210> SEQ ID NO 15
<211> LENGTH: 298
<212> TYPE: PRT
<213> ORGANISM: Homo sapiens

<400> SEQUENCE: 15

Met Val Arg Met Val Pro Val Leu Leu Ser Leu Leu Leu Leu Leu Gly
1               5                   10                  15

Pro Ala Val Pro Gln Glu Asn Gln Asp Gly Arg Tyr Ser Leu Thr Tyr
            20                  25                  30
```

Ile Tyr Thr Gly Leu Ser Lys His Val Glu Asp Val Pro Ala Phe Gln
            35                  40                  45

Ala Leu Gly Ser Leu Asn Asp Leu Gln Phe Phe Arg Tyr Asn Ser Lys
        50                  55                  60

Asp Arg Lys Ser Gln Pro Met Gly Leu Trp Arg Gln Val Glu Gly Met
65                  70                  75                  80

Glu Asp Trp Lys Gln Asp Ser Gln Leu Gln Lys Ala Arg Glu Asp Ile
                85                  90                  95

Phe Met Glu Thr Leu Lys Asp Ile Val Glu Tyr Tyr Asn Asp Ser Asn
            100                 105                 110

Gly Ser His Val Leu Gln Gly Arg Phe Gly Cys Glu Ile Glu Asn Asn
        115                 120                 125

Arg Ser Ser Gly Ala Phe Trp Lys Tyr Tyr Asp Gly Lys Asp Tyr
        130                 135                 140

Ile Glu Phe Asn Lys Glu Ile Pro Ala Trp Val Pro Phe Asp Pro Ala
145                 150                 155                 160

Ala Gln Ile Thr Lys Gln Lys Trp Glu Ala Glu Pro Val Tyr Val Gln
                165                 170                 175

Arg Ala Lys Ala Tyr Leu Glu Glu Cys Pro Ala Thr Leu Arg Lys
            180                 185                 190

Tyr Leu Lys Tyr Ser Lys Asn Ile Leu Asp Arg Gln Asp Pro Pro Ser
        195                 200                 205

Val Val Val Thr Ser His Gln Ala Pro Gly Glu Lys Lys Leu Lys
        210                 215                 220

Cys Leu Ala Tyr Asp Phe Tyr Pro Gly Lys Ile Asp Val His Trp Thr
225                 230                 235                 240

Arg Ala Gly Glu Val Gln Glu Pro Glu Leu Arg Gly Asp Val Leu His
                245                 250                 255

Asn Gly Asn Gly Thr Tyr Gln Ser Trp Val Val Ala Val Pro Pro
            260                 265                 270

Gln Asp Thr Ala Pro Tyr Ser Cys His Val Gln His Ser Ser Leu Ala
        275                 280                 285

Gln Pro Leu Val Val Pro Trp Glu Ala Ser
        290                 295

<210> SEQ ID NO 16
<211> LENGTH: 1049
<212> TYPE: PRT
<213> ORGANISM: Homo sapiens

<400> SEQUENCE: 16

Met Asp Trp Ser Phe Phe Arg Val Val Ala Val Leu Phe Ile Phe Leu
1               5                   10                  15

Val Val Glu Val Asn Ser Glu Phe Arg Ile Gln Val Arg Asp Tyr
            20                  25                  30

Asn Thr Lys Asn Gly Thr Ile Lys Trp His Ser Ile Arg Arg Gln Lys
        35                  40                  45

Arg Glu Trp Ile Lys Phe Ala Ala Ala Cys Arg Glu Gly Glu Asp Asn
    50                  55                  60

Ser Lys Arg Asn Pro Ile Ala Lys Ile His Ser Asp Cys Ala Ala Asn
65                  70                  75                  80

Gln Gln Val Thr Tyr Arg Ile Ser Gly Val Gly Ile Asp Gln Pro Pro
                85                  90                  95

Tyr Gly Ile Phe Val Ile Asn Gln Lys Thr Gly Glu Ile Asn Ile Thr

```
              100                 105                 110
Ser Ile Val Asp Arg Glu Val Thr Pro Phe Ile Ile Tyr Cys Arg
            115                 120                 125

Ala Leu Asn Ser Met Gly Gln Asp Leu Glu Arg Pro Leu Glu Leu Arg
            130                 135                 140

Val Arg Val Leu Asp Ile Asn Asp Asn Pro Val Phe Ser Met Ala
145                 150                 155                 160

Thr Phe Ala Gly Gln Ile Glu Glu Asn Ser Asn Ala Asn Thr Leu Val
                165                 170                 175

Met Ile Leu Asn Ala Thr Asp Ala Asp Glu Pro Asn Asn Leu Asn Ser
            180                 185                 190

Lys Ile Ala Phe Lys Ile Ile Arg Gln Glu Pro Ser Asp Ser Pro Met
            195                 200                 205

Phe Ile Ile Asn Arg Asn Thr Gly Glu Ile Arg Thr Met Asn Asn Phe
210                 215                 220

Leu Asp Arg Glu Gln Tyr Gly Gln Tyr Ala Leu Ala Val Arg Gly Ser
225                 230                 235                 240

Asp Arg Asp Gly Gly Ala Asp Gly Met Ser Ala Glu Cys Glu Cys Asn
                245                 250                 255

Ile Lys Ile Leu Asp Val Asn Asp Asn Ile Pro Tyr Met Glu Gln Ser
            260                 265                 270

Ser Tyr Thr Ile Glu Ile Gln Glu Asn Thr Leu Asn Ser Asn Leu Leu
            275                 280                 285

Glu Ile Arg Val Ile Asp Leu Asp Glu Glu Phe Ser Ala Asn Trp Met
290                 295                 300

Ala Val Ile Phe Phe Ile Ser Gly Asn Glu Gly Asn Trp Phe Glu Ile
305                 310                 315                 320

Glu Met Asn Glu Arg Thr Asn Val Gly Ile Leu Lys Val Val Lys Pro
                325                 330                 335

Leu Asp Tyr Glu Ala Met Gln Ser Leu Gln Leu Ser Ile Gly Val Arg
            340                 345                 350

Asn Lys Ala Glu Phe His His Ser Ile Met Ser Gln Tyr Lys Leu Lys
            355                 360                 365

Ala Ser Ala Ile Ser Val Thr Val Leu Asn Val Ile Glu Gly Pro Val
370                 375                 380

Phe Arg Pro Gly Ser Lys Thr Tyr Val Val Thr Gly Asn Met Gly Ser
385                 390                 395                 400

Asn Asp Lys Val Gly Asp Phe Val Ala Thr Asp Leu Asp Thr Gly Arg
                405                 410                 415

Pro Ser Thr Thr Val Arg Tyr Val Met Gly Asn Asn Pro Ala Asp Leu
            420                 425                 430

Leu Ala Val Asp Ser Arg Thr Gly Lys Leu Thr Leu Lys Asn Lys Val
            435                 440                 445

Thr Lys Glu Gln Tyr Asn Met Leu Gly Gly Lys Tyr Gln Gly Thr Ile
            450                 455                 460

Leu Ser Ile Asp Asp Asn Leu Gln Arg Thr Cys Thr Gly Thr Ile Asn
465                 470                 475                 480

Ile Asn Ile Gln Ser Phe Gly Asn Asp Asp Arg Thr Asn Thr Glu Pro
                485                 490                 495

Asn Thr Lys Ile Thr Thr Asn Thr Gly Arg Gln Glu Ser Thr Ser Ser
            500                 505                 510

Thr Asn Tyr Asp Thr Ser Thr Ser Thr Asp Ser Ser Gln Val Tyr
            515                 520                 525
```

```
Ser Ser Glu Pro Gly Asn Gly Ala Lys Asp Leu Leu Ser Asp Asn Val
    530                 535                 540

His Phe Gly Pro Ala Gly Ile Gly Leu Leu Ile Met Gly Phe Leu Val
545                 550                 555                 560

Leu Gly Leu Val Pro Phe Leu Met Ile Cys Cys Asp Cys Gly Gly Ala
                565                 570                 575

Pro Arg Ser Ala Ala Gly Phe Glu Pro Val Pro Glu Cys Ser Asp Gly
            580                 585                 590

Ala Ile His Ser Trp Ala Val Glu Gly Pro Gln Pro Glu Pro Arg Asp
        595                 600                 605

Ile Thr Thr Val Ile Pro Gln Ile Pro Pro Asp Asn Ala Asn Ile Ile
    610                 615                 620

Glu Cys Ile Asp Asn Ser Gly Val Tyr Thr Asn Glu Tyr Gly Gly Arg
625                 630                 635                 640

Glu Met Gln Asp Leu Gly Gly Glu Arg Met Thr Gly Phe Glu Leu
                645                 650                 655

Thr Glu Gly Val Lys Thr Ser Gly Met Pro Glu Ile Cys Gln Glu Tyr
                660                 665                 670

Ser Gly Thr Leu Arg Arg Asn Ser Met Arg Glu Cys Arg Glu Gly Gly
            675                 680                 685

Leu Asn Met Asn Phe Met Glu Ser Tyr Phe Cys Gln Lys Ala Tyr Ala
690                 695                 700

Tyr Ala Asp Glu Asp Glu Gly Arg Pro Ser Asn Asp Cys Leu Leu Ile
705                 710                 715                 720

Tyr Asp Ile Glu Gly Val Gly Ser Pro Ala Gly Ser Val Gly Cys Cys
                725                 730                 735

Ser Phe Ile Gly Glu Asp Leu Asp Asp Ser Phe Leu Asp Thr Leu Gly
            740                 745                 750

Pro Lys Phe Lys Lys Leu Ala Asp Ile Ser Leu Gly Lys Glu Ser Tyr
        755                 760                 765

Pro Asp Leu Asp Pro Ser Trp Pro Pro Gln Ser Thr Glu Pro Val Cys
    770                 775                 780

Leu Pro Gln Glu Thr Glu Pro Val Val Ser Gly His Pro Pro Ile Ser
785                 790                 795                 800

Pro His Phe Gly Thr Thr Thr Val Ile Ser Glu Ser Thr Tyr Pro Ser
                805                 810                 815

Gly Pro Gly Val Leu His Pro Lys Pro Ile Leu Asp Pro Leu Gly Tyr
            820                 825                 830

Gly Asn Val Thr Val Thr Glu Ser Tyr Thr Thr Ser Asp Thr Leu Lys
        835                 840                 845

Pro Ser Val His Val His Asp Asn Arg Pro Ala Ser Asn Val Val Val
    850                 855                 860

Thr Glu Arg Val Val Gly Pro Ile Ser Gly Ala Asp Leu His Gly Met
865                 870                 875                 880

Leu Glu Met Pro Asp Leu Arg Asp Gly Ser Asn Val Ile Val Thr Glu
                885                 890                 895

Arg Val Ile Ala Pro Ser Ser Ser Leu Pro Thr Ser Leu Thr Ile His
                900                 905                 910

His Pro Arg Glu Ser Ser Asn Val Val Val Thr Glu Arg Val Ile Gln
        915                 920                 925

Pro Thr Ser Gly Met Ile Gly Ser Leu Ser Met His Pro Glu Leu Ala
    930                 935                 940
```

```
Asn Ala His Asn Val Ile Val Thr Glu Arg Val Ser Gly Ala Gly
945                 950                 955                 960

Val Thr Gly Ile Ser Gly Thr Thr Gly Ile Ser Gly Gly Ile Gly Ser
                965                 970                 975

Ser Gly Leu Val Gly Thr Ser Met Gly Ala Gly Ser Gly Ala Leu Ser
            980                 985                 990

Gly Ala Gly Ile Ser Gly Gly Gly Ile Gly Leu Ser Ser Leu Gly Gly
        995                 1000                1005

Thr Ala Ser Ile Gly His Met Arg Ser Ser Ser Asp His His Phe
    1010                1015                1020

Asn Gln Thr Ile Gly Ser Ala Ser Pro Ser Thr Ala Arg Ser Arg
    1025                1030                1035

Ile Thr Lys Tyr Ser Thr Val Gln Tyr Ser Lys
    1040                1045

<210> SEQ ID NO 17
<211> LENGTH: 242
<212> TYPE: PRT
<213> ORGANISM: Homo sapiens

<400> SEQUENCE: 17

Met Ser Asn Pro Arg Ser Leu Glu Glu Glu Lys Tyr Asp Met Ser Gly
1               5                   10                  15

Ala Arg Leu Ala Leu Ile Leu Cys Val Thr Lys Ala Arg Glu Gly Ser
            20                  25                  30

Glu Glu Asp Leu Asp Ala Leu Glu His Met Phe Arg Gln Leu Arg Phe
        35                  40                  45

Glu Ser Thr Met Lys Arg Asp Pro Thr Ala Glu Gln Phe Gln Glu Glu
    50                  55                  60

Leu Glu Lys Phe Gln Gln Ala Ile Asp Ser Arg Glu Asp Pro Val Ser
65                  70                  75                  80

Cys Ala Phe Val Val Leu Met Ala His Gly Arg Glu Gly Phe Leu Lys
                85                  90                  95

Gly Glu Asp Gly Glu Met Val Lys Leu Glu Asn Leu Phe Glu Ala Leu
            100                 105                 110

Asn Asn Lys Asn Cys Gln Ala Leu Arg Ala Lys Pro Lys Val Tyr Ile
        115                 120                 125

Ile Gln Ala Cys Arg Gly Glu Gln Arg Asp Pro Gly Glu Thr Val Gly
    130                 135                 140

Gly Asp Glu Ile Val Met Val Ile Lys Asp Ser Pro Gln Thr Ile Pro
145                 150                 155                 160

Thr Tyr Thr Asp Ala Leu His Val Tyr Ser Thr Val Glu Gly Tyr Ile
                165                 170                 175

Ala Tyr Arg His Asp Gln Lys Gly Ser Cys Phe Ile Gln Thr Leu Val
            180                 185                 190

Asp Val Phe Thr Lys Arg Lys Gly His Ile Leu Glu Leu Leu Thr Glu
        195                 200                 205

Val Thr Arg Arg Met Ala Glu Ala Glu Leu Val Gln Glu Gly Lys Ala
    210                 215                 220

Arg Lys Thr Asn Pro Glu Ile Gln Ser Thr Leu Arg Lys Arg Leu Tyr
225                 230                 235                 240

Leu Gln

<210> SEQ ID NO 18
<211> LENGTH: 2850
```

<212> TYPE: PRT
<213> ORGANISM: Homo sapiens

<400> SEQUENCE: 18

```
Met Pro Lys Leu Leu Gln Gly Val Ile Thr Val Ile Asp Val Phe Tyr
 1               5                  10                  15

Gln Tyr Ala Thr Gln His Gly Glu Tyr Asp Thr Leu Asn Lys Ala Glu
             20                  25                  30

Leu Lys Glu Leu Leu Glu Asn Glu Phe His Gln Ile Leu Lys Asn Pro
         35                  40                  45

Asn Asp Pro Asp Thr Val Asp Ile Ile Leu Gln Ser Leu Asp Arg Asp
 50                  55                  60

His Asn Lys Lys Val Asp Phe Thr Glu Tyr Leu Leu Met Ile Phe Lys
 65                  70                  75                  80

Leu Val Gln Ala Arg Asn Lys Ile Ile Gly Lys Asp Tyr Cys Gln Val
                 85                  90                  95

Ser Gly Ser Lys Leu Arg Asp Asp Thr His Gln His Gln Glu Glu Gln
            100                 105                 110

Glu Glu Thr Glu Lys Glu Glu Asn Lys Arg Gln Glu Ser Ser Phe Ser
        115                 120                 125

His Ser Ser Trp Ser Ala Gly Glu Asn Asp Ser Tyr Ser Arg Asn Val
130                 135                 140

Arg Gly Ser Leu Lys Pro Gly Thr Glu Ser Ile Ser Arg Arg Leu Ser
145                 150                 155                 160

Phe Gln Arg Asp Phe Ser Gly Gln His Asn Ser Tyr Ser Gly Gln Ser
                165                 170                 175

Ser Ser Tyr Gly Glu Gln Asn Ser Asp Ser His Gln Ser Ser Gly Arg
            180                 185                 190

Gly Gln Cys Gly Ser Gly Ser Gln Ser Pro Asn Tyr Gly Gln His
        195                 200                 205

Gly Ser Gly Ser Gly Gln Ser Ser Ser Asn Asp Thr His Gly Ser Gly
    210                 215                 220

Ser Gly Gln Ser Ser Gly Phe Ser Gln His Lys Ser Ser Ser Gly Gln
225                 230                 235                 240

Ser Ser Gly Tyr Ser Gln His Gly Ser Gly Ser Gly His Ser Ser Gly
                245                 250                 255

Tyr Gly Gln His Gly Ser Arg Ser Gly Gln Ser Arg Gly Glu Arg
            260                 265                 270

His Arg Ser Ser Ser Gly Ser Ser Ser Tyr Gly Gln His Gly Ser
        275                 280                 285

Gly Ser Arg Gln Ser Leu Gly His Gly Arg Gly Ser Gly Ser Arg
    290                 295                 300

Gln Ser Pro Ser His Val Arg His Gly Ser Gly His Ser Ser
305                 310                 315                 320

Ser His Gly Gln His Gly Ser Gly Ser Tyr Ser Tyr Ser Arg Gly
                325                 330                 335

His Tyr Glu Ser Gly Ser Gly Gln Thr Ser Gly Phe Gly Gln His Glu
            340                 345                 350

Ser Gly Ser Gly Gln Ser Ser Tyr Ser Lys His Gly Ser Gly Ser
        355                 360                 365

Gly His Ser Ser Gln Gly Gln His Gly Ser Thr Ser Gly Gln Ala
    370                 375                 380

Ser Ser Ser Gly Gln His Gly Ser Ser Arg Gln Ser Ser Ser Tyr
385                 390                 395                 400
```

```
Gly Gln His Glu Ser Ala Ser Arg His Ser Ser Gly Arg Gly Gln His
            405                 410                 415

Ser Ser Gly Ser Gly Gln Ser Pro Gly His Gly Gln Arg Gly Ser Gly
            420                 425                 430

Ser Gly Gln Ser Pro Ser Ser Gly Gln His Gly Thr Gly Phe Gly Arg
            435                 440                 445

Ser Ser Ser Ser Gly Pro Tyr Val Ser Gly Ser Gly Tyr Ser Ser Gly
            450                 455                 460

Phe Gly His His Glu Ser Ser Glu His Ser Ser Gly Tyr Thr Gln
465                 470                 475                 480

His Gly Ser Gly Ser Gly His Ser Ser Gly His Gly Gln His Gly Ser
            485                 490                 495

Arg Ser Gly Gln Ser Ser Arg Gly Glu Arg Gln Gly Ser Ser Ala Gly
            500                 505                 510

Ser Ser Ser Ser Tyr Gly Gln His Gly Ser Gly Ser Arg Gln Ser Leu
            515                 520                 525

Gly His Ser Arg His Gly Ser Gly Gly Gln Ser Pro Ser Pro Ser
            530                 535                 540

Arg Gly Arg His Glu Ser Gly Ser Arg Gln Ser Ser Ser Tyr Gly Pro
545                 550                 555                 560

His Gly Tyr Gly Ser Gly Arg Ser Ser Ser Arg Gly Pro Tyr Glu Ser
            565                 570                 575

Gly Ser Gly His Ser Ser Gly Leu Gly His Gln Glu Ser Arg Ser Gly
            580                 585                 590

Gln Ser Ser Gly Tyr Gly Gln His Gly Ser Ser Ser Gly His Ser Ser
            595                 600                 605

Thr His Gly Gln His Gly Ser Thr Ser Gly Gln Ser Ser Ser Cys Gly
            610                 615                 620

Gln His Gly Ala Thr Ser Gly Gln Ser Ser His Gly Gln His Gly
625                 630                 635                 640

Ser Gly Ser Ser Gln Ser Ser Arg Tyr Gly Gln Gln Gly Ser Gly Ser
            645                 650                 655

Gly Gln Ser Pro Ser Arg Gly Arg His Gly Ser Asp Phe Gly His Ser
            660                 665                 670

Ser Ser Tyr Gly Gln His Gly Ser Gly Ser Gly Trp Ser Ser Ser Asn
            675                 680                 685

Gly Pro His Gly Ser Val Ser Gly Gln Ser Ser Gly Phe Gly His Lys
            690                 695                 700

Ser Gly Ser Gly Gln Ser Ser Gly Tyr Ser Gln His Gly Ser Gly Ser
705                 710                 715                 720

Ser His Ser Ser Gly Tyr Arg Lys His Gly Ser Arg Ser Gly Gln Ser
            725                 730                 735

Ser Arg Ser Glu Gln His Gly Ser Ser Ser Gly Leu Ser Ser Ser Tyr
            740                 745                 750

Gly Gln His Gly Ser Gly Ser His Gln Ser Ser Gly His Gly Arg Gln
            755                 760                 765

Gly Ser Gly Ser Gly His Ser Pro Ser Arg Val Arg His Gly Ser Ser
            770                 775                 780

Ser Gly His Ser Ser His Gly Gln His Gly Ser Gly Thr Ser Cys
785                 790                 795                 800

Ser Ser Ser Cys Gly His Tyr Glu Ser Gly Ser Gly Gln Ala Ser Gly
            805                 810                 815
```

-continued

```
Phe Gly Gln His Glu Ser Gly Ser Gly Gly Tyr Ser Gln His Gly
                820                 825                 830

Ser Ala Ser Gly His Phe Ser Gln Gly Arg His Gly Ser Thr Ser
            835                 840                 845

Gly Gln Ser Ser Ser Ser Gly Gln His Asp Ser Ser Gly Gln Ser
        850                 855                 860

Ser Ser Tyr Gly Gln His Glu Ser Ala Ser His His Ala Ser Gly Arg
865                 870                 875                 880

Gly Arg His Gly Ser Gly Ser Gly Gln Ser Pro Gly His Gly Gln Arg
                885                 890                 895

Gly Ser Gly Ser Gly Gln Ser Pro Ser Tyr Gly Arg His Gly Ser Gly
            900                 905                 910

Ser Gly Arg Ser Ser Ser Ser Gly Arg His Gly Ser Gly Ser Gly Gln
        915                 920                 925

Ser Ser Gly Phe Gly His Lys Ser Ser Ser Gly Gln Ser Ser Gly Tyr
    930                 935                 940

Thr Gln His Gly Ser Gly Ser Gly His Ser Ser Ser Tyr Glu Gln His
945                 950                 955                 960

Gly Ser Arg Ser Gly Gln Ser Ser Arg Ser Glu Gln His Gly Ser Ser
                965                 970                 975

Ser Gly Ser Ser Ser Ser Tyr Gly Gln His Gly Ser Gly Ser Arg Gln
            980                 985                 990

Ser Leu Gly His Gly Gln His Gly Ser Gly Ser Gly Gln Ser Pro Ser
        995                 1000                1005

Pro Ser Arg Gly Arg His Gly Ser Gly Ser Gly Gln Ser Ser Ser
    1010                1015                1020

Tyr Gly Pro Tyr Arg Ser Gly Ser Gly Trp Ser Ser Arg Gly
    1025                1030                1035

Pro Tyr Glu Ser Gly Ser Gly His Ser Ser Gly Leu Gly His Arg
    1040                1045                1050

Glu Ser Arg Ser Gly Gln Ser Ser Gly Tyr Gly Gln His Gly Ser
    1055                1060                1065

Ser Ser Gly His Ser Ser Thr His Gly Gln His Gly Ser Thr Ser
    1070                1075                1080

Gly Gln Ser Ser Ser Cys Gly Gln His Gly Ala Ser Ser Gly Gln
    1085                1090                1095

Ser Ser Ser His Gly Gln His Gly Ser Gly Ser Ser Gln Ser Ser
    1100                1105                1110

Gly Tyr Gly Arg Gln Gly Ser Gly Ser Gly Gln Ser Pro Gly His
    1115                1120                1125

Gly Gln Arg Gly Ser Gly Ser Arg Gln Ser Pro Ser Tyr Gly Arg
    1130                1135                1140

His Gly Ser Gly Ser Gly Arg Ser Ser Ser Ser Gly Gln His Gly
    1145                1150                1155

Ser Gly Leu Gly Glu Ser Ser Gly Phe Gly His His Glu Ser Ser
    1160                1165                1170

Ser Gly Gln Ser Ser Ser Tyr Ser Gln His Gly Ser Gly Ser Gly
    1175                1180                1185

His Ser Ser Gly Tyr Gly Gln His Gly Ser Arg Ser Gly Gln Ser
    1190                1195                1200

Ser Arg Gly Glu Arg His Gly Ser Ser Ser Gly Ser Ser Ser His
    1205                1210                1215

Tyr Gly Gln His Gly Ser Gly Ser Arg Gln Ser Ser Gly His Gly
```

-continued

```
             1220                1225                1230
Arg Gln Gly Ser Gly Ser Gly His Ser Pro Ser Arg Gly Arg His
             1235                1240                1245
Gly Ser Gly Leu Gly His Ser Ser Ser His Gly Gln His Gly Ser
             1250                1255                1260
Gly Ser Gly Arg Ser Ser Ser Arg Gly Pro Tyr Glu Ser Arg Ser
             1265                1270                1275
Gly His Ser Ser Val Phe Gly Gln His Glu Ser Gly Ser Gly His
             1280                1285                1290
Ser Ser Ala Tyr Ser Gln His Gly Ser Gly Ser Gly His Phe Cys
             1295                1300                1305
Ser Gln Gly Gln His Gly Ser Thr Ser Gly Gln Ser Ser Thr Phe
             1310                1315                1320
Asp Gln Glu Gly Ser Ser Thr Gly Gln Ser Ser Ser Tyr Gly His
             1325                1330                1335
Arg Gly Ser Gly Ser Ser Gln Ser Ser Gly Tyr Gly Arg His Gly
             1340                1345                1350
Ala Gly Ser Gly Gln Ser Pro Ser Arg Gly Arg His Gly Ser Gly
             1355                1360                1365
Ser Gly His Ser Ser Ser Tyr Gly Gln His Gly Ser Gly Ser Gly
             1370                1375                1380
Trp Ser Ser Ser Ser Gly Arg His Gly Ser Gly Ser Gly Gln Ser
             1385                1390                1395
Ser Gly Phe Gly His His Glu Ser Ser Ser Trp Gln Ser Ser Gly
             1400                1405                1410
Cys Thr Gln His Gly Ser Gly Ser Gly His Ser Ser Ser Tyr Glu
             1415                1420                1425
Gln His Gly Ser Arg Ser Gly Gln Ser Ser Arg Gly Glu Arg His
             1430                1435                1440
Gly Ser Ser Ser Gly Ser Ser Ser Ser Tyr Gly Gln His Gly Ser
             1445                1450                1455
Gly Ser Arg Gln Ser Leu Gly His Gly Gln His Gly Ser Gly Ser
             1460                1465                1470
Gly Gln Ser Pro Ser Pro Ser Arg Gly Arg His Gly Ser Gly Ser
             1475                1480                1485
Gly Gln Ser Ser Ser Tyr Ser Pro Tyr Gly Ser Gly Ser Gly Trp
             1490                1495                1500
Ser Ser Ser Arg Gly Pro Tyr Glu Ser Gly Ser Ser His Ser Ser
             1505                1510                1515
Gly Leu Gly His Arg Glu Ser Arg Ser Gly Gln Ser Ser Gly Tyr
             1520                1525                1530
Gly Gln His Gly Ser Ser Ser Gly His Ser Ser Thr His Gly Gln
             1535                1540                1545
His Gly Ser Thr Ser Gly Gln Ser Ser Ser Cys Gly Gln His Gly
             1550                1555                1560
Ala Ser Ser Gly Gln Ser Ser Ser His Gly Gln His Gly Ser Gly
             1565                1570                1575
Ser Ser Gln Ser Ser Gly Tyr Gly Arg Gln Gly Ser Gly Ser Gly
             1580                1585                1590
Gln Ser Pro Gly His Gly Gln Arg Gly Ser Gly Ser Arg Gln Ser
             1595                1600                1605
Pro Ser Tyr Gly Arg His Gly Ser Gly Ser Gly Arg Ser Ser Ser
             1610                1615                1620
```

```
Ser Gly Gln His Gly Ser Gly Leu Gly Glu Ser Ser Gly Phe Gly
        1625                1630                1635

His His Glu Ser Ser Ser Gly Gln Ser Ser Tyr Ser Gln His
    1640                1645                1650

Gly Ser Gly Ser Gly His Ser Ser Gly Tyr Gly Gln His Gly Ser
        1655                1660                1665

Arg Ser Gly Gln Ser Ser Arg Gly Glu Arg His Gly Ser Ser Ser
        1670                1675                1680

Arg Ser Ser Ser Arg Tyr Gly Gln His Gly Ser Gly Ser Arg Gln
        1685                1690                1695

Ser Ser Gly His Gly Arg Gln Gly Ser Gly Ser Gly Gln Ser Pro
        1700                1705                1710

Ser Arg Gly Arg His Gly Ser Gly Leu Gly His Ser Ser Ser His
        1715                1720                1725

Gly Gln His Gly Ser Gly Ser Gly Arg Ser Ser Ser Arg Gly Pro
        1730                1735                1740

Tyr Glu Ser Arg Ser Gly His Ser Ser Val Phe Gly Gln His Glu
        1745                1750                1755

Ser Gly Ser Gly His Ser Ser Ala Tyr Ser Gln His Gly Ser Gly
        1760                1765                1770

Ser Gly His Phe Cys Ser Gln Gly Gln His Gly Ser Thr Ser Gly
        1775                1780                1785

Gln Ser Ser Thr Phe Asp Gln Glu Gly Ser Ser Thr Gly Gln Ser
        1790                1795                1800

Ser Ser His Gly Gln His Gly Ser Gly Ser Ser Gln Ser Ser Ser
        1805                1810                1815

Tyr Gly Gln Gln Gly Ser Gly Ser Gly Gln Ser Pro Ser Arg Gly
        1820                1825                1830

Arg His Gly Ser Gly Ser Gly His Ser Ser Ser Tyr Gly Gln His
        1835                1840                1845

Gly Ser Gly Ser Gly Trp Ser Ser Ser Ser Gly Arg His Gly Ser
        1850                1855                1860

Gly Ser Gly Gln Ser Ser Gly Phe Gly His His Glu Ser Ser Ser
        1865                1870                1875

Trp Gln Ser Ser Gly Tyr Thr Gln His Gly Ser Gly Ser Gly His
        1880                1885                1890

Ser Ser Ser Tyr Glu Gln His Gly Ser Arg Ser Gly Gln Ser Ser
        1895                1900                1905

Arg Gly Glu Gln His Gly Ser Ser Ser Gly Ser Ser Ser Ser Tyr
        1910                1915                1920

Gly Gln His Gly Ser Gly Ser Arg Gln Ser Leu Gly His Gly Gln
        1925                1930                1935

His Gly Ser Gly Ser Gly Gln Ser Pro Ser Pro Ser Arg Gly Arg
        1940                1945                1950

His Gly Ser Gly Ser Gly Gln Ser Ser Ser Tyr Gly Pro Tyr Gly
        1955                1960                1965

Ser Gly Ser Gly Trp Ser Ser Ser Arg Gly Pro Tyr Glu Ser Gly
        1970                1975                1980

Ser Gly His Ser Ser Gly Leu Gly His Arg Glu Ser Arg Ser Gly
        1985                1990                1995

Gln Ser Ser Gly Tyr Gly Gln His Gly Ser Ser Ser Gly His Ser
        2000                2005                2010
```

-continued

```
Ser Thr His Gly Gln His Gly Ser Ala Ser Gly Gln Ser Ser Ser
    2015                2020                2025

Cys Gly Gln His Gly Ala Ser Ser Gly Gln Ser Ser His Gly
    2030                2035                2040

Gln His Gly Ser Gly Ser Ser Gln Ser Ser Gly Tyr Gly Arg Gln
    2045                2050                2055

Gly Ser Gly Ser Gly Gln Ser Pro Gly His Gly Gln Arg Gly Ser
    2060                2065                2070

Gly Ser Arg Gln Ser Pro Ser Tyr Gly Arg His Gly Ser Gly Ser
    2075                2080                2085

Gly Arg Ser Ser Ser Gly Gln His Gly Pro Gly Leu Gly Glu
    2090                2095                2100

Ser Ser Gly Phe Gly His His Glu Ser Ser Ser Gly Gln Ser Ser
    2105                2110                2115

Ser Tyr Ser Gln His Gly Ser Gly Ser Gly His Ser Ser Gly Tyr
    2120                2125                2130

Gly Gln His Gly Ser Arg Ser Gly Gln Ser Ser Arg Gly Glu Arg
    2135                2140                2145

His Gly Ser Ser Ser Gly Ser Ser Ser Arg Tyr Gly Gln His Gly
    2150                2155                2160

Ser Gly Ser Arg Gln Ser Ser Gly His Gly Arg Gln Gly Ser Gly
    2165                2170                2175

Ser Gly His Ser Pro Ser Arg Gly Arg His Gly Ser Gly Ser Gly
    2180                2185                2190

His Ser Ser Ser His Gly Gln His Gly Ser Gly Ser Gly Arg Ser
    2195                2200                2205

Ser Ser Arg Gly Pro Tyr Glu Ser Arg Ser Gly His Ser Ser Val
    2210                2215                2220

Phe Gly Gln His Glu Ser Gly Ser Gly His Ser Ala Tyr Ser
    2225                2230                2235

Gln His Gly Ser Gly Ser Gly His Phe Cys Ser Gln Gly Gln His
    2240                2245                2250

Gly Ser Thr Ser Gly Gln Ser Ser Thr Phe Asp Gln Glu Gly Ser
    2255                2260                2265

Ser Thr Gly Gln Ser Ser Ser His Gly Gln His Gly Ser Gly Ser
    2270                2275                2280

Ser Gln Ser Ser Ser Tyr Gly Gln Gln Gly Ser Gly Ser Gly Gln
    2285                2290                2295

Ser Pro Ser Arg Gly Arg His Gly Ser Gly Ser Gly His Ser Ser
    2300                2305                2310

Ser Tyr Gly Gln His Gly Ser Gly Ser Gly Trp Ser Ser Ser Ser
    2315                2320                2325

Gly Arg His Gly Ser Gly Ser Gly Gln Ser Ser Gly Phe Gly His
    2330                2335                2340

His Glu Ser Ser Ser Trp Gln Ser Ser Gly Tyr Thr Gln His Gly
    2345                2350                2355

Ser Gly Ser Gly His Ser Ser Ser Tyr Glu Gln His Gly Ser Arg
    2360                2365                2370

Ser Gly Gln Ser Ser Arg Gly Glu Arg His Gly Ser Ser Ser Gly
    2375                2380                2385

Ser Ser Ser Ser Tyr Gly Gln His Gly Ser Gly Ser Arg Gln Ser
    2390                2395                2400

Leu Gly His Gly Gln His Gly Ser Gly Ser Gly Gln Ser Pro Ser
```

-continued

```
                2405                2410                2415
Pro Ser Arg Gly Arg His Gly Ser Gly Ser Gly Gln Ser Ser Ser
        2420            2425                2430
Tyr Ser Pro Tyr Gly Ser Gly Ser Gly Trp Ser Ser Ser Arg Gly
        2435            2440                2445
Pro Tyr Glu Ser Gly Ser Gly His Ser Ser Gly Leu Gly His Arg
        2450            2455                2460
Glu Ser Arg Ser Gly Gln Ser Ser Gly Tyr Gly Gln His Gly Ser
        2465            2470                2475
Ser Ser Gly His Ser Ser Thr His Gly Gln His Gly Ser Thr Ser
        2480            2485                2490
Gly Gln Ser Ser Ser Cys Gly Gln His Gly Ala Ser Ser Gly Gln
        2495            2500                2505
Ser Ser Ser His Gly Gln His Gly Ser Gly Ser Ser Gln Ser Ser
        2510            2515                2520
Gly Tyr Gly Arg Gln Gly Ser Gly Ser Gly Gln Ser Pro Gly His
        2525            2530                2535
Gly Gln Arg Gly Ser Gly Ser Arg Gln Ser Pro Ser Tyr Gly Arg
        2540            2545                2550
His Gly Ser Gly Ser Gly Arg Ser Ser Ser Gly Gln His Gly
        2555            2560                2565
Ser Gly Leu Gly Glu Ser Ser Gly Phe Gly His His Glu Ser Ser
        2570            2575                2580
Ser Gly Gln Ser Ser Ser Tyr Ser Gln His Gly Ser Gly Ser Gly
        2585            2590                2595
His Ser Ser Gly Tyr Gly Gln His Gly Ser Arg Ser Gly Gln Ser
        2600            2605                2610
Ser Arg Gly Glu Arg His Gly Ser Ser Gly Ser Ser Ser His
        2615            2620                2625
Tyr Gly Gln His Gly Ser Gly Ser Arg Gln Ser Ser Gly His Gly
        2630            2635                2640
Arg Gln Gly Ser Gly Ser Gly Gln Ser Pro Ser Arg Gly Arg His
        2645            2650                2655
Gly Ser Gly Leu Gly His Ser Ser Ser His Gly Gln His Gly Ser
        2660            2665                2670
Gly Ser Gly Arg Ser Ser Ser Arg Gly Pro Tyr Glu Ser Arg Leu
        2675            2680                2685
Gly His Ser Ser Val Phe Gly Gln His Glu Ser Gly Ser Gly His
        2690            2695                2700
Ser Ser Ala Tyr Ser Gln His Gly Ser Gly Ser Gly His Phe Cys
        2705            2710                2715
Ser Gln Gly Gln His Gly Ser Thr Ser Gly Gln Ser Ser Thr Phe
        2720            2725                2730
Asp Gln Glu Gly Ser Ser Thr Gly Gln Ser Ser Ser Tyr Gly His
        2735            2740                2745
Arg Gly Ser Gly Ser Ser Gln Ser Ser Gly Tyr Gly Arg His Gly
        2750            2755                2760
Ala Gly Ser Gly Gln Ser Leu Ser His Gly Arg His Gly Ser Gly
        2765            2770                2775
Ser Gly Gln Ser Ser Ser Tyr Gly Gln His Gly Ser Gly Ser Gly
        2780            2785                2790
Gln Ser Ser Gly Tyr Ser Gln His Gly Ser Gly Ser Gly Gln Asp
        2795            2800                2805
```

```
Gly Tyr Ser Tyr Cys Lys Gly Gly Ser Asn His Asp Gly Gly Ser
        2810                2815                2820

Ser Gly Ser Tyr Phe Leu Ser Phe Pro Ser Ser Thr Ser Pro Tyr
        2825                2830                2835

Glu Tyr Val Gln Glu Gln Arg Cys Tyr Phe Tyr Gln
        2840                2845                2850

<210> SEQ ID NO 19
<211> LENGTH: 427
<212> TYPE: PRT
<213> ORGANISM: Homo sapiens

<400> SEQUENCE: 19

Met Lys Leu Ile Thr Ile Leu Phe Leu Cys Ser Arg Leu Leu Ser
1               5                   10                  15

Leu Thr Gln Glu Ser Gln Ser Glu Glu Ile Asp Cys Asn Asp Lys Asp
            20                  25                  30

Leu Phe Lys Ala Val Asp Ala Ala Leu Lys Lys Tyr Asn Ser Gln Asn
        35                  40                  45

Gln Ser Asn Asn Gln Phe Val Leu Tyr Arg Ile Thr Glu Ala Thr Lys
50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
                85                  90                  95

Lys Asp Ala Ala Lys Ala Ala Thr Gly Glu Cys Thr Ala Thr Val Gly
            100                 105                 110

Lys Arg Ser Ser Thr Lys Phe Ser Val Ala Thr Gln Thr Cys Gln Ile
        115                 120                 125

Thr Pro Ala Glu Gly Pro Val Val Thr Ala Gln Tyr Asp Cys Leu Gly
130                 135                 140

Cys Val His Pro Ile Ser Thr Gln Ser Pro Asp Leu Glu Pro Ile Leu
145                 150                 155                 160

Arg His Gly Ile Gln Tyr Phe Asn Asn Asn Thr Gln His Ser Ser Leu
                165                 170                 175

Phe Met Leu Asn Glu Val Lys Arg Ala Gln Arg Gln Val Val Ala Gly
            180                 185                 190

Leu Asn Phe Arg Ile Thr Tyr Ser Ile Val Gln Thr Asn Cys Ser Lys
        195                 200                 205

Glu Asn Phe Leu Phe Leu Thr Pro Asp Cys Lys Ser Leu Trp Asn Gly
210                 215                 220

Asp Thr Gly Glu Cys Thr Asp Asn Ala Tyr Ile Asp Ile Gln Leu Arg
225                 230                 235                 240

Ile Ala Ser Phe Ser Gln Asn Cys Asp Ile Tyr Pro Gly Lys Asp Phe
                245                 250                 255

Val Gln Pro Pro Thr Lys Ile Cys Val Gly Cys Pro Arg Asp Ile Pro
            260                 265                 270

Thr Asn Ser Pro Glu Leu Glu Glu Thr Leu Thr His Thr Ile Thr Lys
        275                 280                 285

Leu Asn Ala Glu Asn Asn Ala Thr Phe Tyr Phe Lys Ile Asp Asn Val
        290                 295                 300

Lys Lys Ala Arg Val Gln Val Val Ala Gly Lys Lys Tyr Phe Ile Asp
305                 310                 315                 320

Phe Val Ala Arg Glu Thr Thr Cys Ser Lys Glu Ser Asn Glu Glu Leu
```

```
                    325                 330                 335
Thr Glu Ser Cys Glu Thr Lys Lys Leu Gly Gln Ser Leu Asp Cys Asn
                340                 345                 350

Ala Glu Val Tyr Val Val Pro Trp Glu Lys Lys Ile Tyr Pro Thr Val
            355                 360                 365

Asn Cys Gln Pro Leu Gly Met Ile Ser Leu Met Lys Arg Pro Pro Gly
370                 375                 380

Phe Ser Pro Phe Arg Ser Arg Ile Gly Glu Ile Lys Glu Thr
385                 390                 395                 400

Thr Ser His Leu Arg Ser Cys Glu Tyr Lys Gly Arg Pro Pro Lys Ala
                405                 410                 415

Gly Ala Glu Pro Ala Ser Glu Arg Glu Val Ser
                420                 425

<210> SEQ ID NO 20
<211> LENGTH: 418
<212> TYPE: PRT
<213> ORGANISM: Homo sapiens

<400> SEQUENCE: 20

Met Gln Ala Leu Val Leu Leu Leu Cys Ile Gly Ala Leu Leu Gly His
1               5                   10                  15

Ser Ser Cys Gln Asn Pro Ala Ser Pro Pro Glu Glu Gly Ser Pro Asp
            20                  25                  30

Pro Asp Ser Thr Gly Ala Leu Val Glu Glu Asp Pro Phe Phe Lys
        35                  40                  45

Val Pro Val Asn Lys Leu Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
            260                 265                 270
```

```
Ser Ile Ile Phe Phe Leu Pro Leu Lys Val Thr Gln Asn Leu Thr Leu
            275                 280                 285

Ile Glu Glu Ser Leu Thr Ser Glu Phe Ile His Asp Ile Asp Arg Glu
290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
            355                 360                 365

Ala Gly Thr Thr Pro Ser Pro Gly Leu Gln Pro Ala His Leu Thr Phe
370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 21
<211> LENGTH: 101
<212> TYPE: PRT
<213> ORGANISM: Homo sapiens

<400> SEQUENCE: 21

Met Ser Asn Thr Gln Ala Glu Arg Ser Ile Ile Gly Met Ile Asp Met
1               5                   10                  15

Phe His Lys Tyr Thr Arg Arg Asp Asp Lys Ile Glu Lys Pro Ser Leu
                20                  25                  30

Leu Thr Met Met Lys Glu Asn Phe Pro Asn Phe Leu Ser Ala Cys Asp
            35                  40                  45

Lys Lys Gly Thr Asn Tyr Leu Ala Asp Val Phe Glu Lys Lys Asp Lys
        50                  55                  60

Asn Glu Asp Lys Lys Ile Asp Phe Ser Glu Phe Leu Ser Leu Leu Gly
65                  70                  75                  80

Asp Ile Ala Thr Asp Tyr His Lys Gln Ser His Gly Ala Ala Pro Cys
                85                  90                  95

Ser Gly Gly Ser Gln
            100

<210> SEQ ID NO 22
<211> LENGTH: 93
<212> TYPE: PRT
<213> ORGANISM: Homo sapiens

<400> SEQUENCE: 22

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
                20                  25                  30

Asp Leu Lys Lys Leu Leu Glu Thr Glu Cys Pro Gln Tyr Ile Arg Lys
            35                  40                  45

Lys Gly Ala Asp Val Trp Phe Lys Glu Leu Asp Ile Asn Thr Asp Gly
        50                  55                  60

Ala Val Asn Phe Gln Glu Phe Leu Ile Leu Val Ile Lys Met Gly Val
```

```
                 65                  70                  75                  80

Ala Ala His Lys Lys Ser His Glu Glu Ser His Lys Glu
                85                  90

<210> SEQ ID NO 23
<211> LENGTH: 114
<212> TYPE: PRT
<213> ORGANISM: Homo sapiens

<400> SEQUENCE: 23

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro

<210> SEQ ID NO 24
<211> LENGTH: 202
<212> TYPE: PRT
<213> ORGANISM: Homo sapiens

<400> SEQUENCE: 24

Met Ser Ser Val Glu Lys Glu Thr Lys Thr Gln Cys Val Arg Ile Ala
1               5                   10                  15

Thr Lys Ala Ala Ala Thr Glu Glu Pro Glu Val Ile Pro Asp Pro Ala
            20                  25                  30

Lys Gln Thr Asp Arg Val Val Lys Ile Ala Gly Ile Ser Ala Gly Ile
        35                  40                  45

Leu Val Phe Ile Leu Leu Leu Leu Val Val Ile Leu Ile Val Lys Lys
    50                  55                  60

Arg Arg Ser Tyr Tyr Ser Tyr Ser Tyr Tyr Leu Lys Leu Ala Lys Lys
65                  70                  75                  80

Arg Lys Asp Ala Met Gly Asn Thr Arg Gln Glu Met Thr His Met Val
                85                  90                  95

Asn Ala Met Asp Arg Ser Tyr Ala Asp Gln Ser Thr Leu His Ala Glu
            100                 105                 110

Asp Pro Leu Ser Ile Thr Phe Met Asp Gln His Asn Phe Ser Pro Arg
        115                 120                 125

Leu Pro Asn Asp Pro Leu Val Pro Thr Ala Val Leu Asp Glu Asn His
    130                 135                 140

Ser Ala Thr Ala Glu Ser Ser Arg Leu Leu Asp Val Pro Arg Tyr Leu
145                 150                 155                 160

Cys Glu Gly Thr Glu Ser Pro Tyr Gln Thr Gly Gln Leu His Pro Ala
                165                 170                 175

Ile Arg Val Ala Asp Leu Leu Gln His Ile Asn Leu Met Lys Thr Ser
            180                 185                 190
```

Asp Ser Tyr Gly Phe Lys Glu Glu Tyr Glu
        195                 200

<210> SEQ ID NO 25
<211> LENGTH: 484
<212> TYPE: PRT
<213> ORGANISM: Homo sapiens

<400> SEQUENCE: 25

Met Ser Arg Ser Thr Gln Glu Leu Leu Gly Tyr His Cys Arg Leu Gln
1               5                   10                  15

Asp Lys Leu Gln Glu Gln Glu Gly Ser Leu Ala Ala Glu Gly Arg His
            20                  25                  30

Ser Leu Ala Ser Ala Ala Asp His Met Lys Val Val Pro Ser Leu Leu
        35                  40                  45

Leu Ser Val Leu Leu Ala Gln Val Trp Leu Val Pro Gly Leu Ala Pro
    50                  55                  60

Ser Pro Gln Ser Pro Glu Thr Pro Ala Pro Gln Asn Gln Thr Ser Arg
65                  70                  75                  80

Val Val Gln Ala Pro Lys Glu Glu Glu Asp Glu Gln Glu Ala Ser
                85                  90                  95

Glu Glu Lys Ala Ser Glu Glu Glu Lys Ala Trp Leu Met Ala Ser Arg
                100                 105                 110

Gln Gln Leu Ala Lys Glu Thr Ser Asn Phe Gly Phe Ser Leu Leu Arg
            115                 120                 125

Lys Ile Ser Met Arg His Asp Gly Asn Met Val Phe Ser Pro Phe Gly
        130                 135                 140

Met Ser Leu Ala Met Thr Gly Leu Met Leu Gly Ala Thr Gly Pro Thr
145                 150                 155                 160

Glu Thr Gln Ile Lys Arg Gly Leu His Leu Gln Ala Leu Lys Pro Thr
                165                 170                 175

Lys Pro Gly Leu Leu Pro Ser Leu Phe Lys Gly Leu Arg Glu Thr Leu
            180                 185                 190

Ser Arg Asn Leu Glu Leu Gly Leu Thr Gln Gly Ser Phe Ala Phe Ile
        195                 200                 205

His Lys Asp Phe Asp Val Lys Glu Thr Phe Phe Asn Leu Ser Lys Arg
    210                 215                 220

Tyr Phe Asp Thr Glu Cys Val Pro Met Asn Phe Arg Asn Ala Ser Gln
225                 230                 235                 240

Ala Lys Arg Leu Met Asn His Tyr Ile Asn Lys Glu Thr Arg Gly Lys
                245                 250                 255

Ile Pro Lys Leu Phe Asp Glu Ile Asn Pro Glu Thr Lys Leu Ile Leu
            260                 265                 270

Val Asp Tyr Ile Leu Phe Lys Gly Lys Trp Leu Thr Pro Phe Asp Pro
        275                 280                 285

Val Phe Thr Glu Val Asp Thr Phe His Leu Asp Lys Tyr Lys Thr Ile
    290                 295                 300

Lys Val Pro Met Met Tyr Gly Ala Gly Lys Phe Ala Ser Thr Phe Asp
305                 310                 315                 320

Lys Asn Phe Arg Cys His Val Leu Lys Leu Pro Tyr Gln Gly Asn Ala
                325                 330                 335

Thr Met Leu Val Val Leu Met Glu Lys Met Gly Asp His Leu Ala Leu
            340                 345                 350

Glu Asp Tyr Leu Thr Thr Asp Leu Val Glu Thr Trp Leu Arg Asn Met

```
                    355                 360                 365
Lys Thr Arg Asn Met Glu Val Phe Phe Pro Lys Phe Lys Leu Asp Gln
370                 375                 380

Lys Tyr Glu Met His Glu Leu Leu Arg Gln Met Gly Ile Arg Arg Ile
385                 390                 395                 400

Phe Ser Pro Phe Ala Asp Leu Ser Glu Leu Ser Ala Thr Gly Arg Asn
                405                 410                 415

Leu Gln Val Ser Arg Val Leu Gln Arg Thr Val Ile Glu Val Asp Glu
            420                 425                 430

Arg Gly Thr Glu Ala Val Ala Gly Ile Leu Ser Glu Ile Thr Ala Tyr
            435                 440                 445

Ser Met Pro Pro Val Ile Lys Val Asp Arg Pro Phe His Phe Met Ile
            450                 455                 460

Tyr Glu Glu Thr Ser Gly Met Leu Leu Phe Leu Gly Arg Val Val Asn
465                 470                 475                 480

Pro Thr Leu Leu

<210> SEQ ID NO 26
<211> LENGTH: 228
<212> TYPE: PRT
<213> ORGANISM: Homo sapiens

<400> SEQUENCE: 26

Met Pro Gly Ala Gly Asp Gly Gly Lys Ala Pro Ala Arg Trp Leu Gly
1               5                   10                  15

Thr Gly Leu Leu Gly Leu Phe Leu Leu Pro Val Thr Leu Ser Leu Glu
            20                  25                  30

Val Ser Val Gly Lys Ala Thr Asp Ile Tyr Ala Val Asn Gly Thr Glu
        35                  40                  45

Ile Leu Leu Pro Cys Thr Phe Ser Ser Cys Phe Gly Phe Glu Asp Leu
    50                  55                  60

His Phe Arg Trp Thr Tyr Asn Ser Ser Asp Ala Phe Lys Ile Leu Ile
65                  70                  75                  80

Glu Gly Thr Val Lys Asn Glu Lys Ser Asp Pro Lys Val Thr Leu Lys
                85                  90                  95

Asp Asp Asp Arg Ile Thr Leu Val Gly Ser Thr Lys Glu Lys Met Asn
            100                 105                 110

Asn Ile Ser Ile Val Leu Arg Asp Leu Glu Phe Ser Asp Thr Gly Lys
        115                 120                 125

Tyr Thr Cys His Val Lys Asn Pro Lys Glu Asn Asn Leu Gln His His
    130                 135                 140

Ala Thr Ile Phe Leu Gln Val Val Asp Arg Leu Glu Glu Val Asp Asn
145                 150                 155                 160

Thr Val Thr Leu Ile Ile Leu Ala Val Val Gly Gly Val Ile Gly Leu
                165                 170                 175

Leu Ile Leu Ile Leu Leu Ile Lys Lys Leu Ile Ile Phe Ile Leu Lys
            180                 185                 190

Lys Thr Arg Glu Lys Lys Lys Glu Cys Leu Val Ser Ser Ser Gly Asn
        195                 200                 205

Asp Asn Thr Glu Asn Gly Leu Pro Gly Ser Lys Ala Glu Glu Lys Pro
    210                 215                 220

Pro Ser Lys Val
225
```

-continued

```
<210> SEQ ID NO 27
<211> LENGTH: 2214
<212> TYPE: PRT
<213> ORGANISM: Homo sapiens

<400> SEQUENCE: 27
```

Met Ala Thr Arg Ser Ser Arg Arg Glu Ser Arg Leu Pro Phe Leu Phe
1               5                   10                  15

Thr Leu Val Ala Leu Leu Pro Pro Gly Ala Leu Cys Glu Val Trp Thr
            20                  25                  30

Gln Arg Leu His Gly Gly Ser Ala Pro Leu Pro Gln Asp Arg Gly Phe
        35                  40                  45

Leu Val Val Gln Gly Asp Pro Arg Glu Leu Arg Leu Trp Ala Arg Gly
    50                  55                  60

Asp Ala Arg Gly Ala Ser Arg Ala Asp Glu Lys Pro Leu Arg Arg Lys
65                  70                  75                  80

Arg Ser Ala Ala Leu Gln Pro Glu Pro Ile Lys Val Tyr Gly Gln Val
                85                  90                  95

Ser Leu Asn Asp Ser His Asn Gln Met Val Val His Trp Ala Gly Glu
            100                 105                 110

Lys Ser Asn Val Ile Val Ala Leu Ala Arg Asp Ser Leu Ala Leu Ala
        115                 120                 125

Arg Pro Lys Ser Ser Asp Val Tyr Val Ser Tyr Asp Tyr Gly Lys Ser
    130                 135                 140

Phe Lys Lys Ile Ser Asp Lys Leu Asn Phe Gly Leu Gly Asn Arg Ser
145                 150                 155                 160

Glu Ala Val Ile Ala Gln Phe Tyr His Ser Pro Ala Asp Asn Lys Arg
                165                 170                 175

Tyr Ile Phe Ala Asp Ala Tyr Ala Gln Tyr Leu Trp Ile Thr Phe Asp
            180                 185                 190

Phe Cys Asn Thr Leu Gln Gly Phe Ser Ile Pro Phe Arg Ala Ala Asp
        195                 200                 205

Leu Leu Leu His Ser Lys Ala Ser Asn Leu Leu Leu Gly Phe Asp Arg
    210                 215                 220

Ser His Pro Asn Lys Gln Leu Trp Lys Ser Asp Asp Phe Gly Gln Thr
225                 230                 235                 240

Trp Ile Met Ile Gln Glu His Val Lys Ser Phe Ser Trp Gly Ile Asp
                245                 250                 255

Pro Tyr Asp Lys Pro Asn Thr Ile Tyr Ile Glu Arg His Glu Pro Ser
            260                 265                 270

Gly Tyr Ser Thr Val Phe Arg Ser Thr Asp Phe Phe Gln Ser Arg Glu
        275                 280                 285

Asn Gln Glu Val Ile Leu Glu Glu Val Arg Asp Phe Gln Leu Arg Asp
    290                 295                 300

Lys Tyr Met Phe Ala Thr Lys Val Val His Leu Leu Gly Ser Glu Gln
305                 310                 315                 320

Gln Ser Ser Val Gln Leu Trp Val Ser Phe Gly Arg Lys Pro Met Arg
                325                 330                 335

Ala Ala Gln Phe Val Thr Arg His Pro Ile Asn Glu Tyr Tyr Ile Ala
            340                 345                 350

Asp Ala Ser Glu Asp Gln Val Phe Val Cys Val Ser His Ser Asn Asn
        355                 360                 365

Arg Thr Asn Leu Tyr Ile Ser Glu Ala Glu Gly Leu Lys Phe Ser Leu
    370                 375                 380

```
Ser Leu Glu Asn Val Leu Tyr Tyr Ser Pro Gly Ala Gly Ser Asp
385                 390                 395                 400

Thr Leu Val Arg Tyr Phe Ala Asn Glu Pro Phe Ala Asp Phe His Arg
                405                 410                 415

Val Glu Gly Leu Gln Gly Val Tyr Ile Ala Thr Leu Ile Asn Gly Ser
            420                 425                 430

Met Asn Glu Glu Asn Met Arg Ser Val Ile Thr Phe Asp Lys Gly Gly
            435                 440                 445

Thr Trp Glu Phe Leu Gln Ala Pro Ala Phe Thr Gly Tyr Gly Glu Lys
450                 455                 460

Ile Asn Cys Glu Leu Ser Gln Gly Cys Ser Leu His Leu Ala Gln Arg
465                 470                 475                 480

Leu Ser Gln Leu Leu Asn Leu Gln Leu Arg Arg Met Pro Ile Leu Ser
                485                 490                 495

Lys Glu Ser Ala Pro Gly Leu Ile Ile Ala Thr Gly Ser Val Gly Lys
                500                 505                 510

Asn Leu Ala Ser Lys Thr Asn Val Tyr Ile Ser Ser Ala Gly Ala
            515                 520                 525

Arg Trp Arg Glu Ala Leu Pro Gly Pro His Tyr Tyr Thr Trp Gly Asp
530                 535                 540

His Gly Gly Ile Ile Thr Ala Ile Ala Gln Gly Met Glu Thr Asn Glu
545                 550                 555                 560

Leu Lys Tyr Ser Thr Asn Glu Gly Glu Thr Trp Lys Thr Phe Ile Phe
                565                 570                 575

Ser Glu Lys Pro Val Phe Val Tyr Gly Leu Leu Thr Glu Pro Gly Glu
                580                 585                 590

Lys Ser Thr Val Phe Thr Ile Phe Gly Ser Asn Lys Glu Asn Val His
                595                 600                 605

Ser Trp Leu Ile Leu Gln Val Asn Ala Thr Asp Ala Leu Gly Val Pro
610                 615                 620

Cys Thr Glu Asn Asp Tyr Lys Leu Trp Ser Pro Ser Asp Glu Arg Gly
625                 630                 635                 640

Asn Glu Cys Leu Leu Gly His Lys Thr Val Phe Lys Arg Arg Thr Pro
                645                 650                 655

His Ala Thr Cys Phe Asn Gly Glu Asp Phe Asp Arg Pro Val Val Val
                660                 665                 670

Ser Asn Cys Ser Cys Thr Arg Glu Asp Tyr Glu Cys Asp Phe Gly Phe
            675                 680                 685

Lys Met Ser Glu Asp Leu Ser Leu Glu Val Cys Val Pro Asp Pro Glu
690                 695                 700

Phe Ser Gly Lys Ser Tyr Ser Pro Val Pro Cys Pro Val Gly Ser
705                 710                 715                 720

Thr Tyr Arg Arg Thr Arg Gly Tyr Arg Lys Ile Ser Gly Asp Thr Cys
                725                 730                 735

Ser Gly Gly Asp Val Glu Ala Arg Leu Glu Gly Glu Leu Val Pro Cys
            740                 745                 750

Pro Leu Ala Glu Glu Asn Glu Phe Ile Leu Tyr Ala Val Arg Lys Ser
                755                 760                 765

Ile Tyr Arg Tyr Asp Leu Ala Ser Gly Ala Thr Glu Gln Leu Pro Leu
            770                 775                 780

Thr Gly Leu Arg Ala Ala Val Ala Leu Asp Phe Asp Tyr Glu His Asn
785                 790                 795                 800

Cys Leu Tyr Trp Ser Asp Leu Ala Leu Asp Val Ile Gln Arg Leu Cys
```

805                 810                 815
Leu Asn Gly Ser Thr Gly Gln Glu Val Ile Ile Asn Ser Gly Leu Glu
                820                 825                 830

Thr Val Glu Ala Leu Ala Phe Glu Pro Leu Ser Gln Leu Leu Tyr Trp
                835                 840                 845

Val Asp Ala Gly Phe Lys Lys Ile Glu Val Ala Asn Pro Asp Gly Asp
                850                 855                 860

Phe Arg Leu Thr Ile Val Asn Ser Ser Val Leu Asp Arg Pro Arg Ala
865                 870                 875                 880

Leu Val Leu Val Pro Gln Glu Gly Val Met Phe Trp Thr Asp Trp Gly
                885                 890                 895

Asp Leu Lys Pro Gly Ile Tyr Arg Ser Asn Met Asp Gly Ser Ala Ala
                900                 905                 910

Tyr His Leu Val Ser Glu Asp Val Lys Trp Pro Asn Gly Ile Ser Val
                915                 920                 925

Asp Asp Gln Trp Ile Tyr Trp Thr Asp Ala Tyr Leu Glu Cys Ile Glu
                930                 935                 940

Arg Ile Thr Phe Ser Gly Gln Gln Arg Ser Val Ile Leu Asp Asn Leu
945                 950                 955                 960

Pro His Pro Tyr Ala Ile Ala Val Phe Lys Asn Glu Ile Tyr Trp Asp
                965                 970                 975

Asp Trp Ser Gln Leu Ser Ile Phe Arg Ala Ser Lys Tyr Ser Gly Ser
                980                 985                 990

Gln Met Glu Ile Leu Ala Asn Gln Leu Thr Gly Leu Met Asp Met Lys
                995                 1000                1005

Ile Phe Tyr Lys Gly Lys Asn Thr Gly Ser Asn Ala Cys Val Pro
                1010                1015                1020

Arg Pro Cys Ser Leu Leu Cys Leu Pro Lys Ala Asn Asn Ser Arg
                1025                1030                1035

Ser Cys Arg Cys Pro Glu Asp Val Ser Ser Ser Val Leu Pro Ser
                1040                1045                1050

Gly Asp Leu Met Cys Asp Cys Pro Gln Gly Tyr Gln Leu Lys Asn
                1055                1060                1065

Asn Thr Cys Val Lys Glu Glu Asn Thr Cys Leu Arg Asn Gln Tyr
                1070                1075                1080

Arg Cys Ser Asn Gly Asn Cys Ile Asn Ser Ile Trp Trp Cys Asp
                1085                1090                1095

Phe Asp Asn Asp Cys Gly Asp Met Ser Asp Glu Arg Asn Cys Pro
                1100                1105                1110

Thr Thr Ile Cys Asp Leu Asp Thr Gln Phe Arg Cys Gln Glu Ser
                1115                1120                1125

Gly Thr Cys Ile Pro Leu Ser Tyr Lys Cys Asp Leu Glu Asp Asp
                1130                1135                1140

Cys Gly Asp Asn Ser Asp Glu Ser His Cys Glu Met His Gln Cys
                1145                1150                1155

Arg Ser Asp Glu Tyr Asn Cys Ser Ser Gly Met Cys Ile Arg Ser
                1160                1165                1170

Ser Trp Val Cys Asp Gly Asp Asn Asp Cys Arg Asp Trp Ser Asp
                1175                1180                1185

Glu Ala Asn Cys Thr Ala Ile Tyr His Thr Cys Glu Ala Ser Asn
                1190                1195                1200

Phe Gln Cys Arg Asn Gly His Cys Ile Pro Gln Arg Trp Ala Cys
                1205                1210                1215

```
Asp Gly Asp Thr Asp Cys Gln Asp Gly Ser Asp Glu Asp Pro Val
    1220            1225            1230

Asn Cys Glu Lys Lys Cys Asn Gly Phe Arg Cys Pro Asn Gly Thr
    1235            1240            1245

Cys Ile Pro Ser Ser Lys His Cys Asp Gly Leu Arg Asp Cys Ser
    1250            1255            1260

Asp Gly Ser Asp Glu Gln His Cys Glu Pro Leu Cys Thr His Phe
    1265            1270            1275

Met Asp Phe Val Cys Lys Asn Arg Gln Gln Cys Leu Phe His Ser
    1280            1285            1290

Met Val Cys Asp Gly Ile Ile Gln Cys Arg Asp Gly Ser Asp Glu
    1295            1300            1305

Asp Ala Ala Phe Ala Gly Cys Ser Gln Asp Pro Glu Phe His Lys
    1310            1315            1320

Val Cys Asp Glu Phe Gly Phe Gln Cys Gln Asn Gly Val Cys Ile
    1325            1330            1335

Ser Leu Ile Trp Lys Cys Asp Gly Met Asp Asp Cys Gly Asp Tyr
    1340            1345            1350

Ser Asp Glu Ala Asn Cys Glu Asn Pro Thr Glu Ala Pro Asn Cys
    1355            1360            1365

Ser Arg Tyr Phe Gln Phe Arg Cys Glu Asn Gly His Cys Ile Pro
    1370            1375            1380

Asn Arg Trp Lys Cys Asp Arg Glu Asn Asp Cys Gly Asp Trp Ser
    1385            1390            1395

Asp Glu Lys Asp Cys Gly Asp Ser His Ile Leu Pro Phe Ser Thr
    1400            1405            1410

Pro Gly Pro Ser Thr Cys Leu Pro Asn Tyr Tyr Arg Cys Ser Ser
    1415            1420            1425

Gly Thr Cys Val Met Asp Thr Trp Val Cys Asp Gly Tyr Arg Asp
    1430            1435            1440

Cys Ala Asp Gly Ser Asp Glu Glu Ala Cys Pro Leu Leu Ala Asn
    1445            1450            1455

Val Thr Ala Ala Ser Thr Pro Thr Gln Leu Gly Arg Cys Asp Arg
    1460            1465            1470

Phe Glu Phe Glu Cys His Gln Pro Lys Thr Cys Ile Pro Asn Trp
    1475            1480            1485

Lys Arg Cys Asp Gly His Gln Asp Cys Gln Asp Gly Arg Asp Glu
    1490            1495            1500

Ala Asn Cys Pro Thr His Ser Thr Leu Thr Cys Met Ser Arg Glu
    1505            1510            1515

Phe Gln Cys Glu Asp Gly Glu Ala Cys Ile Val Leu Ser Glu Arg
    1520            1525            1530

Cys Asp Gly Phe Leu Asp Cys Ser Asp Glu Ser Asp Glu Lys Ala
    1535            1540            1545

Cys Ser Asp Glu Leu Thr Val Tyr Lys Val Gln Asn Leu Gln Trp
    1550            1555            1560

Thr Ala Asp Phe Ser Gly Asp Val Thr Leu Thr Trp Met Arg Pro
    1565            1570            1575

Lys Lys Met Pro Ser Ala Ser Cys Val Tyr Asn Val Tyr Tyr Arg
    1580            1585            1590

Val Val Gly Glu Ser Ile Trp Lys Thr Leu Glu Thr His Ser Asn
    1595            1600            1605
```

```
Lys Thr Asn Thr Val Leu Lys Val Leu Lys Pro Asp Thr Thr Tyr
1610                1615                1620

Gln Val Lys Val Gln Val Gln Cys Leu Ser Lys Ala His Asn Thr
1625                1630                1635

Asn Asp Phe Val Thr Leu Arg Thr Pro Glu Gly Leu Pro Asp Ala
1640                1645                1650

Pro Arg Asn Leu Gln Leu Ser Leu Pro Arg Glu Ala Glu Gly Val
1655                1660                1665

Ile Val Gly His Trp Ala Pro Pro Ile Thr His Gly Leu Ile
1670                1675                1680

Arg Glu Tyr Ile Val Glu Tyr Ser Arg Ser Gly Ser Lys Met Trp
1685                1690                1695

Ala Ser Gln Arg Ala Ala Ser Asn Phe Thr Glu Ile Lys Asn Leu
1700                1705                1710

Leu Val Asn Thr Leu Tyr Thr Val Arg Val Ala Ala Val Thr Ser
1715                1720                1725

Arg Gly Ile Gly Asn Trp Ser Asp Ser Lys Ser Ile Thr Thr Ile
1730                1735                1740

Lys Gly Lys Val Ile Pro Pro Asp Ile His Ile Asp Ser Tyr
1745                1750                1755

Gly Glu Asn Tyr Leu Ser Phe Thr Leu Thr Met Glu Ser Asp Ile
1760                1765                1770

Lys Val Asn Gly Tyr Val Val Asn Leu Phe Trp Ala Phe Asp Thr
1775                1780                1785

His Lys Gln Glu Arg Arg Thr Leu Asn Phe Arg Gly Ser Ile Leu
1790                1795                1800

Ser His Lys Val Gly Asn Leu Thr Ala His Thr Ser Tyr Glu Ile
1805                1810                1815

Ser Ala Trp Ala Lys Thr Asp Leu Gly Asp Ser Pro Leu Ala Phe
1820                1825                1830

Glu His Val Met Thr Arg Gly Val Arg Pro Pro Ala Pro Ser Leu
1835                1840                1845

Lys Ala Lys Ala Ile Asn Gln Thr Ala Val Glu Cys Thr Trp Thr
1850                1855                1860

Gly Pro Arg Asn Val Val Tyr Gly Ile Phe Tyr Ala Thr Ser Phe
1865                1870                1875

Leu Asp Leu Tyr Arg Asn Pro Lys Ser Leu Thr Thr Ser Leu His
1880                1885                1890

Asn Lys Thr Val Ile Val Ser Lys Asp Glu Gln Tyr Leu Phe Leu
1895                1900                1905

Val Arg Val Val Val Pro Tyr Gln Gly Pro Ser Ser Asp Tyr Val
1910                1915                1920

Val Val Lys Met Ile Pro Asp Ser Arg Leu Pro Pro Arg His Leu
1925                1930                1935

His Val Val His Thr Gly Lys Thr Ser Val Val Ile Lys Trp Glu
1940                1945                1950

Ser Pro Tyr Asp Ser Pro Asp Gln Asp Leu Leu Tyr Ala Ile Ala
1955                1960                1965

Val Lys Asp Leu Ile Arg Lys Thr Asp Arg Ser Tyr Lys Val Lys
1970                1975                1980

Ser Arg Asn Ser Thr Val Glu Tyr Thr Leu Asn Lys Leu Glu Pro
1985                1990                1995

Gly Gly Lys Tyr His Ile Ile Val Gln Leu Gly Asn Met Ser Lys
```

```
                  2000                 2005                2010
Asp Ser Ser Ile Lys Ile Thr Thr Val Ser Leu Ser Ala Pro Asp
        2015                2020                2025

Ala Leu Lys Ile Ile Thr Glu Asn Asp His Val Leu Leu Phe Trp
        2030                2035                2040

Lys Ser Leu Ala Leu Lys Glu Lys His Phe Asn Glu Ser Arg Gly
        2045                2050                2055

Tyr Glu Ile His Met Phe Asp Ser Ala Met Asn Ile Thr Ala Tyr
        2060                2065                2070

Leu Gly Asn Thr Thr Asp Asn Phe Phe Lys Ile Ser Asn Leu Lys
        2075                2080                2085

Met Gly His Asn Tyr Thr Phe Thr Val Gln Ala Arg Cys Leu Phe
        2090                2095                2100

Gly Asn Gln Ile Cys Gly Glu Pro Ala Ile Leu Leu Tyr Asp Glu
        2105                2110                2115

Leu Gly Ser Gly Ala Asp Ala Ser Ala Thr Gln Ala Ala Arg Ser
        2120                2125                2130

Thr Asp Val Ala Ala Val Val Pro Ile Leu Phe Leu Ile Leu
        2135                2140                2145

Leu Ser Leu Gly Val Gly Phe Ala Ile Leu Tyr Thr Lys His Arg
        2150                2155                2160

Arg Leu Gln Ser Ser Phe Thr Ala Phe Ala Asn Ser His Tyr Ser
        2165                2170                2175

Ser Arg Leu Gly Ser Ala Ile Phe Ser Ser Gly Asp Asp Leu Gly
        2180                2185                2190

Glu Asp Asp Glu Asp Ala Pro Met Ile Thr Gly Phe Ser Asp Asp
        2195                2200                2205

Val Pro Met Val Ile Ala
        2210

<210> SEQ ID NO 28
<211> LENGTH: 168
<212> TYPE: PRT
<213> ORGANISM: Homo sapiens

<400> SEQUENCE: 28

Met Arg Ser Phe Leu Leu Val Trp Lys Leu Phe Arg Arg Lys Asp Met
1               5                   10                  15

Lys His Gln Arg Lys Thr Ala Thr Glu Phe Lys Thr Thr Glu Glu Gly
                20                  25                  30

Glu Thr Arg Gln Asp Gly Lys Asp Gly Ser Leu Thr Tyr Arg Ala Asp
            35                  40                  45

Thr Cys Ser Pro Cys Pro Glu Ala Gly Gly Pro Ser Ser Ser Ile
        50                  55                  60

Ala Ser Gly Ser Ser Ile Ser Val Gly Asn Ser Pro Ser His Ser His
65                  70                  75                  80

Ser His Thr Ser Arg Arg Cys Gly Gly Ser Arg Ser Arg Glu Cys
                85                  90                  95

Cys Ser Ser Leu His Ser Ser Arg Gly Ser Arg Gly Ser Ser Trp Ser
            100                 105                 110

Ser Ser Pro Pro Gly Ser Thr Cys Arg Trp Cys Ser Cys His Ser His
        115                 120                 125

His His Ser His His Arg Ser His Arg Ser His Cys Ser His
            130                 135                 140
```

```
His His Ser His His Ser Gly His His Ser His His Asn Phe His
145                 150                 155                 160

Asn His Ser Asn Pro Trp Cys Gln
                165
```

<210> SEQ ID NO 29
<211> LENGTH: 527
<212> TYPE: PRT
<213> ORGANISM: Homo sapiens

<400> SEQUENCE: 29

```
Met Ala Asp Ser Arg Asp Pro Ala Ser Asp Gln Met Gln His Trp Lys
1               5                   10                  15

Glu Gln Arg Ala Ala Gln Lys Ala Asp Val Leu Thr Thr Gly Ala Gly
                20                  25                  30

Asn Pro Val Gly Asp Lys Leu Asn Val Ile Thr Val Gly Pro Arg Gly
            35                  40                  45

Pro Leu Leu Val Gln Asp Val Val Phe Thr Asp Glu Met Ala His Phe
50                  55                  60

Asp Arg Glu Arg Ile Pro Glu Arg Val Val His Ala Lys Gly Ala Gly
65                  70                  75                  80

Ala Phe Gly Tyr Phe Glu Val Thr His Asp Ile Thr Lys Tyr Ser Lys
                85                  90                  95

Ala Lys Val Phe Glu His Ile Gly Lys Lys Thr Pro Ile Ala Val Arg
            100                 105                 110

Phe Ser Thr Val Ala Gly Glu Ser Gly Ser Ala Asp Thr Val Arg Asp
        115                 120                 125

Pro Arg Gly Phe Ala Val Lys Phe Tyr Thr Glu Asp Gly Asn Trp Asp
130                 135                 140

Leu Val Gly Asn Asn Thr Pro Ile Phe Phe Ile Arg Asp Pro Ile Leu
145                 150                 155                 160

Phe Pro Ser Phe Ile His Ser Gln Lys Arg Asn Pro Gln Thr His Leu
                165                 170                 175

Lys Asp Pro Asp Met Val Trp Asp Phe Trp Ser Leu Arg Pro Glu Ser
            180                 185                 190

Leu His Gln Val Ser Phe Leu Phe Ser Asp Arg Gly Ile Pro Asp Gly
        195                 200                 205

His Arg His Met Asn Gly Tyr Gly Ser His Thr Phe Lys Leu Val Asn
210                 215                 220

Ala Asn Gly Glu Ala Val Tyr Cys Lys Phe His Tyr Lys Thr Asp Gln
225                 230                 235                 240

Gly Ile Lys Asn Leu Ser Val Glu Asp Ala Ala Arg Leu Ser Gln Glu
                245                 250                 255

Asp Pro Asp Tyr Gly Ile Arg Asp Leu Phe Asn Ala Ile Ala Thr Gly
            260                 265                 270

Lys Tyr Pro Ser Trp Thr Phe Tyr Ile Gln Val Met Thr Phe Asn Gln
        275                 280                 285

Ala Glu Thr Phe Pro Phe Asn Pro Phe Asp Leu Thr Lys Val Trp Pro
290                 295                 300

His Lys Asp Tyr Pro Leu Ile Pro Val Gly Lys Leu Val Leu Asn Arg
305                 310                 315                 320

Asn Pro Val Asn Tyr Phe Ala Glu Val Glu Gln Ile Ala Phe Asp Pro
                325                 330                 335

Ser Asn Met Pro Pro Gly Ile Glu Ala Ser Pro Asp Lys Met Leu Gln
            340                 345                 350
```

Gly Arg Leu Phe Ala Tyr Pro Asp Thr His Arg His Arg Leu Gly Pro
            355                 360                 365

Asn Tyr Leu His Ile Pro Val Asn Cys Pro Tyr Arg Ala Arg Val Ala
370                 375                 380

Asn Tyr Gln Arg Asp Gly Pro Met Cys Met Gln Asp Asn Gln Gly Gly
385                 390                 395                 400

Ala Pro Asn Tyr Pro Asn Ser Phe Gly Ala Pro Glu Gln Gln Pro
            405                 410                 415

Ser Ala Leu Glu His Ser Ile Gln Tyr Ser Gly Glu Val Arg Arg Phe
            420                 425                 430

Asn Thr Ala Asn Asp Asp Asn Val Thr Gln Val Arg Ala Phe Tyr Val
            435                 440                 445

Asn Val Leu Asn Glu Glu Gln Arg Lys Arg Leu Cys Glu Asn Ile Ala
450                 455                 460

Gly His Leu Lys Asp Ala Gln Ile Phe Ile Gln Lys Lys Ala Val Lys
465                 470                 475                 480

Asn Phe Thr Glu Val His Pro Asp Tyr Gly Ser His Ile Gln Ala Leu
            485                 490                 495

Leu Asp Lys Tyr Asn Ala Glu Lys Pro Lys Asn Ala Ile His Thr Phe
            500                 505                 510

Val Gln Ser Gly Ser His Leu Ala Ala Arg Glu Lys Ala Asn Leu
            515                 520                 525

<210> SEQ ID NO 30
<211> LENGTH: 175
<212> TYPE: PRT
<213> ORGANISM: Homo sapiens

<400> SEQUENCE: 30

Met Asn Ile His Ile His Thr Cys Met His Ile Tyr Thr His Ala His
1               5                   10                  15

Thr His Ala His Ile His Thr Cys Ile His Thr His Thr His Met His
            20                  25                  30

Thr His Thr Leu Thr Tyr Thr His Ile His Met His Thr His Thr Gln
            35                  40                  45

Thr His Ile Tyr Thr Gln Ala His Ile His Ser Cys Thr Gln Ile Asn
        50                  55                  60

Ile Tyr Thr Tyr Ala Tyr Thr Leu Thr Cys Thr Gln Thr His Thr His
65                  70                  75                  80

Ile Cys Thr His Ala His Thr Leu Thr Tyr Thr His Ile His Thr Cys
                85                  90                  95

Thr Tyr Lys Arg Thr Tyr Ile Gln Gly His Ile His Thr His Met His
            100                 105                 110

Thr Tyr Thr Cys Thr Cys Thr His Thr His Lys His Ile His Ala His
            115                 120                 125

Ile His Ile His Thr His Thr His Ile Tyr Thr His Thr Asp Ala Tyr
        130                 135                 140

Thr His Met Asp Thr Tyr Thr His Thr Tyr Pro His Thr His Ile Cys
145                 150                 155                 160

Ile His Ser His Thr His Ala His Thr Tyr Thr His Ile Arg Thr
                165                 170                 175

<210> SEQ ID NO 31
<211> LENGTH: 226
<212> TYPE: PRT

<213> ORGANISM: Homo sapiens

<400> SEQUENCE: 31

Met Ala Arg Leu Leu Gln Ala Ser Cys Leu Leu Ser Leu Leu Leu Ala
1               5                   10                  15

Gly Phe Val Ser Gln Ser Arg Gly Gln Glu Lys Ser Lys Met Asp Cys
            20                  25                  30

His Gly Gly Ile Ser Gly Thr Ile Tyr Glu Tyr Gly Ala Leu Thr Ile
        35                  40                  45

Asp Gly Glu Glu Tyr Ile Pro Phe Lys Gln Tyr Ala Gly Lys Tyr Val
    50                  55                  60

Leu Phe Val Asn Val Ala Ser Tyr Cys Gly Leu Thr Gly Gln Tyr Ile
65                  70                  75                  80

Glu Leu Asn Ala Leu Gln Glu Glu Leu Ala Pro Phe Gly Leu Val Ile
                85                  90                  95

Leu Gly Phe Pro Cys Asn Gln Phe Gly Lys Gln Glu Pro Gly Glu Asn
            100                 105                 110

Ser Glu Ile Leu Pro Thr Leu Lys Tyr Val Arg Pro Gly Gly Gly Phe
        115                 120                 125

Val Pro Asn Phe Gln Leu Phe Glu Lys Gly Asp Val Asn Gly Glu Lys
    130                 135                 140

Glu Gln Lys Phe Tyr Thr Phe Leu Lys Asn Ser Cys Pro Pro Thr Ser
145                 150                 155                 160

Glu Leu Leu Gly Thr Ser Asp Arg Leu Phe Trp Glu Pro Met Lys Val
                165                 170                 175

His Asp Ile Arg Trp Asn Phe Glu Lys Phe Leu Val Gly Pro Asp Gly
            180                 185                 190

Ile Pro Ile Met Arg Trp His His Arg Thr Thr Val Ser Asn Val Lys
        195                 200                 205

Met Asp Ile Leu Ser Tyr Met Arg Arg Gln Ala Ala Leu Gly Val Lys
    210                 215                 220

Arg Lys
225

<210> SEQ ID NO 32
<211> LENGTH: 655
<212> TYPE: PRT
<213> ORGANISM: Homo sapiens

<400> SEQUENCE: 32

Met Gly Arg Trp Ala Trp Val Pro Ser Pro Trp Pro Pro Pro Gly Leu
1               5                   10                  15

Gly Pro Phe Leu Leu Leu Leu Leu Leu Leu Leu Leu Pro Arg Gly
            20                  25                  30

Phe Gln Pro Gln Pro Gly Gly Asn Arg Thr Glu Ser Pro Glu Pro Asn
        35                  40                  45

Ala Thr Ala Thr Pro Ala Ile Pro Thr Ile Leu Val Thr Ser Val Thr
    50                  55                  60

Ser Glu Thr Pro Ala Thr Ser Ala Pro Glu Ala Glu Gly Pro Gln Ser
65                  70                  75                  80

Gly Gly Leu Pro Pro Pro Arg Ala Val Pro Ser Ser Ser Ser Pro
                85                  90                  95

Gln Ala Gln Ala Leu Thr Glu Asp Gly Arg Pro Cys Arg Phe Pro Phe
            100                 105                 110

Arg Tyr Gly Gly Arg Met Leu His Ala Cys Thr Ser Glu Gly Ser Ala

```
            115                 120                 125
His Arg Lys Trp Cys Ala Thr Thr His Asn Tyr Asp Arg Asp Arg Ala
    130                 135                 140

Trp Gly Tyr Cys Val Glu Ala Thr Pro Pro Gly Gly Pro Ala Ala
145                 150                 155                 160

Leu Asp Pro Cys Ala Ser Gly Pro Cys Leu Asn Gly Ser Cys Ser
                165                 170                 175

Asn Thr Gln Asp Pro Gln Ser Tyr His Cys Ser Cys Pro Arg Ala Phe
                180                 185                 190

Thr Gly Lys Asp Cys Gly Thr Glu Lys Cys Phe Asp Glu Thr Arg Tyr
                195                 200                 205

Glu Tyr Leu Glu Gly Gly Asp Arg Trp Ala Arg Val Arg Gln Gly His
    210                 215                 220

Val Glu Gln Cys Glu Cys Phe Gly Gly Arg Thr Trp Cys Glu Gly Thr
225                 230                 235                 240

Arg His Thr Ala Cys Leu Ser Ser Pro Cys Leu Asn Gly Gly Thr Cys
                245                 250                 255

His Leu Ile Val Ala Thr Gly Thr Thr Val Cys Ala Cys Pro Pro Gly
            260                 265                 270

Phe Ala Gly Arg Leu Cys Asn Ile Glu Pro Asp Glu Arg Cys Phe Leu
                275                 280                 285

Gly Asn Gly Thr Gly Tyr Arg Gly Val Ala Ser Thr Ser Ala Ser Gly
290                 295                 300

Leu Ser Cys Leu Ala Trp Asn Ser Asp Leu Leu Tyr Gln Glu Leu His
305                 310                 315                 320

Val Asp Ser Val Gly Ala Ala Ala Leu Leu Gly Leu Gly Pro His Ala
                325                 330                 335

Tyr Cys Arg Asn Pro Asp Asn Asp Glu Arg Pro Trp Cys Tyr Val Val
                340                 345                 350

Lys Asp Ser Ala Leu Ser Trp Glu Tyr Cys Arg Leu Glu Ala Cys Glu
                355                 360                 365

Ser Leu Thr Arg Val Gln Leu Ser Pro Asp Leu Leu Ala Thr Leu Pro
    370                 375                 380

Glu Pro Ala Ser Pro Gly Arg Gln Ala Cys Gly Arg Arg His Lys Lys
385                 390                 395                 400

Arg Thr Phe Leu Arg Pro Arg Ile Ile Gly Gly Ser Ser Ser Leu Pro
                405                 410                 415

Gly Ser His Pro Trp Leu Ala Ala Ile Tyr Ile Gly Asp Ser Phe Cys
                420                 425                 430

Ala Gly Ser Leu Val His Thr Cys Trp Val Val Ser Ala Ala His Cys
                435                 440                 445

Phe Ser His Ser Pro Pro Arg Asp Ser Val Ser Val Val Leu Gly Gln
    450                 455                 460

His Phe Phe Asn Arg Thr Thr Asp Val Thr Gln Thr Phe Gly Ile Glu
465                 470                 475                 480

Lys Tyr Ile Pro Tyr Thr Leu Tyr Ser Val Phe Asn Pro Ser Asp His
                485                 490                 495

Asp Leu Val Leu Ile Arg Leu Lys Lys Lys Gly Asp Arg Cys Ala Thr
                500                 505                 510

Arg Ser Gln Phe Val Gln Pro Ile Cys Leu Pro Glu Pro Gly Ser Thr
                515                 520                 525

Phe Pro Ala Gly His Lys Cys Gln Ile Ala Gly Trp Gly His Leu Asp
                530                 535                 540
```

```
Glu Asn Val Ser Gly Tyr Ser Ser Leu Arg Glu Ala Leu Val Pro
545                 550                 555                 560

Leu Val Ala Asp His Lys Cys Ser Ser Pro Glu Val Tyr Gly Ala Asp
                565                 570                 575

Ile Ser Pro Asn Met Leu Cys Ala Gly Tyr Phe Asp Cys Lys Ser Asp
            580                 585                 590

Ala Cys Gln Gly Asp Ser Gly Gly Pro Leu Ala Cys Glu Lys Asn Gly
        595                 600                 605

Val Ala Tyr Leu Tyr Gly Ile Ile Ser Trp Gly Asp Gly Cys Gly Arg
610                 615                 620

Leu His Lys Pro Gly Val Tyr Thr Arg Val Ala Asn Tyr Val Asp Trp
625                 630                 635                 640

Ile Asn Asp Arg Ile Arg Pro Pro Arg Arg Leu Val Ala Pro Ser
                645                 650                 655

<210> SEQ ID NO 33
<211> LENGTH: 697
<212> TYPE: PRT
<213> ORGANISM: Homo sapiens

<400> SEQUENCE: 33

Met Leu Arg Gly Pro Cys Ser Pro Leu Asn Asp Phe Gln Val Leu Arg
1               5                   10                  15

Gly Thr Glu Leu Gln His Leu Leu His Ala Val Val Pro Gly Pro Trp
            20                  25                  30

Gln Glu Asp Val Ala Asp Ala Glu Glu Cys Ala Gly Arg Cys Gly Pro
        35                  40                  45

Leu Met Asp Cys Arg Ala Phe His Tyr Asn Val Ser Ser His Gly Cys
    50                  55                  60

Gln Leu Leu Pro Trp Thr Gln His Ser Pro His Thr Arg Leu Arg Arg
65                  70                  75                  80

Ser Gly Arg Cys Asp Leu Phe Gln Lys Lys Asp Tyr Val Arg Thr Cys
                85                  90                  95

Ile Met Asn Asn Gly Val Gly Tyr Arg Gly Thr Met Ala Thr Thr Val
            100                 105                 110

Gly Gly Leu Pro Cys Gln Ala Trp Ser His Lys Phe Pro Asn Asp His
        115                 120                 125

Lys Tyr Thr Pro Thr Leu Arg Asn Gly Leu Glu Glu Asn Phe Cys Arg
    130                 135                 140

Asn Pro Asp Gly Asp Pro Gly Gly Pro Trp Cys Tyr Thr Thr Asp Pro
145                 150                 155                 160

Ala Val Arg Phe Gln Ser Cys Gly Ile Lys Ser Cys Arg Glu Ala Ala
                165                 170                 175

Cys Val Trp Cys Asn Gly Glu Glu Tyr Arg Gly Ala Val Asp Arg Thr
            180                 185                 190

Glu Ser Gly Arg Glu Cys Gln Arg Trp Asp Leu Gln His Pro His Gln
        195                 200                 205

His Pro Phe Glu Pro Gly Lys Phe Leu Asp Gln Gly Leu Asp Asp Asn
    210                 215                 220

Tyr Cys Arg Asn Pro Asp Gly Ser Glu Arg Pro Trp Cys Tyr Thr Thr
225                 230                 235                 240

Asp Pro Gln Ile Glu Arg Glu Phe Cys Asp Leu Pro Arg Cys Gly Ser
                245                 250                 255

Glu Ala Gln Pro Arg Gln Glu Ala Thr Thr Val Ser Cys Phe Arg Gly
```

```
                260                 265                 270
Lys Gly Glu Gly Tyr Arg Gly Thr Ala Asn Thr Thr Thr Ala Gly Val
            275                 280                 285

Pro Cys Gln Arg Trp Asp Ala Gln Ile Pro His Gln His Arg Phe Thr
            290                 295                 300

Pro Glu Lys Tyr Ala Cys Lys Asp Leu Arg Glu Asn Phe Cys Arg Asn
305                 310                 315                 320

Pro Asp Gly Ser Glu Ala Pro Trp Cys Phe Thr Leu Arg Pro Gly Met
            325                 330                 335

Arg Ala Ala Phe Cys Tyr Gln Ile Arg Arg Cys Thr Asp Asp Val Arg
            340                 345                 350

Pro Gln Asp Cys Tyr His Gly Ala Gly Glu Gln Tyr Arg Gly Thr Val
            355                 360                 365

Ser Lys Thr Arg Lys Gly Val Gln Cys Gln Arg Trp Ser Ala Glu Thr
            370                 375                 380

Pro His Lys Pro Gln Phe Thr Phe Thr Ser Glu Pro His Ala Gln Leu
385                 390                 395                 400

Glu Glu Asn Phe Cys Arg Asn Pro Asp Gly Asp Ser His Gly Pro Trp
                    405                 410                 415

Cys Tyr Thr Met Asp Pro Arg Thr Pro Phe Asp Tyr Cys Ala Leu Arg
                    420                 425                 430

Arg Cys Ala Asp Asp Gln Pro Pro Ser Ile Leu Asp Pro Pro Asp Gln
            435                 440                 445

Val Gln Phe Glu Lys Cys Gly Lys Arg Val Asp Arg Leu Asp Gln Arg
            450                 455                 460

Arg Ser Lys Leu Arg Val Val Gly Gly His Pro Gly Asn Ser Pro Trp
465                 470                 475                 480

Thr Val Ser Leu Arg Asn Arg Gln Gly Gln His Phe Cys Gly Gly Ser
                    485                 490                 495

Leu Val Lys Glu Gln Trp Ile Leu Thr Ala Arg Gln Cys Phe Ser Ser
                    500                 505                 510

Cys His Met Pro Leu Thr Gly Tyr Glu Val Trp Leu Gly Thr Leu Phe
            515                 520                 525

Gln Asn Pro Gln His Gly Glu Pro Ser Leu Gln Arg Val Pro Val Ala
            530                 535                 540

Lys Met Val Cys Gly Pro Ser Gly Ser Gln Leu Val Leu Leu Lys Leu
545                 550                 555                 560

Glu Arg Ser Val Thr Leu Asn Gln Arg Val Ala Leu Ile Cys Leu Pro
                    565                 570                 575

Pro Glu Trp Tyr Val Val Pro Pro Gly Thr Lys Cys Glu Ile Ala Gly
            580                 585                 590

Trp Gly Glu Thr Lys Gly Thr Gly Asn Asp Thr Val Leu Asn Val Ala
            595                 600                 605

Leu Leu Asn Val Ile Ser Asn Gln Glu Cys Asn Ile Lys His Arg Gly
            610                 615                 620

Arg Val Arg Glu Ser Glu Met Cys Thr Glu Gly Leu Leu Ala Pro Val
625                 630                 635                 640

Gly Ala Cys Glu Gly Asp Tyr Gly Gly Pro Leu Ala Cys Phe Thr His
                    645                 650                 655

Asn Cys Trp Val Leu Glu Gly Ile Ile Ile Pro Asn Arg Val Cys Ala
                    660                 665                 670

Arg Ser Arg Trp Pro Ala Val Phe Thr Arg Val Ser Val Phe Val Asp
            675                 680                 685
```

```
Trp Ile His Lys Val Met Arg Leu Gly
    690             695
```

```
<210> SEQ ID NO 34
<211> LENGTH: 240
<212> TYPE: PRT
<213> ORGANISM: Homo sapiens

<400> SEQUENCE: 34
```

```
Met Thr Pro His Arg Leu Leu Pro Pro Leu Leu Leu Leu Ala Leu
1               5                   10                  15

Leu Leu Ala Ala Ser Pro Gly Gly Ala Leu Ala Arg Cys Pro Gly Cys
            20                  25                  30

Gly Gln Gly Val Gln Ala Gly Cys Pro Gly Gly Cys Val Glu Glu Glu
            35                  40                  45

Asp Gly Gly Ser Pro Ala Glu Gly Cys Ala Glu Ala Glu Gly Cys Leu
        50                  55                  60

Arg Arg Glu Gly Gln Glu Cys Gly Val Tyr Thr Pro Asn Cys Ala Pro
65                  70                  75                  80

Gly Leu Gln Cys His Pro Pro Lys Asp Asp Glu Ala Pro Leu Arg Ala
            85                  90                  95

Leu Leu Leu Gly Arg Gly Arg Cys Leu Pro Ala Arg Ala Pro Ala Val
            100                 105                 110

Ala Glu Glu Asn Pro Lys Glu Ser Lys Pro Gln Ala Gly Thr Ala Arg
            115                 120                 125

Pro Gln Asp Val Asn Arg Arg Asp Gln Gln Arg Asn Pro Gly Thr Ser
    130                 135                 140

Thr Thr Pro Ser Gln Pro Asn Ser Ala Gly Val Gln Asp Thr Glu Met
145                 150                 155                 160

Gly Pro Cys Arg Arg His Leu Asp Ser Val Leu Gln Leu Gln Thr
            165                 170                 175

Glu Val Tyr Arg Gly Ala Gln Thr Leu Tyr Val Pro Asn Cys Asp His
            180                 185                 190

Arg Gly Phe Tyr Arg Lys Arg Gln Cys Arg Ser Ser Gln Gly Gln Arg
            195                 200                 205

Arg Gly Pro Cys Trp Cys Val Asp Arg Met Gly Lys Ser Leu Pro Gly
    210                 215                 220

Ser Pro Asp Gly Asn Gly Ser Ser Ser Cys Pro Thr Gly Ser Ser Gly
225                 230                 235                 240
```

```
<210> SEQ ID NO 35
<211> LENGTH: 88
<212> TYPE: PRT
<213> ORGANISM: Homo sapiens

<400> SEQUENCE: 35
```

```
Met Phe Thr Leu Arg Leu Phe Ala Gly Lys Ala Cys Trp Pro Val Leu
1               5                   10                  15

Tyr Thr Met Leu Lys Glu Val Thr Cys Asp Val Cys Val Cys Val Arg
            20                  25                  30

Ala Arg Ala Cys Thr Cys Met Cys Met Cys Val Cys Glu Cys Met Asp
            35                  40                  45

Val Cys Val Arg Leu Tyr Thr Met Leu Lys Glu Val Thr Cys Asp Met
        50                  55                  60

Cys Val Cys Ala Arg Thr Cys Val His Val Cys Val Ser Ala Trp Met
65                  70                  75                  80
```

Cys Val Cys Thr Cys Thr Gln Cys
                85

<210> SEQ ID NO 36
<211> LENGTH: 1439
<212> TYPE: PRT
<213> ORGANISM: Homo sapiens

<400> SEQUENCE: 36

Met Asp Thr Thr Ala Ala Ala Leu Pro Ala Phe Val Ala Leu Leu
1               5                   10                  15

Leu Leu Ser Pro Trp Pro Leu Leu Gly Ser Ala Gln Gly Gln Phe Ser
            20                  25                  30

Ala Gly Gly Cys Thr Phe Asp Asp Gly Pro Gly Ala Cys Asp Tyr His
            35                  40                  45

Gln Asp Leu Tyr Asp Asp Phe Glu Trp Val His Val Ser Ala Gln Glu
        50                  55                  60

Pro His Tyr Leu Pro Pro Glu Met Pro Gln Gly Ser Tyr Met Ile Val
65                  70                  75                  80

Asp Ser Ser Asp His Asp Pro Gly Glu Lys Ala Arg Leu Gln Leu Pro
                85                  90                  95

Thr Met Lys Glu Asn Asp Thr His Cys Ile Asp Phe Ser Tyr Leu Leu
            100                 105                 110

Tyr Ser Gln Lys Gly Leu Asn Pro Gly Thr Leu Asn Ile Leu Val Arg
        115                 120                 125

Val Asn Lys Gly Pro Leu Ala Asn Pro Ile Trp Asn Val Thr Gly Phe
130                 135                 140

Thr Gly Arg Asp Trp Leu Arg Ala Glu Leu Ala Val Ser Thr Phe Trp
145                 150                 155                 160

Pro Asn Glu Tyr Gln Val Ile Phe Glu Ala Glu Val Ser Gly Gly Arg
                165                 170                 175

Ser Gly Tyr Ile Ala Ile Asp Asp Ile Gln Val Leu Ser Tyr Pro Cys
            180                 185                 190

Asp Lys Ser Pro His Phe Leu Arg Leu Gly Asp Val Glu Val Asn Ala
        195                 200                 205

Gly Gln Asn Ala Thr Phe Gln Cys Ile Ala Thr Gly Arg Asp Ala Val
    210                 215                 220

His Asn Lys Leu Trp Leu Gln Arg Arg Asn Gly Glu Asp Ile Pro Val
225                 230                 235                 240

Ala Gln Thr Lys Asn Ile Asn His Arg Arg Phe Ala Ala Ser Phe Arg
                245                 250                 255

Leu Gln Glu Val Thr Lys Thr Asp Gln Asp Leu Tyr Arg Cys Val Thr
            260                 265                 270

Gln Ser Glu Arg Gly Ser Gly Val Ser Asn Phe Ala Gln Leu Ile Val
        275                 280                 285

Arg Glu Pro Pro Arg Pro Ile Ala Pro Pro Gln Leu Leu Gly Val Gly
    290                 295                 300

Pro Thr Tyr Leu Leu Ile Gln Leu Asn Ala Asn Ser Ile Ile Gly Asp
305                 310                 315                 320

Gly Pro Ile Ile Leu Lys Glu Val Glu Tyr Arg Met Thr Ser Gly Ser
                325                 330                 335

Trp Thr Glu Thr His Ala Val Asn Ala Pro Thr Tyr Lys Leu Trp His
            340                 345                 350

Leu Asp Pro Asp Thr Glu Tyr Glu Ile Arg Val Leu Leu Thr Arg Pro

```
                355                 360                 365
Gly Glu Gly Gly Thr Gly Leu Pro Gly Pro Leu Ile Thr Arg Thr
            370                 375                 380
Lys Cys Ala Glu Pro Met Arg Thr Pro Lys Thr Leu Lys Ile Ala Glu
385                 390                 395                 400
Ile Gln Ala Arg Arg Ile Ala Val Asp Trp Glu Ser Leu Gly Tyr Asn
                405                 410                 415
Ile Thr Arg Cys His Thr Phe Asn Val Thr Ile Cys Tyr His Tyr Phe
            420                 425                 430
Arg Gly His Asn Glu Ser Lys Ala Asp Cys Leu Asp Met Asp Pro Lys
        435                 440                 445
Ala Pro Gln His Val Val Asn His Leu Pro Pro Tyr Thr Asn Val Ser
        450                 455                 460
Leu Lys Met Ile Leu Thr Asn Pro Glu Gly Arg Lys Glu Ser Glu Glu
465                 470                 475                 480
Thr Ile Ile Gln Thr Asp Glu Asp Val Pro Gly Pro Val Pro Val Lys
                485                 490                 495
Ser Leu Gln Gly Thr Ser Phe Glu Asn Lys Ile Phe Leu Asn Trp Lys
            500                 505                 510
Glu Pro Leu Asp Pro Asn Gly Ile Ile Thr Gln Tyr Glu Ile Ser Tyr
        515                 520                 525
Ser Ser Ile Arg Ser Phe Asp Pro Ala Val Pro Val Ala Gly Pro Pro
        530                 535                 540
Gln Thr Val Ser Asn Leu Trp Asn Ser Thr His His Val Phe Met His
545                 550                 555                 560
Leu His Pro Gly Thr Thr Tyr Gln Phe Phe Ile Arg Ala Ser Thr Val
                565                 570                 575
Lys Gly Phe Gly Pro Ala Thr Ala Ile Asn Val Thr Thr Asn Ile Ser
            580                 585                 590
Ala Pro Thr Leu Pro Asp Tyr Glu Gly Val Asp Ala Ser Leu Asn Glu
        595                 600                 605
Thr Ala Thr Thr Ile Thr Val Leu Leu Arg Pro Ala Gln Ala Lys Gly
        610                 615                 620
Ala Pro Ile Ser Ala Tyr Gln Ile Val Val Glu Glu Leu His Pro His
625                 630                 635                 640
Arg Thr Lys Arg Glu Ala Gly Ala Met Glu Cys Tyr Gln Val Pro Val
                645                 650                 655
Thr Tyr Gln Asn Ala Met Ser Gly Gly Ala Pro Tyr Tyr Phe Ala Ala
            660                 665                 670
Glu Leu Pro Pro Gly Asn Leu Pro Glu Pro Ala Pro Phe Thr Val Gly
        675                 680                 685
Asp Asn Arg Thr Tyr Gln Gly Phe Trp Asn Pro Pro Leu Ala Pro Arg
        690                 695                 700
Lys Gly Tyr Asn Ile Tyr Phe Gln Ala Met Ser Ser Val Glu Lys Glu
705                 710                 715                 720
Thr Lys Thr Gln Cys Val Arg Ile Ala Thr Lys Ala Ala Thr Glu Glu
                725                 730                 735
Pro Glu Val Ile Pro Asp Pro Ala Lys Gln Thr Asp Arg Val Val Lys
            740                 745                 750
Ile Ala Gly Ile Ser Ala Gly Ile Leu Val Phe Ile Leu Leu Leu Leu
        755                 760                 765
Val Val Ile Leu Ile Val Lys Lys Ser Lys Leu Ala Lys Lys Arg Lys
        770                 775                 780
```

-continued

Asp Ala Met Gly Asn Thr Arg Gln Glu Met Thr His Met Val Asn Ala
785                 790                 795                 800

Met Asp Arg Ser Tyr Ala Asp Gln Ser Thr Leu His Ala Glu Asp Pro
            805                 810                 815

Leu Ser Ile Thr Phe Met Asp Gln His Asn Phe Ser Pro Arg Tyr Glu
        820                 825                 830

Asn His Ser Ala Thr Ala Glu Ser Ser Arg Leu Leu Asp Val Pro Arg
    835                 840                 845

Tyr Leu Cys Glu Gly Thr Glu Ser Pro Tyr Gln Thr Gly Gln Leu His
850                 855                 860

Pro Ala Ile Arg Val Ala Asp Leu Leu Gln His Ile Asn Leu Met Lys
865                 870                 875                 880

Thr Ser Asp Ser Tyr Gly Phe Lys Glu Glu Tyr Glu Ser Phe Phe Glu
            885                 890                 895

Gly Gln Ser Ala Ser Trp Asp Val Ala Lys Lys Asp Gln Asn Arg Ala
        900                 905                 910

Lys Asn Arg Tyr Gly Asn Ile Ile Ala Tyr Asp His Ser Arg Val Ile
    915                 920                 925

Leu Gln Pro Val Glu Asp Pro Ser Ser Asp Tyr Ile Asn Ala Asn
930                 935                 940

Tyr Ile Asp Gly Tyr Gln Arg Pro Ser His Tyr Ile Ala Thr Gln Gly
945                 950                 955                 960

Pro Val His Glu Thr Val Tyr Asp Phe Trp Arg Met Ile Trp Gln Glu
            965                 970                 975

Gln Ser Ala Cys Ile Val Met Val Thr Asn Leu Val Glu Val Gly Arg
        980                 985                 990

Val Lys Cys Tyr Lys Tyr Trp Pro Asp Asp Thr Glu Val Tyr Gly Asp
    995                 1000                1005

Phe Lys Val Thr Cys Val Glu Met Glu Pro Leu Ala Glu Tyr Val
    1010                1015                1020

Val Arg Thr Phe Thr Leu Glu Arg Arg Gly Tyr Asn Glu Ile Arg
    1025                1030                1035

Glu Val Lys Gln Phe His Phe Thr Gly Trp Pro Asp His Gly Val
    1040                1045                1050

Pro Tyr His Ala Thr Gly Leu Leu Ser Phe Ile Arg Arg Val Lys
    1055                1060                1065

Leu Ser Asn Pro Pro Ser Ala Gly Pro Ile Val Val His Cys Ser
    1070                1075                1080

Ala Gly Ala Gly Arg Thr Gly Cys Tyr Ile Val Ile Asp Ile Met
    1085                1090                1095

Leu Asp Met Ala Glu Arg Glu Gly Val Val Asp Ile Tyr Asn Cys
    1100                1105                1110

Val Lys Ala Leu Arg Ser Arg Arg Ile Asn Met Val Gln Thr Glu
    1115                1120                1125

Glu Gln Tyr Ile Phe Ile His Asp Ala Ile Leu Glu Ala Cys Leu
    1130                1135                1140

Cys Gly Glu Thr Ala Ile Pro Val Cys Glu Phe Lys Ala Ala Tyr
    1145                1150                1155

Phe Asp Met Ile Arg Ile Asp Ser Gln Thr Asn Ser Ser His Leu
    1160                1165                1170

Lys Asp Glu Phe Gln Thr Leu Asn Ser Val Thr Pro Arg Leu Gln
    1175                1180                1185

```
Ala Glu Asp Cys Ser Ile Ala Cys Leu Pro Arg Asn His Asp Lys
    1190                1195                1200

Asn Arg Phe Met Asp Met Leu Pro Pro Asp Arg Cys Leu Pro Phe
    1205                1210                1215

Leu Ile Thr Ile Asp Gly Glu Ser Ser Asn Tyr Ile Asn Ala Ala
    1220                1225                1230

Leu Met Asp Ser Tyr Arg Gln Pro Ala Ala Phe Ile Val Thr Gln
    1235                1240                1245

Tyr Pro Leu Pro Asn Thr Val Lys Asp Phe Trp Arg Leu Val Tyr
    1250                1255                1260

Asp Tyr Gly Cys Thr Ser Ile Val Met Leu Asn Glu Val Asp Leu
    1265                1270                1275

Ser Gln Gly Cys Pro Gln Tyr Trp Pro Glu Glu Gly Met Leu Arg
    1280                1285                1290

Tyr Gly Pro Ile Gln Val Glu Cys Met Ser Cys Ser Met Asp Cys
    1295                1300                1305

Asp Val Ile Asn Arg Ile Phe Arg Ile Cys Asn Leu Thr Arg Pro
    1310                1315                1320

Gln Glu Gly Tyr Leu Met Val Gln Gln Phe Gln Tyr Leu Gly Trp
    1325                1330                1335

Ala Ser His Arg Glu Val Pro Gly Ser Lys Arg Ser Phe Leu Lys
    1340                1345                1350

Leu Ile Leu Gln Val Glu Lys Trp Gln Glu Glu Cys Glu Glu Gly
    1355                1360                1365

Glu Gly Arg Thr Ile Ile His Cys Leu Asn Gly Gly Gly Arg Ser
    1370                1375                1380

Gly Met Phe Cys Ala Ile Gly Ile Val Val Glu Met Val Lys Arg
    1385                1390                1395

Gln Asn Val Val Asp Val Phe His Ala Val Lys Thr Leu Arg Asn
    1400                1405                1410

Ser Lys Pro Asn Met Val Glu Ala Pro Glu Gln Tyr Arg Phe Cys
    1415                1420                1425

Tyr Asp Val Ala Leu Glu Tyr Leu Glu Ser Ser
    1430                1435

<210> SEQ ID NO 37
<211> LENGTH: 1272
<212> TYPE: PRT
<213> ORGANISM: Homo sapiens

<400> SEQUENCE: 37

Met Val Ala Ala Ala Ala Thr Glu Ala Arg Leu Arg Arg Thr
1               5                   10                  15

Ala Ala Thr Ala Ala Leu Ala Gly Arg Ser Gly Gly Pro His Trp Asp
                20                  25                  30

Trp Asp Val Thr Arg Ala Gly Arg Pro Gly Leu Gly Ala Gly Leu Arg
            35                  40                  45

Leu Pro Arg Leu Leu Ser Pro Pro Leu Arg Pro Arg Leu Leu Leu Leu
        50                  55                  60

Leu Leu Leu Leu Ser Pro Pro Leu Leu Leu Leu Leu Pro Cys Glu
65                  70                  75                  80

Ala Glu Ala Ala Ala Ala Ala Ala Val Ser Gly Ser Ala Ala Ala
                85                  90                  95

Glu Ala Lys Glu Cys Asp Arg Pro Cys Val Asn Gly Gly Arg Cys Asn
                100                 105                 110
```

```
Pro Gly Thr Gly Gln Cys Val Cys Pro Ala Gly Trp Val Gly Glu Gln
            115                 120                 125

Cys Gln His Cys Gly Gly Arg Phe Arg Leu Thr Gly Ser Ser Gly Phe
        130                 135                 140

Val Thr Asp Gly Pro Gly Asn Tyr Lys Tyr Lys Thr Lys Cys Thr Trp
145                 150                 155                 160

Leu Ile Glu Gly Gln Pro Asn Arg Ile Met Arg Leu Arg Phe Asn His
                165                 170                 175

Phe Ala Thr Glu Cys Ser Trp Asp His Leu Tyr Val Tyr Asp Gly Asp
            180                 185                 190

Ser Ile Tyr Ala Pro Leu Val Ala Phe Ser Gly Leu Ile Val Pro
            195                 200                 205

Glu Arg Asp Gly Asn Glu Thr Val Pro Glu Val Val Ala Thr Ser Gly
        210                 215                 220

Tyr Ala Leu Leu His Phe Phe Ser Asp Ala Ala Tyr Asn Leu Thr Gly
225                 230                 235                 240

Phe Asn Ile Thr Tyr Ser Phe Asp Met Cys Pro Asn Asn Cys Ser Gly
                245                 250                 255

Arg Gly Glu Cys Lys Ile Ser Asn Ser Ser Asp Thr Val Glu Cys Glu
            260                 265                 270

Cys Ser Glu Asn Trp Lys Gly Glu Ala Cys Asp Ile Pro His Cys Thr
        275                 280                 285

Asp Asn Cys Gly Phe Pro His Arg Gly Ile Cys Asn Ser Ser Asp Val
        290                 295                 300

Arg Gly Cys Ser Cys Phe Ser Asp Trp Gln Gly Pro Gly Cys Ser Val
305                 310                 315                 320

Pro Val Pro Ala Asn Gln Ser Phe Trp Thr Arg Glu Glu Tyr Ser Asn
                325                 330                 335

Leu Lys Leu Pro Arg Ala Ser His Lys Ala Val Val Asn Gly Asn Ile
            340                 345                 350

Met Trp Val Val Gly Gly Tyr Met Phe Asn His Ser Asp Tyr Asn Met
        355                 360                 365

Val Leu Ala Tyr Asp Leu Ala Ser Arg Glu Trp Leu Pro Leu Asn Arg
        370                 375                 380

Ser Val Asn Asn Val Val Val Arg Tyr Gly His Ser Leu Ala Leu Tyr
385                 390                 395                 400

Lys Asp Lys Ile Tyr Met Tyr Gly Gly Lys Ile Asp Ser Thr Gly Asn
            405                 410                 415

Val Thr Asn Glu Leu Arg Val Phe His Ile His Asn Glu Ser Trp Val
        420                 425                 430

Leu Leu Thr Pro Lys Ala Lys Glu Gln Tyr Ala Val Val Gly His Ser
        435                 440                 445

Ala His Ile Val Thr Leu Lys Asn Gly Arg Val Val Met Leu Val Ile
    450                 455                 460

Phe Gly His Cys Pro Leu Tyr Gly Tyr Ile Ser Asn Val Gln Glu Tyr
465                 470                 475                 480

Asp Leu Asp Lys Asn Thr Trp Ser Ile Leu His Thr Gln Gly Ala Leu
            485                 490                 495

Val Gln Gly Gly Tyr Gly His Ser Ser Val Tyr Asp His Arg Thr Arg
            500                 505                 510

Ala Leu Tyr Val His Gly Gly Tyr Lys Ala Phe Ser Ala Asn Lys Tyr
            515                 520                 525
```

```
Arg Leu Ala Asp Asp Leu Tyr Arg Tyr Asp Val Asp Thr Gln Met Trp
        530                 535                 540

Thr Ile Leu Lys Asp Ser Arg Phe Phe Arg Tyr Leu His Thr Ala Val
545                 550                 555                 560

Ile Val Ser Gly Thr Met Leu Val Phe Gly Asn Thr His Asn Asp
                565                 570                 575

Thr Ser Met Ser His Gly Ala Lys Cys Phe Ser Ser Asp Phe Met Ala
            580                 585                 590

Tyr Asp Ile Ala Cys Asp Arg Trp Ser Val Leu Pro Arg Pro Asp Leu
        595                 600                 605

His His Asp Val Asn Arg Phe Gly His Ser Ala Val Leu His Asn Ser
610                 615                 620

Thr Met Tyr Val Phe Gly Gly Phe Asn Ser Leu Leu Leu Ser Asp Ile
625                 630                 635                 640

Leu Val Phe Thr Ser Glu Gln Cys Asp Ala His Arg Ser Glu Ala Ala
                645                 650                 655

Cys Leu Ala Ala Gly Pro Gly Ile Arg Cys Val Trp Asn Thr Gly Ser
            660                 665                 670

Ser Gln Cys Ile Ser Trp Ala Leu Ala Thr Asp Glu Gln Glu Glu Lys
        675                 680                 685

Leu Lys Ser Glu Cys Phe Ser Lys Arg Thr Leu Asp His Asp Arg Cys
690                 695                 700

Asp Gln His Thr Asp Cys Tyr Ser Cys Thr Ala Asn Thr Asn Asp Cys
705                 710                 715                 720

His Trp Cys Asn Asp His Cys Val Pro Arg Asn His Ser Cys Ser Glu
                725                 730                 735

Gly Gln Ile Ser Ile Phe Arg Tyr Glu Asn Cys Pro Lys Asp Asn Pro
            740                 745                 750

Met Tyr Tyr Cys Asn Lys Lys Thr Ser Cys Arg Ser Cys Ala Leu Asp
        755                 760                 765

Gln Asn Cys Gln Trp Glu Pro Arg Asn Gln Glu Cys Ile Ala Leu Pro
770                 775                 780

Glu Asn Ile Cys Gly Ile Gly Trp His Leu Val Gly Asn Ser Cys Leu
785                 790                 795                 800

Lys Ile Thr Thr Ala Lys Glu Asn Tyr Asp Asn Ala Lys Leu Phe Cys
                805                 810                 815

Arg Asn His Asn Ala Leu Leu Ala Ser Leu Thr Thr Gln Lys Lys Val
            820                 825                 830

Glu Phe Val Leu Lys Gln Leu Arg Ile Met Gln Ser Ser Gln Ser Met
        835                 840                 845

Ser Lys Leu Thr Leu Thr Pro Trp Val Gly Leu Arg Lys Ile Asn Val
850                 855                 860

Ser Tyr Trp Cys Trp Glu Asp Met Ser Pro Phe Thr Asn Ser Leu Leu
865                 870                 875                 880

Gln Trp Met Pro Ser Glu Pro Ser Asp Ala Gly Phe Cys Gly Ile Leu
                885                 890                 895

Ser Glu Pro Ser Thr Arg Gly Leu Lys Ala Ala Thr Cys Ile Asn Pro
            900                 905                 910

Leu Asn Gly Ser Val Cys Glu Arg Pro Ala Asn His Ser Ala Lys Gln
        915                 920                 925

Cys Arg Thr Pro Cys Ala Leu Arg Thr Ala Cys Gly Asp Cys Thr Ser
930                 935                 940

Gly Ser Ser Glu Cys Met Trp Cys Ser Asn Met Lys Gln Cys Val Asp
```

```
                    945                 950                 955                 960
Ser Asn Ala Tyr Val Ala Ser Phe Pro Phe Gly Gln Cys Met Glu Trp
                        965                 970                 975
Tyr Thr Met Ser Thr Cys Pro Pro Glu Asn Cys Ser Gly Tyr Cys Thr
                        980                 985                 990
Cys Ser His Cys Leu Glu Gln Pro Gly Cys Gly Trp Cys Thr Asp Pro
                        995                 1000                1005
Ser Asn Thr Gly Lys Gly Lys Cys Ile Glu Gly Ser Tyr Lys Gly
        1010                1015                1020
Pro Val Lys Met Pro Ser Gln Ala Pro Thr Gly Asn Phe Tyr Pro
        1025                1030                1035
Gln Pro Leu Leu Asn Ser Ser Met Cys Leu Glu Asp Ser Arg Tyr
        1040                1045                1050
Asn Trp Ser Phe Ile His Cys Pro Ala Cys Gln Cys Asn Gly His
        1055                1060                1065
Ser Lys Cys Ile Asn Gln Ser Ile Cys Glu Lys Cys Glu Asn Leu
        1070                1075                1080
Thr Thr Gly Lys His Cys Glu Thr Cys Ile Ser Gly Phe Tyr Gly
        1085                1090                1095
Asp Pro Thr Asn Gly Gly Lys Cys Gln Pro Cys Lys Cys Asn Gly
        1100                1105                1110
His Ala Ser Leu Cys Asn Thr Asn Thr Gly Lys Cys Phe Cys Thr
        1115                1120                1125
Thr Lys Gly Val Lys Gly Asp Glu Cys Gln Leu Cys Glu Val Glu
        1130                1135                1140
Asn Arg Tyr Gln Gly Asn Pro Leu Arg Gly Thr Cys Tyr Tyr Thr
        1145                1150                1155
Leu Leu Ile Asp Tyr Gln Phe Thr Phe Ser Leu Ser Gln Glu Asp
        1160                1165                1170
Asp Arg Tyr Tyr Thr Ala Ile Asn Phe Val Ala Thr Pro Asp Glu
        1175                1180                1185
Gln Asn Arg Asp Leu Asp Met Phe Ile Asn Ala Ser Lys Asn Phe
        1190                1195                1200
Asn Leu Asn Ile Thr Trp Ala Ala Ser Phe Ser Ala Gly Thr Gln
        1205                1210                1215
Ala Gly Glu Glu Met Pro Val Val Ser Lys Thr Asn Ile Lys Glu
        1220                1225                1230
Tyr Lys Asp Ser Phe Ser Asn Glu Lys Phe Asp Phe Arg Asn His
        1235                1240                1245
Pro Asn Ile Thr Phe Phe Val Tyr Val Ser Asn Phe Thr Trp Pro
        1250                1255                1260
Ile Lys Ile Gln Val Gln Thr Glu Gln
        1265                1270

<210> SEQ ID NO 38
<211> LENGTH: 289
<212> TYPE: PRT
<213> ORGANISM: Homo sapiens

<400> SEQUENCE: 38

Met Lys Asp Arg Leu Glu Gln Leu Lys Ala Lys Gln Leu Thr Gln Asp
1               5                   10                  15
Asp Asp Thr Asp Ala Val Glu Ile Ala Ile Asp Asn Thr Ala Phe Met
                20                  25                  30
```

```
Asp Glu Phe Phe Ser Glu Ile Glu Glu Thr Arg Leu Asn Ile Asp Lys
             35                  40                  45

Ile Ser Glu His Val Glu Ala Lys Lys Leu Tyr Ser Ile Ile Leu
 50                  55                  60

Ser Ala Pro Ile Pro Glu Pro Lys Thr Lys Asp Asp Leu Glu Gln Leu
 65                  70                  75                  80

Thr Thr Glu Ile Lys Lys Arg Ala Asn Asn Val Arg Asn Lys Leu Lys
                 85                  90                  95

Ser Met Glu Lys His Ile Glu Glu Asp Glu Val Arg Ser Ala Asp
            100                 105                 110

Leu Arg Ile Arg Lys Ser Gln His Ser Val Leu Ser Arg Lys Phe Val
            115                 120                 125

Glu Val Met Thr Lys Tyr Asn Glu Ala Gln Val Asp Phe Arg Glu Arg
130                 135                 140

Ser Lys Gly Arg Ile Gln Arg Gln Leu Glu Ile Thr Gly Lys Lys Thr
145                 150                 155                 160

Thr Asp Glu Glu Leu Glu Met Leu Glu Ser Gly Asn Pro Ala Ile
                165                 170                 175

Phe Thr Ser Gly Ile Ile Asp Ser Gln Ile Ser Lys Gln Ala Leu Ser
            180                 185                 190

Glu Ile Glu Gly Arg His Lys Asp Ile Val Arg Leu Glu Ser Ser Ile
            195                 200                 205

Lys Glu Leu His Asp Met Phe Met Asp Ile Ala Met Leu Val Glu Asn
            210                 215                 220

Gln Gly Glu Met Leu Asp Asn Ile Glu Leu Asn Val Met His Thr Val
225                 230                 235                 240

Asp His Val Glu Lys Ala Arg Asp Glu Thr Lys Lys Ala Val Lys Tyr
                245                 250                 255

Gln Ser Gln Ala Arg Lys Lys Leu Ile Ile Ile Val Leu Val Val
            260                 265                 270

Val Leu Leu Gly Ile Leu Ala Leu Ile Ile Gly Leu Ser Val Gly Leu
            275                 280                 285

Asn

<210> SEQ ID NO 39
<211> LENGTH: 666
<212> TYPE: PRT
<213> ORGANISM: Homo sapiens

<400> SEQUENCE: 39

Met Arg Lys Val Arg Gly Pro Pro Val Ser Cys Ile Lys Arg Asp Ser
 1               5                  10                  15

Pro Ile Gln Cys Ile Gln Ala Ile Ala Glu Asn Arg Ala Asp Ala Val
                 20                  25                  30

Thr Leu Asp Gly Gly Phe Ile Tyr Glu Ala Gly Leu Ala Pro Tyr Lys
             35                  40                  45

Leu Arg Pro Val Ala Ala Glu Val Tyr Gly Thr Glu Arg Gln Pro Arg
 50                  55                  60

Thr His Tyr Tyr Ala Val Ala Val Val Lys Lys Gly Gly Ser Phe Gln
 65                  70                  75                  80

Leu Asn Glu Leu Gln Gly Leu Lys Ser Cys His Thr Gly Leu Arg Arg
                 85                  90                  95

Thr Ala Gly Trp Asn Val Pro Ile Gly Thr Leu Arg Pro Phe Leu Asn
            100                 105                 110
```

-continued

```
Trp Thr Gly Pro Pro Glu Pro Ile Glu Ala Ala Val Ala Arg Phe Phe
        115                 120                 125

Ser Ala Ser Cys Val Pro Gly Ala Asp Lys Gly Gln Phe Pro Asn Leu
130                 135                 140

Cys Arg Leu Cys Ala Gly Thr Gly Glu Asn Lys Cys Ala Phe Ser Ser
145                 150                 155                 160

Gln Glu Pro Tyr Phe Ser Tyr Ser Gly Ala Phe Lys Cys Leu Arg Asp
                165                 170                 175

Gly Ala Gly Asp Val Ala Phe Ile Arg Glu Ser Thr Val Phe Glu Asp
            180                 185                 190

Leu Ser Asp Glu Ala Glu Arg Asp Glu Tyr Glu Leu Leu Cys Pro Asp
        195                 200                 205

Asn Thr Arg Lys Pro Val Asp Lys Phe Lys Asp Cys His Leu Ala Arg
    210                 215                 220

Val Pro Ser His Ala Val Val Ala Arg Ser Val Asn Gly Lys Glu Asp
225                 230                 235                 240

Ala Ile Trp Asn Leu Leu Arg Gln Ala Gln Glu Lys Phe Gly Lys Asp
                245                 250                 255

Lys Ser Pro Lys Phe Gln Leu Phe Gly Ser Pro Ser Gly Gln Lys Asp
                260                 265                 270

Leu Leu Phe Lys Asp Ser Ala Ile Gly Phe Ser Arg Val Pro Pro Arg
        275                 280                 285

Ile Asp Ser Gly Leu Tyr Leu Gly Ser Gly Tyr Phe Thr Ala Ile Gln
    290                 295                 300

Asn Leu Arg Lys Ser Glu Glu Val Ala Ala Arg Arg Ala Arg Val
305                 310                 315                 320

Val Trp Cys Ala Val Gly Glu Gln Glu Leu Arg Lys Cys Asn Gln Trp
                325                 330                 335

Ser Gly Leu Ser Glu Gly Ser Val Thr Cys Ser Ser Ala Ser Thr Thr
                340                 345                 350

Glu Asp Cys Ile Ala Leu Val Leu Lys Gly Glu Ala Asp Ala Met Ser
        355                 360                 365

Leu Asp Gly Gly Tyr Val Tyr Thr Ala Gly Lys Cys Gly Leu Val Pro
    370                 375                 380

Val Leu Ala Glu Asn Tyr Lys Ser Gln Gln Ser Ser Asp Pro Asp Pro
385                 390                 395                 400

Asn Cys Val Asp Arg Pro Val Glu Gly Tyr Leu Ala Val Ala Val Val
                405                 410                 415

Arg Arg Ser Asp Thr Ser Leu Thr Trp Asn Ser Val Lys Gly Lys Lys
                420                 425                 430

Ser Cys His Thr Ala Val Asp Arg Thr Ala Gly Trp Asn Ile Pro Met
        435                 440                 445

Gly Leu Leu Phe Asn Gln Thr Gly Ser Cys Lys Phe Asp Glu Tyr Phe
    450                 455                 460

Ser Gln Ser Cys Ala Pro Gly Ser Asp Pro Arg Ser Asn Leu Cys Ala
465                 470                 475                 480

Leu Cys Ile Gly Asp Glu Gln Gly Glu Asn Lys Cys Val Pro Asn Ser
                485                 490                 495

Asn Glu Arg Tyr Tyr Gly Tyr Thr Gly Ala Phe Arg Cys Leu Ala Glu
                500                 505                 510

Asn Ala Gly Asp Val Ala Phe Val Lys Asp Val Thr Val Leu Gln Asn
        515                 520                 525

Thr Asp Gly Asn Asn Asn Glu Ala Trp Ala Lys Asp Leu Lys Leu Ala
```

```
                530             535             540
Asp Phe Ala Leu Leu Cys Leu Asp Gly Lys Arg Lys Pro Val Thr Glu
545                 550                 555                 560

Ala Arg Ser Cys His Leu Ala Met Ala Pro Asn His Ala Val Val Ser
                565                 570                 575

Arg Met Asp Lys Val Glu Arg Leu Lys Gln Val Leu Leu His Gln Gln
                580                 585                 590

Ala Lys Phe Gly Arg Asn Gly Ser Asp Cys Pro Asp Lys Phe Cys Leu
                595                 600                 605

Phe Gln Ser Glu Thr Lys Asn Leu Leu Phe Asn Asp Asn Thr Glu Cys
                610                 615                 620

Leu Ala Arg Leu His Gly Lys Thr Thr Tyr Glu Lys Tyr Leu Gly Pro
625                 630                 635                 640

Gln Tyr Val Ala Gly Ile Thr Asn Leu Lys Lys Cys Ser Thr Ser Pro
                645                 650                 655

Leu Leu Glu Ala Cys Glu Phe Leu Arg Lys
                660                 665

<210> SEQ ID NO 40
<211> LENGTH: 4655
<212> TYPE: PRT
<213> ORGANISM: Homo sapiens

<400> SEQUENCE: 40

Met Asp Arg Gly Pro Ala Ala Val Ala Cys Thr Leu Leu Leu Ala Leu
1               5                   10                  15

Val Ala Cys Leu Ala Pro Ala Ser Gly Gln Glu Cys Asp Ser Ala His
                20                  25                  30

Phe Arg Cys Gly Ser Gly His Cys Ile Pro Ala Asp Trp Arg Cys Asp
            35                  40                  45

Gly Thr Lys Asp Cys Ser Asp Ala Asp Glu Ile Gly Cys Ala Val
        50                  55                  60

Val Thr Cys Gln Gln Gly Tyr Phe Lys Cys Gln Ser Glu Gly Gln Cys
65                  70                  75                  80

Ile Pro Asn Ser Trp Val Cys Asp Gln Asp Gln Asp Cys Asp Asp Gly
                85                  90                  95

Ser Asp Glu Arg Gln Asp Cys Ser Gln Ser Thr Cys Ser Ser His Gln
                100                 105                 110

Ile Thr Cys Ser Asn Gly Gln Cys Ile Pro Ser Glu Tyr Arg Cys Asp
            115                 120                 125

His Val Arg Asp Cys Pro Asp Gly Ala Asp Glu Asn Asp Cys Gln Tyr
            130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
            180                 185                 190

Gly Glu Cys Ile Pro Arg Ala Tyr Val Cys Asp His Asp Asn Asp Cys
            195                 200                 205

Gln Asp Gly Ser Asp Glu His Ala Cys Asn Tyr Pro Thr Cys Gly Gly
            210                 215                 220

Tyr Gln Phe Thr Cys Pro Ser Gly Arg Cys Ile Tyr Gln Asn Trp Val
225                 230                 235                 240
```

-continued

Cys Asp Gly Glu Asp Asp Cys Lys Asp Asn Gly Asp Glu Asp Gly Cys
            245                 250                 255
Glu Ser Gly Pro His Asp Val His Lys Cys Ser Pro Arg Glu Trp Ser
            260                 265                 270
Cys Pro Glu Ser Gly Arg Cys Ile Ser Ile Tyr Lys Val Cys Asp Gly
            275                 280                 285
Ile Leu Asp Cys Pro Gly Arg Glu Asp Glu Asn Asn Thr Ser Thr Gly
290                 295                 300
Lys Tyr Cys Ser Met Thr Leu Cys Ser Ala Leu Asn Cys Gln Tyr Gln
305                 310                 315                 320
Cys His Glu Thr Pro Tyr Gly Gly Ala Cys Phe Cys Pro Pro Gly Tyr
            325                 330                 335
Ile Ile Asn His Asn Asp Ser Arg Thr Cys Val Glu Phe Asp Asp Cys
            340                 345                 350
Gln Ile Trp Gly Ile Cys Asp Gln Lys Cys Glu Ser Arg Pro Gly Arg
            355                 360                 365
His Leu Cys His Cys Glu Glu Gly Tyr Ile Leu Glu Arg Gly Gln Tyr
            370                 375                 380
Cys Lys Ala Asn Asp Ser Phe Gly Glu Ala Ser Ile Ile Phe Ser Asn
385                 390                 395                 400
Gly Arg Asp Leu Leu Ile Gly Asp Ile His Gly Arg Ser Phe Arg Ile
            405                 410                 415
Leu Val Glu Ser Gln Asn Arg Gly Val Ala Val Gly Val Ala Phe His
            420                 425                 430
Tyr His Leu Gln Arg Val Phe Trp Thr Asp Thr Val Gln Asn Lys Val
            435                 440                 445
Phe Ser Val Asp Ile Asn Gly Leu Asn Ile Gln Glu Val Leu Asn Val
450                 455                 460
Ser Val Glu Thr Pro Glu Asn Leu Ala Val Asp Trp Val Asn Asn Lys
465                 470                 475                 480
Ile Tyr Leu Val Glu Thr Lys Val Asn Arg Ile Asp Met Val Asn Leu
            485                 490                 495
Asp Gly Ser Tyr Arg Val Thr Leu Ile Thr Glu Asn Leu Gly His Pro
            500                 505                 510
Arg Gly Ile Ala Val Asp Pro Thr Val Gly Tyr Leu Phe Phe Ser Asp
            515                 520                 525
Trp Glu Ser Leu Ser Gly Glu Pro Lys Leu Glu Arg Ala Phe Met Asp
            530                 535                 540
Gly Ser Asn Arg Lys Asp Leu Val Lys Thr Lys Leu Gly Trp Pro Ala
545                 550                 555                 560
Gly Val Thr Leu Asp Met Ile Ser Lys Arg Val Tyr Trp Val Asp Ser
            565                 570                 575
Arg Phe Asp Tyr Ile Glu Thr Val Thr Tyr Asp Gly Ile Gln Arg Lys
            580                 585                 590
Thr Val Val His Gly Gly Ser Leu Ile Pro His Pro Phe Gly Val Ser
            595                 600                 605
Leu Phe Glu Gly Gln Val Phe Phe Thr Asp Trp Thr Lys Met Ala Val
            610                 615                 620
Leu Lys Ala Asn Lys Phe Thr Glu Thr Asn Pro Gln Val Tyr Tyr Gln
625                 630                 635                 640
Ala Ser Leu Arg Pro Tyr Gly Val Thr Val Tyr His Ser Leu Arg Gln
            645                 650                 655
Pro Tyr Ala Thr Asn Pro Cys Lys Asp Asn Asn Gly Gly Cys Glu Gln

```
                    660                 665                 670
Val Cys Val Leu Ser His Arg Thr Asp Asn Asp Gly Leu Gly Phe Arg
                675                 680                 685
Cys Lys Cys Thr Phe Gly Phe Gln Leu Asp Thr Asp Glu Arg His Cys
                690                 695                 700
Ile Ala Val Gln Asn Phe Leu Ile Phe Ser Ser Gln Val Ala Ile Arg
705                 710                 715                 720
Gly Ile Pro Phe Thr Leu Ser Thr Gln Glu Asp Val Met Val Pro Val
                725                 730                 735
Ser Gly Asn Pro Ser Phe Phe Val Gly Ile Asp Phe Asp Ala Gln Asp
                740                 745                 750
Ser Thr Ile Phe Phe Ser Asp Met Ser Lys His Met Ile Phe Lys Gln
                755                 760                 765
Lys Ile Asp Gly Thr Gly Arg Glu Ile Leu Ala Ala Asn Arg Val Glu
                770                 775                 780
Asn Val Glu Ser Leu Ala Phe Asp Trp Ile Ser Lys Asn Leu Tyr Trp
785                 790                 795                 800
Thr Asp Ser His Tyr Lys Ser Ile Ser Val Met Arg Leu Ala Asp Lys
                805                 810                 815
Thr Arg Arg Thr Val Val Gln Tyr Leu Asn Asn Pro Arg Ser Val Val
                820                 825                 830
Val His Pro Phe Ala Gly Tyr Leu Phe Phe Thr Asp Trp Phe Arg Pro
                835                 840                 845
Ala Lys Ile Met Arg Ala Trp Ser Asp Gly Ser His Leu Leu Pro Val
                850                 855                 860
Ile Asn Thr Thr Leu Gly Trp Pro Asn Gly Leu Ala Ile Asp Trp Ala
865                 870                 875                 880
Ala Ser Arg Leu Tyr Trp Val Asp Ala Tyr Phe Asp Lys Ile Glu His
                885                 890                 895
Ser Thr Phe Asp Gly Leu Asp Arg Arg Arg Leu Gly His Ile Glu Gln
                900                 905                 910
Met Thr His Pro Phe Gly Leu Ala Ile Phe Gly Glu His Leu Phe Phe
                915                 920                 925
Thr Asp Trp Arg Leu Gly Ala Ile Ile Arg Val Arg Lys Ala Asp Gly
                930                 935                 940
Gly Glu Met Thr Val Ile Arg Ser Gly Ile Ala Tyr Ile Leu His Leu
945                 950                 955                 960
Lys Ser Tyr Asp Val Asn Ile Gln Thr Gly Ser Asn Ala Cys Asn Gln
                965                 970                 975
Pro Thr His Pro Asn Gly Asp Cys Ser His Phe Cys Phe Pro Val Pro
                980                 985                 990
Asn Phe Gln Arg Val Cys Gly Cys Pro Tyr Gly Met Arg Leu Ala Ser
                995                 1000                1005
Asn His Leu Thr Cys Glu Gly Asp Pro Thr Asn Glu Pro Pro Thr
                1010                1015                1020
Glu Gln Cys Gly Leu Phe Ser Phe Pro Cys Lys Asn Gly Arg Cys
                1025                1030                1035
Val Pro Asn Tyr Tyr Leu Cys Asp Gly Val Asp Asp Cys His Asp
                1040                1045                1050
Asn Ser Asp Glu Gln Leu Cys Gly Thr Leu Asn Asn Thr Cys Ser
                1055                1060                1065
Ser Ser Ala Phe Thr Cys Gly His Gly Glu Cys Ile Pro Ala His
                1070                1075                1080
```

-continued

```
Trp Arg Cys Asp Lys Arg Asn Asp Cys Val Asp Gly Ser Asp Glu
    1085            1090            1095

His Asn Cys Pro Thr His Ala Pro Ala Ser Cys Leu Asp Thr Gln
    1100            1105            1110

Tyr Thr Cys Asp Asn His Gln Cys Ile Ser Lys Asn Trp Val Cys
    1115            1120            1125

Asp Thr Asp Asn Asp Cys Gly Asp Gly Ser Asp Glu Lys Asn Cys
    1130            1135            1140

Asn Ser Thr Glu Thr Cys Gln Pro Ser Gln Phe Asn Cys Pro Asn
    1145            1150            1155

His Arg Cys Ile Asp Leu Ser Phe Val Cys Asp Gly Asp Lys Asp
    1160            1165            1170

Cys Val Asp Gly Ser Asp Glu Val Gly Cys Val Leu Asn Cys Thr
    1175            1180            1185

Ala Ser Gln Phe Lys Cys Ala Ser Gly Asp Lys Cys Ile Gly Val
    1190            1195            1200

Thr Asn Arg Cys Asp Gly Val Phe Asp Cys Ser Asp Asn Ser Asp
    1205            1210            1215

Glu Ala Gly Cys Pro Thr Arg Pro Pro Gly Met Cys His Ser Asp
    1220            1225            1230

Glu Phe Gln Cys Gln Glu Asp Gly Ile Cys Ile Pro Asn Phe Trp
    1235            1240            1245

Glu Cys Asp Gly His Pro Asp Cys Leu Tyr Gly Ser Asp Glu His
    1250            1255            1260

Asn Ala Cys Val Pro Lys Thr Cys Pro Ser Ser Tyr Phe His Cys
    1265            1270            1275

Asp Asn Gly Asn Cys Ile His Arg Ala Trp Leu Cys Asp Arg Asp
    1280            1285            1290

Asn Asp Cys Gly Asp Met Ser Asp Glu Lys Asp Cys Pro Thr Gln
    1295            1300            1305

Pro Phe Arg Cys Pro Ser Trp Gln Trp Gln Cys Leu Gly His Asn
    1310            1315            1320

Ile Cys Val Asn Leu Ser Val Val Cys Asp Gly Ile Phe Asp Cys
    1325            1330            1335

Pro Asn Gly Thr Asp Glu Ser Pro Leu Cys Asn Gly Asn Ser Cys
    1340            1345            1350

Ser Asp Phe Asn Gly Gly Cys Thr His Glu Cys Val Gln Glu Pro
    1355            1360            1365

Phe Gly Ala Lys Cys Leu Cys Pro Leu Gly Phe Leu Leu Ala Asn
    1370            1375            1380

Asp Ser Lys Thr Cys Glu Asp Ile Asp Glu Cys Asp Ile Leu Gly
    1385            1390            1395

Ser Cys Ser Gln His Cys Tyr Asn Met Arg Gly Ser Phe Arg Cys
    1400            1405            1410

Ser Cys Asp Thr Gly Tyr Met Leu Glu Ser Asp Gly Arg Thr Cys
    1415            1420            1425

Lys Val Thr Ala Ser Glu Ser Leu Leu Leu Leu Val Ala Ser Gln
    1430            1435            1440

Asn Lys Ile Ile Ala Asp Ser Val Thr Ser Gln Val His Asn Ile
    1445            1450            1455

Tyr Ser Leu Val Glu Asn Gly Ser Tyr Ile Val Ala Val Asp Phe
    1460            1465            1470
```

```
Asp Ser Ile Ser Gly Arg Ile Phe Trp Ser Asp Ala Thr Gln Gly
    1475                1480                1485

Lys Thr Trp Ser Ala Phe Gln Asn Gly Thr Asp Arg Arg Val Val
    1490                1495                1500

Phe Asp Ser Ser Ile Ile Leu Thr Glu Thr Ile Ala Ile Asp Trp
    1505                1510                1515

Val Gly Arg Asn Leu Tyr Trp Thr Asp Tyr Ala Leu Glu Thr Ile
    1520                1525                1530

Glu Val Ser Lys Ile Asp Gly Ser His Arg Thr Val Leu Ile Ser
    1535                1540                1545

Lys Asn Leu Thr Asn Pro Arg Gly Leu Ala Leu Asp Pro Arg Met
    1550                1555                1560

Asn Glu His Leu Leu Phe Trp Ser Asp Trp Gly His His Pro Arg
    1565                1570                1575

Ile Glu Arg Ala Ser Met Asp Gly Ser Met Arg Thr Val Ile Val
    1580                1585                1590

Gln Asp Lys Ile Phe Trp Pro Cys Gly Leu Thr Ile Asp Tyr Pro
    1595                1600                1605

Asn Arg Leu Leu Tyr Phe Met Asp Ser Tyr Leu Asp Tyr Met Asp
    1610                1615                1620

Phe Cys Asp Tyr Asn Gly His His Arg Arg Gln Val Ile Ala Ser
    1625                1630                1635

Asp Leu Ile Ile Arg His Pro Tyr Ala Leu Thr Leu Phe Glu Asp
    1640                1645                1650

Ser Val Tyr Trp Thr Asp Arg Ala Thr Arg Arg Val Met Arg Ala
    1655                1660                1665

Asn Lys Trp His Gly Gly Asn Gln Ser Val Val Met Tyr Asn Ile
    1670                1675                1680

Gln Trp Pro Leu Gly Ile Val Ala Val His Pro Ser Lys Gln Pro
    1685                1690                1695

Asn Ser Val Asn Pro Cys Ala Phe Ser Arg Cys Ser His Leu Cys
    1700                1705                1710

Leu Leu Ser Ser Gln Gly Pro His Phe Tyr Ser Cys Val Cys Pro
    1715                1720                1725

Ser Gly Trp Ser Leu Ser Pro Asp Leu Leu Asn Cys Leu Arg Asp
    1730                1735                1740

Asp Gln Pro Phe Leu Ile Thr Val Arg Gln His Ile Ile Phe Gly
    1745                1750                1755

Ile Ser Leu Asn Pro Glu Val Lys Ser Asn Asp Ala Met Val Pro
    1760                1765                1770

Ile Ala Gly Ile Gln Asn Gly Leu Asp Val Glu Phe Asp Asp Ala
    1775                1780                1785

Glu Gln Tyr Ile Tyr Trp Val Glu Asn Pro Gly Glu Ile His Arg
    1790                1795                1800

Val Lys Thr Asp Gly Thr Asn Arg Thr Val Phe Ala Ser Ile Ser
    1805                1810                1815

Met Val Gly Pro Ser Met Asn Leu Ala Leu Asp Trp Ile Ser Arg
    1820                1825                1830

Asn Leu Tyr Ser Thr Asn Pro Arg Thr Gln Ser Ile Glu Val Leu
    1835                1840                1845

Thr Leu His Gly Asp Ile Arg Tyr Arg Lys Thr Leu Ile Ala Asn
    1850                1855                1860

Asp Gly Thr Ala Leu Gly Val Gly Phe Pro Ile Gly Ile Thr Val
```

-continued

```
            1865                1870                1875
Asp Pro Ala Arg Gly Lys Leu Tyr Trp Ser Asp Gln Gly Thr Asp
        1880                1885                1890

Ser Gly Val Pro Ala Lys Ile Ala Ser Ala Asn Met Asp Gly Thr
        1895                1900                1905

Ser Val Lys Thr Leu Phe Thr Gly Asn Leu Glu His Leu Glu Cys
        1910                1915                1920

Val Thr Leu Asp Ile Glu Glu Gln Lys Leu Tyr Trp Ala Val Thr
        1925                1930                1935

Gly Arg Gly Val Ile Glu Arg Gly Asn Val Asp Gly Thr Asp Arg
        1940                1945                1950

Met Ile Leu Val His Gln Leu Ser His Pro Trp Gly Ile Ala Val
        1955                1960                1965

His Asp Ser Phe Leu Tyr Tyr Thr Asp Glu Gln Tyr Glu Val Ile
        1970                1975                1980

Glu Arg Val Asp Lys Ala Thr Gly Ala Asn Lys Ile Val Leu Arg
        1985                1990                1995

Asp Asn Val Pro Asn Leu Arg Gly Leu Gln Val Tyr His Arg Arg
        2000                2005                2010

Asn Ala Ala Glu Ser Ser Asn Gly Cys Ser Asn Asn Met Asn Ala
        2015                2020                2025

Cys Gln Gln Ile Cys Leu Pro Val Pro Gly Gly Leu Phe Ser Cys
        2030                2035                2040

Ala Cys Ala Thr Gly Phe Lys Leu Asn Pro Asp Asn Arg Ser Cys
        2045                2050                2055

Ser Pro Tyr Asn Ser Phe Ile Val Val Ser Met Leu Ser Ala Ile
        2060                2065                2070

Arg Gly Phe Ser Leu Glu Leu Ser Asp His Ser Glu Thr Met Val
        2075                2080                2085

Pro Val Ala Gly Gln Gly Arg Asn Ala Leu His Val Asp Val Asp
        2090                2095                2100

Val Ser Ser Gly Phe Ile Tyr Trp Cys Asp Phe Ser Ser Ser Val
        2105                2110                2115

Ala Ser Asp Asn Ala Ile Arg Arg Ile Lys Pro Asp Gly Ser Ser
        2120                2125                2130

Leu Met Asn Ile Val Thr His Gly Ile Gly Glu Asn Gly Val Arg
        2135                2140                2145

Gly Ile Ala Val Asp Trp Val Ala Gly Asn Leu Tyr Phe Thr Asn
        2150                2155                2160

Ala Phe Val Ser Glu Thr Leu Ile Glu Val Leu Arg Ile Asn Thr
        2165                2170                2175

Thr Tyr Arg Arg Val Leu Leu Lys Val Thr Val Asp Met Pro Arg
        2180                2185                2190

His Ile Val Val Asp Pro Lys Asn Arg Tyr Leu Phe Trp Ala Asp
        2195                2200                2205

Tyr Gly Gln Arg Pro Lys Ile Glu Arg Ser Phe Leu Asp Cys Thr
        2210                2215                2220

Asn Arg Thr Val Leu Val Ser Glu Gly Ile Val Thr Pro Arg Gly
        2225                2230                2235

Leu Ala Val Asp Arg Ser Asp Gly Tyr Val Tyr Trp Val Asp Asp
        2240                2245                2250

Ser Leu Asp Ile Ile Ala Arg Ile Arg Ile Asn Gly Glu Asn Ser
        2255                2260                2265
```

-continued

```
Glu Val Ile Arg Tyr Gly Ser Arg Tyr Pro Thr Pro Tyr Gly Ile
    2270            2275            2280

Thr Val Phe Glu Asn Ser Ile Ile Trp Val Asp Arg Asn Leu Lys
    2285            2290            2295

Lys Ile Phe Gln Ala Ser Lys Glu Pro Glu Asn Thr Glu Pro Pro
    2300            2305            2310

Thr Val Ile Arg Asp Asn Ile Asn Trp Leu Arg Asp Val Thr Ile
    2315            2320            2325

Phe Asp Lys Gln Val Gln Pro Arg Ser Pro Ala Glu Val Asn Asn
    2330            2335            2340

Asn Pro Cys Leu Glu Asn Asn Gly Gly Cys Ser His Leu Cys Phe
    2345            2350            2355

Ala Leu Pro Gly Leu His Thr Pro Lys Cys Asp Cys Ala Phe Gly
    2360            2365            2370

Thr Leu Gln Ser Asp Gly Lys Asn Cys Ala Ile Ser Thr Glu Asn
    2375            2380            2385

Phe Leu Ile Phe Ala Leu Ser Asn Ser Leu Arg Ser Leu His Leu
    2390            2395            2400

Asp Pro Glu Asn His Ser Pro Pro Phe Gln Thr Ile Asn Val Glu
    2405            2410            2415

Arg Thr Val Met Ser Leu Asp Tyr Asp Ser Val Ser Asp Arg Ile
    2420            2425            2430

Tyr Phe Thr Gln Asn Leu Ala Ser Gly Val Gly Gln Ile Ser Tyr
    2435            2440            2445

Ala Thr Leu Ser Ser Gly Ile His Thr Pro Thr Val Ile Ala Ser
    2450            2455            2460

Gly Ile Gly Thr Ala Asp Gly Ile Ala Phe Asp Trp Ile Thr Arg
    2465            2470            2475

Arg Ile Tyr Tyr Ser Asp Tyr Leu Asn Gln Met Ile Asn Ser Met
    2480            2485            2490

Ala Glu Asp Gly Ser Asn Arg Thr Val Ile Ala Arg Val Pro Lys
    2495            2500            2505

Pro Arg Ala Ile Val Leu Asp Pro Cys Gln Gly Tyr Leu Tyr Trp
    2510            2515            2520

Ala Asp Trp Asp Thr His Ala Lys Ile Glu Arg Ala Thr Leu Gly
    2525            2530            2535

Gly Asn Phe Arg Val Pro Ile Val Asn Ser Ser Leu Val Met Pro
    2540            2545            2550

Ser Gly Leu Thr Leu Asp Tyr Glu Glu Asp Leu Leu Tyr Trp Val
    2555            2560            2565

Asp Ala Ser Leu Gln Arg Ile Glu Arg Ser Thr Leu Thr Gly Val
    2570            2575            2580

Asp Arg Glu Val Ile Val Asn Ala Ala Val His Ala Phe Gly Leu
    2585            2590            2595

Thr Leu Tyr Gly Gln Tyr Ile Tyr Trp Thr Asp Leu Tyr Thr Gln
    2600            2605            2610

Arg Ile Tyr Arg Ala Asn Lys Tyr Asp Gly Ser Gly Gln Ile Ala
    2615            2620            2625

Met Thr Thr Asn Leu Leu Ser Gln Pro Arg Gly Ile Asn Thr Val
    2630            2635            2640

Val Lys Asn Gln Lys Gln Gln Cys Asn Asn Pro Cys Glu Gln Phe
    2645            2650            2655
```

Asn Gly Gly Cys Ser His Ile Cys Ala Pro Gly Pro Asn Gly Ala
2660                    2665                2670

Glu Cys Gln Cys Pro His Glu Gly Asn Trp Tyr Leu Ala Asn Asn
2675                    2680                2685

Arg Lys His Cys Ile Val Asp Asn Gly Glu Arg Cys Gly Ala Ser
2690                    2695                2700

Ser Phe Thr Cys Ser Asn Gly Arg Cys Ile Ser Glu Glu Trp Lys
2705                    2710                2715

Cys Asp Asn Asp Asn Asp Cys Gly Asp Gly Ser Asp Glu Met Glu
2720                    2725                2730

Ser Val Cys Ala Leu His Thr Cys Ser Pro Thr Ala Phe Thr Cys
2735                    2740                2745

Ala Asn Gly Arg Cys Val Gln Tyr Ser Tyr Arg Cys Asp Tyr Tyr
2750                    2755                2760

Asn Asp Cys Gly Asp Gly Ser Asp Glu Ala Gly Cys Leu Phe Arg
2765                    2770                2775

Asp Cys Asn Ala Thr Thr Glu Phe Met Cys Asn Asn Arg Arg Cys
2780                    2785                2790

Ile Pro Arg Glu Phe Ile Cys Asn Gly Val Asp Asn Cys His Asp
2795                    2800                2805

Asn Asn Thr Ser Asp Glu Lys Asn Cys Pro Asp Arg Thr Cys Gln
2810                    2815                2820

Ser Gly Tyr Thr Lys Cys His Asn Ser Asn Ile Cys Ile Pro Arg
2825                    2830                2835

Val Tyr Leu Cys Asp Gly Asp Asn Asp Cys Gly Asp Asn Ser Asp
2840                    2845                2850

Glu Asn Pro Thr Tyr Cys Thr Thr His Thr Cys Ser Ser Ser Glu
2855                    2860                2865

Phe Gln Cys Ala Ser Gly Arg Cys Ile Pro Gln His Trp Tyr Cys
2870                    2875                2880

Asp Gln Glu Thr Asp Cys Phe Asp Ala Ser Asp Glu Pro Ala Ser
2885                    2890                2895

Cys Gly His Ser Glu Arg Thr Cys Leu Ala Asp Glu Phe Lys Cys
2900                    2905                2910

Asp Gly Gly Arg Cys Ile Pro Ser Glu Trp Ile Cys Asp Gly Asp
2915                    2920                2925

Asn Asp Cys Gly Asp Met Ser Asp Glu Asp Lys Arg His Gln Cys
2930                    2935                2940

Gln Asn Gln Asn Cys Ser Asp Ser Glu Phe Leu Cys Val Asn Asp
2945                    2950                2955

Arg Pro Pro Asp Arg Arg Cys Ile Pro Gln Ser Trp Val Cys Asp
2960                    2965                2970

Gly Asp Val Asp Cys Thr Asp Gly Tyr Asp Glu Asn Gln Asn Cys
2975                    2980                2985

Thr Arg Arg Thr Cys Ser Glu Asn Glu Phe Thr Cys Gly Tyr Gly
2990                    2995                3000

Leu Cys Ile Pro Lys Ile Phe Arg Cys Asp Arg His Asn Asp Cys
3005                    3010                3015

Gly Asp Tyr Ser Asp Glu Arg Gly Cys Leu Tyr Gln Thr Cys Gln
3020                    3025                3030

Gln Asn Gln Phe Thr Cys Gln Asn Gly Arg Cys Ile Ser Lys Thr
3035                    3040                3045

Phe Val Cys Asp Glu Asp Asn Asp Cys Gly Asp Gly Ser Asp Glu

-continued

```
              3050             3055             3060
Leu Met His Leu Cys His Thr Pro Glu Pro Thr Cys Pro Pro His
         3065             3070             3075
Glu Phe Lys Cys Asp Asn Gly Arg Cys Ile Glu Met Met Lys Leu
         3080             3085             3090
Cys Asn His Leu Asp Asp Cys Leu Asp Asn Ser Asp Glu Lys Gly
         3095             3100             3105
Cys Gly Ile Asn Glu Cys His Asp Pro Ser Ile Ser Gly Cys Asp
         3110             3115             3120
His Asn Cys Thr Asp Thr Leu Thr Ser Phe Tyr Cys Ser Cys Arg
         3125             3130             3135
Pro Gly Tyr Lys Leu Met Ser Asp Lys Arg Thr Cys Val Asp Ile
         3140             3145             3150
Asp Glu Cys Thr Glu Met Pro Phe Val Cys Ser Gln Lys Cys Glu
         3155             3160             3165
Asn Val Ile Gly Ser Tyr Ile Cys Lys Cys Ala Pro Gly Tyr Leu
         3170             3175             3180
Arg Glu Pro Asp Gly Lys Thr Cys Arg Gln Asn Ser Asn Ile Glu
         3185             3190             3195
Pro Tyr Leu Ile Phe Ser Asn Arg Tyr Tyr Leu Arg Asn Leu Thr
         3200             3205             3210
Ile Asp Gly Tyr Phe Tyr Ser Leu Ile Leu Glu Gly Leu Asp Asn
         3215             3220             3225
Val Val Ala Leu Asp Phe Asp Arg Val Glu Lys Arg Leu Tyr Trp
         3230             3235             3240
Ile Asp Thr Gln Arg Gln Val Ile Glu Arg Met Phe Leu Asn Lys
         3245             3250             3255
Thr Asn Lys Glu Thr Ile Ile Asn His Arg Leu Pro Ala Ala Glu
         3260             3265             3270
Ser Leu Ala Val Asp Trp Val Ser Arg Lys Leu Tyr Trp Leu Asp
         3275             3280             3285
Ala Arg Leu Asp Gly Leu Phe Val Ser Asp Leu Asn Gly Gly His
         3290             3295             3300
Arg Arg Met Leu Ala Gln His Cys Val Asp Ala Asn Asn Thr Phe
         3305             3310             3315
Cys Phe Asp Asn Pro Arg Gly Leu Ala Leu His Pro Gln Tyr Gly
         3320             3325             3330
Tyr Leu Tyr Trp Ala Asp Trp Gly His Arg Ala Tyr Ile Gly Arg
         3335             3340             3345
Val Gly Met Asp Gly Thr Asn Lys Ser Val Ile Ile Ser Thr Lys
         3350             3355             3360
Leu Glu Trp Pro Asn Gly Ile Thr Ile Asp Tyr Thr Asn Asp Leu
         3365             3370             3375
Leu Tyr Trp Ala Asp Ala His Leu Gly Tyr Ile Glu Tyr Ser Asp
         3380             3385             3390
Leu Glu Gly His His Arg His Thr Val Tyr Asp Gly Ala Leu Pro
         3395             3400             3405
His Pro Phe Ala Ile Thr Ile Phe Glu Asp Thr Ile Tyr Trp Thr
         3410             3415             3420
Asp Trp Asn Thr Arg Thr Val Glu Lys Gly Asn Lys Tyr Asp Gly
         3425             3430             3435
Ser Asn Arg Gln Thr Leu Val Asn Thr Thr His Arg Pro Phe Asp
         3440             3445             3450
```

-continued

```
Ile His Val Tyr His Pro Tyr Arg Gln Pro Ile Val Ser Asn Pro
3455                3460                3465

Cys Gly Thr Asn Asn Gly Gly Cys Ser His Leu Cys Leu Ile Lys
3470                3475                3480

Pro Gly Gly Lys Gly Phe Thr Cys Glu Cys Pro Asp Asp Phe Arg
3485                3490                3495

Thr Leu Gln Leu Ser Gly Ser Thr Tyr Cys Met Pro Met Cys Ser
3500                3505                3510

Ser Thr Gln Phe Leu Cys Ala Asn Asn Glu Lys Cys Ile Pro Ile
3515                3520                3525

Trp Trp Lys Cys Asp Gly Gln Lys Asp Cys Ser Asp Gly Ser Asp
3530                3535                3540

Glu Leu Ala Leu Cys Pro Gln Arg Phe Cys Arg Leu Gly Gln Phe
3545                3550                3555

Gln Cys Ser Asp Gly Asn Cys Thr Ser Pro Gln Thr Leu Cys Asn
3560                3565                3570

Ala His Gln Asn Cys Pro Asp Gly Ser Asp Glu Asp Arg Leu Leu
3575                3580                3585

Cys Glu Asn His His Cys Asp Ser Asn Glu Trp Gln Cys Ala Asn
3590                3595                3600

Lys Arg Cys Ile Pro Glu Ser Trp Gln Cys Asp Thr Phe Asn Asp
3605                3610                3615

Cys Glu Asp Asn Ser Asp Glu Asp Ser Ser His Cys Ala Ser Arg
3620                3625                3630

Thr Cys Arg Pro Gly Gln Phe Arg Cys Ala Asn Gly Arg Cys Ile
3635                3640                3645

Pro Gln Ala Trp Lys Cys Asp Val Asp Asn Asp Cys Gly Asp His
3650                3655                3660

Ser Asp Glu Pro Ile Glu Glu Cys Met Ser Ser Ala His Leu Cys
3665                3670                3675

Asp Asn Phe Thr Glu Phe Ser Cys Lys Thr Asn Tyr Arg Cys Ile
3680                3685                3690

Pro Lys Trp Ala Val Cys Asn Gly Val Asp Asp Cys Arg Asp Asn
3695                3700                3705

Ser Asp Glu Gln Gly Cys Glu Arg Thr Cys His Pro Val Gly
3710                3715                3720

Asp Phe Arg Cys Lys Asn His His Cys Ile Pro Leu Arg Trp Gln
3725                3730                3735

Cys Asp Gly Gln Asn Asp Cys Gly Asp Asn Ser Asp Glu Glu Asn
3740                3745                3750

Cys Ala Pro Arg Glu Cys Thr Glu Ser Glu Phe Arg Cys Val Asn
3755                3760                3765

Gln Gln Cys Ile Pro Ser Arg Trp Ile Cys Asp His Tyr Asn Asp
3770                3775                3780

Cys Gly Asp Asn Ser Asp Glu Arg Asp Cys Glu Met Arg Thr Cys
3785                3790                3795

His Pro Glu Tyr Phe Gln Cys Thr Ser Gly His Cys Val His Ser
3800                3805                3810

Glu Leu Lys Cys Asp Gly Ser Ala Asp Cys Leu Asp Ala Ser Asp
3815                3820                3825

Glu Ala Asp Cys Pro Thr Arg Phe Pro Asp Gly Ala Tyr Cys Gln
3830                3835                3840
```

```
Ala Thr Met Phe Glu Cys Lys Asn His Val Cys Ile Pro Pro Tyr
3845                3850                3855

Trp Lys Cys Asp Gly Asp Asp Cys Gly Asp Gly Ser Asp Glu
    3860                3865                3870

Glu Leu His Leu Cys Leu Asp Val Pro Cys Asn Ser Pro Asn Arg
3875                3880                3885

Phe Arg Cys Asp Asn Asn Arg Cys Ile Tyr Ser His Glu Val Cys
3890                3895                3900

Asn Gly Val Asp Asp Cys Gly Asp Gly Thr Asp Glu Thr Glu Glu
3905                3910                3915

His Cys Arg Lys Pro Thr Pro Lys Pro Cys Thr Glu Tyr Glu Tyr
3920                3925                3930

Lys Cys Gly Asn Gly His Cys Ile Pro His Asp Asn Val Cys Asp
3935                3940                3945

Asp Ala Asp Asp Cys Gly Asp Trp Ser Asp Glu Leu Gly Cys Asn
3950                3955                3960

Lys Gly Lys Glu Arg Thr Cys Ala Glu Asn Ile Cys Glu Gln Asn
3965                3970                3975

Cys Thr Gln Leu Asn Glu Gly Gly Phe Ile Cys Ser Cys Thr Ala
3980                3985                3990

Gly Phe Glu Thr Asn Val Phe Asp Arg Thr Ser Cys Leu Asp Ile
3995                4000                4005

Asn Glu Cys Glu Gln Phe Gly Thr Cys Pro Gln His Cys Arg Asn
4010                4015                4020

Thr Lys Gly Ser Tyr Glu Cys Val Cys Ala Asp Gly Phe Thr Ser
4025                4030                4035

Met Ser Asp Arg Pro Gly Lys Arg Cys Ala Ala Glu Gly Ser Ser
4040                4045                4050

Pro Leu Leu Leu Leu Pro Asp Asn Val Arg Ile Arg Lys Tyr Asn
4055                4060                4065

Leu Ser Ser Glu Arg Phe Ser Glu Tyr Leu Gln Asp Glu Glu Tyr
4070                4075                4080

Ile Gln Ala Val Asp Tyr Asp Trp Asp Pro Lys Asp Ile Gly Leu
4085                4090                4095

Ser Val Val Tyr Tyr Thr Val Arg Gly Glu Gly Ser Arg Phe Gly
4100                4105                4110

Ala Ile Lys Arg Ala Tyr Ile Pro Asn Phe Glu Ser Gly Arg Asn
4115                4120                4125

Asn Leu Val Gln Glu Val Asp Leu Lys Leu Lys Tyr Val Met Gln
4130                4135                4140

Pro Asp Gly Ile Ala Val Asp Trp Val Gly Arg His Ile Tyr Trp
4145                4150                4155

Ser Asp Val Lys Asn Lys Arg Ile Glu Val Ala Lys Leu Asp Gly
4160                4165                4170

Arg Tyr Arg Lys Trp Leu Ile Ser Thr Asp Leu Asp Gln Pro Ala
4175                4180                4185

Ala Ile Ala Val Asn Pro Lys Leu Gly Leu Met Phe Trp Thr Asp
4190                4195                4200

Trp Gly Lys Glu Pro Lys Ile Glu Ser Ala Trp Met Asn Gly Glu
4205                4210                4215

Asp Arg Asn Ile Leu Val Phe Glu Asp Leu Gly Trp Pro Thr Gly
4220                4225                4230

Leu Ser Ile Asp Tyr Leu Asn Asn Asp Arg Ile Tyr Trp Ser Asp
```

```
              4235              4240              4245
Phe Lys Glu Asp Val Ile Glu Thr Ile Lys Tyr Asp Gly Thr Asp
    4250              4255              4260
Arg Arg Val Ile Ala Lys Glu Ala Met Asn Pro Tyr Ser Leu Asp
    4265              4270              4275
Ile Phe Glu Asp Gln Leu Tyr Trp Ile Ser Lys Glu Lys Gly Glu
    4280              4285              4290
Val Trp Lys Gln Asn Lys Phe Gly Gln Gly Lys Lys Glu Lys Thr
    4295              4300              4305
Leu Val Val Asn Pro Trp Leu Thr Gln Val Arg Ile Phe His Gln
    4310              4315              4320
Leu Arg Tyr Asn Lys Ser Val Pro Asn Leu Cys Lys Gln Ile Cys
    4325              4330              4335
Ser His Leu Cys Leu Leu Arg Pro Gly Gly Tyr Ser Cys Ala Cys
    4340              4345              4350
Pro Gln Gly Ser Ser Phe Ile Glu Gly Ser Thr Thr Glu Cys Asp
    4355              4360              4365
Ala Ala Ile Glu Leu Pro Ile Asn Leu Pro Pro Pro Cys Arg Cys
    4370              4375              4380
Met His Gly Gly Asn Cys Tyr Phe Asp Glu Thr Asp Leu Pro Lys
    4385              4390              4395
Cys Lys Cys Pro Ser Gly Tyr Thr Gly Lys Tyr Cys Glu Met Ala
    4400              4405              4410
Phe Ser Lys Gly Ile Ser Pro Gly Thr Thr Ala Val Ala Val Leu
    4415              4420              4425
Leu Thr Ile Leu Leu Ile Val Val Ile Gly Ala Leu Ala Ile Ala
    4430              4435              4440
Gly Phe Phe His Tyr Arg Arg Thr Gly Ser Leu Leu Pro Ala Leu
    4445              4450              4455
Pro Lys Leu Pro Ser Leu Ser Ser Leu Val Lys Pro Ser Glu Asn
    4460              4465              4470
Gly Asn Gly Val Thr Phe Arg Ser Gly Ala Asp Leu Asn Met Asp
    4475              4480              4485
Ile Gly Val Ser Gly Phe Gly Pro Glu Thr Ala Ile Asp Arg Ser
    4490              4495              4500
Met Ala Met Ser Glu Asp Phe Val Met Glu Met Gly Lys Gln Pro
    4505              4510              4515
Ile Ile Phe Glu Asn Pro Met Tyr Ser Ala Arg Asp Ser Ala Val
    4520              4525              4530
Lys Val Val Gln Pro Ile Gln Val Thr Val Ser Glu Asn Val Asp
    4535              4540              4545
Asn Lys Asn Tyr Gly Ser Pro Ile Asn Pro Ser Glu Ile Val Pro
    4550              4555              4560
Glu Thr Asn Pro Thr Ser Pro Ala Ala Asp Gly Thr Gln Val Thr
    4565              4570              4575
Lys Trp Asn Leu Phe Lys Arg Lys Ser Lys Gln Thr Thr Asn Phe
    4580              4585              4590
Glu Asn Pro Ile Tyr Ala Gln Met Glu Asn Glu Gln Lys Glu Ser
    4595              4600              4605
Val Ala Ala Thr Pro Pro Pro Ser Pro Ser Leu Pro Ala Lys Pro
    4610              4615              4620
Lys Pro Pro Ser Arg Arg Asp Pro Thr Pro Thr Tyr Ser Ala Thr
    4625              4630              4635
```

-continued

Glu Asp Thr Phe Lys Asp Thr Ala Asn Leu Val Lys Glu Asp Ser
    4640                4645                4650

Glu Val
    4655

<210> SEQ ID NO 41
<211> LENGTH: 4544
<212> TYPE: PRT
<213> ORGANISM: Homo sapiens

<400> SEQUENCE: 41

Met Leu Thr Pro Pro Leu Leu Leu Pro Leu Leu Ser Ala Leu
1               5                   10                  15

Val Ala Ala Ala Ile Asp Ala Pro Lys Thr Cys Ser Pro Lys Gln Phe
                20                  25                  30

Ala Cys Arg Asp Gln Ile Thr Cys Ile Ser Lys Gly Trp Arg Cys Asp
            35                  40                  45

Gly Glu Arg Asp Cys Pro Asp Gly Ser Asp Glu Ala Pro Glu Ile Cys
    50                  55                  60

Pro Gln Ser Lys Ala Gln Arg Cys Gln Pro Asn Glu His Asn Cys Leu
65              70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Gln
                100                 105                 110

Gly Asn Cys Ser Arg Leu Gly Cys Gln His His Cys Val Pro Thr Leu
            115                 120                 125

Asp Gly Pro Thr Cys Tyr Cys Asn Ser Ser Phe Gln Leu Gln Ala Asp
    130                 135                 140

Gly Lys Thr Cys Lys Asp Phe Asp Glu Cys Ser Val Tyr Gly Thr Cys
145             150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
                180                 185                 190

Glu Pro Val Asp Arg Pro Pro Val Leu Leu Ile Ala Asn Ser Gln Asn
            195                 200                 205

Ile Leu Ala Thr Tyr Leu Ser Gly Ala Gln Val Ser Thr Ile Thr Pro
    210                 215                 220

Thr Ser Thr Arg Gln Thr Thr Ala Met Asp Phe Ser Tyr Ala Asn Glu
225             230                 235                 240

Thr Val Cys Trp Val His Val Gly Asp Ser Ala Ala Gln Thr Gln Leu
                245                 250                 255

Lys Cys Ala Arg Met Pro Gly Leu Lys Gly Phe Val Asp Glu His Thr
                260                 265                 270

Ile Asn Ile Ser Leu Ser Leu His His Val Glu Gln Met Ala Ile Asp
            275                 280                 285

Trp Leu Thr Gly Asn Phe Tyr Phe Val Asp Asp Ile Asp Asp Arg Ile
    290                 295                 300

Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys
                325                 330                 335

Val Phe Phe Thr Asp Tyr Gly Gln Ile Pro Lys Val Glu Arg Cys Asp

-continued

```
                340             345             350
Met Asp Gly Gln Asn Arg Thr Lys Leu Val Asp Ser Lys Ile Val Phe
            355                 360             365

Pro His Gly Ile Thr Leu Asp Leu Val Ser Arg Leu Val Tyr Trp Ala
        370                 375             380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu
                405                 410             415

Thr Val Phe Glu Asn Tyr Leu Tyr Ala Thr Asn Ser Asp Asn Ala Asn
            420                 425             430

Ala Gln Gln Lys Thr Ser Val Ile Arg Val Asn Arg Phe Asn Ser Thr
            435                 440             445

Glu Tyr Gln Val Val Thr Arg Val Asp Lys Gly Gly Ala Leu His Ile
        450                 455             460

Tyr His Gln Arg Arg Gln Pro Arg Val Arg Ser His Ala Cys Glu Asn
465                 470                 475             480

Asp Gln Tyr Gly Lys Pro Gly Gly Cys Ser Asp Ile Cys Leu Leu Ala
                485                 490             495

Asn Ser His Lys Ala Arg Thr Cys Arg Cys Arg Ser Gly Phe Ser Leu
            500                 505             510

Gly Ser Asp Gly Lys Ser Cys Lys Lys Pro Glu His Glu Leu Phe Leu
        515                 520             525

Val Tyr Gly Lys Gly Arg Pro Gly Ile Ile Arg Gly Met Asp Met Gly
    530                 535             540

Ala Lys Val Pro Asp Glu His Met Ile Pro Ile Glu Asn Leu Met Asn
545                 550             555                 560

Pro Arg Ala Leu Asp Phe His Ala Glu Thr Gly Phe Ile Tyr Phe Ala
                565                 570             575

Asp Thr Thr Ser Tyr Leu Ile Gly Arg Gln Lys Ile Asp Gly Thr Glu
            580                 585             590

Arg Glu Thr Ile Leu Lys Asp Gly Ile His Asn Val Glu Gly Val Ala
        595                 600             605

Val Asp Trp Met Gly Asp Asn Leu Tyr Trp Thr Asp Asp Gly Pro Lys
    610                 615             620

Lys Thr Ile Ser Val Ala Arg Leu Glu Lys Ala Ala Gln Thr Arg Lys
625                 630                 635             640

Thr Leu Ile Glu Gly Lys Met Thr His Pro Arg Ala Ile Val Val Asp
                645                 650             655

Pro Leu Asn Gly Trp Met Tyr Trp Thr Asp Trp Glu Glu Asp Pro Lys
            660                 665             670

Asp Ser Arg Arg Gly Arg Leu Glu Arg Ala Trp Met Asp Gly Ser His
        675                 680             685

Arg Asp Ile Phe Val Thr Ser Lys Thr Val Leu Trp Pro Asn Gly Leu
    690                 695             700

Ser Leu Asp Ile Pro Ala Gly Arg Leu Tyr Trp Val Asp Ala Phe Tyr
705                 710                 715                 720

Asp Arg Ile Glu Thr Ile Leu Leu Asn Gly Thr Asp Arg Lys Ile Val
                725                 730             735

Tyr Glu Gly Pro Glu Leu Asn His Ala Phe Gly Leu Cys His His Gly
            740                 745             750

Asn Tyr Leu Phe Trp Thr Glu Tyr Arg Ser Gly Ser Val Tyr Arg Leu
        755                 760             765
```

```
Glu Arg Gly Val Gly Gly Ala Pro Pro Thr Val Thr Leu Leu Arg Ser
    770             775                 780

Glu Arg Pro Pro Ile Phe Glu Ile Arg Met Tyr Asp Ala Gln Gln Gln
785                 790                 795                 800

Gln Val Gly Thr Asn Lys Cys Arg Val Asn Asn Gly Gly Cys Ser Ser
                805                 810                 815

Leu Cys Leu Ala Thr Pro Gly Ser Arg Gln Cys Ala Cys Ala Glu Asp
            820                 825                 830

Gln Val Leu Asp Ala Asp Gly Val Thr Cys Leu Ala Asn Pro Ser Tyr
            835                 840                 845

Val Pro Pro Gln Cys Gln Pro Gly Glu Phe Ala Cys Ala Asn Ser
850                 855                 860

Arg Cys Ile Gln Glu Arg Trp Lys Cys Asp Gly Asp Asn Asp Cys Leu
865                 870                 875                 880

Asp Asn Ser Asp Glu Ala Pro Ala Leu Cys His Gln His Thr Cys Pro
                885                 890                 895

Ser Asp Arg Phe Lys Cys Glu Asn Asn Arg Cys Ile Pro Asn Arg Trp
                900                 905                 910

Leu Cys Asp Gly Asp Asn Asp Cys Gly Asn Ser Glu Asp Glu Ser Asn
            915                 920                 925

Ala Thr Cys Ser Ala Arg Thr Cys Pro Pro Asn Gln Phe Ser Cys Ala
            930                 935                 940

Ser Gly Arg Cys Ile Pro Ile Ser Trp Thr Cys Asp Leu Asp Asp Asp
945                 950                 955                 960

Cys Gly Asp Arg Ser Asp Glu Ser Ala Ser Cys Ala Tyr Pro Thr Cys
                965                 970                 975

Phe Pro Leu Thr Gln Phe Thr Cys Asn Asn Gly Arg Cys Ile Asn Ile
            980                 985                 990

Asn Trp Arg Cys Asp Asn Asp Asn Asp Cys Gly Asp Asn Ser Asp Glu
            995                 1000                1005

Ala Gly Cys Ser His Ser Cys Ser Ser Thr Gln Phe Lys Cys Asn
    1010                1015                1020

Ser Gly Arg Cys Ile Pro Glu His Trp Thr Cys Asp Gly Asp Asn
    1025                1030                1035

Asp Cys Gly Asp Tyr Ser Asp Glu Thr His Ala Asn Cys Thr Asn
    1040                1045                1050

Gln Ala Thr Arg Pro Pro Gly Gly Cys His Thr Asp Glu Phe Gln
    1055                1060                1065

Cys Arg Leu Asp Gly Leu Cys Ile Pro Leu Arg Trp Arg Cys Asp
    1070                1075                1080

Gly Asp Thr Asp Cys Met Asp Ser Ser Asp Glu Lys Ser Cys Glu
    1085                1090                1095

Gly Val Thr His Val Cys Asp Pro Ser Val Lys Phe Gly Cys Lys
    1100                1105                1110

Asp Ser Ala Arg Cys Ile Ser Lys Ala Trp Val Cys Asp Gly Asp
    1115                1120                1125

Asn Asp Cys Glu Asp Asn Ser Asp Glu Glu Asn Cys Glu Ser Leu
    1130                1135                1140

Ala Cys Arg Pro Pro Ser His Pro Cys Ala Asn Asn Thr Ser Val
    1145                1150                1155

Cys Leu Pro Pro Asp Lys Leu Cys Asp Gly Asn Asp Asp Cys Gly
    1160                1165                1170
```

```
Asp Gly Ser Asp Glu Gly Glu Leu Cys Asp Gln Cys Ser Leu Asn
1175                1180                1185

Asn Gly Gly Cys Ser His Asn Cys Ser Val Ala Pro Gly Glu Gly
1190                1195                1200

Ile Val Cys Ser Cys Pro Leu Gly Met Glu Leu Gly Pro Asp Asn
1205                1210                1215

His Thr Cys Gln Ile Gln Ser Tyr Cys Ala Lys His Leu Lys Cys
1220                1225                1230

Ser Gln Lys Cys Asp Gln Asn Lys Phe Ser Val Lys Cys Ser Cys
1235                1240                1245

Tyr Glu Gly Trp Val Leu Glu Pro Asp Gly Glu Ser Cys Arg Ser
1250                1255                1260

Leu Asp Pro Phe Lys Pro Phe Ile Ile Phe Ser Asn Arg His Glu
1265                1270                1275

Ile Arg Arg Ile Asp Leu His Lys Gly Asp Tyr Ser Val Leu Val
1280                1285                1290

Pro Gly Leu Arg Asn Thr Ile Ala Leu Asp Phe His Leu Ser Gln
1295                1300                1305

Ser Ala Leu Tyr Trp Thr Asp Val Val Glu Asp Lys Ile Tyr Arg
1310                1315                1320

Gly Lys Leu Leu Asp Asn Gly Ala Leu Thr Ser Phe Glu Val Val
1325                1330                1335

Ile Gln Tyr Gly Leu Ala Thr Pro Glu Gly Leu Ala Val Asp Trp
1340                1345                1350

Ile Ala Gly Asn Ile Tyr Trp Val Glu Ser Asn Leu Asp Gln Ile
1355                1360                1365

Glu Val Ala Lys Leu Asp Gly Thr Leu Arg Thr Thr Leu Leu Ala
1370                1375                1380

Gly Asp Ile Glu His Pro Arg Ala Ile Ala Leu Asp Pro Arg Asp
1385                1390                1395

Gly Ile Leu Phe Trp Thr Asp Trp Asp Ala Ser Leu Pro Arg Ile
1400                1405                1410

Glu Ala Ala Ser Met Ser Gly Ala Gly Arg Arg Thr Val His Arg
1415                1420                1425

Glu Thr Gly Ser Gly Gly Trp Pro Asn Gly Leu Thr Val Asp Tyr
1430                1435                1440

Leu Glu Lys Arg Ile Leu Trp Ile Asp Ala Arg Ser Asp Ala Ile
1445                1450                1455

Tyr Ser Ala Arg Tyr Asp Gly Ser Gly His Met Glu Val Leu Arg
1460                1465                1470

Gly His Glu Phe Leu Ser His Pro Phe Ala Val Thr Leu Tyr Gly
1475                1480                1485

Gly Glu Val Tyr Trp Thr Asp Trp Arg Thr Asn Thr Leu Ala Lys
1490                1495                1500

Ala Asn Lys Trp Thr Gly His Asn Val Thr Val Val Gln Arg Thr
1505                1510                1515

Asn Thr Gln Pro Phe Asp Leu Gln Val Tyr His Pro Ser Arg Gln
1520                1525                1530

Pro Met Ala Pro Asn Pro Cys Glu Ala Asn Gly Gly Gln Gly Pro
1535                1540                1545

Cys Ser His Leu Cys Leu Ile Asn Tyr Asn Arg Thr Val Ser Cys
1550                1555                1560

Ala Cys Pro His Leu Met Lys Leu His Lys Asp Asn Thr Thr Cys
```

-continued

```
            1565                1570                1575
Tyr Glu Phe Lys Lys Phe Leu Leu Tyr Ala Arg Gln Met Glu Ile
       1580                1585                1590
Arg Gly Val Asp Leu Asp Ala Pro Tyr Tyr Asn Tyr Ile Ile Ser
       1595                1600                1605
Phe Thr Val Pro Asp Ile Asp Asn Val Thr Val Leu Asp Tyr Asp
       1610                1615                1620
Ala Arg Glu Gln Arg Val Tyr Trp Ser Asp Val Arg Thr Gln Ala
       1625                1630                1635
Ile Lys Arg Ala Phe Ile Asn Gly Thr Gly Val Glu Thr Val Val
       1640                1645                1650
Ser Ala Asp Leu Pro Asn Ala His Gly Leu Ala Val Asp Trp Val
       1655                1660                1665
Ser Arg Asn Leu Phe Trp Thr Ser Tyr Asp Thr Asn Lys Lys Gln
       1670                1675                1680
Ile Asn Val Ala Arg Leu Asp Gly Ser Phe Lys Asn Ala Val Val
       1685                1690                1695
Gln Gly Leu Glu Gln Pro His Gly Leu Val Val His Pro Leu Arg
       1700                1705                1710
Gly Lys Leu Tyr Trp Thr Asp Gly Asp Asn Ile Ser Met Ala Asn
       1715                1720                1725
Met Asp Gly Ser Asn Arg Thr Leu Leu Phe Ser Gly Gln Lys Gly
       1730                1735                1740
Pro Val Gly Leu Ala Ile Asp Phe Pro Glu Ser Lys Leu Tyr Trp
       1745                1750                1755
Ile Ser Ser Gly Asn His Thr Ile Asn Arg Cys Asn Leu Asp Gly
       1760                1765                1770
Ser Gly Leu Glu Val Ile Asp Ala Met Arg Ser Gln Leu Gly Lys
       1775                1780                1785
Ala Thr Ala Leu Ala Ile Met Gly Asp Lys Leu Trp Trp Ala Asp
       1790                1795                1800
Gln Val Ser Glu Lys Met Gly Thr Cys Ser Lys Ala Asp Gly Ser
       1805                1810                1815
Gly Ser Val Val Leu Arg Asn Ser Thr Thr Leu Val Met His Met
       1820                1825                1830
Lys Val Tyr Asp Glu Ser Ile Gln Leu Asp His Lys Gly Thr Asn
       1835                1840                1845
Pro Cys Ser Val Asn Asn Gly Asp Cys Ser Gln Leu Cys Leu Pro
       1850                1855                1860
Thr Ser Glu Thr Thr Arg Ser Cys Met Cys Thr Ala Gly Tyr Ser
       1865                1870                1875
Leu Arg Ser Gly Gln Gln Ala Cys Glu Gly Val Gly Ser Phe Leu
       1880                1885                1890
Leu Tyr Ser Val His Glu Gly Ile Arg Gly Ile Pro Leu Asp Pro
       1895                1900                1905
Asn Asp Lys Ser Asp Ala Leu Val Pro Val Ser Gly Thr Ser Leu
       1910                1915                1920
Ala Val Gly Ile Asp Phe His Ala Glu Asn Asp Thr Ile Tyr Trp
       1925                1930                1935
Val Asp Met Gly Leu Ser Thr Ile Ser Arg Ala Lys Arg Asp Gln
       1940                1945                1950
Thr Trp Arg Glu Asp Val Val Thr Asn Gly Ile Gly Arg Val Glu
       1955                1960                1965
```

-continued

Gly Ile Ala Val Asp Trp Ile Ala Gly Asn Ile Tyr Trp Thr Asp
1970                1975                1980

Gln Gly Phe Asp Val Ile Glu Val Ala Arg Leu Asn Gly Ser Phe
1985                1990                1995

Arg Tyr Val Val Ile Ser Gln Gly Leu Asp Lys Pro Arg Ala Ile
2000                2005                2010

Thr Val His Pro Glu Lys Gly Tyr Leu Phe Trp Thr Glu Trp Gly
2015                2020                2025

Gln Tyr Pro Arg Ile Glu Arg Ser Arg Leu Asp Gly Thr Glu Arg
2030                2035                2040

Val Val Leu Val Asn Val Ser Ile Ser Trp Pro Asn Gly Ile Ser
2045                2050                2055

Val Asp Tyr Gln Asp Gly Lys Leu Tyr Trp Cys Asp Ala Arg Thr
2060                2065                2070

Asp Lys Ile Glu Arg Ile Asp Leu Glu Thr Gly Glu Asn Arg Glu
2075                2080                2085

Val Val Leu Ser Ser Asn Asn Met Asp Met Phe Ser Val Ser Val
2090                2095                2100

Phe Glu Asp Phe Ile Tyr Trp Ser Asp Arg Thr His Ala Asn Gly
2105                2110                2115

Ser Ile Lys Arg Gly Ser Lys Asp Asn Ala Thr Asp Ser Val Pro
2120                2125                2130

Leu Arg Thr Gly Ile Gly Val Gln Leu Lys Asp Ile Lys Val Phe
2135                2140                2145

Asn Arg Asp Arg Gln Lys Gly Thr Asn Val Cys Ala Val Ala Asn
2150                2155                2160

Gly Gly Cys Gln Gln Leu Cys Leu Tyr Arg Gly Arg Gly Gln Arg
2165                2170                2175

Ala Cys Ala Cys Ala His Gly Met Leu Ala Glu Asp Gly Ala Ser
2180                2185                2190

Cys Arg Glu Tyr Ala Gly Tyr Leu Leu Tyr Ser Glu Arg Thr Ile
2195                2200                2205

Leu Lys Ser Ile His Leu Ser Asp Glu Arg Asn Leu Asn Ala Pro
2210                2215                2220

Val Gln Pro Phe Glu Asp Pro Glu His Met Lys Asn Val Ile Ala
2225                2230                2235

Leu Ala Phe Asp Tyr Arg Ala Gly Thr Ser Pro Gly Thr Pro Asn
2240                2245                2250

Arg Ile Phe Phe Ser Asp Ile His Phe Gly Asn Ile Gln Gln Ile
2255                2260                2265

Asn Asp Asp Gly Ser Arg Arg Ile Thr Ile Val Glu Asn Val Gly
2270                2275                2280

Ser Val Glu Gly Leu Ala Tyr His Arg Gly Trp Asp Thr Leu Tyr
2285                2290                2295

Trp Thr Ser Tyr Thr Thr Ser Thr Ile Thr Arg His Thr Val Asp
2300                2305                2310

Gln Thr Arg Pro Gly Ala Phe Glu Arg Glu Thr Val Ile Thr Met
2315                2320                2325

Ser Gly Asp Asp His Pro Arg Ala Phe Val Leu Asp Glu Cys Gln
2330                2335                2340

Asn Leu Met Phe Trp Thr Asn Trp Asn Glu Gln His Pro Ser Ile
2345                2350                2355

```
Met Arg Ala Ala Leu Ser Gly Ala Asn Val Leu Thr Leu Ile Glu
    2360            2365            2370
Lys Asp Ile Arg Thr Pro Asn Gly Leu Ala Ile Asp His Arg Ala
    2375            2380            2385
Glu Lys Leu Tyr Phe Ser Asp Ala Thr Leu Asp Lys Ile Glu Arg
    2390            2395            2400
Cys Glu Tyr Asp Gly Ser His Arg Tyr Val Ile Leu Lys Ser Glu
    2405            2410            2415
Pro Val His Pro Phe Gly Leu Ala Val Tyr Gly Glu His Ile Phe
    2420            2425            2430
Trp Thr Asp Trp Val Arg Arg Ala Val Gln Arg Ala Asn Lys His
    2435            2440            2445
Val Gly Ser Asn Met Lys Leu Leu Arg Val Asp Ile Pro Gln Gln
    2450            2455            2460
Pro Met Gly Ile Ile Ala Val Ala Asn Asp Thr Asn Ser Cys Glu
    2465            2470            2475
Leu Ser Pro Cys Arg Ile Asn Asn Gly Gly Cys Gln Asp Leu Cys
    2480            2485            2490
Leu Leu Thr His Gln Gly His Val Asn Cys Ser Cys Arg Gly Gly
    2495            2500            2505
Arg Ile Leu Gln Asp Asp Leu Thr Cys Arg Ala Val Asn Ser Ser
    2510            2515            2520
Cys Arg Ala Gln Asp Glu Phe Glu Cys Ala Asn Gly Glu Cys Ile
    2525            2530            2535
Asn Phe Ser Leu Thr Cys Asp Gly Val Pro His Cys Lys Asp Lys
    2540            2545            2550
Ser Asp Glu Lys Pro Ser Tyr Cys Asn Ser Arg Arg Cys Lys Lys
    2555            2560            2565
Thr Phe Arg Gln Cys Ser Asn Gly Arg Cys Val Ser Asn Met Leu
    2570            2575            2580
Trp Cys Asn Gly Ala Asp Asp Cys Gly Asp Gly Ser Asp Glu Ile
    2585            2590            2595
Pro Cys Asn Lys Thr Ala Cys Gly Val Gly Glu Phe Arg Cys Arg
    2600            2605            2610
Asp Gly Thr Cys Ile Gly Asn Ser Ser Arg Cys Asn Gln Phe Val
    2615            2620            2625
Asp Cys Glu Asp Ala Ser Asp Glu Met Asn Cys Ser Ala Thr Asp
    2630            2635            2640
Cys Ser Ser Tyr Phe Arg Leu Gly Val Lys Gly Val Leu Phe Gln
    2645            2650            2655
Pro Cys Glu Arg Thr Ser Leu Cys Tyr Ala Pro Ser Trp Val Cys
    2660            2665            2670
Asp Gly Ala Asn Asp Cys Gly Asp Tyr Ser Asp Glu Arg Asp Cys
    2675            2680            2685
Pro Gly Val Lys Arg Pro Arg Cys Pro Leu Asn Tyr Phe Ala Cys
    2690            2695            2700
Pro Ser Gly Arg Cys Ile Pro Met Ser Trp Thr Cys Asp Lys Glu
    2705            2710            2715
Asp Asp Cys Glu His Gly Glu Asp Glu Thr His Cys Asn Lys Phe
    2720            2725            2730
Cys Ser Glu Ala Gln Phe Glu Cys Gln Asn His Arg Cys Ile Ser
    2735            2740            2745
Lys Gln Trp Leu Cys Asp Gly Ser Asp Asp Cys Gly Asp Gly Ser
```

```
                    2750                2755                2760
Asp Glu  Ala Ala His Cys Glu  Gly Lys Thr Cys  Gly Pro Ser Ser
    2765             2770                 2775

Phe Ser  Cys Pro Gly Thr His  Val Cys Val Pro  Glu Arg Trp Leu
    2780             2785                 2790

Cys Asp  Gly Asp Lys Asp Cys  Ala Asp Gly Ala  Asp Glu Ser Ile
    2795             2800                 2805

Ala Ala  Gly Cys Leu Tyr Asn  Ser Thr Cys Asp  Asp Arg Glu Phe
    2810             2815                 2820

Met Cys  Gln Asn Arg Gln Cys  Ile Pro Lys His  Phe Val Cys Asp
    2825             2830                 2835

His Asp  Arg Asp Cys Ala Asp  Gly Ser Asp Glu  Ser Pro Glu Cys
    2840             2845                 2850

Glu Tyr  Pro Thr Cys Gly Pro  Ser Glu Phe Arg  Cys Ala Asn Gly
    2855             2860                 2865

Arg Cys  Leu Ser Ser Arg Gln  Trp Glu Cys Asp  Gly Glu Asn Asp
    2870             2875                 2880

Cys His  Asp Gln Ser Asp Glu  Ala Pro Lys Asn  Pro His Cys Thr
    2885             2890                 2895

Ser Pro  Glu His Lys Cys Asn  Ala Ser Ser Gln  Phe Leu Cys Ser
    2900             2905                 2910

Ser Gly  Arg Cys Val Ala Glu  Ala Leu Leu Cys  Asn Gly Gln Asp
    2915             2920                 2925

Asp Cys  Gly Asp Ser Ser Asp  Glu Arg Gly Cys  His Ile Asn Glu
    2930             2935                 2940

Cys Leu  Ser Arg Lys Leu Ser  Gly Cys Ser Gln  Asp Cys Glu Asp
    2945             2950                 2955

Leu Lys  Ile Gly Phe Lys Cys  Arg Cys Arg Pro  Gly Phe Arg Leu
    2960             2965                 2970

Lys Asp  Asp Gly Arg Thr Cys  Ala Asp Val Asp  Glu Cys Ser Thr
    2975             2980                 2985

Thr Phe  Pro Cys Ser Gln Arg  Cys Ile Asn Thr  His Gly Ser Tyr
    2990             2995                 3000

Lys Cys  Leu Cys Val Glu Gly  Tyr Ala Pro Arg  Gly Gly Asp Pro
    3005             3010                 3015

His Ser  Cys Lys Ala Val Thr  Asp Glu Glu Pro  Phe Leu Ile Phe
    3020             3025                 3030

Ala Asn  Arg Tyr Tyr Leu Arg  Lys Leu Asn Leu  Asp Gly Ser Asn
    3035             3040                 3045

Tyr Thr  Leu Leu Lys Gln Gly  Leu Asn Asn Ala  Val Ala Leu Asp
    3050             3055                 3060

Phe Asp  Tyr Arg Glu Gln Met  Ile Tyr Trp Thr  Asp Val Thr Thr
    3065             3070                 3075

Gln Gly  Ser Met Ile Arg Arg  Met His Leu Asn  Gly Ser Asn Val
    3080             3085                 3090

Gln Val  Leu His Arg Thr Gly  Leu Ser Asn Pro  Asp Gly Leu Ala
    3095             3100                 3105

Val Asp  Trp Val Gly Gly Asn  Leu Tyr Trp Cys  Asp Lys Gly Arg
    3110             3115                 3120

Asp Thr  Ile Glu Val Ser Lys  Leu Asn Gly Ala  Tyr Arg Thr Val
    3125             3130                 3135

Leu Val  Ser Ser Gly Leu Arg  Glu Pro Arg Ala  Leu Val Val Asp
    3140             3145                 3150
```

-continued

```
Val Gln Asn Gly Tyr Leu Tyr Trp Thr Asp Trp Gly Asp His Ser
3155                3160                3165

Leu Ile Gly Arg Ile Gly Met Asp Gly Ser Ser Arg Ser Val Ile
3170                3175                3180

Val Asp Thr Lys Ile Thr Trp Pro Asn Gly Leu Thr Leu Asp Tyr
3185                3190                3195

Val Thr Glu Arg Ile Tyr Trp Ala Asp Ala Arg Glu Asp Tyr Ile
3200                3205                3210

Glu Phe Ala Ser Leu Asp Gly Ser Asn Arg His Val Val Leu Ser
3215                3220                3225

Gln Asp Ile Pro His Ile Phe Ala Leu Thr Leu Phe Glu Asp Tyr
3230                3235                3240

Val Tyr Trp Thr Asp Trp Glu Thr Lys Ser Ile Asn Arg Ala His
3245                3250                3255

Lys Thr Thr Gly Thr Asn Lys Thr Leu Leu Ile Ser Thr Leu His
3260                3265                3270

Arg Pro Met Asp Leu His Val Phe His Ala Leu Arg Gln Pro Asp
3275                3280                3285

Val Pro Asn His Pro Cys Lys Val Asn Asn Gly Gly Cys Ser Asn
3290                3295                3300

Leu Cys Leu Leu Ser Pro Gly Gly Gly His Lys Cys Ala Cys Pro
3305                3310                3315

Thr Asn Phe Tyr Leu Gly Ser Asp Gly Arg Thr Cys Val Ser Asn
3320                3325                3330

Cys Thr Ala Ser Gln Phe Val Cys Lys Asn Asp Lys Cys Ile Pro
3335                3340                3345

Phe Trp Trp Lys Cys Asp Thr Glu Asp Asp Cys Gly Asp His Ser
3350                3355                3360

Asp Glu Pro Pro Asp Cys Pro Glu Phe Lys Cys Arg Pro Gly Gln
3365                3370                3375

Phe Gln Cys Ser Thr Gly Ile Cys Thr Asn Pro Ala Phe Ile Cys
3380                3385                3390

Asp Gly Asp Asn Asp Cys Gln Asp Asn Ser Asp Glu Ala Asn Cys
3395                3400                3405

Asp Ile His Val Cys Leu Pro Ser Gln Phe Lys Cys Thr Asn Thr
3410                3415                3420

Asn Arg Cys Ile Pro Gly Ile Phe Arg Cys Asn Gly Gln Asp Asn
3425                3430                3435

Cys Gly Asp Gly Glu Asp Glu Arg Asp Cys Pro Glu Val Thr Cys
3440                3445                3450

Ala Pro Asn Gln Phe Gln Cys Ser Ile Thr Lys Arg Cys Ile Pro
3455                3460                3465

Arg Val Trp Val Cys Asp Arg Asp Asn Asp Cys Val Asp Gly Ser
3470                3475                3480

Asp Glu Pro Ala Asn Cys Thr Gln Met Thr Cys Gly Val Asp Glu
3485                3490                3495

Phe Arg Cys Lys Asp Ser Gly Arg Cys Ile Pro Ala Arg Trp Lys
3500                3505                3510

Cys Asp Gly Glu Asp Asp Cys Gly Asp Gly Ser Asp Glu Pro Lys
3515                3520                3525

Glu Glu Cys Asp Glu Arg Thr Cys Glu Pro Tyr Gln Phe Arg Cys
3530                3535                3540
```

-continued

```
Lys Asn Asn Arg Cys Val Pro Gly Arg Trp Gln Cys Asp Tyr Asp
3545                3550                3555

Asn Asp Cys Gly Asp Asn Ser Asp Glu Glu Ser Cys Thr Pro Arg
    3560                3565                3570

Pro Cys Ser Glu Ser Glu Phe Ser Cys Ala Asn Gly Arg Cys Ile
    3575                3580                3585

Ala Gly Arg Trp Lys Cys Asp Gly Asp His Asp Cys Ala Asp Gly
    3590                3595                3600

Ser Asp Glu Lys Asp Cys Thr Pro Arg Cys Asp Met Asp Gln Phe
3605                3610                3615

Gln Cys Lys Ser Gly His Cys Ile Pro Leu Arg Trp Arg Cys Asp
3620                3625                3630

Ala Asp Ala Asp Cys Met Asp Gly Ser Asp Glu Glu Ala Cys Gly
3635                3640                3645

Thr Gly Val Arg Thr Cys Pro Leu Asp Glu Phe Gln Cys Asn Asn
3650                3655                3660

Thr Leu Cys Lys Pro Leu Ala Trp Lys Cys Asp Gly Glu Asp Asp
3665                3670                3675

Cys Gly Asp Asn Ser Asp Glu Asn Pro Glu Glu Cys Ala Arg Phe
3680                3685                3690

Val Cys Pro Pro Asn Arg Pro Phe Arg Cys Lys Asn Asp Arg Val
3695                3700                3705

Cys Leu Trp Ile Gly Arg Gln Cys Asp Gly Thr Asp Asn Cys Gly
3710                3715                3720

Asp Gly Thr Asp Glu Glu Asp Cys Glu Pro Pro Thr Ala His Thr
3725                3730                3735

Thr His Cys Lys Asp Lys Lys Glu Phe Leu Cys Arg Asn Gln Arg
3740                3745                3750

Cys Leu Ser Ser Ser Leu Arg Cys Asn Met Phe Asp Asp Cys Gly
3755                3760                3765

Asp Gly Ser Asp Glu Glu Asp Cys Ser Ile Asp Pro Lys Leu Thr
3770                3775                3780

Ser Cys Ala Thr Asn Ala Ser Ile Cys Gly Asp Glu Ala Arg Cys
3785                3790                3795

Val Arg Thr Glu Lys Ala Ala Tyr Cys Ala Cys Arg Ser Gly Phe
3800                3805                3810

His Thr Val Pro Gly Gln Pro Gly Cys Gln Asp Ile Asn Glu Cys
3815                3820                3825

Leu Arg Phe Gly Thr Cys Ser Gln Leu Cys Asn Asn Thr Lys Gly
3830                3835                3840

Gly His Leu Cys Ser Cys Ala Arg Asn Phe Met Lys Thr His Asn
3845                3850                3855

Thr Cys Lys Ala Glu Gly Ser Glu Tyr Gln Val Leu Tyr Ile Ala
3860                3865                3870

Asp Asp Asn Glu Ile Arg Ser Leu Phe Pro Gly His Pro His Ser
3875                3880                3885

Ala Tyr Glu Gln Ala Phe Gln Gly Asp Glu Ser Val Arg Ile Asp
3890                3895                3900

Ala Met Asp Val His Val Lys Ala Gly Arg Val Tyr Trp Thr Asn
3905                3910                3915

Trp His Thr Gly Thr Ile Ser Tyr Arg Ser Leu Pro Pro Ala Ala
3920                3925                3930

Pro Pro Thr Thr Ser Asn Arg His Arg Arg Gln Ile Asp Arg Gly
```

```
                   3935                3940                3945

Val Thr His Leu Asn Ile Ser Gly Leu Lys Met Pro Arg Gly Ile
        3950                3955                3960

Ala Ile Asp Trp Val Ala Gly Asn Val Tyr Trp Thr Asp Ser Gly
        3965                3970                3975

Arg Asp Val Ile Glu Val Ala Gln Met Lys Gly Glu Asn Arg Lys
        3980                3985                3990

Thr Leu Ile Ser Gly Met Ile Asp Glu Pro His Ala Ile Val Val
        3995                4000                4005

Asp Pro Leu Arg Gly Thr Met Tyr Trp Ser Asp Trp Gly Asn His
        4010                4015                4020

Pro Lys Ile Glu Thr Ala Ala Met Asp Gly Thr Leu Arg Glu Thr
        4025                4030                4035

Leu Val Gln Asp Asn Ile Gln Trp Pro Thr Gly Leu Ala Val Asp
        4040                4045                4050

Tyr His Asn Glu Arg Leu Tyr Trp Ala Asp Ala Lys Leu Ser Val
        4055                4060                4065

Ile Gly Ser Ile Arg Leu Asn Gly Thr Asp Pro Ile Val Ala Ala
        4070                4075                4080

Asp Ser Lys Arg Gly Leu Ser His Pro Phe Ser Ile Asp Val Phe
        4085                4090                4095

Glu Asp Tyr Ile Tyr Gly Val Thr Tyr Ile Asn Asn Arg Val Phe
        4100                4105                4110

Lys Ile His Lys Phe Gly His Ser Pro Leu Val Asn Leu Thr Gly
        4115                4120                4125

Gly Leu Ser His Ala Ser Asp Val Val Leu Tyr His Gln His Lys
        4130                4135                4140

Gln Pro Glu Val Thr Asn Pro Cys Asp Arg Lys Lys Cys Glu Trp
        4145                4150                4155

Leu Cys Leu Leu Ser Pro Ser Gly Pro Val Cys Thr Cys Pro Asn
        4160                4165                4170

Gly Lys Arg Leu Asp Asn Gly Thr Cys Val Pro Val Pro Ser Pro
        4175                4180                4185

Thr Pro Pro Pro Asp Ala Pro Arg Pro Gly Thr Cys Asn Leu Gln
        4190                4195                4200

Cys Phe Asn Gly Gly Ser Cys Phe Leu Asn Ala Arg Arg Gln Pro
        4205                4210                4215

Lys Cys Arg Cys Gln Pro Arg Tyr Thr Gly Asp Lys Cys Glu Leu
        4220                4225                4230

Asp Gln Cys Trp Glu His Cys Arg Asn Gly Gly Thr Cys Ala Ala
        4235                4240                4245

Ser Pro Ser Gly Met Pro Thr Cys Arg Cys Pro Thr Gly Phe Thr
        4250                4255                4260

Gly Pro Lys Cys Thr Gln Gln Val Cys Ala Gly Tyr Cys Ala Asn
        4265                4270                4275

Asn Ser Thr Cys Thr Val Asn Gln Gly Asn Gln Pro Gln Cys Arg
        4280                4285                4290

Cys Leu Pro Gly Phe Leu Gly Asp Arg Cys Gln Tyr Arg Gln Cys
        4295                4300                4305

Ser Gly Tyr Cys Glu Asn Phe Gly Thr Cys Gln Met Ala Ala Asp
        4310                4315                4320

Gly Ser Arg Gln Cys Arg Cys Thr Ala Tyr Phe Glu Gly Ser Arg
        4325                4330                4335
```

```
Cys Glu Val Asn Lys Cys Ser Arg Cys Leu Glu Gly Ala Cys Val
    4340                4345                4350

Val Asn Lys Gln Ser Gly Asp Val Thr Cys Asn Cys Thr Asp Gly
    4355                4360                4365

Arg Val Ala Pro Ser Cys Leu Thr Cys Val Gly His Cys Ser Asn
    4370                4375                4380

Gly Gly Ser Cys Thr Met Asn Ser Lys Met Met Pro Glu Cys Gln
    4385                4390                4395

Cys Pro Pro His Met Thr Gly Pro Arg Cys Glu Glu His Val Phe
    4400                4405                4410

Ser Gln Gln Gln Pro Gly His Ile Ala Ser Ile Leu Ile Pro Leu
    4415                4420                4425

Leu Leu Leu Leu Leu Leu Val Leu Val Ala Gly Val Val Phe Trp
    4430                4435                4440

Tyr Lys Arg Arg Val Gln Gly Ala Lys Gly Phe Gln His Gln Arg
    4445                4450                4455

Met Thr Asn Gly Ala Met Asn Val Glu Ile Gly Asn Pro Thr Tyr
    4460                4465                4470

Lys Met Tyr Glu Gly Gly Glu Pro Asp Asp Val Gly Gly Leu Leu
    4475                4480                4485

Asp Ala Asp Phe Ala Leu Asp Pro Asp Lys Pro Thr Asn Phe Thr
    4490                4495                4500

Asn Pro Val Tyr Ala Thr Leu Tyr Met Gly Gly His Gly Ser Arg
    4505                4510                4515

His Ser Leu Ala Ser Thr Asp Glu Lys Arg Glu Leu Leu Gly Arg
    4520                4525                4530

Gly Pro Glu Asp Glu Ile Gly Asp Pro Leu Ala
    4535                4540

<210> SEQ ID NO 42
<211> LENGTH: 375
<212> TYPE: PRT
<213> ORGANISM: Homo sapiens

<400> SEQUENCE: 42

Met Glu Arg Ala Ser Cys Leu Leu Leu Leu Leu Pro Leu Val His
1               5                   10                  15

Val Ser Ala Thr Thr Pro Glu Pro Cys Glu Leu Asp Asp Glu Asp Phe
                20                  25                  30

Arg Cys Val Cys Asn Phe Ser Glu Pro Gln Pro Asp Trp Ser Glu Ala
            35                  40                  45

Phe Gln Cys Val Ser Ala Val Glu Val Glu Ile His Ala Gly Gly Leu
    50                  55                  60

Asn Leu Glu Pro Phe Leu Lys Arg Val Asp Ala Asp Ala Asp Pro Arg
65                  70                  75                  80

Gln Tyr Ala Asp Thr Val Lys Ala Leu Arg Val Arg Arg Leu Thr Val
                85                  90                  95

Gly Ala Ala Gln Val Pro Ala Gln Leu Leu Val Gly Ala Leu Arg Val
                100                 105                 110

Leu Ala Tyr Ser Arg Leu Lys Glu Leu Thr Leu Glu Asp Leu Lys Ile
            115                 120                 125

Thr Gly Thr Met Pro Pro Leu Pro Leu Glu Ala Thr Gly Leu Ala Leu
    130                 135                 140

Ser Ser Leu Arg Leu Arg Asn Val Ser Trp Ala Thr Gly Arg Ser Trp
```

```
        145                 150                 155                 160
Leu Ala Glu Leu Gln Gln Trp Leu Lys Pro Gly Leu Lys Val Leu Ser
                    165                 170                 175

Ile Ala Gln Ala His Ser Pro Ala Phe Ser Cys Glu Gln Val Arg Ala
                180                 185                 190

Phe Pro Ala Leu Thr Ser Leu Asp Leu Ser Asp Asn Pro Gly Leu Gly
            195                 200                 205

Glu Arg Gly Leu Met Ala Ala Leu Cys Pro His Lys Phe Pro Ala Ile
        210                 215                 220

Gln Asn Leu Ala Leu Arg Asn Thr Gly Met Glu Thr Pro Thr Gly Val
225                 230                 235                 240

Cys Ala Ala Leu Ala Ala Gly Val Gln Pro His Ser Leu Asp Leu
                245                 250                 255

Ser His Asn Ser Leu Arg Ala Thr Val Asn Pro Ser Ala Pro Arg Cys
            260                 265                 270

Met Trp Ser Ser Ala Leu Asn Ser Leu Asn Leu Ser Phe Ala Gly Leu
        275                 280                 285

Glu Gln Val Pro Lys Gly Leu Pro Ala Lys Leu Arg Val Leu Asp Leu
    290                 295                 300

Ser Cys Asn Arg Leu Asn Arg Ala Pro Gln Pro Asp Glu Leu Pro Glu
305                 310                 315                 320

Val Asp Asn Leu Thr Leu Asp Gly Asn Pro Phe Leu Val Pro Gly Thr
                325                 330                 335

Ala Leu Pro His Glu Gly Ser Met Asn Ser Gly Val Val Pro Ala Cys
            340                 345                 350

Ala Arg Ser Thr Leu Ser Val Gly Val Ser Gly Thr Leu Val Leu Leu
        355                 360                 365

Gln Gly Ala Arg Gly Phe Ala
    370                 375

<210> SEQ ID NO 43
<211> LENGTH: 198
<212> TYPE: PRT
<213> ORGANISM: Homo sapiens

<400> SEQUENCE: 43

Met Ala Ser Gly Asn Ala Arg Ile Gly Lys Pro Ala Pro Asp Phe Lys
1               5                   10                  15

Ala Thr Ala Val Val Asp Gly Ala Phe Lys Glu Val Lys Leu Ser Asp
                20                  25                  30

Tyr Lys Gly Lys Tyr Val Val Leu Phe Phe Tyr Pro Leu Asp Phe Thr
            35                  40                  45

Phe Val Cys Pro Thr Glu Ile Ile Ala Phe Ser Asn Arg Ala Glu Asp
        50                  55                  60

Phe Arg Lys Leu Gly Cys Glu Val Leu Gly Val Ser Val Asp Ser Gln
65                  70                  75                  80

Phe Thr His Leu Ala Trp Ile Asn Thr Pro Arg Lys Glu Gly Gly Leu
                85                  90                  95

Gly Pro Leu Asn Ile Pro Leu Leu Ala Asp Val Thr Arg Arg Leu Ser
            100                 105                 110

Glu Asp Tyr Gly Val Leu Lys Thr Asp Glu Gly Ile Ala Tyr Arg Gly
        115                 120                 125

Leu Phe Ile Ile Asp Gly Lys Gly Val Leu Arg Gln Ile Thr Val Asn
    130                 135                 140
```

-continued

```
Asp Leu Pro Val Gly Arg Ser Val Asp Glu Ala Leu Arg Leu Val Gln
145                 150                 155                 160

Ala Phe Gln Tyr Thr Asp Glu His Gly Glu Val Cys Pro Ala Gly Trp
                165                 170                 175

Lys Pro Gly Ser Asp Thr Ile Lys Pro Asn Val Asp Asp Ser Lys Glu
            180                 185                 190

Tyr Phe Ser Lys His Asn
            195

<210> SEQ ID NO 44
<211> LENGTH: 124
<212> TYPE: PRT
<213> ORGANISM: Homo sapiens

<400> SEQUENCE: 44

Ser Phe Ser Ser Met Glu Ala Ser Ala Leu Cys Trp Gly Val Met
1               5                   10                  15

Ala Ser Ser Leu Leu Ala Ser Leu Ala Ile Glu Arg Val Met Arg Pro
                20                  25                  30

Leu Arg Leu Pro Trp Leu Leu Ala Val Leu Arg Pro Leu Glu Ala Thr
            35                  40                  45

Ala Ser Phe Ser Ser Leu Ser Ser Pro Glu Val Ser Ser Val Phe Ser
        50                  55                  60

Leu Arg Arg Ser Ser Leu Ser Phe Ser Thr Ser Gly Phe Ser Ser Ser
65                  70                  75                  80

Phe Ser Ala Ser Phe Ser Phe Ser Phe Ser Ser Phe Ser Ser Trp Leu
                85                  90                  95

Leu Arg Gly Met Gly Cys Cys Cys Cys Cys Cys Cys Cys Cys Cys
                100                 105                 110

Cys Cys Cys Cys Cys Trp Leu Leu Pro Arg Arg Arg
            115                 120
```

BIOMARKERS FOR MYOCARDIAL ISCHEMIA

CROSS-REFERENCE TO RELATED APPLICATIONS

This application is a continuation of U.S. patent application 12/994,034, filed Sep. 15, 2001, now U.S. Pat. No. 8,497,078, issued Jul. 30, 2013, which is a 35U.S.C. §371 U.S. national entry of International Application PCT/US2009/045168, having an international filing date of May 26, 2009, which claims the benefit of U.S. Provisional Application No. 61/128,688, filed May 23, 2008, the content of each of the aforementioned applications is herein incorporated by reference in their entirety.

BACKGROUND INFORMATION

Coronary heart disease is the most common single cause of death in the western world, representing about 20% of all deaths. This is equivalent to about 2 million deaths in Europe per year or four people per minute. In the US, over 8 million people exhibit acute (chest pain) symptoms in the Emergency Department (ED) of hospitals, with 1.5 million individuals having confirmed acute coronary symptom (ACS) events, accounting for 500,000 short term deaths. In patients presenting to the emergency room with chest pain, fewer than 15% are ultimately diagnosed as having ischemia or acute myocardial infarction (MI). Currently, blood tests for the cardiac specific isoform of troponin I or troponin T (TnI or TnT, respectively) are generally used for the diagnosis of acute myocardial infarction (due to cardiac muscle (cell) death). Creatine kinase (CK) MB and myoglobin can also be used, but are considered to be less specific for cardiac injury. However, although these cardiac biomarkers can identify patients with even small amounts of myocardial necrosis, there is an earlier time point in which the heart is in ischemia but is not yet in necrosis, and the diagnosis of cardiac ischemia in the absence of necrosis cannot currently be made with accuracy.

It would be useful to be able to identify subjects in this diagnostic window (having non-necrotic ischemia). Such a diagnostic tool would be of great value for triage in the emergency department. For example, it would allow earlier intervention, including earlier perfusion, to allow increased salvage of the injured myocardium; and it would prevent unnecessary admittance to the hospital of patients with non-cardiac chest pain. Furthermore, such an assay could delay therapy in subjects who do not exhibit diagnostic electrocardiographic (ECG) changes, and could help to improve the accuracy of current provocative tests for ischemia, such as exercise stress testing. The sooner intervention can be carried out, the less cardiac damage will occur. Reduced damage is correlated with an increase in long term survival.

DESCRIPTION OF THE DRAWINGS

1. Two additional proteins were observed in each protein spot. Caspase 14 was observed to change in AMI (individual) 15 and by 1 DLC for individuals (1-10) that underwent atrial pacing
2. Most stringent—greater than 2 fold increase (3.2) in ⅔ ischemia or AMI patients as well as fluctuation in other individuals
3. Reduced stringency (fold change reduced (2.2)) greater than 1.5 fold change
4. Reduced stringency—greater than 2 fold increase in ⅔ ischemia or AMI patients but fluctuates with individuals
5. LPLNECA-1=isoform 1 of Long palate, lung and nasal epithelium carcinoma-associated protein 1
6. LMW and HMW kinnogen-1 were detected but it was the bradykinin peptide that was elevated

DESCRIPTION

Figure 1:
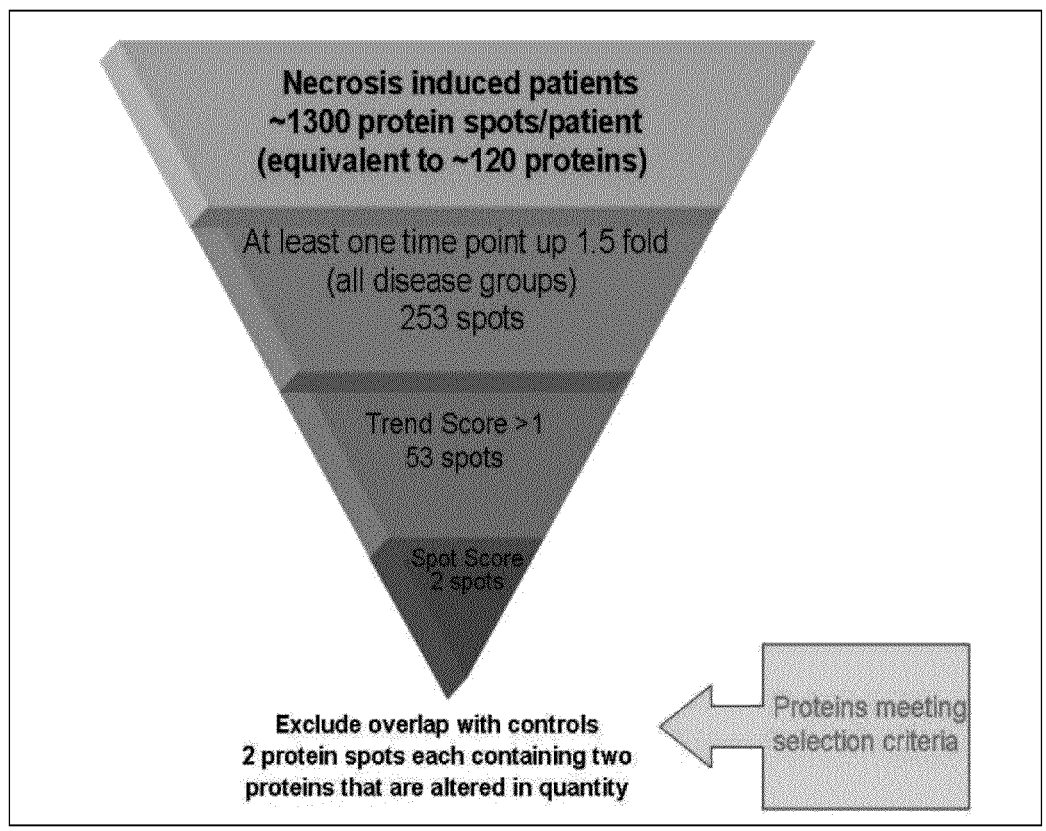
FIG. 1 shows a schematic representation of protein spot attrition due to stringent criteria, based on a cohort that underwent atrial pacing to induce demand on the heart such that the blood flow was inadequate, thereby potentially causing myocardial ischemia. Blood samples were drawn from the coronary sinuses of individuals subjected to atrial pacing. The change in lactate acid level was an indication of induced ischemia, while the detection of cTnI or cTnT was indicative of cardiac necrosis. Those subjects that did not exhibit any change in lacate acid level or cTnT/cTnT were considered controls.
Figure 2:
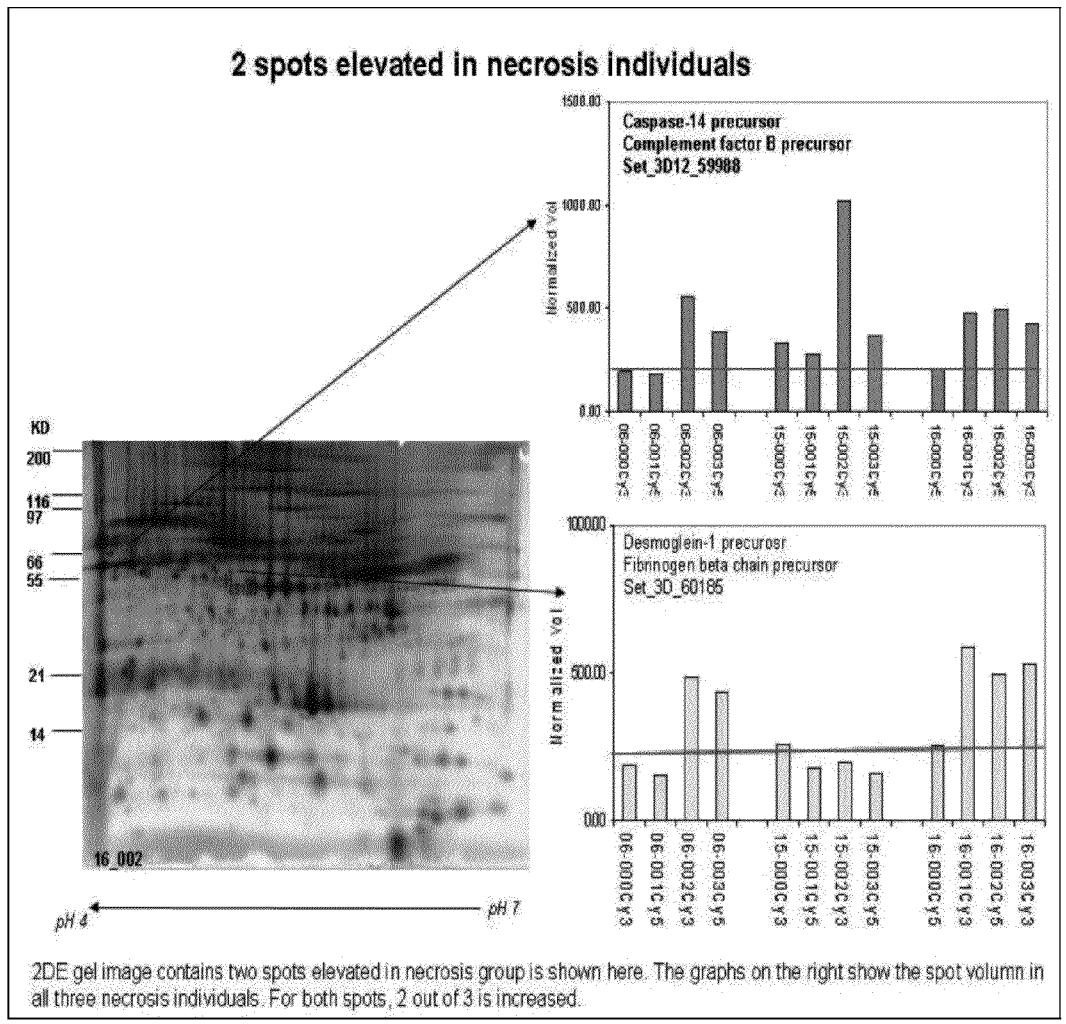
FIG. 2 shows a 2DE gel image showing two spots that are elevated in necrosis individuals. Serum samples were initially depleted of immunoglobins (IgG) and albumin, then separated based on pI and MW using gel electrophorisis. The majority of the spots did not change in all of the individuals subjected to atrial pacing. The graphs on the right show the spot volume in all three necrosis individuals. For both spots, 2 out of 3 were increased for those individuals which had cTnI detected after atrial pacing in their coronary sinus blood samples.
Figure 3:
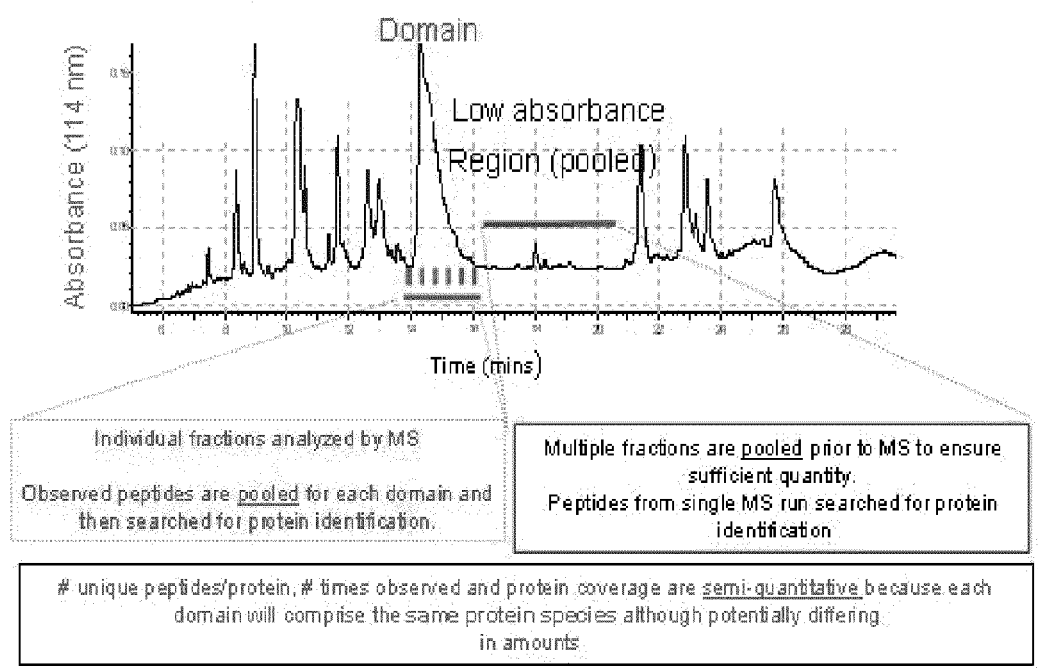
FIG. 3 shows 1DLC fractions strategy used in MS analysis. Samples were depleted of immunoglobins (IgG, IgM and IgA) and albumin, then separated based on hydrophobicity (Reversed phase high performance liquid chromatography, RPLC, 1DLC). The number of unique peptides/protein observed, and the number of times observed and protein coverage are semi-quantitative, because each domain will comprise the same protein species, although potentially differing in amounts.
Figure 4:
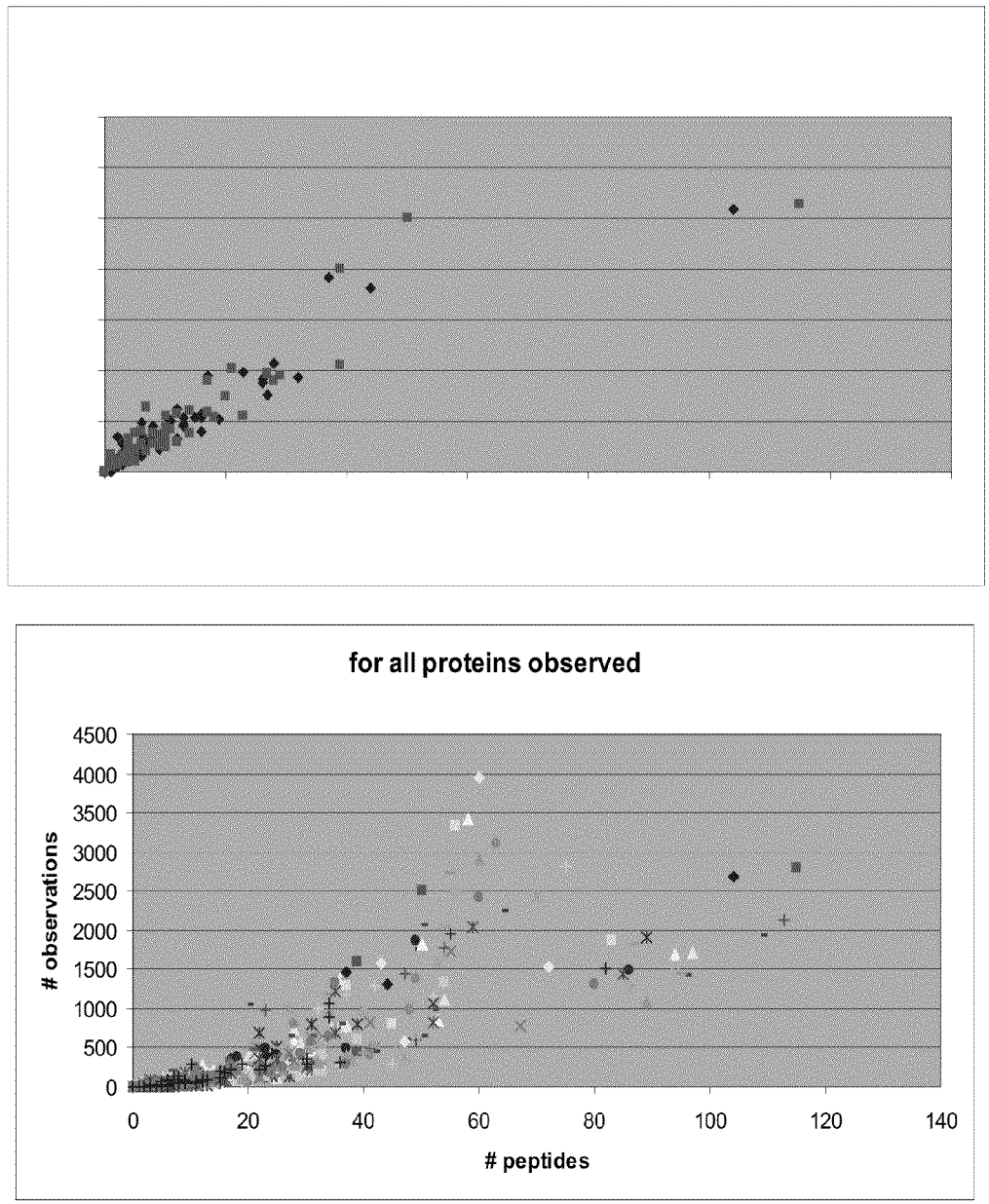
FIG. 4 shows the number of peptides observed vs. the number of spectra count for all individuals and all time points obtained by 1DLC (hydrophobicity, RPLC-MS run 1).

The present inventors have identified a number of protein markers for cardiac (myocardial) ischemia, including non-necrotic cardiac (myocardial) ischemia.

Three different types of protein analysis were performed to identify these markers, in order to cover as broad a base as possible of proteome coverage, e.g. to allow the enhanced detection of isoforms and of post-translational modifications (PTM). These types of analysis were two-dimensional electrophoresis (2DE, separating proteins based on pI and molecular weight), two-dimensional liquid chromatography (2DLC, separating proteins based on pI and hydrophobicity) and one-dimensional liquid chromatography (1DLC, separating proteins based on hydrophobicity). Note that the starting pH differs between 2DLC and 1DLC: pH 8.5 and 2.3, respectively. Two different cohorts were analyzed—increased metabolic demand (cohort 1) and reduced supply (cohort 2).

In a first study, ischemia was induced in a first cohort of subjects by metabolic demand: subjects were stimulated by atrial pacing, which makes the heart beat faster and induces ischemia, as indicated by an increase in lactate, and potentially myocardial necrosis (based on detection of cTnI or cTnT in blood). In some cases, individuals did not exhibit any increase in lactate or detectable cTnI/cTnT. These latter individuals were considered controls. Multiple serum samples were obtained for each individual. Differences between baseline (prior to pacing) and those at peaking pacing and up to 60 minutes after were analyzed. Those proteins that were elevated compared to the baseline in the majority of ischemic or necroiss individuals (and not elevated in controls) were considered to be of interest.

This procedure mimics naturally occurring metabolic cardiac events, such as ministrokes, that might precede a full MI. Ischemia is a heterogeneous group of conditions, resulting from different underlying mechanisms, such as demand and supply limitation. We have "mimicked" these two conditions in the different cohorts used in the analysis. Thus, these cohorts are expected to reflect markers that are overexpressed in subjects suffering from ischemia resulting from a variety of such underlying mechanisms. Samples from demand (atrial pacing) were evaluated by 2DE, 2DLC and 1DLC.

In a second study, ischemia was induced in a second cohort by coronary blockage: subjects undergoing valve replacement surgery exhibited ischemia because of blood loss during the procedure. This procedure mimics naturally occurring events in which ischemia is induced by coronary blood vessel blockage. This cohort was evaluated only by 1DLC, the procedure which provided a comparison to the most useful results with the first cohort. Those proteins found to be altered in both cohorts are considered to be "tier one" markers, although strong hits in either cohort may also be considered to be prime candidate markers.

The results of the studies with these two cohorts are summarized in Table 13. Taken together, these studies show that three proteins are implicated as the most highly correlated markers (sometimes referred to herein as "first tier" markers, as they are observed to be elevated in both cohorts) for ischemia, regardless of the cause of the ischemia: Lumican; Extracellular matrix protein 1 (ECM-1); and Carboxypeptidase N (e.g., the catalytic chain).

Three markers in addition to Lumican, ECM-1 and Carboxypeptidase N are implicated as first tier markers for at least subjects similar to those in the first cohort: Angiogenin; Semenogelin (e.g., isoforms 1 and 2); and Long palate, lung and nasal epithelium carcinoma-associated protein 1 (LPL-NECA-1) (e.g., isoform 1; isoforms 2-4 are also present, but the method of analysis employed in this study, although it supports isoform 1, cannot distinguish among the four isoforms, which are splice variants, so isoforms 2-4 cannot be ruled out due to sequence homology).

Ten markers in addition to Lumican, ECM-1 and Carboxypeptidase N are implicated as first tier markers for at least subjects similar to those in the second cohort: Perioxiredoxin isoform 2; S100 isoforms A7, A8 and A9 (other S100 isoforms were detected and not observed to be altered); Sortilin-related receptor; Catalase; Low density lipoprotein receptor related proteins 1 and 2; and Syntaxin 3.

In addition to these first tier markers, Table 13 lists some "second tier" markers which can also be used for identifying subjects similar to those in both cohorts I and II; in cohort I; or in cohort II. These include, e.g., Alpha-2-HS-glycoprotein; Galectin-7; Hornerin; Proteoglycan-4; Profilaggrin (also called Filaggrin); Vitamin D binding protein; C4b-binding protein alpha chain; Thyroxine binding globulin; Alpha-2-glycoprotein 1, zinc; protease, serine 3; Caspase 14; Desmogelin; Kininogen-1 (we observed the peptide for the intact protein, but our data cannot distinguish between changes to the LMW or HMW, which could also be present); Hepatocyte growth factor like protein; Hepatocyte growth factor activator; and Insulin like growth factor protein 6.

In some embodiments of the invention, it is desirable to distinguish between subjects whose ischemia is induced by metabolic causes (similar to the subjects of cohort I), and subjects whose ischemia is induced by coronary blood vessel blockage (similar to the subjects of cohort II), because different treatment methods can be used for the two classes of subjects. The markers of the invention can be used to make such distinctions.

This invention relates, e.g., to a method for determining if a subject has myocardial ischemia, comprising measuring in a sample from the subject the amount of at least one of the following proteins, compared to a baseline value:

a) Lumican and/or b) Extracellular matrix protein 1 and/or c) Carboxypeptidase N, wherein a significant amount (e.g., at least a statistically significant amount) of over-expression of the protein(s) compared to the baseline value is indicative of myocardial ischemia (e.g., indicates that the subject has, or is likely to have, myocardial ischemia). The amount of expression may be determined for any combination of 1, 2, or all 3, of these proteins, and the determinations can be conducted simultaneously, or in any order.

Another aspect of the invention is a method for identifying subjects that have myocardial ischemia that is induced by a metabolic-induced ischemic event [due to a metabolic limitation, in which the heart is unable to meet metabolic need; (excessive) metabolic demand], comprising determining in the sample from the subject the amount, compared to a baseline value, of at least one of proteins a), b), c) above, d) Angiogenin, e) Semenogelin, and/or f) Long palate, lung and nasal epithelium carcinoma-associated protein 1. The amount of expression may be determined for any combination of 1, 2, 3, 4, 5, or 6 of these proteins, and the determinations can be conducted simultaneously, or in any order.

Another aspect of the invention is a method for identifying subjects that have myocardial ischemia that is induced by coronary blood vessel blockage, which limits the supply of blood, comprising determining in the sample from the subject the amount, compared to a baseline value, of at least one of proteins a), b), c) above, g) Syntaxin,
h) Perioxiredoxin isoform 2,
i) S100 isoform A7,
j) S100 isoform A8,
k) S100 isoform A9,
l) Sortilin-related receptor
m) Catalase
n) Low density lipoprotein receptor related protein 1, and/or
o) Low density lipoprotein receptor related protein 2. The amount of expression may be determined for any combination of 1, 2, 3, 4, 5, 6, 7, 8, 9, 10, 11 or 12 of these proteins, and the determinations can be conducted simultaneously, or in any order.

In addition to the proteins noted above, one of more of the "second tier" proteins indicated in Table 13 can also be measured. A skilled worker will recognize which of these markers are indicative of a cohort I-type of condition, and which are indicative of a cohort II-type of condition.

Another aspect of the invention is a method for determining if a subject has myocardial ischemia, comprising determining in a sample from the subject the amount, compared to a baseline value, of at least one (e.g., at least four) of at least proteins a)-p) as noted above. The amount of expression may be determined for any combination of 1, 2, 3, 4, 5, 6, 7, 8, 9, 10, 11, 12, 13, 14, or 15 of these proteins; and the determinations can be conducted simultaneously, or in any order.

In a method of the invention, a determination that increasing numbers of protein markers of the invention are overexpressed in a subject can further indicate that the subject has (or is likely to have) myocardial ischemia.

A method as above may further comprise measuring in the sample the amount of one or more other markers that have been reported to be diagnostic of cardiac necrosis, including cardiac specific isoforms of troponin I (TnI) and/or troponin T (TnT) (although CK-MB, myoglobin, have been used in the past, cTnI and cTnT are the current gold standards), wherein a significant increase (e.g., at least a statistically significant increase) of the one or more markers further is further indicative that the subject has myocardial ischemia.

As noted above, ischemia is a heterogeneous condition caused by a variety of underlying mechanisms. Even if a single marker of the invention is capable of detecting a subject having ischemia resulting from a particular mechanism, it is possible for some markers that the marker is also upregulated in a disease other than myocardial ischemia. In such a case, it would be desirable to screen for upregulation of at least one additional marker that is associated with ischemia caused by a different underlying mechanism. The column labeled "Function" in Table 13 shows that some of the markers of the invention can be divided into particular groups on the basis of their functions. A skilled worker, studying this table, could readily identify markers associated with different mechanisms. In one embodiment of the invention, markers associated with 2, 3, 4 or more underlying mechanisms can be tested together in an assay of the invention.

Another aspect of the method is a method for deciding how to treat a subject suspected of having myocardial ischemia, or a subject that is at high risk for having myocardial ischemia, comprising determining by a method as above if the subject has (or is likely to have) myocardial ischemia and, (1) if the subject is determined to have (or to be likely to have) myocardial ischemia, deciding to treat the subject aggressively [such as with angioplasty (mechanical widening in opening blood vessels), treating with an anti-thrombolysis agent or, if possible, with percutaneous coronary intervention (PCI, or TPA), or undergoing coronary bypass surgery to replace the injuried/blocked coronary artery], or (2) if the subject is determined not to have (or not to be likely to have) myocardial ischemia, deciding to treat the subject non-aggressively [such as with asprin and/or thrombolysis (e.g., TPA), with periodic monitoring to ensure no future MI events, or by recommending changes in life style. This method can be used to confirm that a subject does not have ischemia (especially if myocardial ischemia is not detectable by cTnI or cTnT elevation), and thus to allow the subject to be released from hospital care.]

Another aspect of the invention is a method for treating a subject suspected of having myocardial ischemia, or a subject that is at high risk for having myocardial ischemia, comprising determining by a method as above if the subject has (or is likely to have) myocardial ischemia and, (1) if the subject is determined to have (or to be likely to have) myocardial ischemia, treating the subject aggressively, as indicated above, or (2) if the subject is determined not to have (or not to be likely to have) myocardial ischemia, treating the subject non-aggressively, as indicated above.

Another aspect of the invention is a kit for detecting the presence of ischemia in a subject, comprising reagents for detecting the amounts of at least one (e.g., any combination of 1, 2, 3, 4, 5, 6, 7, 8, 9, 10, 11, 12, 13, 14, or 15 of at least proteins a)-o) as noted above.

This invention relates, e.g., to a method for determining if a subject has myocardial ischemia, comprising
(a) providing a sample obtained from a subject suspected of having myocardial ischemia;
(b) determining in the sample the amount of at least one of at least proteins a)-p) as noted above (e.g., any combination of 1, 2, 3, 4, 5, 6, 7, 8, 9, 10, 11, 12, 13, 14, or 15) of the proteins); and
(c) comparing the amount(s) of the protein(s) to a baseline value that is indicative of the amount of the protein in a subject that does not have myocardial ischemia, wherein an increased amount (e.g., a statistically significantly increased amount) of the protein(s) compared to the baseline value is indicative of myocardial ischemia.

In one embodiment of the invention, the amount(s) of the protein(s) is compared over time to the baseline value and/or to levels known to be associated with necrosis. The kinetic rise and fall of combinations of proteins is indicative of impending myocardial ischemia (or other cardio and vascular events, such as stroke. A method of the invention can also be used to determine risk in subjects (patients) with stable or unstable angina.

A sample which is "provided" can be obtained by the person (or machine) conducting the assay, or it can have been obtained by another, and transferred to the person (or machine) carrying out the assay.

By a "sample" (e.g. a test sample) from a subject meant a sample that might be expected to contain elevated levels of the protein markers of the invention in a subject having myocardial ischemia. Many suitable sample types will be evident to a skilled worker. In one embodiment of the invention, the sample is a blood sample, such as whole blood, plasma, or serum (plasma from which clotting factors have been removed). For example, peripheral, arterial or venous plasma or serum can be used. In another embodiment, the sample is urine, sweat, or another body fluid into which proteins are sometimes removed from the blood stream. In the case of urine, for example, the protein is likely to be broken down, so diagnostic fragments of the proteins of the invention can be screened for. In another embodiment, the sample is cardiac tissue, which is harvested, e.g., after a heart transplant or the insertion of a pacemaker or defibrillator. Methods for obtaining samples and preparing them for analysis (e.g., for detection of the amount of protein) are conventional and well-known in the art. Some suitable methods are described in the Examples herein or in the references cited therein.

A "subject," as used herein, includes any animal that has, or is suspected of having, myocaridal ischemia. Suitable subjects (patients) include laboratory animals (such as mouse, rat, rabbit, guinea pig or pig), farm animals, sporting animals (e.g. dogs or horses) and domestic animals or pets (such as a horse, dog or cat). Non-human primates and human patients are included. For example, human subjects who present with chest pain or other symptoms of cardiac distress, including, e.g. shortness of breath, nausea, vomiting, sweating, weakness, fatigue, or palpitations, can be evaluated by a method of the invention. About ¼ of MI are silent and without chest pain. Furthermore, patients who have been evaluated in an emergency room or in an ambulance or physician's office and then dismissed as not being ill according to current tests for infarction have an increased risk of having a heart attack in the next 24-48 hours; such patients can be monitored by a method of the invention to determine if and when they begin express markers of the invention, which indicates that, e.g., they are beginning to exhibit ischemia. Subjects can also be monitored by a method of the invention to improve the accuracy of current provocative tests for ischemia, such as exercise stress testing. An individual can be monitored by a method of the invention during exercise stress tests of Dobutamine stress tests to determine if the individual is at risk for ischemia; such monitoring can supplement or replace the test that is currently carried out. Athletes (e.g., humans, racing dogs or race horses) can be monitored during training to ascertain if they are exerting themselves too vigorously and are in danger of undergoing an MI.

In another embodiment of the invention, the method is used as a screen in order to identify a drug (or to improve a cardioplegic solution) that protects the heart from ischemia and necrosis. The detection of one or more of the proteins of the invention in blood (or media if cell culture is used) is indicative of ischemia, and the quantity of the protein(s) is indicative of the severity of the ischemia.

The properties and amino acid sequences of the proteins of the invention are well-known and can be determined routinely, as well as downloaded from various known databases. See, e.g., the database, International Protein Index (IPI) at the world wide web site, ebi.ac.uk/IPI/xrefs.html. A summary of some properties of some of the proteins discussed herein, including their IPI ID number and amino acid sequences, is provided in Examples II and IV. This information is accurate as of the date of filing of this application. However, some of this information, including the sequences, is routinely updated (e.g. to correct mistakes in the previous entries), so updated (corrected) information about the proteins is included in this application. Information provided in the IPI database is incorporated by reference in the present application.

Although much of the data presented in the Examples herein are directed to particular forms of proteins of interest (or peptides thereof), it will be evident to a skilled worker that a variety of forms of these proteins may be indicative of the presence of myocardial ischemia in a subject. For example, the protein may be an intact, full-length protein. If a protein undergoes processing naturally (e.g., is converted from a pre-pro-hormone to a pro-hormone to a fully processed hormone; the N-terminal methionine is cleaved off; the signal sequence is removed, often accompanied by a post-translational modification, such as acetylation; etc.), any of these forms of the protein are included in the invention. Furthermore, in some instances, a protein of the invention may be broken down or degraded (e.g., proteins that are found in the urine). In such a case, an investigator can determine the level of one or more of the fragments or degradation products. A "diagnostic protein fragment," as used herein, is a fragment that is unique to the protein being identified, as detected by the assay. For example, a diagnostic fragment is recognized specifically by an antibody used to detect the full-length protein. Certain isoforms or post translational modifications (PTM) may also be encompassed by the invention. For example, the inventors have obtained data indicating PTM for C4b binding proteins; protease, serine; 3 alpha-2-glycoprotein 1; and zinc caspase 14.

The proteins and combinations of proteins discussed herein are sometimes referred to herein as "proteins (or protein markers) of the invention."

A variety of tests that have been used to detect myocardial events (particularly late occurring events, such as necrotic myocardial ischemia). These include, e.g., determining the levels of cardiac specific isoform(s) of troponin I (TnI) and/or troponin T (TnT), CK-MB (Creatine Kinase-MB), or myoglobin, although only the former two are the current gold standard. CK MB and myoglobin are not cardiac-specific. However, none of these markers is completely satisfactory for the detection of myocardial ischemia. For example, they fail to detect early stages of heart disease, such as non-necrotic myocardial ischemia. The new markers described herein can be used in conjunction with these types of assays.

When the values of more than one protein are being analyzed, a statistical method such as multi-variant analysis or principal component analysis (PCA) is used which takes into account the levels of the various proteins (e.g., using a linear regression score). For verification, we will use either immunoassay or multiple reaction monitoring (MRM, a MS-based targeted method that quantifies peptides that are unique to the protein of interest) on individuals (control, ischemia and MI).

In some embodiments, it is desirable to express the results of an assay in terms of an increase (e.g., a statistically significant increase) in a value (or combination of values) compared to a baseline value.

A "significant" increase in a value, as used herein, can refer to a difference which is reproducible or statistically significant, as determined using statistical methods that are appropriate and well-known in the art, generally with a probability value of less than five percent chance of the change being due to random variation. In general, a statistically significant value is at least two standard deviations from the value in a "normal" healthy control subject. Suitable statistical tests will be evident to a skilled worker. For example, a significant increase in the amount of a protein compared to a baseline value can be about 50%, 2-fold, or more higher. A significantly elevated amount of a protein of the invention compared to a suitable baseline value, then, is indicative that a test subject has myocardial ischemia (indicates that the subject is likely to have myocardial ischemia). A subject is "likely" to have myocardial ischemia if the subject has levels of the marker protein(s) significantly above those of a healthy control or his own baseline (taken at an earlier time point). The extent of the increased levels correlates to the % chance. For example, the subject can have greater than about a 50% chance, e.g., greater than about 70%, 80% 90%, 95% or higher chance, of having the ischemia. In general, the presence of an elevated amount of a marker of the invention is a strong indication that the subject has ischemia.

As used herein, a "baseline value" generally refers to the level (amount) of a protein in a comparable sample (e.g., from the same type of tissue as the tested tissue, such as blood or serum), from a "normal" healthy subject that does not exhibit myocardial ischemia. If desired, a pool or population of the same tissues from normal subjects can be used, and the baseline value can be an average or mean of the measurements. Suitable baseline values can be determined by those of skill in the art without undue experimentation. Suitable baseline values may be available in a database compiled from the values and/or may be determined based on published data or on retrospective studies of patients' tissues, and other information as would be apparent to a person of ordinary skill implementing a method of the invention. Suitable baseline values may be selected using statistical tools that provide an appropriate confidence interval so that measured levels that fall outside the standard value can be accepted as being aberrant from a diagnostic perspective, and predictive of ischemia.

It is generally not practical in a clinical or research setting to use patient samples as sources for baseline controls. Therefore, one can use any of variety of reference values in which the same or a similar level of expression is found as in a subject that does not have myocardial ischemia.

It will be appreciated by those of skill in the art that a baseline or normal level need not be established for each assay as the assay is performed but rather, baseline or normal levels can be established by referring to a form of stored information regarding a previously determined baseline levels for a given protein or panel of proteins, such as a baseline level established by any of the above-described methods. Such a form of stored information can include, for example, a reference chart, listing or electronic file of population or individual data regarding "normal levels" (negative control) or positive controls; a medical chart for the patient recording data from previous evaluations; a receiver-operator characteristic (ROC) curve; or any other source of data regarding baseline levels that is useful for the patient to be diagnosed. In one embodiment of the invention, the amount of the proteins in a combination of proteins, compared to a baseline value, is expressed as a linear regression score, as described, e.g., in Irwin, in Neter, Kutner, Nachtsteim, Wasserman (1996) Applied Linear Statistical Models, $4^{th}$ edition, page 295.

In an embodiment in which the progress of a treatment is being monitored, a baseline value can be based on earlier measurements taken from the same subject, before the treatment was administered.

The amount of a protein can be measured using any suitable method. Some methods involve the use of antibodies, binding ligands, or mass spectrometry tagged peptides specific for a protein of interest. Antibodies suitable for use in assays of the invention are commercially available, or can be prepared routinely. Methods for preparing and using antibodies in assays for proteins of interest are conventional, and are described, e.g., in Green et al., Production of Polyclonal Antisera, in *Immunochemical Protocols* (Manson, ed.), (Humana Press 1992); Coligan et al., in *Current Protocols in Immunology*, Sec. 2.4.1 (1992); Kohler & Milstein (1975), *Nature* 256, 495; Coligan et al., sections 2.5.1-2.6.7; and Harlow et al., Antibodies: A Laboratory Manual, page 726 (Cold Spring Harbor Laboratory Pub. 1988).

Any of a variety of antibodies can be used in methods of the invention. Such antibodies include, e.g., polyclonal, monoclonal (mAbs), recombinant, humanized or partially humanized, single chain, Fab, and fragments thereof. The antibodies can be of any isotype, e.g., IgM, various IgG isotypes such as $IgG_1$'$IgG_{2a}$, etc., and they can be from any animal species that produces antibodies, including goat, rabbit, mouse, chicken or the like. The term, an antibody "specific for" a protein, means that the antibody recognizes a defined sequence of amino acids, or epitope in the protein. An antibody that is "specific for" a polypeptide refers to an antibody that binds selectively to the polypeptide and not generally to other polypeptides unintended for binding to the antibody. The parameters required to achieve such specificity can be determined routinely, using conventional methods in the art. Conditions that are effective for binding a protein to an antibody which is specific for it are well-known and conventional.

In one embodiment of the invention, antibodies specific for a (one or more) protein of the invention are immobilized on a surface (e.g., are reactive elements on an array, such as a microarray, or are on another surface, such as used for surface plasmon resonance (SPR)-based technology, such as Biacore), and proteins in the sample are detected by virtue of their ability to bind specifically to the antibodies. Alternatively, proteins in the sample can be immobilized on a surface, and detected by virtue of their ability to bind specifically to the antibodies. Methods of preparing the surfaces and performing the analyses, including conditions effective for specific binding, are conventional and well-known in the art.

Among the many types of suitable immunoassays are immunohistochemical staining, ELISA, Western blot (immunoblot), immunoprecipitation, radioimmuno assay (RIA), fluorescence-activated cell sorting (FACS), etc. Assays used in a method of the invention can be based on colorimetric readouts, fluorescent readouts, mass spectrometry, visual inspection, etc. Assays can be carried out, e.g., with suspension beads, or with arrays, in which antibodies or cell or blood samples are attached to a surface such as a glass slide or a chip.

In one embodiment, a tissue sample (e.g. a cardiac tissue sample) is stained with a suitable antibody in a conventional immunohistochemical assay for those proteins which are present in the myocardium. Note that it can be difficult to obtain human tissue unless an individual is undergoing surgery or a routine biopsy (e.g. following heart transplantation), and such subjects are likely to be ischemic to some degree.

Mass spectrometry (MS) can also be used to determine the amount of a protein, using conventional methods. Some typical such methods are described in the Examples herein. Relative ratio between multiple samples can be determined using label free methods (as done in the present Examples), based on spectral count (and the number of unique peptides and the number of observation of each peptide). In the Examples herein, we used a LTQ-Orbitrap LC/MS/MS instrument to obtain the data. Alternatively, quantitative data can be obtained using multiple reaction monitoring (MRM), most often carried out using a triple quadripole mass spectrometer. In this case, peptides that are unique to a given protein are selected in the MS instrument and quantified. Absolute quantification can be obtained if a known labeled synthetic peptide is used. For detailed methods see, e.g., Qin Fu and J E Van Eyk, in Clinical Proteomics: from diagnostics to therapy (Van Eyk J E and Dunn M, eds), Wiley and Son Press; Current Protocols in Molecular Biology, Preparation of Proteins and Peptides for Mass Spectrometry Analysis in a Bottom-Up Proteomics Workflow, Gundry et al., chapter 10, 2009, in press)

In general, molecular biology methods referred to herein are well-known in the art and are described, e.g., in Sambrook et al., Molecular Cloning: A Laboratory Manual, current edition, Cold Spring Harbor Laboratory, Cold Spring Harbor, N.Y., and Ausubel et al., Current Protocols in Molecular Biology, John Wiley & sons, New York, N.Y.

A detection (diagnostic) method of the invention can be adapted for many uses. For example, it can be used to follow the progression of cardiac ischemia. In one embodiment of the invention, the detection is carried out both before (or at approximately the same time as), and after, the administration of a treatment, and the method is used to monitor the effectiveness of the treatment. A subject can be monitored in this way to determine the effectiveness for that subject of a particular drug regimen, or a drug or other treatment modality can be evaluated in a pre-clinical or clinical trial. If a treatment method is successful, the levels of the protein markers of the invention are expected to decrease.

A method of the invention can be used to suggest a suitable method of treatment for a subject. For example, if a subject is determined by a method of the invention to be likely to have myocardial ischemia, a decision can be made to treat the subject with an aggressive form of treatment; and, in one embodiment, the treatment is then administered. Suitable aggressive treatment modalities include, for example, angioplasty (mechanical widening to open blood vessels); treating with an anti-thrombolysis agent or, if possible, with percutaneous coronary intervention (PCI, or TPA); or undergoing coronary bypass surgery to replace the injuried/blocked coronary artery. Methods for carrying out such treatments are conventional and well-known. By contrast, if a subject is determined not to be likely to have myocardial ischemia, a decision can be made to adopt a less aggressive treatment regimen; and, in one embodiment, the subject is then treated with this less aggressive forms of treatment. Suitable less aggressive forms of treatment include, for example, treatment with asprin and/or agents that bring about thrombolysis (e.g., TPA); periodic monitoring to ensure no future MI events; or recommending changes in life style. A subject that does not have myocardial ischemia is thus spared the unpleasant side-effects associated with the unnecessary, more aggressive forms of treatment. By "treated" is meant that an effective amount of a drug or other anti-heart disease procedure is administered to the subject. An "effective" amount of an agent refers to an amount that elicits a detectable response (e.g. of a therapeutic response) in the subject.

One aspect of the invention is a kit for detecting whether a subject is likely to have myocardial ischemia, comprising one or more agents for detecting the amount of a protein of the invention. As used herein, the singular forms "a," "an" and "the" include plural referents unless the context clearly dictates otherwise. For example, "a" protein of the invention, as used above, includes 2, 3, 4, 5 or more of the proteins. In addition, other markers for ischemia (e.g., as discussed elsewhere herein) can also be present in a kit. If mass spectrometry is to be used to measure protein levels, the following reagents can be included in the kit: known amounts of a labeled (e.g. stable isotope) peptide (synthetic or recombinant) standard for each peptide to be assessed, separately or combined into a single mixture containing all peptides; optionally, a different peptide standard for assessing reproducibility of the assay; and/or, optionally, dilutent and trypsin for preparation of the sample. If an antibody-based method is to be used to measure protein levels, the agents in the kit can encompass antibodies specific for the proteins. The kit may also include additional agents suitable for detecting, measuring and/or quantitating the amount of protein, including conventional analytes for creation of standard curves. Among other uses, kits of the invention can be used in experimental applications. A skilled worker will recognize components of kits suitable for carrying out a method of the invention.

Optionally, a kit of the invention may comprise instructions for performing the method. Optional elements of a kit of the invention include suitable buffers, containers, or packaging materials. The reagents of the kit may be in containers in which the reagents are stable, e.g., in lyophilized form or stabilized liquids. The reagents may also be in single use form, e.g., for the performance of an assay for a single subject. In one embodiment of the invention, the kit is a "home chest pain test kit," that can be used to test blood, urine, or other body fluids for the presence (and/or level) of protein markers of the invention. Thus, a patient who has been released from an Emergency Department (ED) or a cardiac ward, but who is at risk over the next about 48 hours, can take the test over time at home and, if the test produces positive results, return to the ED.

In the foregoing and in the following examples, all temperatures are set forth in uncorrected degrees Celsius; and, unless otherwise indicated, all parts and percentages are by weight.

EXAMPLES

Example I

Identification of Novel Cardiac Biomarkers that are Rapidly Released into the Coronary Sinus in Response to Cardiac Ischemia, Even in the Absence of Detectable Myocyte Necrosis A. Overview of the Studies Rapid atrial pacing has been reported to produce reversible and controlled myocardial ischemia, as measured by a coronary sinus lactate concentration that rises above arterial lactate concentration, in approximately ⅔ of patients with fixed epicardial coronary artery disease (>70% diameter stenosis in at least one coronary artery). (Dehmer et al. (1983) *Am Heart J* 106, 114-24; Markham et al. (1983) *Am J Cardiol* 51, 1589-94). Therefore, in the experiments shown in this Example, atrial pacing was used as the human demand ischemia model.

In the studies shown in this Example, three types of protein analysis were conducted to identify protein markers of the invention. There is normally less than 40% overlap (e.g., 3-5) in the proteins observed between the different types of analysis platforms. This is because every protein is intrinsically different with respect to its pI, hydrophobicity and mass. Furthermore, post translational modifications (PTM) alter the intrinsic nature of the protein and thus may display quite different separation or enrichment characteristics. As such, the choice of technology or group of technologies should be dictated by the characteristics of the proteins targeted by the experimental question. In the case of biomarker discovery (and based on the lessons learnt from the biomarker, cTnI), multiple protein separation strategies should (and do) increase proteome coverage.

The present inventors and collaborators have found that the combination of intact protein separation technologies of 2DE (two-dimensional electrophoresis), 2DLC (two-dimensional liquid chromatography) and 1DLC (one-dimensional liquid chromatography) increases the proteome coverage while allowing enhanced detection of isoforms and PTM. 2DE of serum (and plasma) was optimized for separation by using pH 4-7 and 10% Bis-Tris gel (Graham et al. (20050) *Proteomics* 5 2309-14; Fu et al. (2005) *Proteomics* 5, 2656-64), as were the liquid chromatography methods. The combination of chemical depletion and optimized 2DE conditions can achieve good reproducibility (~20% CV) (Fu et al. (supra)). Liquid chromatography (LC) separates proteins based on one or more of their intrinsic properties: mass (size exclusion), isoelectric point (pI, chromatographic focusing or ion exchange), hydrophobicity (reversed phase) or affinity chromatography (bio-specificity). Our laboratory has optimized 2DLC combining chromatographic focusing and reversed phase HPLC with the commercial Beckman Coulter instrument, the Two-Dimensional Protein Fractionation (PF2D) system (McDonald et al. (2006) *Mol Cell Proteomics* 5, 2392-411; Sheng et al. (2006) *Mol Cell Proteomics* 5, 26-34; Stasna et al. Protein separation: Liquid chromatography, In "Proteomic and Genomic Analysis of Cardiovascular Disease" (eds. Van Eyk J E and Dunn M) 2008 Wiley and Son Press, page 241). Briefly, samples are loaded onto the first dimension column (ion exchange column) at pH 8.5 in presence of urea and detergent and separated based on pI by decreasing the pH to 4.0 (Graham et al. (2006) (supra). Proteins that are bound tightly to the column or have a pI below 4.0 are eluted using 1M salt. We found that including 20% isopropanol in the buffers can eliminate "artificial" binding of a subset of proteins to the first dimension. Fractions are collected throughout the chromatographic separation and each fraction is subsequently separated by reversed phase chromatography using a linear gradient composed of aqueous trifloroacetic acid (TFA), pH 2.3 and TFA/acetronitrile, pH 2.3. The second dimension elution profile is monitored at 214 nm (peptide bonds) and is semi-quantitative. On average, fractions contain 1-100 proteins in each peak (McDonald et al. (2006); Graham et al. (2006) (both supra)). These samples can be further analyzed by electrophoresis (ME or 2DE) or analyzed directly by mass spectrometry (MS). If so, due to the complexity of the reversed phase fractions they must undergo further online LC separation prior to MS. An overview outlining the process is summarized in Fu et al. (2008) (supra).

B. Cohort Information for Atria Pacing Human Model—Cohort I

1. Research Design

Patients >20 years old with stable exertional angina referred for cardiac catheterization were recruited Exclusion criteria were atrial fibrillation, valvular heart disease, prior coronary artery bypass surgery, depressed left ventricular systolic function, acute coronary syndrome, and/or left bundle branch block. As well, patients were excluded if they reported angina within 48 hours of the catheterization. 19 individuals were recruited. The study was approved by the Institutional Review Boards of UT Southwestern and Parkland Hospital. All patients have signed written informed consent.

A 7 or 8 Fr Gorlin catheter was advanced to the coronary sinus from the right brachial vein. Coronary sinus, peripheral arterial, and peripheral venous serum samples were obtained prior to start of the atrial pacing. The left atrium was paced at 20 beats/minute above the resting heart rate and this was increased every 3 minutes by 20 beats/minute until one of the following occurs: chest pain, AV block, or a heart rate of 160 beats/minutes is achieved. The patient was maximally paced at this rate for 3 minutes. At the end of the three-minute period, repeat blood samples were collected from the coronary sinus and peripheral artery. Repeat sampling from the coronary sinus was performed at 30 and 60 minutes after pacing termination.

TABLE 1

Timing line for serum sample collection

| Location | Baseline | Immediate post-pacing | 30 minutes post-pacing | 60 minutes post-pacing |
|---|---|---|---|---|
| Coronary Sinus | X | X | X | X |

Blood was immediately placed on ice and was transported to the processing center within 30 minutes of collection. Samples were centrifuged, serum (and plasma) separated, and specimens aliquoted into 100 µL tubes using an automated micropipette system. No samples were at room temperature for longer than 10 minutes. The longest duration between sample collection and freezing was less than one hour. Lactate and cardiac troponin T (TnT) was measured in heparinized plasma a (see table 2)

2. Cohort and Experimental Group Designation

The cohort was designated based on the following criteria:
1) Cases (n=19) Significant coronary artery disease (at least one vessel with a diameter stenosis ≥70%) and coronary sinus lactate>arterial lactate after pacing (data not shown).
2) Controls are individuals with no or little change in lactate pre vs. post.
3) Moderate or severe ischemia: individuals with increase in lactate and are cTnT negative.
4) Necrosis designation was for individuals with increase in lactate and are cTnT positive.
5)

TABLE 2 coronary sinus values

| PATIENT | age | csLpre | csLpost | TnT-cs0 | TnT-cs1 | TnT-cs2 | TnT-cs3 | Definition |
|---|---|---|---|---|---|---|---|---|
| 1 | 50 | 0.4 | 0.7 | <0.01 | <0.01 | <0.01 | <0.01 | mI |
| 2 | 40 | 0.8 | 0.6 | <0.01 | <0.01 | <0.01 | <0.01 | C |
| 3 | 60 | 0.7 | 0.7 | <0.01 | <0.01 | <0.01 | <0.01 | C |
| 4 | 56 | 0.8 | 1 | <0.01 | <0.01 | <0.01 | <0.01 | mI |
| 5 | 63 | 0.8 | 0.9 | <0.01 | <0.01 | <0.01 | <0.01 | C |
| 6 | 51 | 0.7 | 0.7 | <0.01 | <0.01 | 0.016 | 0.029 | N |
| 7 | 51 | 0.4 | 1.2 | <0.01 | <0.01 | <0.01 | <0.01 | sI |
| 8 | 52 | 0.3 | 0.4 | <0.01 | <0.01 | <0.01 | <0.01 | C |
| 9 | 45 | 0.6 | 0.6 | <0.01 | <0.01 | NA | NA | C |
| 10 | 56 | 0.7 | 1.3 | <0.01 | <0.01 | <0.01 | <0.01 | sI |
| 11 | 50 | 0.5 | 0.9 | <0.01 | <0.01 | <0.01 | <0.01 | sI |
| 12 | 47 | 0.3 | 0.5 | <0.01 | <0.01 | <0.01 | <0.01 | mI |
| 13 | 57 | 1.1 | 0.9 | <0.01 | <0.01 | NA | NA | excluded |
| 14 | 62 | 0.9 | 1 | <0.01 | <0.01 | <0.01 | <0.01 | excluded |
| 15 | 43 | 0.3 | 0.8 | <0.01 | <0.01 | 0.026 | 0.109 | N |
| 16 | 52 | 1.22 | 1.48 | <0.01 | <0.01 | <0.01 | 0.041 | N |
| 17 | 47 | COAG | 0.28 | <0.01 | <0.01 | <0.01 | <0.01 | excluded |
| 18 | 47 | 0.23 | 0.46 | <0.01 | <0.01 | <0.01 | <0.01 | mI |
| 19 | 53 | 0.17 | 0.16 |  |  |  |  | C |

Pre and post define samples taken at baseline and after maximum pacing

Definition defines, control (c) as no change in lactate and TnT negative, ischemia (I) as increase in lactate and TnT negative and differentiated in to moderate (mI) or severe (sI); necrosis (n) TnT positive and excluded for LC analysis (but included for 2DE).

C. 2-dimensional Gel Electrophoresis Analysis 1. 2DE Cohort

All patients and all time points were analyzed.

2. 2DE Methods

Serum was depleted of IgG using protein G affinity chromatography and depleted of albumin using our in-house affinity/chemical depletion method (Fu et al. (2005) (supra). Protein concentration was determined using BCA assay (Pierce) for each depleted sample. 50 ug of each time point (baseline time point 1, 2 and 3) per individual was labeled with one of the three Cy dyes (Applied Biosystems Inc.). As well, a pool sample was created from equal amounts of each time point of a single patient sample. For each individual, equal amount of two labeled sample (two time points) were mixed with the pool sample and then separated simultaneously using optimized pH 4-7 gel, followed by 10% Bis-Tris SDS PAGE. The gels were then imaged on a fluorescent gel imager at the Cy3, Cy5 and Cy2 wavelengths. Subsequently, the gels were stained with silver to allow visualization for spot picking. Gel images were analyzed by Ludesi Inc (.http://www.ludesi.com/). Gels were aligned, spots matched and quantified. For example, gel images were prepared for an individual that became ischemic or underwent necrosis with pacing. Comparisons were made between baseline and the other subsequent time points for each individual. To avoid a nondetected (zero) value 0.1 was added to all values.

3. Selection Criteria.

Selection criteria for 2DE was based on analysis of all individual in each group (induced ischemia and induced necrosis) and are as follows:
 i) Equal or greater than 1.5 fold increase compared to time point 0 (baseline).
 ii) The spot volume was above (100 units) to allow protein identification by mass spectrometry.
 iii) The spot was resolved.
 iv) The change in the profile remains above baseline once elevated.
 v) A changed in 3 out of the 3 or 2 out of the 3 individuals in a designated group (induced ischemia or induced necrosis) at any time point.

4. Results for 2DE

Approximately 1200 protein spots were resolved on each 2DE gel. Due to stringent criteria for cut offs, most protein spots were deemed not to change or biological variability was too great to be significant (FIG. 1, see breakdown). Caspase 14 and complement factor B (isoform 1) increased specifically in patients with necrosis while fibrinogen beta chain and desmoglein-1 increased in patients with severe ischemia and necrosis (table 3).

TABLE 3 summary of changes detected by 2DE

| Protein name | observed at baseline | control | large ischemia | moderate ischemia | necrosis |
|---|---|---|---|---|---|
| Caspase-14 | yes | 1 out of 5 | 1 out of 3 | 0 out of 4 | 2 out of 3 |
| Isoform 1 of Complement factor B | yes | 1 out of 5 | 1 out of 3 | 0 out of 4 | 2 out of 3 |
| Fibrinogen beta chain | yes | 2 out of 5 | 1 out of 3 | 2 out of 4 | 2 out of 3 |
| Desmoglein-1 | yes | 2 out of 5 | 1 out of 3 | 2 out of 4 | 2 out of 3 |

The majority of proteins observed by 2DE, high abundant soluble proteins, do not change with induced ischemia or necrosis. Without wishing to be bound by any particular mechanism, Caspase 14 (IPI00013885) is proposed to be involved in the death receptor and granzyme B apoptotic pathways. It may act as a downstream signal transducer of cell death. Desmoglein-1 (IPI00025753) is a component of the cell desmosome junctions which are distinct plasma membrane domains. It has a single transmembrane domain. Desmosomes are the most common type of intercellular junction in vertebrate epithelial cells but found in other cell types. This protein is part of a complex comprising plakophilin 1, plakophilin 2, desmoplakin, desmoglein 1, desmoglein 4, plako- globin and corneodesmosin. Other proteins of the desmosome complex as well as caspase 14 are found by 1DLC and 2DLC in a few individuals.

Information sheets summarizing some of the properties of these and other proteins discussed herein are provided as Example II.

D. 1DLC Work Flow 1. 1DLC Cohort

Each individual time sample outlined below (table 4) was analyzed using reversed phase HPLC. The control group samples were selected based on having similar prelacate concentrations compared to the two disease groups.

TABLE 4

| 1DLC | | |
|---|---|---|
| Group designation | Patient numbers | Time points |
| control | 3, 5 | 0 and 1 |
| ischemia | 7, 10, 11 | 0, 1, 2, 3 |
| necrosis | 6, 15, 16 | 0, 1, 3 |

2. 1DLC Method

Figure 5:
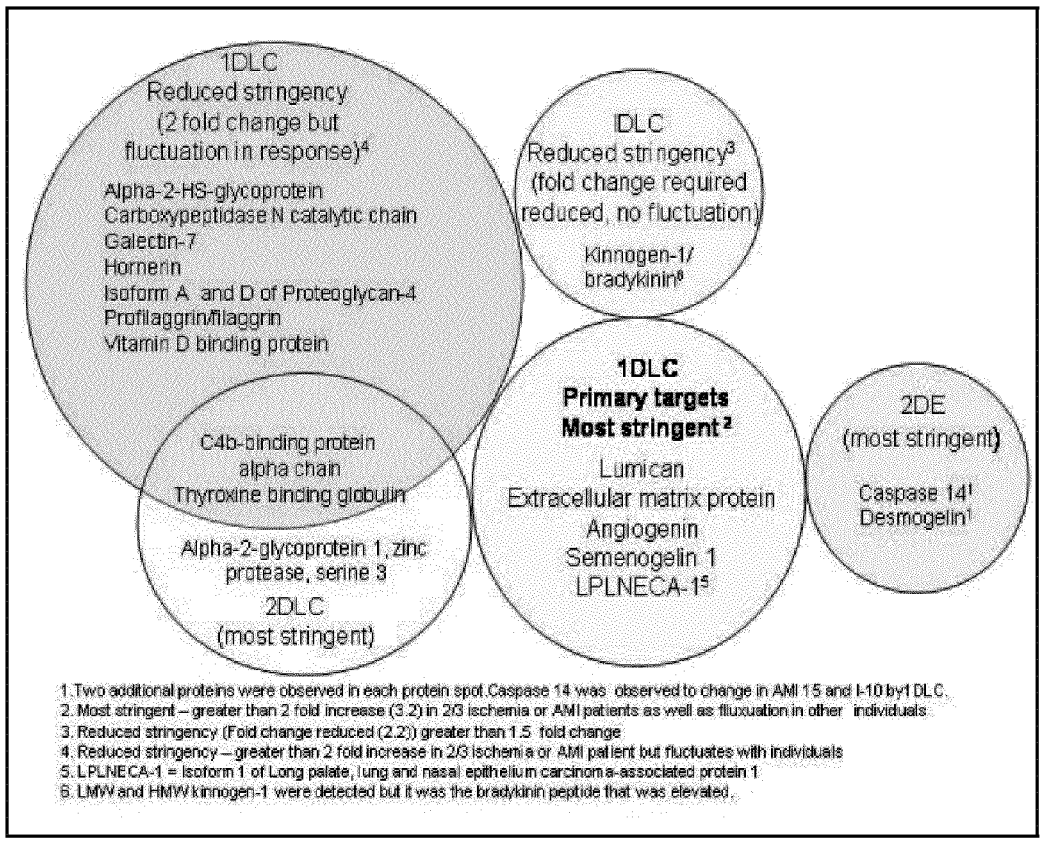
FIG. 5 schematically illustrates the overlap between the three different proteomic methods used: 2DE, 1DLC and 2DLC. For 2DLC, the serum samples were depleted of immunoglobins (IgG, IgM and IgA) and albumin, then separated based on chromatographic focusing (pH from 8.5 to 4.0) and reversed phase HPLC (1DLC). Fractions from areas found to be different in the 2DLC were analyzed by MS. Differences in spectral counting and or number of peptides observed were included as changed. Superscripts 1-6 refer to the following.

Serum was depleted using an affinity chromatography comprised of IgY antibodies specific for all forms of immunoglobins (IgG, IgA and IgM) and then depleted of albumin using our in-house affinity/chemical depletion method. This was done in order to reduce background of the chromatogram. Protein concentration was determined using BCA assay (Pierce) for each depleted sample. Samples were analyzed on the same 1DLC columns. 50 ug of each sample was run (in duplicate) using our optimized gradient. One set was used for mass spectrometric analysis; the other set was stored at −80° C. Fractions were collected into 96-well plates, stored at −80° C. until analyzed. Protein standard was run every morning to ensure good, consistent and reproducible performance of HPLC system. Extensive washing was carried out between runs to eliminate possible cross-over contamination. Chromatographic images were compared and regions/domains with acceptable intensities from each experimental sample were selected or combined (FIG. 5). Total 650 fractions (26 fractions per sample) were dried down, neutralized, and digested with trypsin. 50% of the digested sample was applied to the LC LTQ-Orbitrap MS.

For LC-MS/MS experiments on the LTQ-Orbitrap (ThermoFinnigan, San Jose, Calif.), peptides were dissolved in 6 µl resuspension buffer (4% acetonitrile in water with 0.1% formic acid). Samples (3 µl) were loaded onto a 75 um×10 cm BioBasic C18 column (New Objective, Woburn, Mass.). Peptides were eluted into an LTQ-Orbitrap (ThermoFinnigan, San Jose, Calif.) using an Agilent 1200 nano-LC system (Agilent, Santa Clara, Calif.). The HPLC gradient was 5% to 60% B (90% acetonitrile/water in 0.1% Formic acid) over 30 or 60 min depended on sample complexity. The mass spectrometer was operated in data-dependent mode in which every FT-MS scan (survey 350-2000 Da) was followed by MS/MS scans of the 5 most abundant ions.

All mass spectrometry data was analyzed according to a pipeline established and already used in our laboratory, designed to meet stringent criteria from the proteomics community. Data from the LTQ-Orbitrap was searched against the IPI databases where possible, using Sorcerer Sequest (Sagen, San Jose, Calif.). Search results were validated and analyzed using Scaffold (Proteome Systems, Portland, Oreg.). Protein identifications based upon a single peptide observation were handled carefully through manual inspection of the tandem MS (MS/MS) spectra, BLAST searching of the sequence to ensure it matches only the reported protein, requiring a minimum of 8 amino acids and a peptide probability score of >0.9.

Data analysis was based on the following: peptide redundancy removed, protein name redundancy removed, the number of unique peptides and number of observation for each peptide regardless of charge state (2+. 3+ or 4+) were determined for each protein. The protein was proposed to have a potential PTM if it was identified in multiple non-sequential domain/fractions. This was noted and all data regardless of the fraction was included for quantitation of the protein.

Data reanalysis was carried out using a version of the published algorithm for spectral counting (Old et al. (2005) *Molecular and Cellular Proteomics* 4.10, 1487-502) that added a 1.25 correction factor value to all numbers, in order to eliminate any zero values (non detectable values). The algorithm $R_p = \text{Log}_{10}$ (Px+1.25)/(P0+1.25)+$\text{Log}_{10}$ (TP0−P0+1.25)/(TPx−Px +1.25)) and $R_{sc} = \text{Log}_{10}$) (SCx+1.25)/(SC0+SCx+1.25)+$\text{Log}_{10}$) (TSC0−SC0+1.25)/(TSCx −SCx+1.25), where $R_p$ is the $\text{Log}_{10}$ ratio of number of unique peptides between time points 0 and x, $R_{sc}$ is the $\text{Log}_{10}$ ratio of spectral counts between time points 0 and x, P0 or Px is the number of unique peptides or at baseline (0) or another time point (x) for the specific protein of interest. TP0 or TPx is the number of all unique peptides for the complete data set for that individual at that specific time point (0 or x). SC0 and SCx are the spectral counts at time points 0 and x for the protein. TSC0 and TSCx are the total number of spectral counts in the experiment at time points 0 and x. There is a linear correlation between number of peptides observed and the spectra count (under 70 peptides/protein). However, for very abundant protein with 100's of peptides and observations the relationship is more non-linear. A cut off of 0.3 (2 fold) was used to indicate a change.

3. Duplicate MS Analysis

Two independent MS analyses were done on each LC fraction. In both cases, LC fractions were stored (−80° C.) following an independent LC separation of the intact proteins. Image analysis was carried out between the various LC runs to match the fractions as closely as possible. However, the fractions analyzed were not completely identical due to variation in the LC run and exact timing of the fraction collection. The stored fractions were dried down, neutralized and digested with trypsin. The digested sample was applied to the LC LTQ-Orbitrap MS and number of peptides and spectra count were determined (table 5). The total number of peptide and counts for each time points is shown in table 6. This is taken into account when calculating change.

TABLE 5

MS replicate on frozen intact protein sample
cohort I, two protein LC runs, separated digestion and MS run sample: AMI-15-003 (F = fraction number)

| | # peptides F1 + 2 + 3 + 4-duplicate | # peptides F1 + 2 + 3 + 4-original | # peptides F15 + 16-duplicate | # peptides F15 + 16-original | # peptides F25-original | # peptides F25-duplicate |
|---|---|---|---|---|---|---|
| alpha-1 antiproteinase | 1 | 2 | 20 | 25 | 16 | 16 |
| alpha1-antichymotrypsin | 0 | 0 | 1 | 8 | 7 | 6 |
| alpha-1-microglobulin/bikunin | 0 | 0 | 2 | 0 | 0 | 0 |
| Alpha-2-macroglobulin | 0 | 0 | 7 | 2 | 32 | 31 |
| alpha-2-plasmin inhibitor | 0 | 0 | 0 | 0 | 0 | 2 |
| Angiotensinogen | 0 | 0 | 0 | 0 | 2 | 13 |
| Apolipoprotein A-I | 2 | 0 | 9 | 7 | 13 | 15 |
| apolipoprotein A-IV | 0 | 0 | 5 | 4 | 2 | 10 |
| Apolipoprotein C-I | 0 | 0 | 2 | 3 | 0 | 0 |
| apolipoprotein E | 0 | 0 | 0 | 0 | 2 | 8 |
| Beta2- Glycoprotein | 0 | 2 | 0 | 0 | 0 | 0 |
| B-factor, properdin | 0 | 0 | 15 | 19 | 2 | 8 |
| C9 complement protein | 0 | 0 | 8 | 2 | 0 | 1 |
| carboxypeptidase N | 0 | 0 | 6 | 0 | 0 | 0 |
| caspase 14 | 2 | 0 | 0 | 0 | 0 | 0 |
| cathelicidin antimicrobial peptide | 0 | 0 | 2 | 0 | 0 | 0 |
| coagulation factor II (thrombin) | 0 | 0 | 4 | 3 | 0 | 0 |
| coagulation factor XIII B subunit | 2 | 3 | 0 | 0 | 0 | 0 |
| complement component 1, s | 0 | 0 | 0 | 2 | 0 | 0 |
| complement component 2 | 0 | 0 | 0 | 0 | 3 | 2 |
| complement component 3 | 2 | 2 | 33 | 14 | 71 | 81 |
| complement component 4 binding protein, alpha chain | 0 | 0 | 3 | 0 | 0 | 0 |
| complement component 5 | 0 | 0 | 0 | 0 | 0 | 5 |
| complement component 7 | 0 | 0 | 3 | 5 | 0 | 0 |
| complement component 8, alpha | 0 | 0 | 3 | 3 | 0 | 0 |
| complement component 8, gamma | 0 | 0 | 3 | 6 | 0 | 0 |
| complement component C4A | 0 | 0 | 32 | 19 | 16 | 29 |
| complement component C6 | 0 | 0 | 3 | 2 | 0 | 0 |
| complement component C8 beta chain | 0 | 0 | 1 | 9 | 0 | 0 |
| complement factor H | 17 | 20 | 9 | 7 | 1 | 3 |
| complement factor I | 0 | 0 | 4 | 0 | 0 | 0 |
| dermcidin | 2 | 2 | 0 | 0 | 0 | 0 |
| filaggrin 2 | 1 | 0 | 0 | 0 | 0 | 0 |
| gelsolin | 0 | 0 | 13 | 3 | 0 | 5 |
| hemopexin | 0 | 0 | 5 | 2 | 0 | 0 |
| histidine-rich glycoprotein | 0 | 0 | 3 | 0 | 0 | 0 |
| hornerin | 2 | 0 | 0 | 0 | 0 | 0 |

TABLE 5-continued

MS replicate on frozen intact protein sample
cohort I, two protein LC runs, separated digestion and MS run sample: AMI-15-003 (F = fraction number)

| Protein name | # peptides F1 + 2 + 3 + 4-duplicate | # peptides F1 + 2 + 3 + 4-original | # peptides F15 + 16-duplicate | # peptides F15 + 16-original | # peptides F25-original | # peptides F25-duplicate |
|---|---|---|---|---|---|---|
| hyaluronan binding protein 2 | 0 | 0 | 0 | 3 | 0 | 0 |
| Insulin-like growth factor-binding protein 3 | 4 | 4 | 0 | 0 | 0 | 0 |
| Inter-alpha-trypsin inhibitor heavy chain H1 | 0 | 0 | 9 | 6 | 6 | 9 |
| Inter-alpha-trypsin inhibitor heavy chain H2 | 0 | 0 | 8 | 3 | 6 | 15 |
| Inter-alpha-trypsin inhibitor heavy chain H3 | 0 | 0 | 6 | 0 | 0 | 0 |
| Inter-alpha-trypsin inhibitor heavy chain H4 | 0 | 0 | 10 | 2 | 0 | 4 |
| kallikrein B, plasma (Fletcher factor) 1 | 0 | 0 | 0 | 4 | 0 | 0 |
| kininogen-1 | 0 | 0 | 1 | 2 | 0 | 0 |
| leucine-rich alpha-2-glycoprotein 1 | 0 | 0 | 5 | 0 | 0 | 0 |
| lumican | 0 | 0 | 4 | 5 | 0 | 0 |
| pigment epithelium-derived factor precursor (PEDF) | 0 | 0 | 0 | 0 | 10 | 0 |
| plasma protease (C1) inhibitor | 0 | 0 | 0 | 0 | 0 | 3 |
| amyloid P | 0 | 0 | 6 | 2 | 0 | 0 |
| profilaggrin | 0 | 1 | 0 | 0 | 0 | 0 |
| S100 calcium-binding protein A7 | 3 | 4 | 0 | 0 | 0 | 0 |
| S100 calcium-binding protein A8 | 1 | 2 | 0 | 0 | 0 | 1 |
| S100 calcium-binding protein A9 | 1 | 2 | 0 | 0 | 0 | 1 |
| transferrin | 0 | 0 | 13 | 18 | 7 | 10 |
| transthyretin | 0 | 0 | 6 | 6 | 0 | 0 |
| vitronectin | 0 | 0 | 2 | 2 | 0 | 0 |

TABLE 6 total number of peptide and spectra count in MS run 1 and 2

| sample | peptides time point 0 | run 1 counts TP 0 | run 1 peptides TP 1 | run 1 counts TP 1 | run 1 peptides TP 2 | run 1 counts TP 2 | run 2 peptides TP 0 | run 2 counts TP 0 | run 2 peptides TP 1 |
|---|---|---|---|---|---|---|---|---|---|
| A-15 | 976 | 10694 | 820 | 10527 | 767 | 9761 | 530 | 3005 | 770 |
| A-16 | 715 | 9250 | 737 | 8615 | 682 | 7908 | 728 | 4724 | 709 |

| | time point 0 | run 1 TP 0 | run 1 TP 1 | run 1 TP 1 | run 1 TP 2 | run 1 TP 2 | run 1 TP 3 | run 1 TP 3 | run 2 TP 0 |
|---|---|---|---|---|---|---|---|---|---|---|
| 1-7 | 794 | 10673 | 788 | 10661 | 806 | 10806 | 828 | 10529 | 652 |
| 1-10 | 763 | 12629 | 810 | 11952 | 873 | 12868 | 894 | 12353 | 693 |
| 1-11 | 997 | 10783 | 830 | 11027 | 645 | 15836 | 830 | 10666 | 661 |

| sample | run 2 counts TP 1 | run 2 peptides TP 2 | run 2 counts TP 2 |
|---|---|---|---|
| A-15 | 4702 | 802 | 4621 |
| A-16 | 4962 | 695 | 4683 |

| | run 2 TP 0 | run 2 TP 1 | run 2 TP 1 | run 2 TP 2 | run 2 TP 2 | run 2 TP 3 | run 2 TP 3 |
|---|---|---|---|---|---|---|---|
| 1-7 | 3880 | 654 | 3338 | 621 | 4338 | 715 | 3370 |
| 1-10 | 3398 | 589 | 3486 | 489 | 2904 | 746 | 3493 |
| 1-11 | 4501 | 604 | 4012 | 603 | 3865 | 595 | 3791 |

4. Criteria Selection for 1DLC

Selection criteria for 1DLC was based on analysis of all individuals in each group (induced necrosis or induced ischemia) and are as follows:

i) Changes in the number of unique peptides or the number of time each peptide was observed regardless of charge state (2+. 3+ or 4+) were compared to the equivalent protein (if observed) at time point 0. Changes are based on $R_p$ or $R_{sc}$ values of 0.30 or greater. The fold changes associated with these R values depend on the number of observations and range from 1:4 ratio (R=0.36 before total observation correction, 4 fold change) to a 300:600 (R=0.3001 before total observation correction, 2 fold change). The total observation correction will shift the R value depending on the different in size of the 2 sample groups and the proportion of observations for a the protein of interest relative to the entire sample. A 10% difference in sample size between the compared samples could increase or decrease the R value by 0.045ii)

ii) Changes in 2 out of the 3 or 3 out of the 3 individuals in a designated group (induced ischemia or induced necrosis) at any time point.

5. Results

Although the number of unique peptides observed between MS run 1 and 2 were similar, the number of peptide observations was reduced in the second run (Table 6). This did not overly affect the number of proteins observed except for the lower abundant proteins. There were 25 different serum samples analyzed, giving raise to 650 fractions being analyzed per MS analysis (1300 total MS runs). This resulted in, for both MS runs, over 41,000 unique peptides being identified, with these peptides observed over 410,600 times. Table 7 outlines the proteins that met the criteria above and whether they were observed to change by 2DLC.

An additional level of stringency was added in which the variation within an individual was taken into account. The first tier proteins are found consistently to remain elevated. These are highlighted in bold type. Those proteins with variation between patients or time points were ranked as second tier. Bradykinin peptide was also included (rather than kininogen, the parent protein which had a weaker correlation) based on reducing the fold change required to 1.5 fold. It was the only additional protein that met this weaker criterion. For details regarding the proteins see Example II.

TABLE 7 summary of protein changes observed by 1DLC

| protein name | accession | up in ischemia 2 or 3 of 3 | up in necrosis 2 or 3 of 3 | Protein change detected by 2DLC |
|---|---|---|---|---|
| Alpha-2-HS-glycoprotein precursor | IPI00022431 | yes | | |
| Angiogenin | IPI00008554 | yes | | |
| Carboxypeptidase N catalytic chain | IPI00010295 | yes | | |
| Extracellular matrix protein 1 | IPI00645849 | yes | | |
| Galectin-7 | IPI00219221 | yes | | |
| Hornerin | IPI00398625 | yes | | |
| Isoform 1 of Long palate, lung and nasal epithelium carcinoma-associated protein 1 | IPI00291410 | yes | | |
| Isoform 2 of Semenogelin-1 | IPI00414684 | yes | | |
| Lumican | IPI00020986 | | yes | |
| Profilaggrin | IPI00654788 | yes | | |
| Thyroxine-binding globulin | IPI00292946 | yes | | yes |
| Vitamin D-binding protein | IPI00555812 | yes | | |
| Isoform LMW of Kininogen-1 (specifically bradykinin) | IPI00215894 | | yes | |
| C4b-binding protein alpha chain | IPI00021727 | yes | | yes |
| Proteoglycan-4 (isoforms A and D) | IPI00655676/ | yes | | |

E. 2-dimensional Liquid Chromatography 1. 2DLC Cohort

Since 2DLC requires 2 mg of protein or greater for each analysis and the quantity of sample for the atria pacing cohort was limited so pooling was required for each group as outlined in table 8.

TABLE 8

2DLC pool

| Group designation | Patient numbers pooled | Time points analyzed |
|---|---|---|
| control | 3, 19, 9 | 0 (2 mg protein) |
| | 3, 19 | 3 (2 mg protein) |
| ischemia | 7, 10, 11 | 0 (2 mg protein) |
| | 7, 10, 11 | 1 (2 mg protein) |
| | 7, 10, 11 | 2 and 3 (equal amounts) (2 mg protein) |

TABLE 8-continued

2DLC pool

| Group designation | Patient numbers pooled | Time points analyzed |
|---|---|---|
| necrosis | 15, 16 | 0 and 1 (equal amounts) (1.9 mg protein) |
| | 15, 16 | 2 and 3 (equal amounts) (1.9 mg protein) |

2. 2DLC Method

Serum was depleted using an affinity chromatography comprised of IgY antibodies specific for 3 major forms of immunoglobins (IgG, IgA and IgM) and then depleted of albumin using our in-house affinity/chemical depletion method. This was done in order to reduce background of the chromatogram. Protein concentration was determined using BCA assay (Pierce). Samples were analyzed on the same set of first and second dimension columns. 2 mg of sample from each time point were sequentially injected on the HPCF first dimension column, followed by HPRF second dimension separation. Fractions were collected into 96-well plates and stored at −80 C until analyzed. Extensive washing was carried out between runs to eliminate possible cross-over contamination.

Chromatographic images were compared and the same regions/domains from multiple-pH fractions were combined based on profile and previous identification. Fractions from high salt wash were analyzed individually without pooling. Total 315 fractions from 7 time points were dried down, neutralized, and digested with trypsin. 50% of the digested sample was applied to the LC LTQ-Orbitrap MS.

For LC-MS/MS experiments on the LTQ-Orbitrap (ThermoFinnigan, San Jose, Calif.), peptides from the digestion of LC fraction were resuspended in 6 μA resuspension buffer (4% acetonitrile in water with 0.1% formic acid). Samples (3 μl) were loaded onto a 75 um×10 cm BioBasic C18 column (New Objective, Woburn, Mass.). Peptides were eluted into an LTQ-Orbitrap (ThermoFinnigan, San Jose, Calif.) using an Agilent 1200 nano-LC system (Agilent, Santa Clara, Calif.). The HPLC gradient was 5% to 60% B (90% acetonitrile/water in 0.1% Formic acid) over 30 or 60 min dependent on sample complexity. The mass spectrometer was operated in data-dependent mode in which every FT-MS scan (survey 350-2000 Da) was followed by MS/MS scans of the 5 most abundant ions.

All mass spectrometry data was analyzed according to the pipeline established and already used in the Van Eyk laboratory, designed to meet stringent criteria from the proteomics community. Data from the LTQ-Orbitrap was searched against the IPI databases where possible, using Sorcerer Sequest (Sagen, San Jose, Calif.). Search results were validated and analyzed using Scaffold (Proteome Systems, Portland, Oreg.). Protein identifications based upon a single peptide observation were handled carefully through manual inspection of the tandem MS (MS/MS) spectra, BLAST searching of the sequence to ensure it matches only the reported protein, requiring a minimum of 8 amino acids and a peptide probability score of >0.9.

Data analysis flow was based on the following: peptide redundancy removed, protein name redundancy removed, the number of unique peptides and number of observation for each peptide regardless of charge state were determined for each protein and, in the cases where the protein was observed in multiple domains as an indicator of potential PTM this was noted and all data for the protein was included for quantitation.

factor of 1.25 was used in all R value calculations with a R>0.3 as indicative of change. See 1DLC for more detail.

3. Criteria Selection for 2DLC
A) Individual in Each Group (Induced Necrosis or Induced Ischemia)
   i) Changes in the number of unique peptides or the number of times each peptide was observed regardless of charge state (+2. +3 or +4) were compared to the equivalent protein (if observed) at time point 0. All proteins only seen in time points after baseline were included.
   ii) Changes in 3 out of the 3 or 2 out of the 3 individuals in a designated group (induced ischemia or induced necrosis) at any time point.
B) Group
   i) proteins that met the above criteria for either induced ischemia or induced necrosis that did not change in all of the control (non ischemic) samples at any time point.

4. 2DLC Results

Over 7500 specta were analyzed per pooled sample and thus, over 52,5000 spectra in total. Spectra were removed based on poor quality and each mass was assigned to a single peptide sequence resulting in ~5500 spectra remaining. The number of the proteins that met the criteria are listed below in table 9. See Example II for detailed protein information.

TABLE 9 protein observed changed by 2DLC

| Protein name | IPI accession number | increased in Ischemia | increased in necrosis | potential PTM in any sample | present at baseline | Ischemia T1/T0 | Ischemia T2/T0 | present at baseline | necrosis T1/T0 | Control present at baseline | Control_ T1/T0 |
|---|---|---|---|---|---|---|---|---|---|---|---|
| Protease, serine, 3 | IPI00748381 | yes | yes | no | 0 | 0 | > | 0 | > | 0 | 0 |
| C4b-binding protein alpha chain | IPI00021727 | yes | yes | yes | yes | 0 | > | yes | > | yes | = |
| Alpha-2-glycoprotein 1, zinc (no) | IPI00166729 | yes | yes | yes | 0 | > | > | 0 | > | 0 | 0 |
| Thyroxine-binding globulin precursor | IPI00292946 | no | yes | no | yes | 0 | 0 | 0 | > | 0 | 0 |

Criteria was that both number of peptide and number of count must increased increased in ischemia = if protein is increases over baseline in the POOLED sample comprising severe ischemia patients. Ischemia was based on increase in lactate over time and no detectable cTnT increased in necrosis = if protein is increases over baseline in the POOLED sample comprising necrosis patients analyzed. Necrosis was based on detectable cTnT (at time point 2 and or 3)

PTM = protein found in multiple fractions in any of the pooled sample.

Note,
if sequential maybe reflect not PTM but rather large quantity of protein eluting over multiple fractions
yes = present at baseline
0 not detected,
> greater than baseline
< less than baseline
= equal to baseline
yes - detected at baseline
control pool: all T0 = baseline from 13, 19, 9; T1 = time point 1 for 13, 19 and 9
ischemia pool: T0 = baseline from 7, 10, 11; T1 = time point 1 from 7, 10, 11; T2 = time point 2 and 3 from 7, 10, 11
necrosis pool: T0 = baseline and time point 1 for 16, 15; T2 = time points 2 and 3 of patient 16 and 15

The number of unique peptides and total number of counts (number of times each peptide is observed) were dependently used to semi-quantify each protein that was observed. To deal with proteins which peptides were only observed at some but not all time points (resulting in no information) a correction Interestingly, two proteins, junction plakoglobin, desmoplakin, that are part of the desmonsomal protein complex were detected in a few patients but not enough to make it meet the criteria. Desmoglein-1, the other protein of the same complex was found elevated in necrosis individual with 2DE.

| name | IPI # | Increase in ischemia | Increase in necrosis | Potential PTM | Ischemia TP1 | Ischemia TP2 | Ischemia TP3 |
|---|---|---|---|---|---|---|---|
| Junction plakoglobin (catenin gamma isoform 1) | IPI00554711 | yes | no | no | 0 | > | 0 |
| DPII isoform (most likely also DPI) Desmoplakin | IPI00217182 (IPI0013933) | yes | no | no | 0 | > | 0 |

F. Final Summary of all Protein Changes with Three Methods of Proteomic Analysis Coronary sinus serum samples were analyzed from patients undergoing atrial pacing. Patients were designated into control, ischemia or necrosis groups based on the presence of cTnT at any time point (necrosis group) and an increase in lactate during the pacing protocol (ischemia and necrosis groups). Depleted samples were analyzed for all patients and all time points by 2DE. Depleted samples for 3 patients that were control, ischemia or necrosis were analyzed at multiple time points by 1DLC. Pooling of these individuals (2 or 3) from control, necrosis and ischemia were required for analyzed by 2DLC due to the amount of protein required for this technology. Proteins selection criteria for each method and MS-based quantitation for each method are described above.

The following proteins have been selected as primary or secondary targets based on the robustness of their changes with ischemia and or necrosis and known biological functions. The overlap is schematically shown in FIG. 5. Detailed information about each target is located in Example II.

Primary Targets
Lumican
Extracellular matrix protein 1
Angiogenin
Semenogelin (all isoforms 1 and 2)
Long palate, lung and nasal epithelium carcinoma-associated protein 1 (all isoforms, 1 and 2)
Secondary Targets
Alpha-2-HS-glycoprotein
Carboxypeptidase N (all subunits including catalytic chain)
Galectin-7
Hornerin
Proteoglycan-4 (Isoform A and D)
Profilaggrin (Filaggrin)
Vitamin D binding protein
C4b-binding protein alpha chain
Thyroxine binding globulin
Alpha-2-glycoprotein 1, zinc
protease, serine 3
Caspase 14
Desmogelin
Kininogen-1 (LMW and HMW and bradykinin)

Example II

Summary of Some of the Properties of Proteins Discussed with Regard to Cohort I

A. Vitamin D-Binding Protein
Name: Vitamin D-binding protein
IPI ID: IPI00555812
UniProtKB/Swiss-Prot entry ID: P02774, Q16309, Q16310
Length: 474 aa, molecular weight: 52964 Da (of precursor)
1. Basic Information from UniProtKB/Swiss-Prot Entry
  FUNCTION: Multifunctional protein found in plasma, ascitic fluid, cerebrospinal fluid, and urine and on the surface of many cell types. In plasma, it carries the vitamin D sterols and prevents polymerization of actin by binding its monomers. DBP associates with membrane-bound immunoglobulin on the surface of B-lymphocytes and with IgG Fc receptor on the membranes of T-lymphocytes.
  SUBCELLULAR LOCATION: Secreted.
  POLYMORPHISM: Over 80 variants of human DBP have been identified. The three most common alleles are called GC*1F, GC*1S, and GC*2. The sequence shown is that of the GC*2 allele
2. Sequence (SEQ ID NO: 1)
MKRVLVLLLAVAFGHALERGRDYEKNKVCKEFSHLGKEDFTSLSLVLY

SRKFPSGTFEQVSQLVKEVVSLTEACCAEGADPDCYDTRTSALSAKSCE

SNSPFPVHPGTAECCTKEGLERKLCMAALKHQPQEFPTYVEPTNDEICE

AFRKDPKEYANQFMWEYSTNYGQAPLSLLVSYTKSYLSMVGSCCTSASP

TVCFLKERLQLKHLSLLTTLSNRVCSQYAAYGEKKSRLSNLIKLAQKVP

TADLEDVLPLAEDITNILSKCCESASEDCMAKELPEHTVKLCDNLSTKN

SKFEDCCQEKTAMDVFVCTYFMPAAQLPELPDVELPTNKDVCDPGNTKV

MDKYTFELSRRTHLPEVFLSKVLEPTLKSLGECCDVEDSTTCFNAKGPL

LKKELSSFIDKGQELCADYSENTFTEYKKKLAERLKAKLPDATPKELAK

LVNKRSDFASNCCSINSPPLYCDSEIDAELKNIL 1-16 Leader Sequence.

Peptides used in the MS analysis described in this application are indicated by highlighting (shading) in the protein sequences shown herein. A skilled worker can use peptides for some of the proteins which have been described previously by others who have performed MS on those proteins. The sequences of peptides is dependent on the particular type of MS used. For example, the peptides for MALDI can be different from those in ESI. The studies performed herein were ESI.

3. Alternative Names: DBP, Group-specific Component, Gc-globulin, VDB
4. Additional Information on Function
  Serum vitamin D3-binding protein (Gc protein) is the precursor for the principal macrophage activating factor (MAF).
  Gc protein was deglycosylated by serum alpha-N-acetyl-galactosaminidase (Nagalase)
  The level of Gc globulin is reduced in patients with fulminate hepatic failure, septic shock and trauma. Furthermore, low levels of Gc globulin in patients with fulminant hepatic failure and multiple trauma have been found to correlate with the morbidity and mortality of patients. It has not been studied in heart disease.
5. Summary
  Assays are available for total Vitamin D binding protein and for the amount of protein which is either free or bound to actin. This protein is known to be diagnostic for several diseases. It seems to be change with cellular injury and decrease with long term chronic disease. Clinical studies and animal models have shown that Gc-globulin has an important role in the clearance of procoagulant actin from the circulation after its release during cell necrosis and tissue injury but it is not known if it is in the heart.

B. Thyroxine-binding Globulin
Name: Thyroxine-binding globulin precursor
IPI ID: IPI00292946
UniProtKB/Swiss-Prot entry ID: P05543
Length: 415 aa, molecular weight: 46325 Da (precursor)
1. Basic Information from UniProtKB/Swiss-Prot Entry
   FUNCTION: Major thyroid hormone transport protein in serum.
   SUBCELLULAR LOCATION: Secreted.
   TISSUE SPECIFICITY: Expressed by the liver and secreted in plasma.
   DISEASE: Defects in SERPINA7 are a cause of TBG deficiency [MIM:314200]. Mutations in the SERPINA7 gene can result as a whole spectrum of deficiencies, characterized by either reduced or increased TBG levels in the serum. Patients show, respectively, reduced or elevated protein-bound iodine but are euthyroid.
2. Sequence

```
(SEQ ID NO: 2)
MSPFLYLVLLVLGLHATIHCASPEGKVTACHSSQPNATLYKMSSINADFAFNLYRRFTVE

TPDKNIFFSPVSISAALVMLSFGACCSTQTEIVETLGFNLTDTPMVEIQHGEFQHLICSLN

FPKKELELQIGNALFIGKHLKPLAKFLNDVKTLYETEVFSTGDFSNISAAKQEINSHVEMQ

TKGKVVGLIQDLKPNTIMVLVNYIHFKAQWANPFDPSKTEDSSSFLIDKTTTVQVPMMHQ

MEQYYHLVDMELNCTVLQMDYSKNALALFVLPKEGQMESVEAAMSSKTLKKWNRLLQKGW

VDLFVPKFSISATYDLGATLLKMGIQHAYSENADFSGLTEDNGLKLSNAAHKAVLHIGEK

GTEAAAVPEVELSDQPENTFLHPIIQIDRSFMLLILERSTRSILFLGKVVNPTEA
```

1-20 Signal Sequence
3. Alternative Names: T4-binding Globulin, Serpin A7
4. Summary
Thyroxine-binding globulin binds with high-affinity to the thyroid hormone. It is proposed to be a biomarker for senescence and aging. Chronic treatment with perindopril, an angiotensin I-converting enzyme inhibitor used in cardiac and renal disease, enhanced thyroxine-binding capacity and possibility the protein level itself. In a study on ACS, thyroxine binding globulin was measured in those with acute myocardial infarction after 14 days and there was no change compared to control. It has not been studied in myocardial ischemia or events leading up to MI.

C. Lumican

Name: Lumican

IPI ID: IPI00020986

UniProtKB/Swiss-Prot entry ID:

Length: 338 aa, molecular weight: 38429 Da, (of precursor)

1. Basic Information from UniProtKB/Swiss-Prot Entry

SUBUNIT Binds to laminin (By similarity).

SUBCELLULAR LOCATION Secreted, extracellular space, extracellular matrix (By similarity).

2. Sequence

```
(SEQ ID NO: 3)
MSLSAFTLFLALIGGTSGQYYDYDFPLSIYGQSSPNCAPECNCPESYPSAMYCDELKLKS

VPMVPPGIKYLYLRNNQIDHIDEKAFENVTDLQWLILDHNLLENSKIKGRVFSKLKQLKK

LHINHNNLTESVGPLPKSLEDLQLTHNKITKLGSFEGLVNLTFIHLQHNRLKEDAVSAAF

KGLKSLEYLDLSFNQIARLPSGLPVSLLTLYLDNNKISNIPDEYFKRFNALQYLRLSHNE

LADSGIPGNSFNVSSLVELDLSYNKLKNIPTVNENLENYYLEVNQLEKFDIKSFCKILGP

LSYSKIKHLRLDGNRISETSLPPDMYECLRVANEVTLN
```

1-18 Signal Sequence
3. Alternative Names:
   (Keratan Sulfate Proteoglycan Lumican) (KSPG Lumican).
4. Summary
   Protein involved in injury response in a number of tissues and is a secreted protein. In a study on the lumican in fibrosis with chronic ischemic and reperfused rat heart (which is not the acute myocardial infaction model, but rather would induce heart failure), the level of lumican mRNA increased, peaking at the fourth week. The protein level was not investigated. This protein is also known to inhibits cell adhesion and neurite outgrowth and be involved in wound healing of the cornea. It plays an important role in cell migration and proliferation during embryonic development, tissue repair, and tumor growth. It has not been studied in the context of myocardial ischemia or events leading up to MI.

D. Galectin-7
Name: Galectin-7
IPI ID: IPI00219221
UniProtKB/Swiss-Prot entry ID:
Length: 136 aa, molecular weight: 15075 Da
1. Basic Information from UniProtKB/Swiss-Prot Entry
FUNCTION Could be involved in cell-cell and/or cell-matrix interactions necessary for normal growth control. Pro-apoptotic protein that functions intracellularly upstream of JNK activation and cytochrome c release.
SUBCELLULAR LOCATION Cytoplasm. Nucleus. Secreted (Potential). Note=May be secreted by a non-classical secretory pathway.
TISSUE SPECIFICITY Mainly in stratified squamous epithelium.
2. Sequence

```
                                                 (SEQ ID NO: 4)
MSNVPHKSSLPEGIRPGTVLRIRGLVPPNASRFHVNLLCGEEQGSDAALHFNPRLDTSEV

VFNSKEQGSWGREERGPGVPFQRGQPFEVLIIASDDGFKAVVGDAQYHHFRHRLPLARVR

LVEVGGDVQLDSVRIF
```

Initial Met is Removed
3. Alternative Names:
Galectin-7 (Gal-7) (HKL-14) (PI7) (p53-induced gene 1 protein).
Homologous 100% to Q6IB87_HUMAN LGALS7 protein (HCG1776519) (HCG42850) [LGALS7]
Note on Sequence:
Note only 36% homology with galectin 3 which is known to be involved in cancer.
4. Additional Information on Function
The literature suggests that galectin 7 is involved in apoptosis. It is most likely is secreted and forms dimers. Galectin 7 is an emerging marker involved in the epidermal development of pluristratified epithelia and in epidermal cell migration. It is elevated in wound healing. It has not been studied in the context of myocardial ischemia or events leading up to MI.

E. Extracellular Matrix Protein 1
Name: Extracellular matrix protein 1
IPI ID: IPI00645849
UniProtKB/Swiss-Prot entry ID: Q5T5G4
Length: 567 AA (includes signal sequence)
Molecular weight: 63563 Da (includes signal sequence)
1. Basic Information from UniProtKB/Swiss-Prot Entry
FUNCTION: Not known
SUBCELLULAR LOCATION: Secreted, extracellular space.
DISEASE: Defects in ECM1 are the cause of lipoid proteinosis (LiP); also known as lipoid proteinosis of Urbach and Wiethe or hyalinosis cutis et mucosae. LiP is a rare autosomal recessive disorder characterized by generalized thickening of skin, mucosae and certain viscera. Classical features include beaded eyelid papules and laryngeal infiltration leading to hoarseness. Histologically, there is widespread deposition of hyaline material and disruption/reduplication of basement membrane.

2. Sequence Information from 1DLC

```
                                                           (SEQ ID NO: 5)
MGTTARAALVLTYLAVASAASEGGFTATGQRQLRPEHFQEVGYAAPPSPPLSRSLPMDHPD

SSQHGPPFEGQSGKEGRGPRPHSQPWLGERVGCSHIPPSIVQPPPSQEATPLQQEKLLPAQ

LPAEKEVGPPLPQEAVPLQKELPSLQHPNEQKEGTPAPFGDQSHPEPESWNAAQHCQQDRS

QGGWGHRLDGFPPGRPSPDNLNQICLPNRQHVVYGPWNLPQSSYSHLTRQGETLNFLEIGY

SRCCHCRSHTNRLECAKLVWEEAMSRFCEAEFSVKTRPHWCCTRQGEARFSCFQEEAFQPH

YQLRACPSHQPDISSGLELPFPPGVPTLDNIKNICHLRRFRSVPRNLPATDPLQRELLALI

QLEREFQRCCRQGNNHTCTWKAWEDTLDKYCDREYAVKTHHHLCCRHPPSPTRDECFARRA

PYPNYDRDILTIDIGRVTPNLMGHLCGNQRVLTKHKHIPGLIHNMTARCCDLPFPEQACCA

EEEKLTFINDLCGPRRNIWRDPALCCYLSPGDEQVNCFNINYLRNVALVSGDTENAKGQGE

QGSTGGTNISSTSEPKEE
```

3. Alternative Names: Secretory Component p85; Q5T5G5, Q8IZ60, Q5T5G6, Q16610
Note on Sequence:
  Signal sequence 1-19 is removed in the mature protein.
4. Summary
  Mutations of this protein result in lipoid proteinosis, a rare recessive disorder of the skin and mucosae. It binds perlecan, MMP9 and fibulin in the skin. It can inhibit MMP9. Auto antibodies to this protein occur with lichen sclerosus. Neither disease is common and so specificity to ischemia is likely. It has not been studied in the context of myocardial ischemia or events leading up to MI.

F. Semenogelin 1
Name: Semenogelin 1
IPI ID: IPI00414684 (Semenogelin-2 precursor IPI00025415)
UniProtKB/Swiss-Prot entry ID: P04279, Q6X4I9, Q6Y809, Q6Y822, Q6Y823, Q86U64, Q96QM3
Length: 402 aa, molecular weight: 45322 Da 1. Basic Information from UniProtKB/Swiss-Prot Entry
FUNCTION Predominant protein in semen. It participates in the formation of a gel matrix entrapping the accessory gland secretions and ejaculated spermatozoa. Fragments of semenogelin and/or fragments of the related proteins may contribute to the activation of progressive sperm movements as the gel-forming proteins are fragmented by KLK3/PSA.
FUNCTION Alpha-inhibin-92 and alpha-inhibin-31, derived from the proteolytic degradation of semenogelin, inhibit the secretion of pituitary follicle-stimulating hormone.
SUBUNIT Occurs in disulfide-linked complexes which may also contain two less abundant 71- and 76-kDa semenogelin-related polypeptides.
SUBCELLULAR LOCATION Secreted.
ALTERNATIVE PRODUCTS
  Event=Alternative splicing; Named isoforms=2;
  Name=1;
  IsoId=P04279-1; Sequence=Displayed;
  Name=2;
  IsoId=P04279-2; Sequence=VSP_004385;
  Note=No experimental confirmation available;
TISSUE SPECIFICITY Seminal vesicle. However references show it is also present in other tissues including skeletal muscle
2. Sequence 1-23 Signal Sequence
3. Alternative Names:
  SEMG
4. Summary
  SGI isoform is found in skeletal muscle as well as epithelial cells. Isoform expression is tissue specific and SGI isoform is found in skeletal muscle as well as epithelial cells. The peptides produced by cleavage of semenogelin I, the predominant human semen coagulum protein, had high levels of antibacterial activity. It has not been studied in the context of myocardial ischemia or events leading up to MI.

G. Isoform 1 of Long Palate, Lung and Nasal Epithelium Carcinoma-associated Protein 1
Name: Isoform 1 of Long palate, lung and nasal epithelium carcinoma-associated protein 1
IPI ID: IPI00291410,
UniProtKB/Swiss-Prot entry ID: Q8TDL5-1
Length: 484 aa, molecular weight: 52442 Da 1. Basic Information from UniProtKB/Swiss-Prot Entry
FUNCTION May play a role in innate immunity in mouth, nose and lungs.
SUBCELLULAR LOCATION Secreted (By similarity).
ALTERNATIVE PRODUCTS
  Event=Alternative splicing; Named isoforms=2;
  Name=1;
  IsoId=Q8TDL5-1; Sequence=Displayed;
  Name=2;
  IsoId=Q8TDL5-2; Sequence=VSP_015285, VSP_015286,
  VSP 015287,
  VSP 015288;
  Note=No experimental confirmation available;
TISSUE SPECIFICITY Detected in trachea, nasal septal epithelium and lung. 0 hits (SEQ ID NO: 6)

MKPNIIFVLSLLLILEKQAAVMGQKGGSKGRLPSEFSQFPHGQKGQHYSGQKGKQQTESK

GSFSIQYTYHVDANDHDQSRKSQQYDLNALHKTTKSQRHLGGSQQLLHNKQEGRDHDKSK

GHFHRVVIHHKGGKAHRGTQNPSQDQGNSPSGKGISSQYSNTEERLWVHGLSKEQTSVSG

AQKGRKQGGSQSSYVLQTEELVANKQQRETKNSHQNKGHYQNVVEVREEHSSKVQTSLCP

AHQDKLQHGSKDIFSTGDELLVYNKNQHQTKNLNQDQQHGRKANKISYQSSSTEERRLHY

GENGVQKDVSQRSIYSQTEKLVAGKSQIQAPNPKQEPWHGENAKGESGQSTNREQDLLSH

EQKGRHQHGSHGGLDIVIIEQEDDSDRHLAQHLNNDRNPLFT

2. Sequence (SEQ ID NO: 7)
MAGPWTFTLLCGLLAATLIQATLSPTAVLILGPKVIKEKLTQELKDHNATSILQQLPLLS

AMREKPAGGIPVLGSLVNTVLKHIIWLKVITANILQLQVKPSANDQELLVKIPLDMVAGF

NTPLVKTIVEFHMTTEAWATIRMDTSASGPTRLVLSDCATSHGSLRIQLLHKLSFLVNAL

AKQVMNLLVPSLPNLVKNQLCPVIEASFNGMYADLLQLVKVPISLSIDRLEFDLLYPAIK

GDTIQLYLGAKLLDSQGKVTKWFNNSAASLTMPTLDNIPFSLIVSQDVVKAAVAAVLSPE

EFMVLLDSVLPESAHRLKSSIGLINEKAADKLGSTQIVKILTQDTPEFFIDQGHAKVAQL

IVLEVFPSSEALRPLFTLGIEASSEAQFYTKGDQLILNLNNISSDRIQLMNSGIGWFQPD

VLKNIITEIIHSILLPNQNGKLRSGVPVSLSVKALGFEAAESSLTKDALVLTPASWKPSS

PVSQ 1-21 potential signal sequence. Isoform 2 is truncated at N-terminus. Also have insert (underlined) which has no peptides. Therefore, cannot distinguish between isoform one and two SIMILARITY: Belongs to the pancreatic ribonuclease family.

It is uncertain whether Met-1 or Met-3 is the initiator.

2. Sequence Information from 1DLC (SEQ ID NO: 8)
MVMGLGVLLL VFVLGLGLTP PTLAQDNSRY THFLTQHYDA KPQGRDDRYC ESIMRRRGLT

SPCKDINTFI HGNKRSIKAI CENKNGNPHR ENLRISKSSF QVTTCKLHGG SPWPPCQYRA

TAGFRNVVVA CENGLPVHLD QSIFRRP

3. Alternative Names: C20orf114
4. Summary
   Little is known about this protein or its shorter isoform (2). It has not been studied in the context of myocardial ischemia or events leading up to MI.

H. Angiogenin
Name: Angiogenin, precursor
IPI ID: IPI00008554
UniProtKB/Swiss-Prot entry ID: P03950
Length: 147 AA [This is the length of the unprocessed precursor]
Molecular weight: 42051 Da [This is the MW of the unprocessed precursor
1. Basic Information from UniProtKB/Swiss-Prot Entry
   FUNCTION: May function as a tRNA-specific ribonuclease that binds to actin on the surface of endothelial cells; once bound, angiogenin is endocytosed and translocated to the nucleus, thereby promoting the endothelial invasiveness necessary for blood vessel formation. Angiogenin induces vascularization of normal and malignant tissues. Abolishes protein synthesis by specifically hydrolyzing cellular tRNAs.
   INTERACTIONS: May bind alpha-actinin P35609
   SUBCELLULAR LOCATION: Secreted
   TISSUE SPECIFICITY: Expressed predominantly in the liver.
   DEVELOPMENTAL STAGE: Low level expression in the developing fetus, increased in the neonate, and maximal in the adult Multiple Peptides
3. Alternative Names: RNASE5, Ribonuclease A Family, 5, RNASE4 Protein, ANG Protein Q53×86, Q6P5T2
   Note on Sequence:
     Most likely have either intact molecule or the mature processed form.
     Signal peptide residues 1-24
   Additional information on function Angiogenin is a normal constituent of the circulation and contained in a vasculature that rarely undergoes proliferation, but in some physiological and pathological conditions its levels increase in blood, promoting neovascularization. This is a potentially important physiological protein involved in angiogenesis.
4. Summary
   Interestingly, this protein may play a role in angiogenesis. Recently it has been potentially linked to poor outcome in ACS patients, which is a chronic condition that can result from many different etiologies. Plasma angiogenin levels was increased in ACS also with ischemic brain damage. However, it has not been studied in the context of myocardial ischemia or events leading up to MI.

I. C4b-binding Protein
Name: C4b-binding protein (alpha chain)r
IPI ID: IPI00021727
UniProtKB/Swiss-Prot entry ID: P04003
Length: 597 AA [This is the length of the unprocessed precursor]
Molecular weight: 67033 Da [This is the MW of the unprocessed precursor]

1. Basic Information from UniProtKB/Swiss-Prot Entry
    FUNCTION: Controls the classical pathway of complement activation. It binds as a cofactor to C3b/C4b inactivator (C3bINA), which then hydrolyzes the complement fragment C4b. It also accelerates the degradation of the C4bC2a complex (C3 convertase) by dissociating the complement fragment C2a. Alpha chain binds C4b. It interacts also with anticoagulant protein S and with serum amyloid P component.
    SUBUNIT: Disulfide-linked complex of alpha and beta chains of 3 possible sorts: a 570 kDa complex of 7 alpha chains and 1 beta chain, a 530 kDa homoheptamer of alpha chains or a 500 kDa complex of 6 alpha chains and 1 beta chain. The central body of the alpha chain homopolymer supports tentacles, each with the binding site for C4b at the end.
    SUBCELLULAR LOCATION: Secreted
    TISSUE SPECIFICITY: Chylomicrons in the plasma.
    It is uncertain whether Met-1 or Met-17 is the initiator
Additional Information
    CRP binds C4b binding proteins and regulations it inhibition of complement system (Regulation of Complement Activation by C-Reactive Protein: Targeting of the Inhibitory Activity of C4b-Binding Protein[1] AP Sjöberg et al., J. Immuno. 2006, 176: 7612-7620).
    C4b-binding protein (C4BP), binds strongly to necrotic cells, irrespective of the cell type used or the method of induction. (C4b-binding protein binds to necrotic cells and DNA, limiting DNA release and inhibiting complement activation L A. Trouw et al., JEM, 2005, 201, 1937-1948)

2. Sequence

3. Alternative Names: IC4b binding protein, C4b binding protein alpha chain, C4b receptor, C4bP, C4bPA, C4bPAL1, Complement component 4 binding protein, alpha like 1, PRP, Proline rich protein Complement component 4 binding protein, alpha. Q5VVQ8
Note on Sequence:
    Most likely intact protein. Several patients had protein present in multiple fractions and although sequential appears to be due to PTM rather than bleed over between two fractions. E do not know what the PTM is at this time. This protein has not been studied in the context of myocardial ischemia or events leading up to MI.

J. Carboxypeptidase N Catalytic Chain
Name: Carboxypeptidase N catalytic chain precursor
IPI ID: IPI00021439
UniProtKB/Swiss-Prot entry ID: P15169
Length: 458 AA [This is the length of the unprocessed precursor]
Molecular weight: 52286 Da [This is the MW of the unprocessed precursor]

1. Basic Information from UniProtKB/Swiss-Prot Entry
    FUNCTION: Protects the body from potent vasoactive and inflammatory peptides containing C-terminal Arg or Lys (such as kinins or anaphylatoxins) which are released into the circulation. Note cleaves bradykinin!
    CATALYTIC ACTIVITY: Release of a C-terminal basic amino acid, preferentially lysine.
    SUBUNIT: Tetramer of two catalytic chains and two glycosylated inactive chains.
    SUBCELLULAR LOCATION: Secreted/extracellular space
    SIMILARITY: Belongs to the peptidase M14 family

```
                                                            (SEQ ID NO: 9)
MHPPKTPSGA LHRKRKMAAW PFSRLWKVSD PILFQMTLIA ALLPAVLGNC GPPPTLSFAA

PMDITLTETR FKTGTTLKYT CLPGYVRSHS TQTLTCNSDG EWVYNTFCIY KRCRHPGELR

NGQVEIKTDL SFGSQIEFSC SEGFFLIGST TSRCEVQDRG VGWSHPLPQC EIVKCKPPPD

IRNGRHSGEE NFYAYGFSVT YSCDPRFSLL FHASISCTVE NETIGVWRPS PPTCEKITCR

KPDVSHGEMV SGFGPIYNYK DTIVFKCQKG FVLRGSSVIH CDADSKWNPS PPACEPNSCI

NLPDIPHASW ETYPRPTKED VYVYGTVLRY RCHPGYKPTT DEPTTVICQK NLRWTPYQGC

EALCCPEPKL NNGEITQHRK SRPANHCVYF YGDEISFSCH ETSRFSAICQ GDGTWSPRTP

SCGDICNFPP KIAHGHYKQS SSYSFFKEEI IYECDKGYIL VGQAKLSCSY SHWSAPAPQC

KALCRKPELV NGRLSVDKDQ YVEPENVTIQ CDSGYGVVGP QSITCSGNRT WYPEVPKCEW

ETPEGCEQVL TGKRLMQCLP NPEDVKMALE VYKLSLEIEQ LELQRDSARQ STLDKEL
```

Green both 1DLC and 2DLC
Glue only 2DLC

2. Sequence (SEQ ID NO: 10)

*MSDLLSVFLH LLLLFKLVAP* VTFRHHRYDD LVRTLYKVQN ECPGITRVYS IGRSVEGRHL

YVLEFSDHPG IHEPLEPEVK YVGNMHGNEA LGRELMLQLS EFLCEEFRNR NQRIVQLIQD

TRIHILPSMN PDGYEVAAAQ GPNKPGYLVG RNNANGVDLN RNFPDLNTYI YYNEKYGGPN

HHLPLPDNWK SQVEPETRAV IRWMHSFNFV LSANLHGGAV VANYPYDKSF EHRVRGVRRT

ASTPTPDDKL FQKLAKVYSY AHGWMFQGWN CGDYFPDGIT NGASWYSLSK GMQDFNYLHY

NCFEITLELS CDKFPPEEEL QREWLGNREA LIQFLEQVHQ GIKGMVLDEN YNNLANAVIS

VSGINHDVTS GDHGDYFRLL LPGIYTVSAT APGYDPETVT VTVGPAEPTL VNFHLKRSIP

QVSPVRRAPS RRHGVRAKVQ PQARKKEMEM RQLQRGPA

3. Alternative Names: CPN, Carboxypeptidase N polypeptide 1, Carboxypeptidase N small subunit; Lysine carboxypeptidase, Arginine carboxypeptidase, Kininase-1, Serum carboxypeptidase NSCPN, Anaphylatoxin inactivator, Plasma carboxypeptidase B Q5T287
Note on Sequence: Signal Sequence 1-20
4. Summary
Interesting protein, which may alter bradykinin levels and creatine kinase levels. Involved in early inflammatory response. Has been shown to be elevated after AMI based on activity assays. Although it has been shown that there is a high degree of variability in carboxypeptidase N in healthy subjects and does not change with acute myocardial infarction patients but may reach maximum at 48 h after onset of chest pain. It has not been studied in the context of myocardial ischemia or events leading up to MI.
K. Profilaggrin/Filaggrin
Name: Profilaggrin (Filaggrin)
IPI ID: IPI00746718
UniProtKB/Swiss-Prot entry ID: P20930 (note only 70% homology)
Length: 4061AA
Molecular weight: 435170 Da 1. Basic Information from UniProtKB/Swiss-Prot Entry
FUNCTION: Aggregates keratin intermediate filaments and promotes disulfide-bond formation among the intermediate filaments during terminal differentiation of mammalian epidermis
PTM: Filaggrin is initially synthesized as a large, insoluble, highly phosphorylated precursor containing many tandem copies of 324 AA, which are not separated by "large linker". The precursor is deposited as keratohyalin granules. During terminal differentiation it is dephosphorylated and proteolytically cleaved.
PTM: Undergoes deimination of some arginine residues (citrullination).
DISEASE: Defects in FLG are the cause of ichthyosis vulgaris [MIM:146700]; also known as ichthyosis simplex. The phenotypic characteristics of ichthyosis vulgaris include palmar hyperlinearity, keratosis pilaris and a fine scale that is most prominent over the lower abdomen, arms, and legs. Ichthyosis vulgaris is characterized histologically by absent or reduced keratohyalin granules in the epidermis and mild hyperkeratosis. The disease can be associated with frequent asthma, eczema or hay fever. Inheritance is autosomal dominant.
2. Sequence (IPI Sequence)

(SEQ ID NO: 11)
MSTLLENIFAIINLFKQYSKKDKNTDTLSKKELKELLEKEFRQILKNPDDPDMVDVFMDH

LDIDHNKKIDFTEFLLMVFKLAQAYYESTRKENLPISGHKHRKHSHHDKHEDNKQEENKE

NRKRPSSLERRNNRKGNKGRSKSPRETGGKRHESSSEKKERKGYSPTHREEEYGKNHHNS

SKKEKNKTENTRLGDNRKRLSERLEEKEDNEEGVYDYENTGRMTQKWIQSGHIATYYTIQ

DEAYDTTDSLLEENKIYERSRSSDGKSSSQVNRSRHENTSQVPLQESRTRKRRGSRVSQD

RDSEGHSEDSERHSGSASRNHHGSAWEQSRDGSRHPRSHDEDRASHGHSADSSRQSGTRH

AETSSRGQTASSHEQARSSPGERHGSGHQQSADSSRHSATGRGQASSAVSDRGHRGSSGS

QASDSEGHSENSDTQSVSGHGKAGLRQQSHQESTRGRSGERSGRSGSFIYQVSTHEQSES

AHGRTRTSTGRRQGSGGEQARDSSRHSASQEGQDTIRAHPGSRRGGRQGSHHEQSVDRSG

HSGSHHSHTTSQGRSDVSRGQSGSRSVSRQTRNEKQSGDGSRHSGSRHHEASSRADSSRH

SQVGQGQSSGPRTSRNQGSSVSQDSDSQGHSEDSERRSGSASRNHHGSAQEQSRDGSRHP

RSHHEDRAHGHGSAESSRQSGTHHAENSSGGQAASSHEQARSSAGERHGSHHQQSADSSR

```
HSGIGHGQASSAVRDSGHRGSSGSQASDSEGHSEDSDTQSVSAHGQAGPHQQSHQESTRG

RSAGRSGRSGSFLYQVSTHEQSESAHGRTRTSTGRRQGSHHEQARDSSRHSASQEGQDTI

RGHPGSSRRGRQGSHYEQSVDRSGHSGSGGSGTTSQGTSDASRGQSGSRSASRQTRNDEQ

SGDGSRHSWSHHHEASTQADSSRHSQSGQGQSAGPRTSRNQGSSVSQDSDSQGHSEDSER

WSGSASRNHRGSAQEQSRDGSRHPTSHHEDRAGHGHSAESSRQSGTHHAENSSGGQAASS

HEQARSSAGERHGSHHQQSADSSRHSGIGHGQASSAVRDSGHRGSSGSQASDSEGHSEDS

DTQSVSAHGQAGPHQQSHQESTRGRSAGRSGRSGSFLYQVSTHEQSESAHGRAGPSTGGR

QGSRHEQARDSSRHSASQEGQDTIRGHPGSRRGGRQGSYHEQSVDRSGNSGSHHSHTTSQ

GRSDASHGQSGS
```

3. Summary

Peptides observed are unique to Filaggrin (and not to Ifapsoriasin or Hornerin). This protein has not been studied in the context of myocardial ischemia or events leading up to MI.

L. Proteoglycan-4

Name: Isoform A and D of Proteoglycan-4 (we cannot distinguish isoforms due to high degree of sequence homology)

IPI ID: IPI00024825 and IPI00655676

UniProtKB/Swiss-Prot entry ID: Q92954, Q6DNC4, Q6DNC5, Q6ZMZ5, Q9BX49

Length: 1404 aa, molecular weight: 151077 Da

1. Sequence

```
                                                    (SEQ ID NO: 12)
MAWKTLPTYLLLLLSVFVIQQVSSQDLSSCAGRCGEGYSRDATCNCDYNCQHYMECCPDF

KRVCTAELSCKGRCFESFERGRECDCDAQCKKYDKCCPDYESFCAEVHNPTSPPSSKKAP

PPSGASQTIKSTTKRSPKPPNKKKTKKVIESEEITEEHSVSENQESSSSSSSSSSSSTIR

KIKSSKNSAANRELQKKLKVKDNKKNRTKKKPTPKPPVVDEAGSGLDNGDFKVTTPDTST

TQHNKVSTSPKITTAKPINPRPSLPPNSDTSKETSLTVNKETTVETKETTTTNKQTSTDG

KEKTTSAKETQSIEKTSAKDLAPTSKVLAKPTPKAETTTKGPALTTPKEPTPTTPKEPAS

TTPKEPTPTTIKSAPTTPKEPAPTTTKSAPTTPKEPAPTTTKEPAPTTPKEPAPTTTKEP

APTTTKSAPTTPKEPAPTTPKKPAPTTPKEPAPTTPKEPTPTTPKEPAPTTKEPAPTTPK

EPAPTAPKKPAPTTPKEPAPTTPDEPAPTTTKEPSPTTPKEPAPTTTKSAPTTTKEPAPT

TTKSAPTTPKEPSPTTTKEPAPTTPKEPAPTTPKKPAPTTPKEPAPTTPKEPAPTTTKKP

APTTPKEPAPTTPKETAPTTPKKLTPTTPEKLAPTTPEKPAPTTPEELAPTTPEEPTPTT

PEEPAPTTPKAAAPNTPKEPAPTTPKEPAPTTPKEPAPTTPKETAPTTPKGTAPTTLKEP

APTTPKKPAPKELAPTTTKEPTSTTCDKPAPTTPKGTAPTTPKEPAPTTPKEPAPTTPKG

TAPTTLKEPAPTTPKKPAPKELAPTTTKGPTSTTSDKPAPTTPKETAPTTPKEPAPTTPK

KPAPTTPETPPPTTSEVSTPTTTKEPTTIHKSPDESTPELSAEPTKALENSPKEPGVPT

TKTPAATKPEMTTTAKDKTTERDLRTTPETTTAAPKMTKETATTTEKTTESKITATTTQV

TSTTTQDTTPFKITTLKTTTLAPKVTTTKKTITTTEIMNKPEETAKPKDRATNSKATTPK

PQKPTKAPKKPTSTKKPKTMPRVRKPKTTPTPRKMTSTMPELNPTSRIAEAMLQTTTRPN

QTPNSKLVEVNPKSEDAGGAEGETPHMLLRPHVFMPEVTPDMDYLPRVPNQGIIINPMLS

DETNICNGKPVDGLTTLRNGTLVAFRGHYFWMLSPFSPPSPARRITEVWGIPSPIDTVFT

RCNCEGKTFFFKDSQYWRFTNDIKDAGYPKPIFKGFGGLTGQIVAALSTAKYKNWPESVY

FFKRGGSIQQYIYKQEPVQKCPGRRPALNYPVYGETTQVRRRRFERAIGPSQTHTIRIQY
```

```
SPARLAYQDKGVLHNEVKVSILWRGLPNVVTSAISLPNIRKPDGYDYYAFSKDQYYNIDV

PSRTARAITTRSGQTLSKVWYNCP
```

```
1      24   24   Potential. signal
25   1404 1380   Proteoglycan-4.
1307 1404   98   Proteoglycan-4 C-terminal part.
26     66   41   Missing (in isoform B, isoform D and isoform E).
107   199   93   Missing (in isoform C and isoform D).
157   199   43   Missing (in isoform F).
412   841  430   Missing (in isoform E).
```

2. Alternative Names: Proteoglycan-4 precursor (Lubricin) (Megakaryocyte-stimulating factor) (Superficial zone proteoglycan) [Contains: Proteoglycan-4 C-terminal part].

3. Summary

PRG4 (proteoglycan 4) is a megakaryocyte stimulating factor and articular superficial zone protein which is expressed in cartilage, liver, heart, lung, and bone. It is known to be involved in the lubrication of mammalian joints. This protein has not been studied in the context of myocardial ischemia or events leading up to MI.

M. Alpha-2-HS-Glycoprotein

Name: Alpha-2-HS-glycoprotein
IPI ID: IPI00022431
UniProtKB/Swiss-Prot entry ID: P02765
Length: 367 aa, molecular weight: 39325 Da 1. Basic Information from UniProtKB/Swiss-Prot Entry FUNCTION Promotes endocytosis, possesses opsonic properties and influences the mineral phase of bone. Shows affinity for calcium and barium ions.

SUBUNIT Alpha-2-HS glycoprotein derives from this precursor, when the connecting peptide is cleaved off. The two chains A and B are held together by a single disulfide bond.

SUBCELLULAR LOCATION Secreted.

TISSUE SPECIFICITY Synthesized in liver and selectively concentrated in bone matrix. Secreted in plasma. It is also found in dentin in much higher quantities than other plasma proteins.

2. Sequence (SEQ ID NO: 13)
```
MKSLVLLLCLAQLWGCHSAPHGPGLIYRQPNCDDPETEEAALVAIDYINQ

NLPWGYKHTLNQIDEVKVWPQQPSGELFEIEIDTLETTCHVLDPTPVARC

SVRQLKEHAVEGDCDFQLLKLDGKFSVVYAKCDSSPDSAEDVRKVCQDC

PLLAPLNDTRVVHAAKAALAAFNAQNNGSNFQLEEISRAQLVPLPPSTY

VEFTVSGTDCVAKEATEAAKCNLLAEKQYGFCKATLSEKLGGAEVAVTC
```

```
-continued
TVFQTQPVTSQPQPEGANEAVPTPVVDPDAPPSPPLGAPGLPPAGSPP

DSHVLLAAPPGHQLHRAHYDLRHTFMGVVSLGSPSGEVSHPRKTRTVVQ

PSVGAAAGPVVPPCPGRIRHFKV
```

1-18 Signal Sequence

3. Alternative Names:
Alpha-2-HS-glycoprotein precursor (Fetuin-A) (Alpha-2-Z-globulin) (Ba-alpha-2-glycoprotein) [Contains: Alpha-2-HS-glycoprotein chain A; Alpha-2-HS-glycoprotein chain B].

4. Summary Very high abundant protein and found to change in many diseases and acts as a calcification inhibitor. It inhibits inflammation. It is elevated late after acute myocardial infarction but did not correlate with peak cardiac troponin values. This protein has not been studied in the context of myocardial ischemia or events leading up to MI.

N. Protease, Serine, 3 (Mesotrypsinogen) IPI00748381

Name: Protease, serine, 3
IPI ID: IPI00748381
UniProtKB/Swiss-Prot entry ID: Q5JT15
Length: 249AA [This is the length of the unprocessed precursor]
Molecular weight: 26914 Da [This is the MW of the unprocessed precursor 1. Basic Information from UniProtKB/Swiss-Prot Entry FUNCTION (mesotrypsinogen data): Preferential cleavage: Arg-|-Xaa, Lys-|-Xaa. Cofactor Binds 1 calcium ion per subunit.

INTERACTIONS: This protein binds to Amyloid beta A4 (which we observe but do not see changed) and tissue factor pathway inhibitor (see HPRD)

SUBCELLULAR LOCATION: Secreted.

TISSUE SPECIFICITY: Pancreas and brain.

2. Sequence Information from 2DLC

Note: this protein was identified in different fractions for ischemia vs AMI. This suggests that this protein has undergone a PTM with AMI and thus is physically distinct from the form present during ischemia. We do not know what this PTM(s) is at this time.

Sequence (SEQ ID NO: 14)
```
MSPFLILAFVGAAGEVAVPFDDDDKIVGGYTCEENSLPYQVSLNSGSHFCGGSLISEQWV

VSAAHCYKTRIQVRLGEHNIKVLEGNEQFINAAKIIRHPKYNRDTLDNDIMLIKLSSPAV

INARVSTISLPTTPPAAGTECLISGWGNTLSFGADYPDELKCLDAPVLTQAECKASYPGK

ITNSMFCVGFLEGGKDSCQRDSGGPVVCNGQLQGVVSWGHGCAWKNRPGVYTKVYNYVDW

IKDTIAANS
``` bold amino acids are trypsin-like domain

3. Alternative Names:

Uncharacterized protein PRSS3 A6NN76, Mesotrypsin C Q6ISJ4, Mesotrypsinogen C P35030-3 (98% homologous and not in region of the observed peptides), Isoform C of P35030 P35030-3, Isoform B of P35030 P35030-2. Based on HPRD this is the same protein as trypsinogen IV (has same sequence), protease serine, 4, TRY3, TRY4, trypsin 3, trypsin 4 (Brain), trypsinogen III (pancreatic).

Note: In swiss prot, mesotrysinogen has three isoforms—two of which are longer proteins at the N-terminus. We can not distinguish between the three isoforms.

Note on Sequence:

We cannot distinguish between the three highly conserved isoforms of mesotrypsinogen based on MS data.

4. Summary

Mesotrypsin is an inhibitor-resistant protease and is secreted from pancreatic juice. Whether it is present in the heart is not known. This protein has not been studied in the context of myocardial ischemia or events leading up to MI.

O. Alpha-2-Glycoprotein 1, zinc IPI00166729

Name: alpha-2-glycoprotein 1, zinc

IPI ID: IPI00166729

UniProtKB/Swiss-Prot entry ID: Q8N4N0 Q5XKQ4

Length: 298 AA [This is the length of the unprocessed precursor]

Molecular weight: 34259 Da [This is the MW of the unprocessed precursor

1. Basic Information from UniProtKB/Swiss-Prot Entry

FUNCTION: Stimulates lipid degradation in adipocytes and causes the extensive fat losses associated with some advanced cancers. May bind polyunsaturated fatty acids.

SUBCELLULAR LOCATION: Secreted.

TISSUE SPECIFICITY: Blood plasma, seminal plasma, urine, saliva, sweat, epithelial cells of various human glands, liver.

2. Sequence

3. Alternative Names: Alpha-2-glycoprotein 1 Q5XKQ4, zinc binding; zinc-alpha-2-glycoprotein P25311 (295 AA and 33872 Da, over 95% homology)

4. Summary Zinc-alpha2-glycoprotein (ZAG) is a a lipid mobilizing factor found in adipose tissue. It is increased in a number of cancers. Nothing is known about with respect to the heart and myocardial ischemia. It has not been studied in the context of myocardial ischemia or events leading up to MI.

P. Desmoglein-1

Name: Desmoglein-1

IPI ID: IPI00025753

UniProtKB/Swiss-Prot: Q02413

Length: 1049 AA [This is the length of the unprocessed precursor]

Molecular Weight: 113716 Da

1. Basic Information from UniProtKB/Swiss-Prot Entry Q02413

FUNCTION: Component of intercellular desmosome junctions. Involved in the interaction of plaque proteins and intermediate filaments mediating cell-cell adhesion.

SUBCELLULAR LOCATION: Cell membrane; Single-pass type I membrane protein (By similarity).

SIMILARITY: Contains 4 cadherin domains

TISSUE SPECIFICITY: Epidermis, tongue, tonsil and esophagus.

DISEASE: Defects in DSG1 are the cause of keratosis palmoplantaris striata I (PPKS1) [MIM:148700]; also known as striate palmoplantar keratoderma I (SPPK1). PPKS1 is an autosomal dominant disease characterized by thickening of the skin on the palms and soles, and longitudinal hyperkeratotic lesions on the palms, running the length of each finger.

Protein ID data

SEPARATION METHOD: 2DE

EXPECTED MOLECULAR WEIGHT/PI: 113716 Da/4.90

```
                                                    (SEQ ID NO: 15)
MVRMVPVLLSLLLLLGPAVPQENQDGRYSLTYIYTGLSKHVEDVPAFQALGSLNDLQFFR

YNSKDRKSQPMGLWRQVEGMEDWKQDSQLQKAREDIFMETLKDIVEYYNDSNGSHVLQGR

FGCEIENNRSSGAFWKYYYDGKDYIEFNKEIPAWVPFDPAAQITKQKWEAEPVYVQRAKA

YLEEECPATLRKYLKYSKNILDRQDPPSVVVTSHQAPGEKKKLKCLAYDFYPGKIDVHWT

RAGEVQEPELRGDVLHNGNGTYQSWVVVAVPPQDTAPYSCHVQHSSLAQPLVVPWEAS
```

Note on sequence: note initiating Met is cleaved. There maybe a PTM with ischemia as the peptides elute at different fractions at T-1 and T-2. We do not know what the PTM is.

OBSERVED MOLECULAR WEIGHT/PI: 59 KD/5.8

NOTE: It could be processed the product.

2. Sequence

```
                                                    (SEQ ID NO: 16)
MDWSFFRVVAVLFIFLVVVEVNSEFRIQVRDYNTKNGTIKWHSIRRQKREWIKFAAACRE

GEDNSKRNPIAKIHSDCAANQQVTYRISGVGIDQPPYGIFVINQKTGEINITSIVDREVT

PFFIIYCRALNSMGQDLERPLELRVRVLDINDNPPVFSMATFAGQIEENSNANTLVMILN

ATDADEPNNLNSKIAFKIIRQEPSDSPMFIINRNTGEIRTMNNFLDREQYGQYALAVRGS

DRDGGADGMSAECECNIKILDVNDNIPYMEQSSYTIEIQENTLNSNLLEIRVIDLDEEFS
```

```
ANWMAVIFFISGNEGNWFEIEMNERTNVGILKVVKPLDYEAMQSLQLSIGVRNKAEFHHS

IMSQYKLKASAISVTVLNVIEGPVFRPGSKTYVVTGNMGSNDKVGDFVATDLDTGRPSTT

VRYVMGNNPADLLAVDSRTGKLTLKNKVTKEQYNMLGGKYQGTILSIDDNLQRTCTGTIN

INIQSFGNDDRTNTEPNTKITTNTGRQESTSSTNYDTSTTSTDSSQVYSSEPGNGAKDLL

SDNVHFGPAGIGLLIMGFLVLGLVPFLMICCDCGGAPRSAAGFEPVPECSDGAIHSWAVE

GPQPEPRDITTVIPQIPPDNANIIECIDNSGVYTNEYGGREMQDLGGGERMTGFELTEGV

KTSGMPEICQEYSGTLRRNSMRECREGGLMNFMESYFCQKAYAYADEDEGRPSNDCLLI

YDIEGVGSPAGSVGCCSFIGEDLDDSFLDTLGPKFKKLADISLGKESYPDLDPSWPPQST

EPVCLPQETEPVVSGHPPISPHFGTTTVISESTYPSGPGVLHPKPILDPLGYGNVTVTES

YTTSDTLKPSVHVHDNRPASNVVVTERVVGPISGADLHGMLEMPDLRDGSNVIVTERVIA

PSSSLPTSLTIHHPRESSNVVVTERVIQPTSGMIGSLSMHPELANAHNVIVTERVVSGAG

VTGISGTTGISGGIGSSGLVGTSMGAGSGALSGAGISGGGIGLSSLGGTASIGHMRSSSD

HHFNQTIGSASPSTARSRITKYSTVQYSK
```

3. Summary This protein is part of the desmosome cell junctions in many cell types including the heart. The protein is the antigen for Pemphigus foliaceus is an autoimmune skin disease. It binds to plakophilin 1, plakophilin 2, desmoplakin, desmoglein 1, desmoglein 4, plakoglobin and corneodesmosin, all of which maybe potential biomarkers in myocardial ischemia. It has not been studied in the context of myocardial ischemia or events leading up to MI.

Protein ID data
Separation method: 2DE
Expected molecular weight/pI: 27680 Da/5.44 (pro-caspase-14=242 AA)
Observed molecular weight/pI: 68000 Da/6.8,
Note: There is difference in observed and expected MW, multiple proteins complex?
2. Sequence

```
                                                    (SEQ ID NO: 17)
MSNPRSLEEE KYDMSGARLA LILCVTKARE GSEEDLDALE HMFRQLRFES TMKRDPTAEQ

FQEELEKFQQ AIDSREDPVS CAFVVLMAHG REGFLKGEDG EMVKLENLFE ALNNKNCQAL

RAKPKVYIIQ ACRGEQRDPG ETVGGDEIVM VIKDSPQTIP TYTDALHVYS TVEGYIAYRH

DQKGSCFIQT LVDFTKRKG HILELLTEVT RRMAEAELVQ EGKARKTNPE IQSTLRKRLY

LQ
```

Q. Caspase-14
Name: Caspase-14
IPI ID: IPI00013885
UniProtKB/Swiss-Prot: P31944
Length: 242 AA [this is the length of the unprocessed precursor]
  propeptide=1-? AA
  sub-unit 1=?-146 AA,
  sub-unit 2=147-242 AA
Molecular Weight: 27680 Da [this is the MW of the unprocessed precursor]
1. Basic information from UniProtKB/Swiss-Prot Entry P31944
  FUNCTION: May be involved in the death receptor and granzyme B apoptotic pathways. May function as a downstream signal transducer of cell death.
  SUBUNIT: May dimerize with large prodomain caspases.
  SUBCELLULAR LOCATION: Cytoplasm (By similarity).

3. Summary
  Casp14 may play a role in ontogenesis and skin physiology. CASP14 cDNA and determined that CASP14 contains 7 exons encoding a 242-amino acid protein, 2 CASP14 transcripts (CASP14a and CASP14b) differ in the C terminus while an alternative splice acceptor site within intron 5 results in a 74-nucleotide insertion in CASP14b. CASP14b lacks homology with the caspase consensus sequence. CASP14 has been found in epidermis, hair follicles, the sebaceous gland. NO treatment of neonatal mouse cardiomyocytes in culture causes increase in caspase 14. There is also increase in this protein in canine brain during cardiac arrest and resuscitation. This protein has not been studied in the context of myocardial ischemia or events leading up to MI.
R. Hornerin
Name: HORNERIN
IPI ID: IPI00398625
UniProtKB/Swiss-Prot ID: Q86YZ3
Length: 2850 aa, molecular weight: 282390 Da

1. Basic Information from UniProtKB/Swiss-Prot Entry:

| FUNCTION | May play a role in cornification. |
|---|---|
| SUBCELLULAR LOCATION | Cytoplasmic granule (By similarity). Note = Found in keratohyalin granules in the granular cells of the epidermis (By similarity). |

2. Sequence:

(SEQ ID NO: 18)

```
MPKLLQGVITVIDVFYQYATQHGEYDTLNKAELKELLENEFHQILKNPND
PDTVDIILQSLDRDHNKKVDFTEYLLMIFKLVQARNKIIGKDYCQVSGSK
LRDDTHQHQEEQEETEKEENKRQESSFSHSSWSAGENDSYSRNVRGSLKP
GTESISRRLSFQRDFSGQHNSYSGQSSSYGEQNSDSHQSSGRGQCGSGSG
QSPNYGQHGSGSGQSSSNDTHGSGSGQSSGFSQHKSSGQSSGYSQHGSG
SGHSSGYGQHGSRSGQSSRGERHRSSSGSSSYGQHGSGSRQSLGHGRQG
SGSRQSPSHVRHGSGSGHSSSHGQHGSGSSYSYSRGHYESGSGQTSGFGQ
HESGSGQSSGYSKHGSGSGHSSSGQGHGSTSGQASSSGQHGSSSRQSSSY
GQHESASRHSSGRGQHSSGSGQSPGHGQRGSGSGQSPSSGQHGTGFGRSS
SSGPYVSGSGYSSGFGHHESSSEHSSGYTQHGSGSGHSSGHGQHGSRSGQ
SSRGERQGSSAGSSSSYGQHGSGSRQSLGHSRHGSGSGQSPSPSRGRHES
GSRQSSSYGPHGYGSGRSSSRGPYESGSGHSSGLGHQESRSGQSSGYGQH
GSSSGHSSTHGQHGSTSGQSSSCGQHGATSGQSSSHGQHGSGSSQSSRYG
QQGSGSGQSPSRGRHGSDFGHSSSYGQHGSGSGWSSSNGPHGSVSGQSSG
FGHKSGSGQSSGYSQHGSGSSHSSGYRKHGSRSGQSSRSEQHGSSSGLSS
SYGQHGSGSHQSSGHGRQGSGSGHSPSRVRHGSSSGHSSSHGQHGSGTSC
SSSCGHYESGSGQASGFGQHESGSGQGYSQHGSASGHFSSQGRHGSTSGQ
SSSSGQHDSSSGQSSSYGQHESASHHASGRGRHGSGSGQSPGHGQRGSGS
GQSPSYGRHGSGSGRSSSSGRHGSGSGQSSGFGHKSSGQSSGYTQHGSG
SGHSSSYEQHGSRSGQSSRSEQHGSSSGSSSYGQHGSGSRQSLGHGQHG
SGSGQSPSPSRGRHGSGSGQSSSYGPYRSGSGWSSSRGPYESGSGHSSGL
GHRESRSGQSSGYGQHGSSSGHSSTHGQHGSTSGQSSSCGQHGASSGQSS
SHGQHGSGSSQSSGYGRQGSGSGQSPGHGQRGSGSRQSPSYGRHGSGSGR
SSSSGQHGSGLGESSGFGHHESSSGQSSSYQHGSGSGHSSGYGQHGSRS
GQSSRGERHGSSSGSSSHYGQHGSGSRQSSGHGRQGSGSGHSPSRGRHGS
GLGHSSSHGQHGSGSGRSSSRGPYESRSGHSSVFGQHESGSGHSSAYSQH
GSGSGHFCSQGQHGSTSGQSSTFDQEGSSTGQSSSYGHRGSGSSQSSGYG
RHGAGSGQSPSRGRHGSGSGHSSSYGQHGSGSGWSSSSGRHGSGSGQSSG
FGHHESSSWQSGCTQHGSGSGHSSSYEQHGSRSGQSSRGERHGSSSGSS
SSYGQHGSGSRQSLGHGQHGSGSGQSPSPSRGRHGSGSGQSSSYSPYGSG
SGWSSSRGPYESGSSHSSGLGHRESRSGQSSGYGQHGSSSGHSSTHGQHG
STSGQSSSCGQHGASSGQSSSHGQHGSGSSQSSGYGRQGSGSGQSPGHGQ
RGSGSRQSPSYGRHGSGSGRSSSSGQHGSGLGESSGFGHHESSSGQSSSY
SQHGSGSGHSSGYGQHGSRSGQSSRGERHGSSSRSSSRYGQHGSGSRQSS
GHGRQGSGSGQSPSRGRHGSGLGHSSSHGQHGSGSGRSSSRGPYESRSGH
SSVFGQHESGSGHSSAYSQHGSGSGHFCSQGQHGSTSGQSSTFDQEGSST
GQSSSHGQHGSGSSQSSSYGQQGSGSGQSPSRGRHGSGSGHSSSYGQHGS
GSGWSSSSGRHGSGSGQSSGFGHHESSSWQSSGYTQHGSGSGHSSSYEQH
GSRSGQSSRGEQHGSSSGSSSYGQHGSGSRQSLGHGQHGSGSGQSPSPS
RGRHGSGSGQSSSYGPYGSGSGWSSSRGPYESGSGHSSGLGHRESRSGQS
SGYGQHGSSSGHSSTHGQHGSASGQSSSCGQHGASSGQSSSHGQHGSGSS
QSSGYGRQGSGSGQSPGHGQRGSGSRQSPSYGRHGSGSGRSSSSGQHGPG
LGESSGFGHHESSSGQSSSYSQHGSGSGHSSGYGQHGSRSGQSSRGERHG
SSSGSSSRYGQHGSGSRQSSGHGRQGSGSGHSPSRGRHGSGSGHSSSHGQ
HGSGSGRSSSRGPYESRSGHSSVFGQHESGSGHSSAYSQHGSGSGHFCSQ
GQHGSTSGQSSTFDQEGSSTGQSSSHGQHGSGSSQSSSYGQQGSGSGQSP
SRGRHGSGSGHSSSYGQHGSGSGWSSSSGRHGSGSGQSSGFGHHESSSWQ
SSGYTQHGSGSGHSSSYEQHGSRSGQSSRGERHGSSGSSSSYGQHGSGS
RQSLGHGQHGSGSGQSPSPSRGRHGSGSGQSSSYSPYGSGSGWSSSRGPY
ESGSGHSSGLGHRESRSGQSSGYGQHGSSSGHSSTHGQHGSTSGQSSSCG
QHGASSGQSSSHGQHGSGSSQSSGYGRQGSGSGQSPGHGQRGSGSRQSPS
YGRHGSGSGRSSSSGQHGSGLGESSGFGHHESSSGQSSSYSQHGSGSGHS
SGYGQHGSRSGQSSRGERHGSSSGSSSHYGQHGSGSRQSSGHGRQGSGSG
QSPSRGRHGSGLGHSSSHGQHGSGSGRSSSRGPYESRLGHSSVFGQHESG
SGHSSAYSQHGSGSGHFCSQGQHGSTSGQSSTFDQEGSSTGQSSSYGHRG
SGSSQSSGYGRHGAGSGQSLSHGRHGSGSGQSSSYGQHGSGSGQSSGYSQ
HGSGSGQDGYSYCKGGSNHDGGSSGSYFLSFPSSTSPYEYVQEQRCYFYQ
```

Little is known about this protein. It has not been studied in the context of myocardial ischemia or events leading up to MI.

S. Kininogen
Name: ISOFORM LMW OF KININOGEN-1
IPI ID: IPI00215894
UniProtKB/Swiss-Prot ID: P01042
Length: 427 aa, molecular weight: 47883 Da (of Precursor)

1. Basic Information from UniProtKB/Swiss-Prot Entry:

| | |
|---|---|
| FUNCTION | (1) Kininogens are inhibitors of thiol proteases; (2) HMW-kininogen plays an important role in blood coagulation by helping to position optimally prekallikrein and factor XI next to factor XII; (3) HMW-kininogen inhibits the thrombin- and plasmin- induced aggregation of thrombocytes; (4) the active peptide bradykinin that is released from HMW-kininogen shows a variety of physiological effects: (4A) influence in smooth muscle contraction, (4B) induction of hypotension, (4C) natriuresis and diuresis, (4D) decrease in blood glucose level, (4E) it is a mediator of inflammation and causes (4E1) increase in vascular permeability, (4E2) stimulation of nociceptors (4E3) release of other mediators of inflammation (e.g. prostaglandins), (4F) it has a cardioprotective effect (directly via bradykinin action, indirectly via endothelium-derived relaxing factor action); (5) LMW-kininogen inhibits the aggregation of thrombocytes; (6) LMW-kininogen is in contrast to HMW-kininogen not involved in blood clotting. |
| SUBCELLULAR LOCATION | Secreted, extracellular space. |

2. Sequence:

(SEQ ID NO: 19)
MKLITILFLCSRLLLSLTQESQSEEIDCNDKDLFKAVDAALKKYNSQN

QSNNQFVLYRITEATKTVGSDTFYSFKYEIKEGDCPVQSGKTWQDCE

YKDAAKAATGECTATVGKRSSTKFSVATQTCQITPAEGPVVTAQYD

CLGCVHPISTQSPDLEPILRHGIQYFNNNTQHSSLFMLNEVKRAQRQ

VVAGLNFRITYSIVQTNCSKENFLFLTPDCKSLWNGDTGECTDNAYI

DIQLRIASFSQNCDIYPGKDFVQPPTKICVGCPRDIPTNSPELEETLTH

TITKLNAENNATFYFKIDNVKKARVQVVAGKKYFIDFVARETTCSKES

NEELTESCETKKLGQSLDCNAEVYVVPWEKKIYPTVNCQPLGMISL

MKRPPGFSPFRSSRIGEIKEETTSHLRSCEYKGRPPKAGAEPASER

EVS

3. Alternative Name(s): High molecular weight kininogen, Short name=HMWK; Williams-Fitzgerald-Flaujeac factor; Fitzgerald factor; Alpha-2-thiol proteinase inhibitor
This protein has not been studied in the context of myocardial ischemia or events leading up to MI.

Example III

Further Studies to Identify Cardiac Biomarkers, Using as a Cohort of Patients, a Valve Replacement Cardioplegia Human Model (Cohort II)

A. Overview of the Studies

Figure 6:
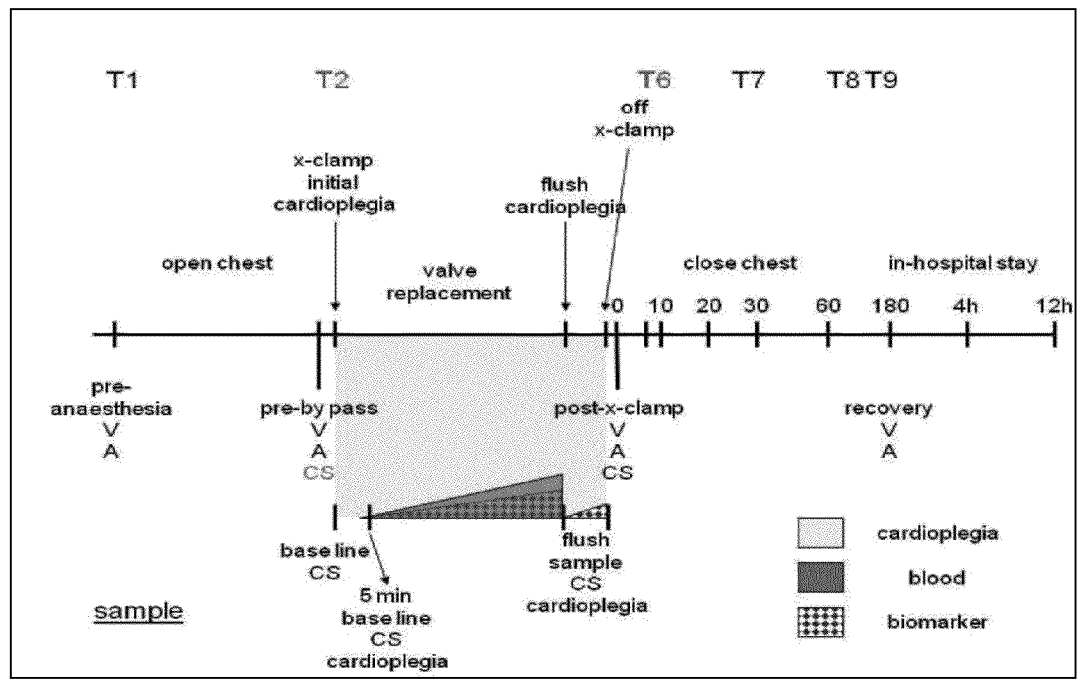
FIG. 6 shows schematically the collection during valve replacement. In this chorot, coronary sinus samples were obtained from individuals who underwent induced ischemia due to stopping of the heart (with cardioplegia) during valve replacement. Coronary sinus samples were obtained and depleted prior to being separated by 1DLC (as outlined above). Proteins found to be increased with ischemia in the majority of individuals were considered first teir. However, it must be recognized that lower abundant proteins may only be observed in a few patients due to inherent detection limits of this type of MS analysis. These proteins might be actually elevated in many patients and just not observed with this approach.
Figure 7:
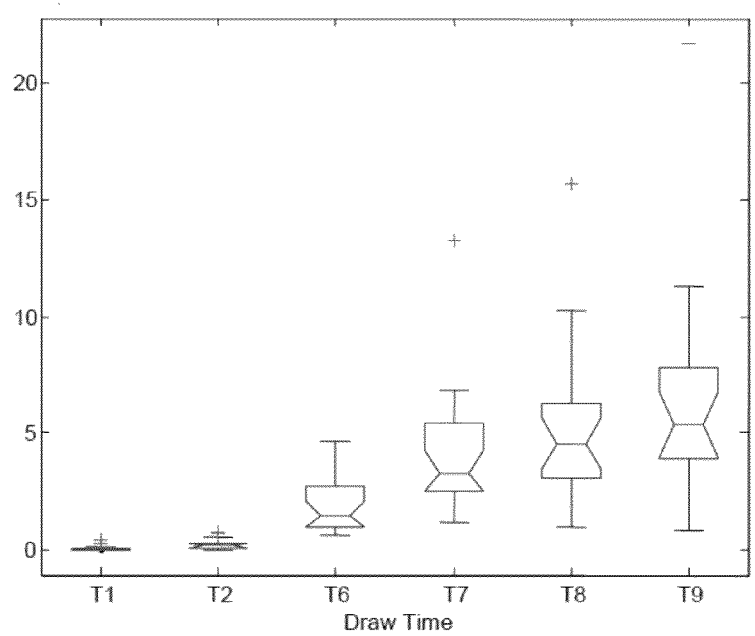
FIG. 7 shows a box plot of cTn1 at all time points for the individuals that under went valve replacement. Note that all individuals eventually had detectable cTnI/cTnT in their serum, indicating necrosis. However, at the time points at which de novo discovery was undertaken, none of the individuals had detectable cTnT or cTnI. This shows that all were ischemic at the time of study.

The 21 patients in this cohort all underwent aortic valve replacement surgery (See FIGS. 6 and 7). Table 10 provides cohort information of this model.

TABLE 10 patient sampling

| | |
|---|---|
| T1 | pre-op sample (before incision). |
| T2 | immediately before the heart gets stopped (prior to CPB). |
| T6 | 5 min after the heart went off CPB and was beating on its own again. |
| T7 | 30 min after bypass |
| T8 | 60 min after bypass |
| T9 | 120 min after bypass |

There were 6 plasma samples taken. Note that only 19 (out of 21) patients have samples at T9. The sample were normalized to total protein concentration for both targeted and de novo discovery. In the targeted analysis, 15 biomarkers were determined for each sample, specifically, CRP, GM-CSF, IFNγ, IL10, IL12p70, IL1β, IL-2, IL-6, IL-8, NT proBNP, SAA, TNFα, cTnI, sICAM, sVCAM. All time points were analyzed. These analyses were done using the MESOSCALE multiplex assay in triplicate. FIG. 7 shows the box blot for cTnI measurement for all patients. For de novo discovery, only T2 and T6 were analyzed.

B. Methods

1. High Abundant Protein Depletion

IgY depletion of the top 12 abundant proteins of samples from each individual sample.

2. Intact Protein Separation by Hydrophobicity

1DLC analysis was carried out for cohort II (20 patients with two time points). All 1DLC analyses were done in duplicate using the optimized gradient developed to eliminate the interference of the unknown contaminates that eluted at the beginning and end of the run. Optimization was required as the contaminants were not MS compatible and co-eluted with proteins found to be interesting in cohort I. The duplicate run for each patient time point were collected into a single plate and stored at −80° C. until analyzed. A total of 80 @ 1DLC runs were carried out (20×2×2=80 (2 time points, 20 patients, in duplicate)). The fractions obtained for each 1DLC run were pooled into 16 fractions, neutralized and dried down, prior to resolublization in buffer compatible for tryptic digestion.

3. MS Analysis

MS analysis for each digested fraction was carried using the LTQ Orbitrap LC MSMS instrument. Each fraction was run in duplicate. A total 1216 MS runs were carried out (19×2×16×2=1216 (19 patients, 16 fractions per time point, two time points, in duplicate). For LC-MS/MS experiments on the LTQ-Orbitrap (ThermoFinnigan, San Jose, Calif.), peptides were dissolved in 6 µl resuspension buffer (4% acetonitrile in water with 0.1% formic acid). Samples (3 µl were loaded onto a 75 um×10 cm BioBasic C18 column (New Objective, Woburn, Mass.). Peptides were eluted into an LTQ-Orbitrap (ThermoFinnigan, San Jose, Calif.) using an Agilent 1200 nano-LC system (Agilent, Santa Clara, Calif.). The HPLC gradient was 5% to 60% B (90% acetonitrile/water in 0.1% Formic acid) over 30 or 60 min depended on sample complexity. The mass spectrometer was operated in data-dependent mode in which every FT-MS scan (survey 350-2000 Da) was followed by MS/MS scans of the 5 most abundant ions.

Mass spectrometry data were analyzed, and data reanalysis was carried out, as described in Example 1D2 above.

C. Results

1. Optimization of 1DLC

In order for cohort II to be analyzed, optimization of the 1DLC gradient was required to resolve a contaminating peak eluting early on the chromatogram. The contaminating peak overlaid a region in which we found several potential biomarkers and resulted in suppression of the peptides of interest.

2. Optimization and Testing of Reproducibility of MS Analysis

In table 11, the MS reproducibility of several fractions is shown.

TABLE 11

MS reproducibility cohort II sequential. MS run 1 vs. run 2
Same LC fraction, digested, split and MS analyzed

| Method for cohort II<br>Fraction 1<br>Protein name | run 1<br># peptides<br>Fraction 1 | run 2<br># peptides<br>fraction 1 | run 1<br># total spectra<br>Fraction 1 | run 2<br># total spectra<br>Fraction 1 |
|---|---|---|---|---|
| histidine-rich glycoprotein | 14 | 13 | 35 | 32 |
| factor H | 12 | 11 | 27 | 24 |
| Kininogen 1 | 10 | 11 | 15 | 18 |
| complement component 4 binding protein | 8 | 10 | 14 | 19 |
| Lactoferrin | 7 | 8 | 16 | 14 |
| apolipoprotein H | 5 | 4 | 12 | 13 |
| Transferrin | 5 | 5 | 20 | 18 |
| alpha-1-acid glycoprotein 1 | 4 | 4 | 13 | 11 |
| haptoglobin | 3 | 4 | 6 | 7 |
| fibrinogen, alpha p | 3 | 3 | 5 | 5 |
| plasminogen | 3 | 3 | 6 | 6 |
| Alpha-1B-glycoprotein | 2 | 0 | 2 | 0 |
| alpha2-HS glycoprotein | 2 | 2 | 3 | 3 |
| collagen 1 pro-alpha-2 chain | 2 | 1 | 3 | 2 |
| selenoprotein P | 2 | 2 | 5 | 6 |
| Extracellular matrix protein 1 | 2 | 2 | 3 | 4 |
| Fraction 2<br>Protein name | # peptides<br>Fraction 2 | # peptides<br>Fraction 2 | # total spectra<br>Fraction 2 | # total spectra<br>Fraction 2 |
| complement component C4 | 27 | 26 | 49 | 47 |
| Antithrombin | 22 | 20 | 52 | 78 |
| complement component 3 | 22 | 24 | 42 | 50 |
| Fibronectin 1 | 21 | 24 | 38 | 55 |
| Ceruloplasmin | 19 | 21 | 49 | 52 |
| Inter-alpha-trypsin inhibitor heavy chain H4 | 14 | 12 | 29 | 25 |
| Inter-alpha-trypsin inhibitor heavy chain H2 | 13 | 15 | 29 | 30 |
| Alpha-1B-glycoprotein | 11 | 10 | 28 | 24 |
| Alpha1 Antichymotrypsin | 10 | 11 | 46 | 50 |
| Complement factor B | 9 | 11 | 23 | 28 |
| gelsolin isoform b | 9 | 9 | 19 | 16 |
| leucine-rich alpha-2-glycoprotein 1 | 9 | 7 | 28 | 16 |
| Inter-alpha-trypsin inhibitor heavy chain H1 | 9 | 8 | 28 | 37 |
| Kininogen | 8 | 10 | 18 | 20 |
| histidine-rich glycoprotein | 7 | 7 | 15 | 13 |
| apolipoprotein A-IV | 6 | 9 | 12 | 16 |
| alpha2-HS glycoprotein | 5 | 5 | 8 | 9 |
| peroxiredoxin 2 isoform | 5 | 4 | 10 | 19 |
| Transthyretin | 4 | 4 | 9 | 10 |
| complement component C6 | 4 | 2 | 13 | 4 |
| lumican | 3 | 3 | 14 | 5 |
| carboxypeptidase B2 isoform a preproprotein | 3 | 2 | 5 | 6 |
| apolipoprotein H precursor | 2 | 4 | 6 | 21 |
| Transferrin | 2 | 2 | 3 | 3 |
| amyloid P | 2 | 0 | 2 | 0 |
| alpha-1-microglobulin | 2 | 2 | 4 | 4 |
| Retinol binding protein 4 | 2 | 2 | 3 | 4 |
| complement component 8, alpha | 2 | 1 | 3 | 1 |
| serine or cysteine proteinase inhibitor | 2 | 2 | 2 | 2 |
| complement component 4 binding protein | 1 | 1 | 2 | 1 |
| hemoglobin | 1 | 0 | 3 | 0 |
| C9 complement protein | 1 | 0 | 2 | 0 |
| alpha-1-acid glycoprotein 1 | 0 | 0 | 0 | 0 |
| complement factor H-related 1 | 0 | 1 | 0 | 2 |
| alpha-1-antichymotrypsin | 0 | 2 | 0 | 8 |

3. Cohort II Analysis 343 non-redundant proteins were compared. Table 12 shows those proteins which were most significantly increased in T6 compared to T0 for cohort II.

TABLE 12

Target proteins in cohort II

Top hits from cohort II clustered based on related protein family. Below listed the number of individuals the protein was elevated in T6 compared to T2 (increased due to induced ischemia). 20 individuals were analyzed.

1. PRDX2 Peroxiredoxin 2 - increased in 17 patients
2. S100A9 Protein S100-A9 - increased in 17 patients
   S100 A8 - increased in 11 patients
   S100 A7- increased in 4 patients
3. Lactotransferrin increased in 14 patients
4. CA1 Carbonic anhydrase 1 - increased in 17 patients
   CA2 Carbonic anhydrase 2 - increased in 3 patients
5. Conserved hypothetical protein - increased in 12 patients
6. NCOR2 CTG26 alternate open reading frame (Fragment) - increased in 11 patients
7. LOC729968 Conserved hypothetical protein - increased in 11 patients
8. Conserved hypothetical protein - increased in 9 patients
9. SORL1 Sortilin-related receptor - increased in 11 patients
10. COL1A1 Collagen alpha-1(I) chain precursor - increased in 11 patients
    COL1A2 130 kDa protein - increased in 10 patients
11. CPB2 Isoform 1 of Carboxypeptidase B2 precursor - increased in 10 patients
    Carboxypeptidase subunit 2 - increased in 8 patients
12. HBB Hemoglobin subunit beta - increased in 12 patients
    HBA Hemoglobin subunit alpha - increased in 4 patients
13. Lactotransferrin - increased in 12 patients
14. LRP1 Prolow-density lipoprotein receptor-related protein 1 precursor - increased in 9 patients
    LRP2 Low-density lipoprotein receptor-related protein 2 precursor - increased in 9 patients
    Together a total of 13 unique patients
15. CAT Catalase - increased in 11 patients
16. STX3 Isoform A of Syntaxin-3 - increased in 9 patients
17. ECM1 Extracellular matrix protein 1 - increased in 10 patients
18. SERPINA10 Protein Z-dependent protease inhibitor precursor - increased in 8 patients
19. PTPRK Isoform 1 of Receptor-type tyrosine-protein phosphatase kappa precursor increased in 8 patients
20. ATRN Isoform 2 of Attractin precursor - increased in 8 patients
21. PTPRK Protein tyrosine phosphatase, receptor type, K increased in 6 patients Others of interest due to biology (there are low abundant proteins and may not be observed in higher number of patients due to detection issues)

22. MST1 Hepatocyte growth factor-like protein precursor - increased in 7 patients
    HGFAC Hepatocyte growth factor activator precursor - increased in 4 patients
23. IGFBP6 Insulin-like growth factor-binding protein 6 precursor - increased in 5 patients
    IGFBP5 Insulin-like growth factor-binding protein 5 precursor - increased in 1 patients
    IGFBP2 Insulin-like growth factor-binding protein 2 precursor - increased in 7 patients (same ones as 7)
    IGFBP7 Insulin-like growth factor-binding protein 7 precursor - increased in 7 patients (same ones as 2)
    IGFALS Insulin-like growth factor-binding protein complex acid labile chain precursor - increased in 3 patients
    Total for group 8 patients
24. SERPINF1 Pigment epithelium-derived factor precursor - increased in 4 patients
25. GPX3 Glutathione peroxidase 3 precursor - increased in 4 patients
26. CD14 Monocyte differentiation antigen CD14 precursor - increased in 4 patients
27. Note there are interesting proteins seen in 2-3 patients which may still be important alternations which are not seen in more patients due to their low abundance. These should be discussed.
    A summary of some of the properties of these proteins is presented in Example IV.

4. Cohort II and I Comparison
Comparison of the top candidate proteins between cohort I and II are shown in Table 13.

TABLE 13

| Protein | IPI number | Cohort I | Cohort II | FUNCTION | Is protein secreted? |
|---|---|---|---|---|---|
| Tier One | | | | | |
| Lumican | IPI00020986 | Top | Found | May be involved in cell response to injury | Yes |
| Extracellular matrix protein | IPI00645849 | Top | Found | Involved in extracellular matrix compostition | Yes |
| Carboxypeptidase N catalytic chain | IPI00010295 | Mid | Found | Protease involved in regulation of vasoactive and inflammatory peptides | Yes |
| angiogenin | IPI00008554 | Top | no | May be involved in angiogeneisis | Yes |
| semenogelin | IPI00414684 | Top | no | Forms gel matrix around sperm, unknown role in other cells | Yes |
| Lung PLNECA-1 | IPI00291410 | Top | no | May play a role in innate immunity | Yes |
| Perioxiredoxin 2 | IPI00027350 | No | Elevated in 17, Top | Involved in redox regulation of the cell. | No |
| S100 A9 | IPI00027462 | No | Elevated in 17, Top | Expressed by macrophages in acutely inflamed tissues and in chronic inflammations. | No |
| S100 A8 | IPI00007047 | No | Elevated in 11, Top | Expressed by macrophages in chronic inflammations. Also expressed in epithelial cells constitutively or induced during dermatoses. | unknown |
| S100 A7 | IPI00219806 | No | Elevated in 4, Lower | unknown | Secreted |
| Sortilin-related receptor | IPI00022608 | No | Elevated in 11, Mid | Likely to be a multifunctional endocytic receptor, which implicates it in the uptake of lipoproteins and of proteases. | No, is a plasma membrane protein |
| Catalase | IPI00465436 | No | Elevated in 11, Mid | Serves to protect cells from the toxic effects of hydrogen peroxide. | No |
| Low density lipoprotein receptor related protein 1 | IPI00020557 | No | Elevated in 9, Mid | Endocytic receptor involved in endocytosis and in phagocytosis of apoptotic cells. | No |
| Low density lipoprotein receptor related protein 2 | IPI00024292 | No | Elevated in 9, Top | Acts together with cubilin to mediate HDL endocytosis (By similarity). | No |
| Syntaxin-3 | IPI00395768 | No | Evelated in 9, Mid | Potentially involved in docking of synaptic vesicles at presynaptic active zones. | No |
| Tier two | | | | | |
| Hepatocyte growth factor like protein | IPI00292218 | | + | Unknown | Unknown |
| Hepatocyte growth factor activator | IPI00029193 | | + | Activates hepatocyte growth factor (HGF). | Secreted. |
| Insulin like growth factor protein 6 | IPI00029235 | | + | GF-binding proteins prolong the half-life of the IGFs. | Secreted. |
| Pigment epithelium-derived factor | IPI00006114 | | + | Neurotrophic protein; induces extensive neuronal differentiation in retinoblastoma cells. Potent inhibitor of angiogenesis. | Secreted. |
| Glutathione peroxidase 3 | IPI00026199 | | + | Protects cells and enzymes from oxidative damage. | Secreted. |
| Monocyte differentiation antigen CD14 | IPI00029260 | | + | Involved in the innate immune response to bacterial lipopolysaccharide (LPS). | No |
| Lactotransferrin, cDNA FLJ58679, highly similar to Lactotransferrin | IPI00789477 | | + | unknown | unknown |
| Attractin | IPI00162735 | | | Involved in the initial immune cell clustering during inflammatory response. | Secreted |
| Conserved hypothetical protein | IPI00883661 | | + | Unknown | Unknown |
| NCOR2 CTG26 | IPI00006659 | | + | unknown | unknown |

TABLE 13-continued

| Protein | IPI number | Cohort I | Cohort II | FUNCTION | Is protein secreted? |
|---|---|---|---|---|---|
| alternate open reading frame LOC729968 | IPI00884334 | | + | unknown | unknown |
| Conserved hypothetical protein Protein Z-dependent protease inhibitor | IPI00007199 | | + | Inhibits factor Xa activity. | Secreted. |
| Conserved hypothetical protein | IPI00847894 | | | unknown | unknown |
| Isoform 1 of Receptor-type tyrosine-protein phosphatase kappa | IPI00015756 | | + | Regulation of processes involving cell contact and adhesion such as growth control, tumor invasion, and metastasis. | No, but present on plasma membrane |
| Protein tyrosine phosphatase, receptor type, K | IPI00552690 | | + | Receptor | Unknown, but present on plasma membrane |
| Sodium channel subunit beta-4 | IPI00217376 | | Elevated in 7 people | Part of sodium channel | No, but present on plasma membrane |
| Alpha2-HS-glycoprotein | IPI00022431 | + | Elevated in 4 people | See previous write up for cohort I | See previous write up for cohort I |
| Galectin 7 | IPI00219221 | + | – | See previous write up for cohort I | See previous write up for cohort I |
| Hornerin | IPI00398625 | + | Elevated and seen only in one person | See previous write up for cohort I | See previous write up for cohort I |
| Proteoglycan 4 (isoforms A and D) | IPI00655676 | + | Elevated in 4 people | See previous write up for cohort I | See previous write up for cohort I |
| Proflaggrin (Filaggrin) | IPI00654788 | + | – | See previous write up for cohort I | See previous write up for cohort 1 |
| Vitamin D binding protein | IPI00555812 | + | – | See previous write up for cohort I | See previous write up for cohort 1 |
| C4b binding proteins | IPI00021727 | + | – | See previous write up for cohort I | See previous write up for cohort 1 |
| Thyroxine binding globulin | IPI00292946 | + | – | See previous write up for cohort I | See previous write up for cohort 1 |
| Alpha 2 glycoprotein 1, zinc | IPI00166729 | + | Elevated in 3 people | See previous write up for cohort I | See previous write up for cohort I |
| Caspase 14 | | | + | See previous write up for cohort I | See previous write up for cohort 1 |
| Desmogelin | | | + | See previous write up for cohort I | See previous write up for cohort 1 |
| Kininogen -1 | IPI00215894 | + | | See previous write up for cohort I | See previous write up for cohort I |

Some additional proteins were found to be elevated in a subset of the patients in cohort II that exhibit ischemia. See Table 14 below for details.

TABLE 14

| Protein name | Protein accession numbers | # individual with ischemic induced increase (max. 20) |
|---|---|---|
| PRDX2 Peroxiredoxin-2 | IPI00027350 | 17 |
| S100A9 Protein S100-A9 | IPI00027462 | 17 |

TABLE 14-continued

| Protein name | Protein accession numbers | # individual with ischemic induced increase (max. 20) |
|---|---|---|
| LTF Similar to Lactotransferrin | IPI00789477 | 14 |
| Conserved hypothetical protein | IPI00883661 | 12 |
| HBB Hemoglobin subunit beta | IPI00654755 | 12 |
| NCOR2 CTG26 alternate open reading frame | IPI00006659 | 11 |
| S100A8 Protein S100-A8 | IPI00007047 | 11 |
| SORL1 Sortilin-related receptor | IPI00022608 | 11 |
| CA1 Carbonic anhydrase 1 | IPI00215983 | 11 |
| COL1A1 Collagen alpha-1(I) chain | IPI00297646 | 11 |
| CAT Catalase | IPI00465436 | 11 |
| ALB Isoform 1 of Serum albumin | IPI00745872 | 11 |
| LOC729968 Conserved hypothetical protein | IPI00884334 | 11 |
| CFI Complement factor I | IPI00291867 | 10 |
| CPB2 Isoform 1 of Carboxypeptidase B2 | IPI00329775 | 10 |
| Ig heavy chain V-II region OU | IPI00382534 | 10 |
| Ig kappa chain V-I region Ka | IPI00387095 | 10 |
| COL1A2 130 kDa protein | IPI00873137 | 10 |
| ECM1 Extracellular matrix protein 1 | IPI00645849 | 10 |
| LRP1 Prolow-density lipoprotein receptor-related protein 1 | IPI00020557 | 9 |
| LRP2 Low-density lipoprotein receptor-related protein 2 | IPI00024292 | 9 |
| C7 Complement component C7 | IPI00296608 | 9 |
| STX3 Isoform A of Syntaxin-3 | IPI00395768 | 9 |
| SERPINA1 Isoform 1 of Alpha-1-antitrypsin | IPI00553177 | 9 |
| LOC440786 Ig kappa chain V-II region TEW | IPI00736885 | 9 |
| Conserved hypothetical protein | IPI00847894 | 9 |
| SERPINA10 Protein Z-dependent protease inhibitor | IPI00007199 | 8 |
| PTPRK Isoform 1 of Receptor-type tyrosine-protein phosphatase kappa | IPI00015756 | 8 |
| AMBP AMBP protein | IPI00022426 | 8 |
| TF Serotransferrin | IPI00022463 | 8 |
| C5 Complement C5 | IPI00032291 | 8 |
| ATRN Isoform 2 of Attractin | IPI00162735 | 8 |
| C1QB complement component 1, q subcomponent, B chain | IPI00477992 | 8 |
| CPN2 Carboxypeptidase N subunit 2 | IPI00479116 | 8 |
| SERPINA5 Plasma serine protease inhibitor | IPI00007221 | 7 |
| LUM Lumican | IPI00020986 | 7 |
| APOB Apolipoprotein B-100 | IPI00022229 | 7 |
| C1QC Complement C1q subcomponent subunit C | IPI00022394 | 7 |
| SHBG Isoform 1 of Sex hormone-binding globulin | IPI00023019 | 7 |
| SCN4B Isoform 1 of Sodium channel subunit beta-4 | IPI00217376 | 7 |
| MST1 Hepatocyte growth factor-like protein | IPI00292218 | 7 |
| MDFI 19 kDa protein | IPI00385435 | 7 |
| QSOX1 Isoform 2 of Sulfhydryl oxidase 1 | IPI00465016 | 7 |
| FETUB GUGU beta form | IPI00552199 | 7 |
| SEPP1 selenoprotein P isoform 2 | IPI00847381 | 7 |
| HBA2; HBA1 Alpha 2 globin variant (Fragment) | IPI00853068 | 7 |
| CPN1 Carboxypeptidase N catalytic chain | IPI00010295 | 6 |
| AFM Afamin | IPI00019943 | 6 |
| SOD1 Superoxide dismutase | IPI00218733 | 6 |
| VTN Vitronectin | IPI00298971 | 6 |
| SERPINA4 Kallistatin | IPI00328609 | 6 |
| SERPINA4 Kallistatin | IPI00328609 | 6 |
| PTPRK Protein tyrosine phosphatase, receptor type, K | IPI00552690 | 6 |
| SERPINA3 Isoform 1 of Alpha-1-antichymotrypsin | IPI00847635 | 6 |
| OU domain class 5 transcription factor 1 (Fragment) | IPI00868800 | 6 |
| ORM1 orosomucoid 1 | IPI00884926 | 6 |
| F12 Coagulation factor XII | IPI00019581 | 5 |
| APOA1 Apolipoprotein A-I | IPI00021841 | 5 |
| IGFBP6 Insulin-like growth factor-binding protein 6 | IPI00029235 | 5 |
| FN1 Isoform 3 of Fibronectin | IPI00339223 | 5 |
| g heavy chain V-III region CAM | IPI00382482 | 5 |
| LOC388720 similar to ubiquitin and ribosomal protein S27a | IPI00397808 | 5 |
| CLU clusterin isoform 1 | IPI00400826 | 5 |
| BTD Uncharacterized protein BTD (Fragment) | IPI00744685 | 5 |
| PROS1 80 kDa protein | IPI00873445 | 5 |
| SERPINF1 Pigment epithelium-derived factor | IPI00006114 | 4 |
| C8G Complement component C8 gamma chain | IPI00011261 | 4 |
| ORM1 Alpha-1-acid glycoprotein 1 | IPI00022429 | 4 |
| AHSG Alpha-2-HS-glycoprotein | IPI00022431 | 4 |
| GGH Gamma-glutamyl hydrolase | IPI00023728 | 4 |
| EFNB1 Ephrin-B1 | IPI00024307 | 4 |
| GPX3 Glutathione peroxidase 3 | IPI00026199 | 4 |
| HGFAC Hepatocyte growth factor activator | IPI00029193 | 4 |
| CD14 Monocyte differentiation antigen CD14 | IPI00029260 | 4 |

TABLE 14-continued

| Protein name | Protein accession numbers | # individal with ischemic induced increase (max. 20) |
|---|---|---|
| FGA Isoform 2 of Fibrinogen alpha chain | IPI00029717 | 4 |
| LRP1B Similar to Candidate tumor suppressor protein | IPI00032063 | 4 |
| S100A7 Protein S100-A7 | IPI00219806 | 4 |
| C8B Complement component C8 beta chain | IPI00294395 | 4 |
| DMXL1 DmX-like protein 1 | IPI00294728 | 4 |
| ARSB Arylsulfatase B | IPI00306576 | 4 |
| LRP8 Isoform 3 of Low-density lipoprotein receptor-related protein 8 | IPI00384247 | 4 |
| HBA2; HBA1 Hemoglobin subunit alpha | IPI00410714 | 4 |
| ASPN ASPN protein | IPI00418431 | 4 |
| A2M Alpha-2-macroglobulin | IPI00478003 | 4 |
| CDH3 Isoform 2 of Cadherin-3 | IPI00645614 | 4 |
| KLKB1 Plasma kallikrein | IPI00654888 | 4 |
| SERPINA1 Isoform 2 of Alpha-1-antitrypsin | IPI00790784 | 4 |
| ICAM2 28 kDa protein | IPI00793958 | 4 |
| C1RL cDNA FLJ14022 fis, clone HEMBA1003538, weakly similar to COMPLEMENT C1R COMPONENT | IPI00795055 | 4 |
| B2M B2M protein | IPI00796379 | 4 |
| APOA1 Apolipoprotein A1 | IPI00853525 | 4 |
| Transthyretin | IPI00855916 | 4 |
| ITIH3 Uncharacterized protein ITIH3 | IPI00873416 | 4 |
| MB 16 kDa protein | IPI00878623 | 4 |
| SERPINF2 Alpha-2-antiplasmin | IPI00879231 | 4 |
| COL5A2 Collagen alpha-2(V) chain | IPI00844306 | 4 |
| JUP Junction plakoglobin | IPI00554711 | 4 |
| PRG4 Isoform D of Proteoglycan-4 | IPI00655676 | 4 |
| GPR37 Probable G-protein coupled receptor 37 | IPI00006166 | 3 |
| F13B Coagulation factor XIII B chain | IPI00007240 | 3 |
| CLEC3B Tetranectin | IPI00009028 | 3 |
| C6 Complement component 6 | IPI00009920 | 3 |
| C8A Complement component C8 alpha chain | IPI00011252 | 3 |
| DSP Isoform DPI of Desmoplakin | IPI00013933 | 3 |
| COPS2 Isoform 2 of COP9 signalosome complex subunit 2 | IPI00018813 | 3 |
| F2 Prothrombin (Fragment) | IPI00019568 | 3 |
| IGFALS Insulin-like growth factor-binding protein complex acid labile chain | IPI00020996 | 3 |
| ACTG1 Actin, cytoplasmic 2 | IPI00021440 | 3 |
| FGA Isoform 1 of Fibrinogen alpha chain | IPI00021885 | 3 |
| RBP4 Plasma retinol-binding protein | IPI00022420 | 3 |
| RBP4 Retinol binding protein 4, plasma | IPI00022420 | 3 |
| HPX Hemopexin | IPI00022488 | 3 |
| NPR1 Atrial natriuretic peptide receptor A | IPI00027200 | 3 |
| SEPP1 Selenoprotein P | IPI00029061 | 3 |
| ZAK Isoform 2 of Mitogen-activated protein kinase kinase kinase MLT | IPI00029643 | 3 |
| CST3 Cystatin-C | IPI00032293 | 3 |
| AZGP1 alpha-2-glycoprotein 1, zinc | IPI00166729 | 3 |
| CA2 Carbonic anhydrase 2 | IPI00218414 | 3 |
| SELL L-selectin | IPI00218795 | 3 |
| FGG Isoform Gamma-A of Fibrinogen gamma chain | IPI00219713 | 3 |
| IGSF5 Immunoglobulin superfamily member 5 | IPI00245940 | 3 |
| LYVE1 Lymphatic vessel endothelial hyaluronic acid receptor 1 | IPI00290856 | 3 |
| SERPING1 Plasma protease C1 inhibitor | IPI00291866 | 3 |
| C17orf13; ACYP1; C1R Complement C1r subcomponent | IPI00296165 | 3 |
| F9 Coagulation factor IX | IPI00296176 | 3 |
| FGB Fibrinogen beta chain | IPI00298497 | 3 |
| LILRB2 leukocyte immunoglobulin-like receptor, subfamily B, member 2 isoform 1 | IPI00303952 | 3 |
| IGHG1 Putative uncharacterized protein DKFZp686N02209 | IPI00384938 | 3 |
| cDNA FLJ43303 fis, clone NOVAR2000136, moderately similar to Calsequestrin, skeletal muscle isoform | IPI00445889 | 3 |
| IGHM IGHM protein | IPI00472610 | 3 |
| PTGDS Prostaglandin D2 synthase 21 kDa | IPI00513767 | 3 |
| GC Vitamin D-binding protein | IPI00555812 | 3 |
| HP Haptoglobin | IPI00641737 | 3 |
| LCN2 Lipocalin 2, Neutrophil gelatinase-associated lipocalin | IPI00643623 | 3 |
| ITIH2 Inter-alpha (Globulin) inhibitor H2 | IPI00645038 | 3 |
| FETUB GUGU beta form, Fetuin-B | IPI00743766 | 3 |
| HABP2 Hyaluronan-binding protein 2 | IPI00746623 | 3 |
| C1S Uncharacterized protein C1S | IPI00749179 | 3 |
| LRP1B Low-density lipoprotein receptor-related protein 1B | IPI00877809 | 3 |
| SERPIND1 Heparin cofactor 2 | IPI00879573 | 3 |
| APOA4 Apolipoprotein A-IV | IPI00304273 | 3 |
| CDH22 Cadherin-22 | IPI00000436 | 2 |

TABLE 14-continued

| Protein name | Protein accession numbers | # individual with ischemic induced increase (max. 20) |
|---|---|---|
| TAF9 Transcription initiation factor TFIID subunit 9 | IPI00002993 | 2 |
| MBL2 Mannose-binding protein C | IPI00004373 | 2 |
| CRISP3 cDNA FLJ75207 | IPI00004798 | 2 |
| EFNA4 Isoform 1 of Ephrin-A4 | IPI00005125 | 2 |
| COMT Isoform Membrane-bound of Catechol O-methyltransferase | IPI00011284 | 2 |
| LRRC4C Netrin-G1 ligand | IPI00014223 | 2 |
| IGFBP7 Insulin-like growth factor-binding protein 7 | IPI00016915 | 2 |
| C1S Complement C1s subcomponent | IPI00017696 | 2 |
| GGT1 Isoform 1 of Gamma-glutamyltranspeptidase 1 | IPI00018901 | 2 |
| PLG Plasminogen | IPI00019580 | 2 |
| ORM2 Alpha-1-acid glycoprotein 2 | IPI00020091 | 2 |
| PLXNA3 Plexin-A3 | IPI00020884 | 2 |
| C4BPA C4b-binding protein alpha chain | IPI00021727 | 2 |
| SERPINB3 Serpin B3 | IPI00022204 | 2 |
| BAI1 Brain-specific angiogenesis inhibitor 1 | IPI00022333 | 2 |
| HRG Histidine-rich glycoprotein | IPI00022371 | 2 |
| APCS Serum amyloid P-component | IPI00022391 | 2 |
| C1QA Complement C1q subcomponent subunit A | IPI00022392 | 2 |
| C9 Complement component C9 | IPI00022395 | 2 |
| NRGN Neurogranin | IPI00022640 | 2 |
| CDH1 Epithelial cadherin | IPI00025861 | 2 |
| SOD3 Extracellular superoxide dismutase [Cu—Zn] | IPI00027827 | 2 |
| KNG1 Isoform HMW of Kininogen-1 | IPI00032328 | 2 |
| PTH2 Tuberoinfundibular peptide of 39 residues | IPI00059307 | 2 |
| PTPRU protein tyrosine phosphatase, receptor type, U isoform 3 | IPI00107472 | 2 |
| PTPRF Receptor-type tyrosine-protein phosphatase F | IPI00107831 | 2 |
| UBA52 ubiquitin and ribosomal protein L40 , UBB; RPS27A; UBC ubiquitin and ribosomal protein S27a | IPI00179330 | 2 |
| UBB; RPS27A; UBC ubiquitin and ribosomal protein S27a | IPI00179330 | 2 |
| TTN Isoform 7 of Titin | IPI00179357 | 2 |
| CLCN6 Isoform A of Chloride channel protein 6 | IPI00180121 | 2 |
| HIST1H1C Histone H1.2 | IPI00217465 | 2 |
| MB Myoglobin | IPI00217493 | 2 |
| HRC Sarcoplasmic reticulum histidine-rich calcium-binding protein | IPI00219226 | 2 |
| SP140 Isoform LYSp100-A of Nuclear body protein SP140 | IPI00219535 | 2 |
| PTPRO Receptor-type tyrosine-protein phosphatase O | IPI00241041 | 2 |
| CLU Clusterin | IPI00291262 | 2 |
| SLC44A2 Isoform 2 of Choline transporter-like protein 2 | IPI00293074 | 2 |
| ITIH4 Isoform 1 of Inter-alpha-trypsin inhibitor heavy chain H4 | IPI00294193 | 2 |
| IGFBP2 Insulin-like growth factor-binding protein 2 | IPI00297284 | 2 |
| LTF Growth-inhibiting protein 12 | IPI00298860 | 2 |
| LCN2 Neutrophil gelatinase-associated lipocalin | IPI00299547 | 2 |
| THBS4 Thrombospondin-4 | IPI00328550 | 2 |
| Ig heavy chain V-III region TEI | IPI00382494 | 2 |
| VASN Vasorin | IPI00395488 | 2 |
| FLG2 Ifapsoriasin | IPI00397801 | 2 |
| SEMG1 Isoform 2 of Semenogelin-1 | IPI00414684 | 2 |
| IGHG1 Putative uncharacterized protein DKFZp686N02209 | IPI00423466 | 2 |
| HUWE1 Isoform 2 of E3 ubiquitin-protein ligase HUWE1 | IPI00445401 | 2 |
| PTPRK Protein tyrosine phosphatase, receptor type, K | IPI00470937 | 2 |
| HP HP protein | IPI00478493 | 2 |
| FCGR3A Fc fragment of IgG, low affinity IIIa, receptor for | IPI00640044 | 2 |
| C2 Complement component 2 | IPI00643506 | 2 |
| CPN2 similar to Carboxypeptidase N subunit 2 | IPI00738433 | 2 |
| A1BG alpha 1 B-glycoprotein | IPI00745089 | 2 |
| LOC732428 Uncharacterized protein ENSP00000375150 | IPI00787862 | 2 |
| SOD1 Uncharacterized protein SOD1 | IPI00789078 | 2 |
| CLEC3B Putative uncharacterized protein DKFZp686H17246 | IPI00792115 | 2 |
| 8 kDa protein | IPI00792845 | 2 |
| FCGR3B Protein | IPI00795501 | 2 |
| C5 Complement component 5 variant (Fragment) | IPI00816741 | 2 |
| PRAP1 Isoform 4 of Proline-rich acidic protein 1 | IPI00855875 | 2 |
| SH3BGRL 13 kDa protein | IPI00872670 | 2 |

Example IV

Summary of Some of the Properties of Proteins Discussed with Regard to Cohort II A. Pigment Epithelium-Derived Factor
Name: PIGMENT EPITHELIUM-DERIVED FACTOR
IPI ID: IPI00006114
UniProtKB/Swiss-Prot ID: P36955
Length: 418 aa, molecular weight: 46342 Da
1. Basic Information from UniProtKB/Swiss-Prot Entry:

| | |
|---|---|
| FUNCTION | Neurotrophic protein; induces extensive neuronal differentiation in retinoblastoma cells. Potent inhibitor of angiogenesis. As it does not undergo the S (stressed) to R (relaxed) conformational transition characteristic of active serpins, it exhibits no serine protease inhibitory activity. |
| SUBCELLULAR LOCATION | Secreted. Melanosome. Note = Enriched in stage I melanosomes. |
| PTM | The N-terminus is blocked. Extracellular phosphorylation enhances antiangiogenic activity. |

2. Sequence:

(SEQ ID NO: 20)
MQALVLLLCIGALLGHSSCQNPASPPEEGSPDPDSTGALVEEEDPFFKV

PVNKLAAAVSNFGYDLYRVRSSMSPTTNVLLSPLSVATALSALSLGAEQR

TESIIHRALYYDLISSPDIHGTYKELLDTVTAPQKNLKSASRIVFEKKL

RIKSSFVAPLEKSYGTRPRVLTGNPRLDLQEINNWVQAQMKGKLARSTKE

IPDEISILLLGVAHFKGQWVTKFDSRKTSLEDFYLDEERTVRVPMMSDP

KAVLRYGLDSDLSCKIAQLPLTGSMSIIFFLPLKVTQNLTLIEESLTSE

FIHDIDRELKTVQAVLTVPKLKLSYEGEVTKSLQEMKLQSLFDSPDFS

KITGKPIKLTQVEHRAGFEWNEDGAGTTPSPGLQPAHLTFPLDYHLNQ

PFIFVLRDTDTGALLFIGKILDPRGP

3. Alternative Name(s): Serpin-F1, EPC-1
Has been used in treatment of retinal ischemic injury. As well, increased levels are observed with retinal diseases and diabetes but none have been related to heart disease including myocardial ischemia.

B. Protein S100-A7
Name: Protein S100-A7
IPI ID: IPI00219806
UniProtKB/Swiss-Prot ID: P31151
Length: 101 aa, molecular weight: 11471 Da
1. Basic Information from UniProtKB/Swiss-Prot Entry:

| | |
|---|---|
| Subcellular location | Cytoplasm. Secreted. |
| Subunit structure | Interacts with RANBP9. |

2. Sequence:

(SEQ ID NO: 21)
MSNTQAERSIIGMIDMFHKYTRRDDKIEKPSLLTMMKENFPNFLSACDK

KGTNYLADVFEKKDKNEDKKIDFSEFLSLLGDIATDYHKQSHGAAPCS

GGSQ

3. Alternative Name(s): S100 Calcium-binding Protein A7; Psoriasin
This protein has not been linked to myocardial ischemia or events leading up to MI.

C. Protein S100-A8
Name: Protein S100 A8
IPI ID: IPI00007047
UniProtKB/Swiss-Prot ID: P05109
Length: 93 aa, molecular weight: 10835 Da
1. Basic Information from UniProtKB/Swiss-Prot Entry:
Function: Expressed by macrophages in chronic inflammations. Also expressed in epithelial cells constitutively or induced during dermatoses. May interact with components of the intermediate filaments in monocytes and epithelial cells.
2. Sequence:

(SEQ ID NO: 22)
MLTELEKALNSIIDVYHKYSLIKGNFHAVYRDDLKKLLETECPQYIRKK

GADVWFKELDINTDGAVNFQEFLILVIKMGVAAHKKSHEESHKE

3. Alternative Name(s):
S100 calcium-binding protein A8
   Calgranulin-A
   Migration inhibitory factor-related protein 8
      Short name=MRP-8
      Short name=P8
   Cystic fibrosis antigen
      Short name=CFAG
   Leukocyte L1 complex light chain
   Calprotectin L1L subunit
   Urinary stone protein band A
   This protein has not been linked to myocardial ischemia or events leading up to MI.

D. Protein S100-A9
Name: PROTEIN S100-A9
IPI ID: IPI00027462
UniProtKB/Swiss-Prot ID: P06702
Length: 114 aa, molecular weight: 13242 Da
1. Basic Information from UniProtKB/Swiss-Prot Entry:
Function: Expressed by macrophages in acutely inflammated tissues and in chronic inflammations. Seem to be an inhibitor of protein kinases. Also expressed in epithelial cells constitutively or induced during dermatoses. May interact with components of the intermediate filaments in monocytes and epithelial cells.
Subcellular location: cytoplasm and nucleus.
2. Sequence:

(SEQ ID NO: 23)
MTCKMSQLERNIETIINTFHQYSVKLGHPDTLNQGEFKELVRKDLQNFL

KKENKNEKVIEHIMEDLDTNADKQLSFEEFIMLMARLTWASHEKMHE

GDEGPGHHHKPGLGEGTP

3. Alternative Name(s):
   Full=S 100 calcium-binding protein A9;
   Full=Calgranulin-B;
   Full=Migration inhibitory factor-related protein 14;
   Short=MRP-14;
   Short=P14;
   Full=Leukocyte L1 complex heavy chain;
   Full=Calprotectin L1H subunit;
   The mRNA levels of 5100 A9 have been shown to increase after ischemic brain injury and after stroke. The protein level was not determined. This protein has not been linked to myocardial ischemia or events leading up to MI.

E. Protein Tyrosine Phosphatase, Receptor Type, K
Name: PROTEIN TYROSINE PHOSPHATASE, RECEPTOR TYPE, K
IPI ID: IPI00552690
UniProtKB/TrEMBL ID: Q5JY45
Length: 202 aa, molecular weight: 22792 Da
Sequence:

(SEQ ID NO: 24)
MSSVEKETKTQCVRIATKAAATEEPEVIPDPAKQTDRVVKIAGISAGI

LVFILLLLVVILIVKKRRSYYSYSYYLKLAKKRKDAMGNTRQEMTHMVN

AMDRSYADQSTLHAEDPLSITFMDQHNFSPRLPNDPLVPTAVLDEN

HSATAESSRLLDVPRYLCEGTESPYQTGQLHPAIRVADLLQHINLMK

TSDSYGFKEEYE

This protein has not been linked to myocardial ischemia or events leading up to MI.

F. Protein Z-dependent Protease Inhibitor
Name: Protein Z-dependent protease inhibitor
IPI ID: IPI00007199
UniProtKB/Swiss-Prot ID: Q9UK55
Length: 484 aa, molecular weight: 55114 Da (of Precursor)
1. Basic Information from UniProtKB/Swiss-Prot Entry:

| FUNCTION | Inhibits factor Xa activity in the presence of protein Z, calcium and phospholipid. |
|---|---|
| SUBCELLULAR LOCATION | Secreted. |

2. Sequence:

(SEQ ID NO: 25)
MSRSTQELLGYHCRLQDKLQEQEGSLAAEGRHSLASAADHMKVVPSLLL

SVLLAQVWLVPGLAPSPQSPETPAPQNQTSRVVQAPKEEEEDEQEASEE

KASEEEKAWLMASRQQLAKETSNFGFSLLRKISMRHDGNMVFSPFGMSL

AMTGLMLGATGPTETQIKRGLHLQALKPTKPGLLPSLFKGLRETLSRNLE

LGLTQGSFAFIHKDFDVKETFFNLSKRYFDTECVPMNFRNASQAKRLMN

HYINKETRGKIPKLFDEINPETKLILVDYILFKGKWLTPFDPVFTEVDTF

HLDKYKTIKVPMMYGAGKFASTFDKNFRCHVLKLPYQGNATMLVVLMEK

MGDHLALEDYLTTDLVETWLRNMKTRNMEVFFPKFKLDQKYEMHELL

RQMGIRRIFSPFADLSELSATGRNLQVSRVLQRTVIEVDERGTEAVAGIL

SEITAYSMPPVIKVDRPFHFMIYEETSGMLLFLGRVVNPTLL

3. Alternative Name(s): Serpin A10

Protein Z was recently shown to act as an essential cofactor for protein Z-dependent protease inhibitor, a potent down-regulator of coagulation Factor Xa. Low levels of protein Z have been correlated with increased risk of stroke. However, protein Z dependent protease inhibitor was not studied. This protein has not been linked to myocardial ischemia or events leading up to MI.

G. Sodium Channel Subunit Beta-4
Name: ISOFORM 10F SODIUM CHANNEL SUBUNIT BETA-4
IPI ID: IPI00217376
UniProtKB/Swiss-Prot ID: Q81WT1-1
Length: 228 aa, molecular weight: 24969 Da (of Precursor)
1. Basic Information from UniProtKB/Swiss-Prot Entry:

| FUNCTON | Modulates channel gating kinetics. Causes negative shifts in the voltage dependence of activation of certain alpha sodium channels, but does not affect the voltage dependence of inactivation (By similarity). |
|---|---|
| SUBCELLULAR LOCATION | Membrane; Single-pass type I membrane protein (Probable). |

2. Sequence:

(SEQ ID NO: 26)
MPGAGDGGKAPARWLGTGLLGLFLLPVTLSLEVSVGKATDIYAVNGT

EILLPCTFSSCFGFEDLHFRWTYNSSDAFKILIEGTVKNEKSDPKVTLK

DDDRITLVGSTKEKMNNISIVLRDLEFSDTGKYTCHVKNPKENNLQHH

ATIFLQVVDRLEEVDNTVTLIILAVVGGVIGLLILILLIKKLIIFILKKT

REKKKECLVSSSGNDNTENGLPGSKAEEKPPSKV

This protein has not been linked to myocardial ischemia or events leading up to MI.

H. Sortilin-Related Receptor
Name: SORTILIN-RELATED RECEPTOR
IPI ID: IPI00022608
UniProtKB/Swiss-Prot ID: Q92673
Length: 2214 aa, molecular weight: 248441 Da (of Precursor)
1. Basic Information from UniProtKB/Swiss-Prot Entry:

| FUNTION | Likely to be a multifunctional endocytic receptor, that may be implicated in the uptake of lipoproteins and of proteases. Binds LDL, the major cholesterol-carrying lipoprotein of plasma, and transports it into cells by endocytosis. Binds the receptor-associated protein (RAP). Could play a role in cell-cell interaction. |
|---|---|
| SUBCELLULAR LOCATION | Membrane; Single-pass type I membrane protein (Potential). |

2. Sequence:

(SEQ ID NO: 27)
MATRSSRRESRLPFLFTLVALLPPGALCEVWTQRLHGGSAPLPQDRGFLV

VQGDPRELRLWARGDARGASRADEKPLRRKRSAALQPEPIKVYGQVSLND

SHNQMVVHWAGEKSNVIVALARDSLALARPKSSDVYVSYDYGKSFKKISD

KLNFGLGNRSEAVIAQFYHSPADNKRYIFADAYAQYLWITFDFCNTLQGF

SIPFRAADLLLHSKASNLLLGFDRSHPNKQLWKSDDFGQTWIMIQEHVKS

FSWGIDPYDKPNTIYIERHEPSGYSTVFRSTDFFQSRENQEVILEEVRDF

QLRDKYMFATKVVHLLGSEQQSSVQLWVSFGRKPMRAAQFVTRHPINEYY

IADASEDQVFVCVSHSNNRTNLYISEAEGLKFSLSLENVLYYSPGGAGSD

TLVRYFANEPFADFHRVEGLQGVYIATLINGSMNEENMRSVITFDKGGTW

EFLQAPAFTGYGEKINCELSQGCSLHLAQRLSQLLNLQLRRMPILSKESA

PGLIIATGSVGKNLASKTNVYISSSAGARWREALPGPHYYTWGDHGGIIT

AIAQGMETNELKYSTNEGETWKTFIFSEKPVFVYGLLTEPGEKSTVFTIF

GSNKENVHSWLILQVNATDALGVPCTENDYKLWSPSDERGNECLLGHKTV

FKRRTPHATCFNGEDFDRPVVVSNCSCTREDYECDFGFKMSEDLSLEVCV

-continued

```
PDPEFSGKSYSPPVPCPVGSTYRRTRGYRKISGDTCSGGDVEARLEGELV

PCPLAEENEFILYAVRKSIYRYDLASGATEQLPLTGLRAAVALDFDYEHN

CLYWSDLALDVIQRLCLNGSTGQEVIINSGLETVEALAFEPLSQLLYWVD

AGFKKIEVANPDGDFRLTIVNSSVLDRPRALVLVPQEGVMFWTDWGDLKP

GIYRSNMDGSAAYHLVSEDVKWPNGISVDDQWIYWTDAYLECIERITFSG

QQRSVILDNLPHPYAIAVFKNEIYWDDWSQLSIFRASKYSGSQMEILANQ

LTGLMDMKIFYKGKNTGSNACVPRPCSLLCLPKANNSRSCRCPEDVSSSV

LPSGDLMCDCPQGYQLKNNTCVKEENTCLRNQYRCSNGNCINSIWWCDFD

NDCGDMSDERNCPTTICDLDTQFRCQESGTCIPLSYKCDLEDDCGDNSDE

SHCEMHQCRSDEYNCSSGMCIRSSWVCDGDNDCRDWSDEANCTAIYHTCE

ASNFQCRNGHCIPQRWACDGDTDCQDGSDEDPVNCEKKCNGFRCPNGTCI

PSSKHCDGLRDCSDGSDEQHCEPLCTHFMDFVCKNRQQCLFHSMVCDGII

QCRDGSDEDAAFAGCSQDPEFHKVCDEFGFQCQNGVCISLIWKCDGMDDC

GDYSDEANCENPTEAPNCSRYFQFRCENGHCIPNRWKCDRENDCGDWSDE

KDCGDSHILPFSTPGPSTCLPNYYRCSSGTCVMDTWVCDGYRDCADGSDE

EACPLLANVTAASTPTQLGRCDRFEFECHQPKTCIPNWKRCDGHQDCQDG

RDEANCPTHSTLTCMSREFQCEDGEACIVLSERCDGFLDCSDESDEKACS

DELTVYKVQNLQWTADFSGDVTLTWMRPKKMPSASCVYNVYYRVVGESIW

KTLETHSNKTNTVLKVLKPDTTYQVKVQVQCLSKAHNTNDFVTLRTPEGL

PDAPRNLQLSLPREAEGVIVGHWAPPIHTHGLIREYIVEYSRSGSKMWAS

QRAASNFTEIKNLLVNTLYTVRVAAVTSRGIGNWSDSKSITTIKGKVIPP

PDIHIDSYGENYLSFTLTMESDIKVNGYVVNLFWAFDTHKQERRTLNFRG

SILSHKVGNLTAHTSYEISAWAKTDLGDSPLAFEHVMTRGVRPPAPSLKA

KAINQTAVECTWTGPRNVVYGIFYATSFLDLYRNPKSLTTSLHNKTVIVS

KDEQYLFLVRVVVPYQGPSSDYVVVKMIPDSRLPPRHLHVVHTGKTSVVI

KWESPYDSPDQDLLYAIAVKDLIRKTDRSYKVKSRNSTVEYTLNKLEPGG

KYHIIVQLGNMSKDSSIKITTVSLSAPDALKIITENDHVLLFWKSLALKE

KHFNESRGYEIHMFDSAMNITAYLGNTTDNFFKISNLKMGHNYTFTVQAR

CLFGNQICGEPAILLYDELGSGADASATQAARSTDVAAVVVPILFLILLS

LGVGFAILYTKHRRLQSSFTAFANSHYSSRLGSAIFSSGDDLGEDDEDAP

MITGFSDDVPMVIA
```

3. Alternative Name(s):

Sorting protein-related receptor containing LDLR class A repeats

Short name=SorLA

SorLA-1

Low-density lipoprotein receptor relative with 11 ligand-binding repeats

Short name=LDLR relative with 11 ligand-binding repeats

Short name=LR11

This protein has not been linked to myocardial ischemia or events leading up to MI.

I. Conserved Hypothetical Protein

Name Conserved hypothetical protein
IPI ID: IPI00884334
Length: 168 aa, molecular weight: 18798 Da
Sequence:

(SEQ ID NO: 28)
```
MRSFLLVWKLFRRKDMKHQRKTATEFKTTEEGETRQDGKDGSLTYRADT

CSPCPEAGGPPSSSIASGSSISVGNSPSHSHSHTSRRCGGSSRSRECCS

SLHSSRGSRGSSWSSSPPGSTCRWCSCHSHHHSHHRSHHRSHHCSHH

HSHHHSGHHSHHNFHNHSNPWCQ
```

This protein has not been linked to myocardial ischemia or events leading up to MI.

J. Catalase

Name: Catalase
IPI ID: IPI00465436
UniProtKB/Swiss-Prot ID: P04040
Length: 527 aa, molecular weight: 59756 Da

1. Basic Information from UniProtKB/Swiss-Prot Entry:

| | |
|---|---|
| Function | Occurs in almost all aerobically respiring organisms and serves to protect cells from the toxic effects of hydrogen peroxide. Promotes growth of cells including T-cells, B-cells, myeloid leukemia cells, melanoma cells, mastocytoma cells and normal and transformed fibroblast cells. |
| Subcellular location | Peroxisome. |

2. Sequence:

(SEQ ID NO: 29)
```
MADSRDPASDQMQHWKEQRAAQKADVLTTGAGNPVGDKLNVITVGPRG

PLLVQDVVFTDEMAHFDRERIPERVVHAKGAGAFGYFEVTHDITKYSKAK

VFEHIGKKTPIAVRFSTVAGESGSADTVRDPRGFAVKFYTEDGNWDLVGN

NTPIFFIRDPILFPSFIHSQKRNPQTHLKDPDMVWDFWSLRPESLHQVSF

LFSDRGIPDGHRHMNGYGSHTFKLVNANGEAVYCKFHYKTDQGIKNLSVE

DAARLSQEDPDYGIRDLFNAIATGKYPSWTFYIQVMTFNQAETFPFNPFD

LTKVWPHKDYPLIPVGKLVLNRNPVNYFAEVEQIAFDPSNMPPGIEASPD

KMLQGRLFAYPDTHRHRLGPNYLHIPVNCPYRARVANYQRDGPMCMQDN

QGGAPNYYPNSFGAPEQQPSALEHSIQYSGEVRRFNTANDDNVTQVRAF

YVNVLNEEQRKRLCENIAGHLKDAQIFIQKKAVKNFTEVHPDYGSHIQA

LLDKYNAEKPKNAIHTFVQSGSHLAAREKANL
```

Catalase is an important enzyme in the heart's regulation of oxidative stress. It has been linked to preconditioning in the heart tissue. As a serum marker, it has not been linked to myocardial ischemia or events leading up to MI.

K. Conserved Hypothetical Protein

Name: Conserved hypothetical protein
IPI ID: IPI00883661
UniProt/TrEMBL ID: A6NFT5
Length: 175 aa, molecular weight: 20933 Da

2. Sequence:

(SEQ ID NO: 30)
```
MNIHIHTCMHIYTHAHTHAHIHTCIHTHTHMHTHTLTYTHIHMHTHTQTH

IYTQAHIHSCTQINIYTYAYTLTCTQTHTHICTHAHTLTYTHIHTCTYKR
```

TYIQGHIHTHMHTYTCTCTHTHKHIHAHIHIHTHTHIYTHTDAYTHMDTY

THTYPHTHICIHSHTHAHTYTHIRT

This protein has not been linked to myocardial ischemia or events leading up to MI.

L. Glutathione peroxidase 3
Name: Glutathione peroxidase 3
IPI ID: IPI00026199
UniProtKB/Swiss-Prot ID: P22352
Length: 226 aa, molecular weight: 25505 Da
1. Basic Information from UniProtKB/Swiss-Prot Entry:

| FUNCTION | Protects cells and enzymes from oxidative damage, by catalyzing the reduction of hydrogen peroxide, lipid peroxides and organic hydroperoxide, by glutathione. |
|---|---|
| SUBCELLULAR LOCATION | Secreted. |
| TISSUE SPECIFICITY | Secreted in plasma. |

2. Sequence:

(SEQ ID NO: 31)
MARLLQASCLLSLLLAGFVSQSRGQEKSKMDCHGGISGTIYEYGALTIDG

EEYIPFKQYAGKYVLFVNVASYCGLTGQYIELNALQEELAPFGLVILGFP

CNQFGKQEPGENSEILPTLKYVRPGGGFVPNFQLFEKGDVNGEKEQKFYT

FLKNSCPPTSELLGTSDRLFWEPMKVHDIRWNFEKFLVGPDGIPIMRWHH

RTTVSNVKMDILSYMRRQAALGVKRK

3. Alternative Name(s):
   GSHPx-3
      Short name=GPx-3
   Extracellular glutathione peroxidase
   Plasma glutathione peroxidase
   GSHPx-P
      Short name=GPx-P GPx 3 is an important enzyme involved in many cells regulation of oxidative stress. As a serum marker it has not been linked to myocardial ischemia or events leading up to MI.

M. Hepatocyte Growth Factor Activator
Name: HEPATOCYTE GROWTH FACTOR ACTIVATOR
IPI ID: IPI00029193
UniProtKB/Swiss-Prot ID: Q04756
Length: 655 aa, molecular weight: 70682 Da (of Precursor)
1. Basic Information from UniProtKB/Swiss-Prot Entry:

| FUNCTION | Activates hepatocyte growth factor (HGF) by converting it from a single chain to a heterodimeric form. |
|---|---|
| SUBCELLULAR LOCATION | Secreted. Note = Secreted as an inactive single-chain precursor and is then activated to a heterodimeric form. |

2. Sequence:

(SEQ ID NO: 32)
MGRWAWVPSPWPPPGLGPFLLLLLLLLLLPRGFQPQPGGNRTESPEPNAT

ATPAIPTILVTSVTSETPATSAPEAEGPQSGGLPPPPRAVPSSSSPQAQA

LTEDGRPCRFPFRYGGRMLHACTSEGSAHRKWCATTHNYDRDRAWGYCVE

ATPPPGGPAALDPCASGPCLNGGSCSNTQDPQSYHCSCPRAFTGKDCGTE

KCFDETRYEYLEGGDRWARVRQGHVEQCECFGGRTWCEGTRHTACLSSPC

LNGGTCHLIVATGTTVCACPPGFAGRLCNIEPDERCFLGNGTGYRGVAST

SASGLSCLAWNSDLLYQELHVDSVGAAALLGLGPHAYCRNPDNDERPWCY

VVKDSALSWEYCRLEACESLTRVQLSPDLLATLPEPASPGRQACGRRHKK

RTFLRPRIIGGSSSLPGSHPWLAAIYIGDSFCAGSLVHTCWVVSAAHCFS

HSPPRDSVSVVLGQHFFNRTTDVTQTFGIEKYIPYTLYSVFNPSDHDLVL

IRLKKKGDRCATRSQFVQPICLPEPGSTFPAGHKCQIAGWGHLDENVSGY

SSSLREALVPLVADHKCSSPEVYGADISPNMLCAGYFDCKSDACQGDSGG

PLACEKNGVAYLYGIISWGDGCGRLHKPGVYTRVANYVDWINDRIRPPRR

LVAPS

This protein has not been linked to myocardial ischemia or events leading up to MI.

N. Hepatocyte Growth Factor-Like Protein Homolog
Name: HEPATOCYTE GROWTH FACTOR-LIKE PROTEIN HOMOLOG
IPI ID: IPI00292218
UniProtKB/TrEMBL ID: B7Z557
Length: 697 aa, molecular weight: 78787 Da
Sequence:

(SEQ ID NO: 33)
MLRGPCSPLNDFQVLRGTELQHLLHAVVPGPWQEDVADAEECAGRCGPLM

DCRAFHYNVSSHGCQLLPWTQHSPHTRLRRSGRCDLFQKKDYVRTCIMNN

GVGYRGTMATTVGGLPCQAWSHKFPNDHKYTPTLRNGLEENFCRNPDGDP

GGPWCYTTDPAVRFQSCGIKSCREAACVWCNGEEYRGAVDRTESGRECQR

WDLQHPHQHPFEPGKFLDQGLDDNYCRNPDGSERPWCYTTDPQIEREFCD

LPRCGSEAQPRQEATTVSCFRGKGEGYRGTANTTTAGVPCQRWDAQIPHQ

HRFTPEKYACKDLRENFCRNPDGSEAPWCFTLRPGMRAAFCYQIRRCTDD

VRPQDCYHGAGEQYRGTVSKTRKGVQCQRWSAETPHKPQFTFTSEPHAQL

EENFCRNPDGDSHGPWCYTMDPRTPFDYCALRRCADDQPPSILDPPDQVQ

FEKCGKRVDRLDQRRSKLRVVGGHPGNSPWTVSLRNRQGQHFCGGSLVKE

QWILTARQCFSSCHMPLTGYEVWLGTLFQNPQHGEPSLQRVPVAKMVCGP

SGSQLVLLKLERSVTLNQRVALICLPPEWYVVPPGTKCEIAGWGETKGTG

NDTVLNVALLNVISNQECNIKHRGRVRESEMCTEGLLAPVGACEGDYGGP

LACFTHNCWVLEGIIIPNRVCARSRWPAVFTRVSVFVDWIHKVMRLG

This protein has not been linked to myocardial ischemia or events leading up to MI O. Insulin-Like Growth Factor-Binding Protein 6
Name: INSULIN-LIKE GROWTH FACTOR-BINDING PROTEIN 6
IPI ID: IPI00029235
UniProtKB/Swiss-Prot ID: P24592
Length: 240 aa, molecular weight: 25322 Da (of Precursor)
1. Basic Information from UniProtKB/Swiss-Prot Entry:

| FUNCTION | IGF-binding proteins prolong the half-life of the IGFs and have been shown to either inhibit or stimulate the growth promoting effects of the IGFs on cell culture. |
|---|---|

| | They alter the interaction of IGFs with their cell surface receptors. |
|---|---|
| SUBCELLULAR LOCATION | Secreted. |

2. Sequence:

(SEQ ID NO: 34)
MTPHRLLPPLLLLLALLLAASPGGALARCPGCGQGVQAGCPGGCVEEEDG

GSPAEGCAEAEGCLRREGQECGVYTPNCAPGLQCHPPKDDEAPLRALLLG

RGRCLPARAPAVAEENPKESKPQAGTARPQDVNRRDQQRNPGTSTTPSQP

NSAGVQDTEMGPCRRHLDSVLQQLQTEVYRGAQTLYVPNCDHRGFYRKRQ

CRSSQGQRRGPCWCVDRMGKSLPGSPDGNGSSSCPTGSSG

3. Synonym: IBP-6

In a swine model of myocardial injury, studied at 3-24, 72, or 168 hrs, it was shown that there was an increased level of mRNA of IGFBP-6 at all time points. In situ hybridisation identified myocytes as the main producers of IGFBP-6 mRNA. However, the protein itself was not investigated. As well, this protein was found to be elevated in a young multiple myeloma patient with high-output cardiac failure. To date, there has been no study indicating the association of this protein with myocardial ischemia or events leading up to MI.

P. Conserved Hypothetical Protein
Name: Conserved hypothetical protein
IPI ID: IPI00847894
Length: 88 aa, molecular weight: 9931 Da
Sequence:

(SEQ ID NO: 35)
MFTLRLFAGKACWPVLYTMLKEVTCDVCVCVRARACTCMCMCVCECMDVC

VRLYTMLKEVTCDMCVCARTCVHVCVSAWMCVCTCTQC

This protein has not been linked to myocardial ischemia or events leading up to MI.

Q. Isoform 1 of Receptor-Type Tyrosine-Protein Phosphatase Kappa
Name: ISOFORM 10F RECEPTOR-TYPE TYROSINE-PROTEIN PHOSPHATASE KAPPA
IPI ID: IPI00015756
UniProtKB/Swiss-Prot ID: Q15262-1
Length: 1439 aa, molecular weight: 162102 Da (of Precursor)
1. Basic Information from UniProtKB/Swiss-Prot Entry:

| FUNCTION | Regulation of processes involving cell contact and adhesion such as growth control, tumor invasion, and metastasis. Forms complexes with beta-catenin and gamma-catenin/plakoglobin. Beta-catenin may be a substrate for the catalytic activity of PTP-kappa. |
|---|---|
| SUBCELLULAR LOCATION | Cell junction, adherens junction. Cell membrane; Single-pass type I membrane protein. |

2. Sequence:

(SEQ ID NO: 36)
MDTTAAAALPAFVALLLLSPWPLLGSAQGQFSAGGCTFDDGPGACDYHQD

LYDDFEWVHVSAQEPHYLPPEMPQGSYMIVDSSDHDPGEKARLQLPTMKE

NDTHCIDFSYLLYSQKGLNPGTLNILVRVNKGPLANPIWNVTGFTGRDWL

RAELAVSTFWPNEYQVIFEAEVSGGRSGYIAIDDIQVLSYPCDKSPHFLR

LGDVEVNAGQNATFQCIATGRDAVHNKLWLQRRNGEDIPVAQTKNINHRR

FAASFRLQEVTKTDQDLYRCVTQSERGSGVSNFAQLIVREPPRPIAPPQL

LGVGPTYLLIQLNANSIIGDGPIILKEVEYRMTSGSWTETHAVNAPTYKL

WHLDPDTEYEIRVLLTRPGEGGTGLPGPPLITRTKCAEPMRTPKTLKIAE

IQARRIAVDWESLGYNITRCHTFNVTICYHYFRGHNESKADCLDMDPKAP

QHVVNHLPPYTNVSLKMILTNPEGRKESEETIIQTDEDVPGPVPVKSLQG

TSFENKIFLNWKEPLDPNGIITQYEISYSSIRSFDPAVPVAGPPQTVSNL

WNSTHHVFMHLHPGTTYQFFIRASTVKGFGPATAINVTTNISAPTLPDYE

GVDASLNETATTITVLLRPAQAKGAPISAYQIVVEELHPHRTKREAGAME

CYQVPVTYQNAMSGGAPYYFAAELPPGNLPEPAPFTVGDNRTYQGFWNPP

LAPRKGYNIYFQAMSSVEKETKTQCVRIATKAATEEPEVIPDPAKQTDRV

VKIAGISAGILVFILLLLVVILIVKKSKLAKKRKDAMGNTRQEMTHMVNA

MDRSYADQSTLHAEDPLSITFMDQHNFSPRYENHSATAESSRLLDVPRYL

CEGTESPYQTGQLHPAIRVADLLQHINLMKTSDSYGFKEEYESFFEGQSA

SWDVAKKDQNRAKNRYGNIIAYDHSRVILQPVEDDPSSDYINANYIDGYQ

RPSHYIATQGPVHETVYDFWRMIWQEQSACIVMVTNLVEVGRVKCYKYWP

DDTEVYGDFKVTCVEMEPLAEYVVRTFTLERRGYNEIREVKQFHFTGWPD

HGVPYHATGLLSFIRRVKLSNPPSAGPIVVHCSAGAGRTGCYIVIDIMLD

MAEREGVVDIYNCVKALRSRRINMVQTEEQYIFIHDAILEACLCGETAIP

VCEFKAAYFDMIRIDSQTNSSHLKDEFQTLNSVTPRLQAEDCSIACLPRN

HDKNRFMDMLPPDRCLPFLITIDGESSNYINAALMDSYRQPAAFIVTQYP

LPNTVKDFWRLVYDYGCTSIVMLNEVDLSQGCPQYWPEEGMLRYGPIQVE

CMSCSMDCDVINRIFRICNLTRPQEGYLMVQQFQYLGWASHREVPGSKRS

FLKLILQVEKWQEECEEGEGRTIIHCLNGGGRSGMFCAIGIVVEMVKRQN

VVDVFHAVKTLRNSKPNMVEAPEQYRFCYDVALEYLESS

This protein has not been linked to myocardial ischemia or events leading up to MI.

R. Isoform 2 of Attractin
Name: ISOFORM 20F ATTRACTIN
IPI ID: IPI00162735
UniProtKB/Swiss-Prot ID: O75882-2
Length: 1272 aa, molecular weight: 141429 Da (of Precursor)
1. Basic Information from UniProtKB/Swiss-Prot Entry:

| FUNCTION | Involved in the initial immune cell clustering during inflammatory response and may regulate chemotactic activity of chemokines. May play a role in melanocortin signaling pathways that regulate energy homeostasis and hair color. Low-affinity receptor for agouti (By similarity). Has a critical role in normal myelination in the central nervous system (By similarity). |
|---|---|
| SUBCELLULAR LOCATION | Secreted. |

2. Sequence:

```
                                        (SEQ ID NO: 37)
MVAAAAATEARLRRRTAATAALAGRSGGPHWDWDVTRAGRPGLGAGLRLP

RLLSPPLRPRLLLLLLLLSPPLLLLLLPCEAEAAAAAAAVSGSAAAEAKE

CDRPCVNGGRCNPGTGQCVCPAGWVGEQCQHCGGRFRLTGSSGFVTDGPG

NYKYKTKCTWLIEGQPNRIMRLRFNHFATECSWDHLYVYDGDSIYAPLVA

AFSGLIVPERDGNETVPEVVATSGYALLHFFSDAAYNLTGFNITYSFDMC

PNNCSGRGECKISNSSDTVECECSENWKGEACDIPHCTDNCGFPHRGICN

SSDVRGCSCFSDWQGPGCSVPVPANQSFWTREEYSNLKLPRASHKAVVNG

NIMWVVGGYMFNHSDYNMVLAYDLASREWLPLNRSVNNVVVRYGHSLALY

KDKIYMYGGKIDSTGNVTNELRVFHIHNESWVLLTPKAKEQYAVVGHSAH

IVTLKNGRVVMLVIFGHCPLYGYISNVQEYDLDKNTWSILHTQGALVQGG

YGHSSVYDHRTRALYVHGGYKAFSANKYRLADDLYRYDVDTQMWTILKDS

RFFRYLHTAVIVSGTMLVFGGNTHNDTSMSHGAKCFSSDFMAYDIACDRW

SVLPRPDLHHDVNRFGHSAVLHNSTMYVFGGFNSLLLSDILVFTSEQCDA

HRSEAACLAAGPGIRCVWNTGSSQCISWALATDEQEEKLKSECFSKRTLD

HDRCDQHTDCYSCTANTNDCHWCNDHCVPRNHSCSEGQISIFRYENCPKD

NPMYYCNKKTSCRSCALDQNCQWEPRNQECIALPENICGIGWHLVGNSCL

KITTAKENYDNAKLFCRNHNALLASLTTQKKVEFVLKQLRIMQSSQSMSK

LTLTPWVGLRKINVSYWCWEDMSPFTNSLLQWMPSEPSDAGFCGILSEPS

TRGLKAATCINPLNGSVCERPANHSAKQCRTPCALRTACGDCTSGSSECM

WCSNMKQCVDSNAYVASFPFGQCMEWYTMSTCPPENCSGYCTCSHCLEQP

GCGWCTDPSNTGKGKCIEGSYKGPVKMPSQAPTGNFYPQPLLNSSMCLED

SRYNWSFIHCPACQCNGHSKCINQSICEKCENLTTGKHCETCISGFYGDP

TNGGKCQPCKCNGHASLCNTNTGKCFCTTKGVKGDECQLCEVENRYQGNP

LRGTCYYTLLIDYQFTFSLSQEDDRYYTAINFVATPDEQNRDLDMFINAS

KNFNLNITWAASFSAGTQAGEEMPVVSKTNIKEYKDSFSNEKFDFRNHPN

ITFFVYVSNFTWPIKIQVQTEQ
```

3. Alternative Name(s): Mahogany homolog; DPPT-L

This protein has not been linked to myocardial ischemia and events leading up to MI.

S. Isoform a of Syntaxin-3
Name: Syntaxin-3 (STX3A)
IPI ID: IPI00395768
UniProtKB/Swiss-Prot ID: Q13277-1 and Q13277-2
Length: 289 aa, molecular weight: 33155 Da-------- Q13277-1
1. Basic Information from UniProtKB/Swiss-Prot Entry:

| FUNCTION | Potentially involved in docking of synaptic vesicles at presynaptic active zones. |
|---|---|
| SUBCELLULAR LOCATION | Membrane; Single-pass type IV membrane protein (Potential). |

2. Sequence:

```
                                        (SEQ ID NO: 38)
MKDRLEQLKAKQLTQDDDTDAVEIAIDNTAFMDEFFSEIEETRLNIDKIS

EHVEEAKKLYSIILSAPIPEPKTKDDLEQLTTEIKKRANNVRNKLKSMEK

HIEEDEVRSSADLRIRKSQHSVLSRKFVEVMTKYNEAQVDFRERSKGRIQ

RQLEITGKKTTDEELEEMLESGNPAIFTSGIIDSQISKQALSEIEGRHKD

IVRLESSIKELHDMFMDIAMLVENQGEMLDNIELNVMHTVDHVEKARDET

KKAVKYQSQARKKLIIIIVLVVVLLGILALIIGLSVGLN
```

This protein has not been linked to myocardial ischemia and events leading up to MI.

T. Lactotransferrin
Name: Lactotransferrin
IPI ID: IPI00789477
UniProtKB/TrEMBL ID: B2MV14, B7Z4X2
Length: 666 aa, molecular weight: 73161 Da
Sequence:

```
                                        (SEQ ID NO: 39)
MRKVRGPPVSCIKRDSPIQCIQAIAENRADAVTLDGGFIYEAGLAPYKLR

PVAAEVYGTERQPRTHYYAVAVVKKGGSFQLNELQGLKSCHTGLRRTAGW

NVPIGTLRPFLNWTGPPEPIEAAVARFFSASCVPGADKGQFPNLCRLCAG

TGENKCAFSSQEPYFSYSGAFKCLRDGAGDVAFIRESTVFEDLSDEAERD

EYELLCPDNTRKPVDKFKDCHLARVPSHAVVARSVNGKEDAIWNLLRQAQ

EKFGKDKSPKFQLFGSPSGQKDLLFKDSAIGFSRVPPRIDSGLYLGSGYF

TAIQNLRKSEEEVAARRARVVWCAVGEQELRKCNQWSGLSEGSVTCSSAS

TTEDCIALVLKGEADAMSLDGGYVYTAGKCGLVPVLAENYKSQQSSDPDP

NCVDRPVEGYLAVAVVRRSDTSLTWNSVKGKKSCHTAVDRTAGWNIPMGL

LFNQTGSCKFDEYFSQSCAPGSDPRSNLCALCIGDEQGENKCVPNSNERY

YGYTGAFRCLAENAGDVAFVKDVTVLQNTDGNNNEAWAKDLKLADFALLC

LDGKRKPVTEARSCHLAMAPNHAVVSRMDKVERLKQVLLHQQAKFGRNGS

DCPDKFCLFQSETKNLLFNDNTECLARLHGKTTYEKYLGPQYVAGITNLK

KCSTSPLLEACEFLRK
```

Levels have been shown to increase with leukocyte activation. Therefore, there are increases found during ischemic stroke, following by-pass surgery and after direct stenting in patients with angina. However, no studies that have linked this protein to myocardial ischemia or events leading up to MI.

U. Low-Density Lipoprotein Receptor-Related Protein 2
Name: LOW-DENSITY LIPOPROTEIN RECEPTOR-RELATED PROTEIN 2
IPI ID: IPI00024292
UniProtKB/Swiss-Prot ID: P98164
Length: 4655 aa, molecular weight: 521958 Da (of Precursor)
1. Basic Information from UniProtKB/Swiss-Prot Entry:

| FUNCTION | Acts together with cubilin to mediate HDL endocytosis (By similarity). May participate in regulation of parathyroid-hormone and para-thyroid-hormone-related protein release. |
|---|---|
| SUBCELLULAR LOCATION | Membrane; Single-pass type I membrane protein. Membrane, coated pit. |

2. Sequence:

(SEQ ID NO: 40)
MDRGPAAVACTLLLALVACLAPASGQECDSAHFRCGSGHCIPADWRCDGT
KDCSDDADEIGCAVVTCQQGYFKCQSEGQCIPNSWVCDQDQDCDDGSDER
QDCSQSTCSSHQITCSNGQCIPSEYRCDHVRDCPDGADENDCQYPTCEQL
TCDNGACYNTSQKCDWKVDCRDSSDEINCTEICLHNEFSCGNGECIPRAY
VCDHDNDCQDGSDEHACNYPTCGGYQFTCPSGRCIYQNWVCDGEDDCKDN
GDEDGCESGPHDVHKCSPREWSCPESGRCISIYKVCDGILDCPGREDENN
TSTGKYCSMTLCSALNCQYQCHETPYGGACFCPPGYIINHNDSRTCVEFD
DCQIWGICDQKCESRPGRHLCHCEEGYILERGQYCKANDSFGEASIIFSN
GRDLLIGDIHGRSFRILVESQNRGVAVGVAFHYHLQRVFWTDTVQNKVFS
VDINGLNIQEVLNVSVETPENLAVDWVNNKIYLVETKVNRIDMVNLDGSY
RVTLITENLGHPRGIAVDPTVGYLFFSDWESLSGEPKLERAFMDGSNRKD
LVKTKLGWPAGVTLDMISKRVYWVDSRFDYIETVTYDGIQRKTVVHGGSL
IPHPFGVSLFEGQVFFTDWTKMAVLKANKFTETNPQVYYQASLRPYGVTV
YHSLRQPYATNPCKDNNGGCEQVCVLSHRTDNDGLGFRCKCTFGFQLDTD
ERHCIAVQNFLIFSSQVAIRGIPFTLSTQEDVMVPVSGNPSFFVGIDFDA
QDSTIFFSDMSKHMIFKQKIDGTGREILAANRVENVESLAFDWISKNLYW
TDSHYKSISVMRLADKTRRTVVQYLNNPRSVVVHPFAGYLFFTDWFRPAK
IMRAWSDGSHLLPVINTTLGWPNGLAIDWAASRLYWVDAYFDKIEHSTFD
GLDRRRLGHIEQMTHPFGLAIFGEHLFFTDWRLGAIIRVRKADGGEMTVI
RSGIAYILHLKSYDVNIQTGSNACNQPTHPNGDCSHFCFPVPNFQRVCGC
PYGMRLASNHLTCEGDPTNEPPTEQCGLFSFPCKNGRCVPNYYLCDGVDD
CHDNSDEQLCGTLNNTCSSSAFTCGHGECIPAHWRCDKRNDCVDGSDEHN
CPTHAPASCLDTQYTCDNHQCISKNWVCDTDNDCGDGSDEKNCNSTETCQ
PSQFNCPNHRCIDLSFVCDGDKDCVDGSDEVGCVLNCTASQFKCASGDKC
IGVTNRCDGVFDCSDNSDEAGCPTRPPGMCHSDEFQCQEDGICIPNFWEC
DGHPDCLYGSDEHNACVPKTCPSSYFHCDNGNCIHRAWLCDRDNDCGDMS
DEKDCPTQPFRCPSWQWQCLGHNICVNLSVVCDGIFDCPNGTDESPLCNG
NSCSDFNGGCTHECVQEPFGAKCLCPLGFLLANDSKTCEDIDECDILGSC
SQHCYNMRGSFRCSCDTGYMLESDGRTCKVTASESLLLLVASQNKIIADS
VTSQVHNIYSLVENGSYIVAVDFDSISGRIFWSDATQGKTWSAFQNGTDR
RVVFDSSIILTETIAIDWVGRNLYWTDYALETIEVSKIDGSHRTVLISKN
LTNPRGLALDPRMNEHLLFWSDWGHHPRIERASMDGSMRTVIVQDKIFWP
CGLTIDYPNRLLYFMDSYLDYMDFCDYNGHHRRQVIASDLIIRHPYALTL
FEDSVYWTDRATRRVMRANKWHGGNQSVVMYNIQWPLGIVAVHPSKQPNS
VNPCAFSRCSHLCLLSSQGPHFYSCVCPSGWSLSPDLLNCLRDDQPFLIT
VRQHIIFGISLNPEVKSNDAMVPIAGIQNGLDVEFDDAEQYIYWVENPGE
IHRVKTDGTNRTVFASISMVGPSMNLALDWISRNLYSTNPRTQSIEVLTL
HGDIRYRKTLIANDGTALGVGFPIGITVDPARGKLYWSDQGTDSGVPAKI
ASANMDGTSVKTLFTGNLEHLECVTLDIEEQKLYWAVTGRGVIERGNVDG

TDRMILVHQLSHPWGIAVHDSFLYYTDEQYEVIERVDKATGANKIVLRDN
VPNLRGLQVYHRRNAAESSNGCSNNMNACQQICLPVPGGLFSCACATGFK
LNPDNRSCSPYNSFIVVSMLSAIRGFSLELSDHSETMVPVAGQGRNALHV
DVDVSSGFIYWCDFSSSVASDNAIRRIKPDGSSLMNIVTHGIGENGVRGI
AVDWVAGNLYFTNAFVSETLIEVLRINTTYRRVLLKVTVDMPRHIVVDPK
NRYLFWADYGQRPKIERSFLDCTNRTVLVSEGIVTPRGLAVDRSDGYVYW
VDDSLDIIARIRINGENSEVIRYGSRYPTPYGITVFENSIIWVDRNLKKI
FQASKEPENTEPPTVIRDNINWLRDVTIFDKQVQPRSPAEVNNNPCLENN
GGCSHLCFALPGLHTPKCDCAFGTLQSDGKNCAISTENFLIFALSNSLRS
LHLDPENHSPPFQTINVERTVMSLDYDSVSDRIYFTQNLASGVGQISYAT
LSSGIHTPTVIASGIGTADGIAFDWITRRIYYSDYLNQMINSMAEDGSNR
TVIARVPKPRAIVLDPCQGYLYWADWDTHAKIERATLGGNFRVPIVNSSL
VMPSGLTLDYEEDLLYWVDASLQRIERSTLTGVDREVIVNAAVHAFGLTL
YGQYIYWTDLYTQRIYRANKYDGSGQIAMTTNLLSQPRGINTVVKNQKQQ
TCNNPCEQFNGGCSHICAPGPNGAECQCPHEGNWYLANNRKHCIVDNGER
CGASSFCSNGRCISEEWKCDNDNDCGDGSDEMESVCALHTCSPTAFTCAN
GRCVQYSYRCDYYNDCGDGSDEAGCLFRDCNATTEFMCNNRRCIPREFIC
NGVDNCHDNNTSDEKNCPDRTCQSGYTKCHNSNICIPRVYLCDGDNDCGD
NSDENPTYCTTHTCSSSEFQCASGRCIPQHWYCDQETDCFDASDEPASCG
HSERTCLADEFKCDGGRCIPSEWICDGDNDCGDMSDEDKRHQCQNQNCSD
SEFLCVNDRPPDRRCIPQSWVCDGDVDCTDGYDENQNCTRRTCSENEFTC
GYGLCIPKIFRCDRHNDCGDYSDERGCLYQTCQQNQFTCQNGRCISKTFV
CDEDNDCGDGSDELMHLCHTPEPTCPPHEFKCDNGRCIEMMKLCNHLDDC
LDNSDEKGCGINECHDPSISGCDHNCTDTLTSFYCSCRPGYKLMSDKRTC
VDIDECTEMPFVCSQKCENVIGSYICKCAPGYLREPDGKTCRQNSNIEPY
LIFSNRYYLRNLTIDGYFYSLILEGLDNVVALDFDRVEKRLYWIDTQRQV
IERMFLNKTNKETIINHRLPAAESLAVDWVSRKLYWLDARLDGLFVSDLN
GGHRRMLAQHCVDANNTFCFDNPRGLALHPQYGYLYWADWGHRAYIGRVG
MDGTNKSVIISTKLEWPNGITIDYTNDLLYWADAHLGYIEYSDLEGHHRH
TVYDGALPHPFAITIFEDTIYWTDWNTRTVEKGNKYDGSNRQTLVNTTHR
PFDIHVYHPYRQPIVSNPCGTNNGGCSHLCLIKPGGKGFTCECPDDFRTL
QLSGSTYCMPMCSSTQFLCANNEKCIPIWWKCDGQKDCSDGSDELALCPQ
RFCRLGQFQCSDGNCTSPQTLCNAHQNCPDGSDEDRLLCENHHCDSNEWQ
CANKRCIPESWQCDTFNDCEDNSDEDSSHCASRTCRPGQFRCANGRCIPQ
AWKCDVDNDCGDHSDEPIEECMSSAHLCDNFTEFSCKTNYRCIPKWAVCN
GVDDCRDNSDEQGCEERTCHPVGDFRCKNHHCIPLRWQCDGQNDCGDNSD
EENCAPRECTESEFRCVNQQCIPSRWICDHYNDCGDNSDERDCEMRTCHP
EYFQCTSGHCVHSELKCDGSADCLDASDEADCPTRFPDGAYCQATMFECK
NHVCIPPYWKCDGDDDCGDGSDEELHLCLDVPCNSPNRFRCDNNRCIYSH
EVCNGVDDCGDGTDETEEHCRKPTPKPCTEYEYKCGNGHCIPHDNVCDDA

```
DDCGDWSDELGCNKGKERTCAENICEQNCTQLNEGGFICSCTAGFETNVF

DRTSCLDINECEQFGTCPQHCRNTKGSYECVCADGFTSMSDRPGKRCAAE

GSSPLLLLPDNVRIRKYNLSSERFSEYLQDEEYIQAVDYDWDPKDIGLSV

VYYTVRGEGSRFGAIKRAYIPNFESGRNNLVQEVDLKLKYVMQPDGIAVD

WVGRHIYWSDVKNKRIEVAKLDGRYRKWLISTDLDQPAAIAVNPKLGLMF

WTDWGKEPKIESAWMNGEDRNILVFEDLGWPTGLSIDYLNNDRIYWSDFK

EDVIETIKYDGTDRRVIAKEAMNPYSLDIFEDQLYWISKEKGEVWKQNKF

GQGKKEKTLVVNPWLTQVRIFHQLRYNKSVPNLCKQICSHLCLLRPGGYS

CACPQGSSFIEGSTTECDAAIELPINLPPPCRCMHGGNCYFDETDLPKCK

CPSGYTGKYCEMAFSKGISPGTTAVAVLLTILLIVVIGALAIAGFFHYRR

TGSLLPALPKLPSLSSLVKPSENGNGVTFRSGADLNMDIGVSGFGPETAI

DRSMAMSEDFVMEMGKQPIIFENPMYSARDSAVKVVQPIQVTVSENVDNK

NYGSPINPSEIVPETNPTSPAADGTQVTKWNLFKRKSKQTTNFENPIYAQ

MENEQKESVAATPPPSPSLPAKPKPPSRRDPTPTYSATEDTFKDTANLVK
EDSEV
```

3. Alternative Name(s): Megalin; Glycoprotein 330; Short name=gp330

This protein has not been directly linked to myocardial ischemia or events leading up to MI.

V. Prolow Density Lipoprotein Receptor Related Protein 1
Name: Prolow density lipoprotein receptor related protein 1
IPI ID: IPI00020557
UniProtKB/Swiss-Prot ID: Q07954
Length: 4544 aa, molecular weight: 504575 Da (of Precursor)
1. Basic Information from UniProtKB/Swiss-Prot Entry:
   Function: Endocytic receptor involved in endocytosis and in phagocytosis of apoptotic cells. Required for early embryonic development. Involved in cellular lipid homeostasis. Involved in the plasma clearance of chylomicron remnants and activated LRPAP1 (alpha 2-macroglobulin), as well as the local metabolism of complexes between plasminogen activators and their endogenous inhibitors. May modulate cellular events, such as APP metabolism, kinase-dependent intracellular signaling, neuronal calcium signaling as well as neurotransmission.
   Subcellular location: Low-density lipoprotein receptor-related protein 1 85 kDa subunit: Cell membrane; Single-pass type I membrane protein. Membrane>coated pit. Low-density lipoprotein receptor-related protein 1 515 kDa subunit: Cell membrane; Peripheral membrane protein; Extracellular side. Membrane>coated pit. Low-density lipoprotein receptor-related protein 1 intracellular domain: Cytoplasm. Nucleus. Note=After cleavage, the intracellular domain (LRPICD) is detected both in the cytoplasm and in the nucleus.
2. Sequence:

```
                                         (SEQ ID NO: 41)
MLTPPLLLLLPLLSALVAAAIDAPKTCSPKQFACRDQITCISKGWRCDGE

RDCPDGSDEAPEICPQSKAQRCQPNEHNCLGTELCVPMSRLCNGVQDCMD

GSDEGPHCRELQGNCSRLGCQHHCVPTLDGPTCYCNSSFQLQADGKTCKD

FDECSVYGTCSQLCTNTDGSFICGCVEGYLLQPDNRSCKAKNEPVDRPPV

LLIANSQNILATYLSGAQVSTITPTSTRQTTAMDFSYANETVCWVHVGDS

AAQTQLKCARMPGLKGFVDEHTINISLSLHHVEQMAIDWLTGNFYFVDDI

DDRIFVCNRNGDTCVTLLDLELYNPKGIALDPAMGKVFFTDYGQIPKVER

CDMDGQNRTKLVDSKIVFPHGITLDLVSRLVYWADAYLDYIEVVDYEGKG

RQTIIQGILIEHLYGLTVFENYLYATNSDNANAQQKTSVIRVNRFNSTEY

QVVTRVDKGGALHIYHQRRQPRVRSHACENDQYGKPGGCSDICLLANSHK

ARTCRCRSGFSLGSDGKSCKKPEHELFLVYGKGRPGIIRGMDMGAKVPDE

HMIPIENLMNPRALDFHAETGFIYFADTTSYLIGRQKIDGTERETILKDG

IHNVEGVAVDWMGDNLYWTDDGPKKTISVARLEKAAQTRKTLIEGKMTHP

RAIVVDPLNGWMYWTDWEEDPKDSRRGRLERAWMDGSHRDIFVTSKTVLW

PNGLSLDIPAGRLYWVDAFYDRIETILLNGTDRKIVYEGPELNHAFGLCH

HGNYLFWTEYRSGSVYRLERGVGGAPPTVTLLRSERPPIFEIRMYDAQQQ

QVGTNKCRVNNGGCSSLCLATPGSRQCACAEDQVLDADGVTCLANPSYVP

PPQCQPGEFACANSRCIQERWKCDGDNDCLDNSDEAPALCHQHTCPSDRF

KCENNRCIPNRWLCDGDNDCGNSEDESNATCSARTCPPNQFSCASGRCIP

ISWTCDLDDDCGDRSDESASCAYPTCFPLTQFTCNNGRCININWRCDNDN

DCGDNSDEAGCSHSCSSTQFKCNSGRCIPEHWTCDGDNDCGDYSDETHAN

CTNQATRPPGGCHTDEFQCRLDGLCIPLRWRCDGDTDCMDSSDEKSCEGV

THVCDPSVKFGCKDSARCISKAWVCDGDNDCEDNSDEENCESLACRPPSH

PCANNTSVCLPPDKLCDGNDDCGDGSDEGELCDQCSLNNGGCSHNCSVAP

GEGIVCSCPLGMELGPDNHTCQIQSYCAKHLKCSQKCDQNKFSVKCSCYE

GWVLEPDGESCRSLDPFKPFIIFSNRHEIRRIDLHKGDYSVLVPGLRNTI

ALDFHLSQSALYWTDVVEDKIYRGKLLDNGALTSFEVVIQYGLATPEGLA

VDWIAGNIYWVESNLDQIEVAKLDGTLRTTLLAGDIEHPRAIALDPRDGI

LFWTDWDASLPRIEAASMSGAGRRTVHRETGSGGWPNGLTVDYLEKRILW

IDARSDAIYSARYDGSGHMEVLRGHEFLSHPFAVTLYGGEVYWTDWRTNT

LAKANKWTGHNVTVVQRTNTQPFDLQVYHPSRQPMAPNPCEANGGQGPCS

HLCLINYNRTVSCACPHLMKLHKDNTTCYEFKKFLLYARQMEIRGVDLDA

PYYNYIISFTVPDIDNVTVLDYDAREQRVYWSDVRTQAIKRAFINGTGVE

TVVSADLPNAHGLAVDWVSRNLFWTSYDTNKKQINVARLDGSFKNAVVQG

LEQPHGLVVHPLRGKLYWTDGDNISMANMDGSNRTLLFSGQKGPVGLAID

FPESKLYWISSGNHTINRCNLDGSGLEVIDAMRSQLGKATALAIMGDKLW

WADQVSEKMGTCSKADGSGSVVLRNSTTLVMHMKVYDESIQLDHKGTNPC

SVNNGDCSQLCLPTSETTRSCMCTAGYSLRSGQQACEGVGSFLLYSVHEG

IRGIPLDPNDKSDALVPVSGTSLAVGIDFHAENDTIYWVDMGLSTISRAK

RDQTWREDVVTNGIGRVEGIAVDWIAGNIYWTDQGFDVIEVARLNGSFRY

VVISQGLDKPRAITVHPEKGYLFWTEWGQYPRIERSRLDGTERVVLVNVS

ISWPNGISVDYQDGKLYWCDARTDKIERIDLETGENREVVLSSNNMDMFS

VSVFEDFIYWSDRTHANGSIKRGSKDNATDSVPLRTGIGVQLKDIKVFNR

DRQKGTNVCAVANGGCQQLCLYRGRGQRACACAHGMLAEDGASCREYAGY

LLYSERTILKSIHLSDERNLNAPVQPFEDPEHMKNVIALAFDYRAGTSPG
```

```
TPNRIFFSDIHFGNIQQINDDGSRRITIVENVGSVEGLAYHRGWDTLYWT

SYTTSTITRHTVDQTRPGAFERETVITMSGDDHPRAFVLDECQNLMFWTN

WNEQHPSIMRAALSGANVLTLIEKDIRTPNGLAIDHRAEKLYFSDATLDK

IERCEYDGSHRYVILKSEPVHPFGLAVYGEHIFWTDWVRRAVQRANKHVG

SNMKLLRVDIPQQPMGIIAVANDTNSCELSPCRINNGGCQDLCLLTHQGH

VNCSCRGGRILQDDLTCRAVNSSCRAQDEFECANGECINFSLTCDGVPHC

KDKSDEKPSYCNSRRCKKTFRQCSNGRCVSNMLWCNGADDCGDGSDEIPC

NKTACGVGEFRCRDGTCIGNSSRCNQFVDCEDASDEMNCSATDCSSYFRL

GVKGVLFQPCERTSLCYAPSWVCDGANDCGDYSDERDCPGVKRPRCPLNY

FACPSGRCIPMSWTCDKEDDCEHGEDETHCNKFCSEAQFECQNHRCISKQ

WLCDGSDDCGDGSDEAAHCEGKTCGPSSFSCPGTHVCVPERWLCDGDKDC

ADGADESIAAGCLYNSTCDDREFMCQNRQCIPKHFVCDHDRDCADGSDES

PECEYPTCGPSEFRCANGRCLSSRQWECDGENDCHDQSDEAPKNPHCTSP

EHKCNASSQFLCSSGRCVAEALLCNGQDDCGDSSDERGCHINECLSRKLS

GCSQDCEDLKIGFKCRCRPGFRLKDDGRTCADVDECSTTFPCSQRCINTH

GSYKCLCVEGYAPRGGDPHSCKAVTDEEPFLIFANRYYLRKLNLDGSNYT

LLKQGLNNAVALDFDYREQMIYWTDVTTQGSMIRRMHLNGSNVQVLHRTG

KLSNPDGLAVDWVGGNLYWCDGRDTIEVSKLNGAYRTVLVSSGLREPRAL

VVDVQNGYLYWTDWGDHSLIGRIGMDGSSRSVIVDTKITWPNGLTLDYVT

ERIYWADAREDYIEFASLDGSNRHVVLSQDIPHIFALTLFEDYVYWTDWE

TKSINRAHKTTGTNKTLLISTLHRPMDLHVFHALRQPDVPNHPCKVNNGG

CSNLCLLSPGGGHKCACPTNFYLGSDGRTCVSNCTASQFVCKNDKCIPFW

WKCDTEDDCGDHSDEPPDCPEFKCRPGQFQCSTGICTNPAFICDGDNDCQ

DNSDEANCDIHVCLPSQFKCTNTNRCIPGIFRCNGQDNCGDEDERDCPE

VTCAPNQFQCSITKRCIPRVWVCDRDNDCVDGSDEPANCTQMTCGVDEFR

CKDSGRCIPARWKCDGEDDCGDGSDEPKEECDERTCEPYQFRCKNNRCVP

GRWQCDYDNDCGDNSDEESCTPRPCSESEFSCANGRCIAGRWKCDGDHDC

ADGSDEKDCTPRCDMDQFQCKSGHCIPLRWRCDADADCMDGSDEEACGTG

VRTCPLDEFQCNNTLCKPLAWKCDGEDDCGDNSDENPEECARFVCPPNRP

FRCKNDRVCLWIGRQCDGTDNCGDGTDEEDCEPPTAHTTHCKDKKEFLCR

NQRCLSSSLRCNMFDDCGDGSDEEDCSIDPKLTSCATNASICGDEARCVR

TEKAAYCACRSGFHTVPGQPGCQDINECLRFGTCSQLCNNTKGGHLCSCA

RRNFMKTHNTCKAEGSEYQVLYIADDNEIRSLFPGHPHSAYEQAFQGDES

VIDAMDVHVKAGRVYWTNWHTGTISYRSLPPAAPPTTSNRHRRQIDRGVT

RHLNISGLKMPGIAIDWVAGNVYWTDSGRDVIEVAQMKGENRKTLISGMI

DEPHAIVVDPLRGTMYWSDWGNHPKIETAAMDGTLRETLVQDNIQWPTGL

AVDYHNERLYWADAKLSVIGSIRLNGTDPIVAADSKRGLSHPFSIDVFED

YIYGVTYINNRVFKIHKFGHSPLVNLTGGLSHASDVVLYHQHKQPEVTNP

CDRKKCEWLCLLSPSGPVCTCPNGKRLDNGTCVPVPSPTPPPDAPRPGTC

NLQCFNGGSCFLNARRQPKCRCQPRYTGDKCELDQCWEHCRNGGTCAASP

SGMPTCRCPTGFTGPKCTQQVCAGYCANNSTCTVNQGNQPQCRCLPGFLG

DRCQYRQCSGYCENFGTCQMAADGSRQCRCTAYFEGSRCEVNKCSRCLEG

ACVVNKQSGDVTCNCTDGRVAPSCLTCVGHCSNGGSCTMNSKMMPECQCP

PHMTGPRCEEHVFSQQQPGHIASILIPLLLLLLLVLVAGVVFWYKRRVQG

AKGFQHQRMTNGAMNVEIGNPTYKMYEGGEPDDVGGLLDADFALDPDKPT

NFTNPVYATLYMGGHGSRHSLASTDEKRELLGRGPEDEIGDPLA
```

3. Alternative Name(s):
   Alpha-2-macroglobulin receptor
      Short name=A2MR
   Apolipoprotein E receptor
      Short name=APOER
   CD_antigen=CD91
   This protien has not been directly linked to myocardial ischemia or events leading up to MI.

W. Monocyte Differentiation Antigen CD14
Name: MONOCYTE DIFFERENTIATION ANTIGEN CD14
IPI ID: IPI00029260
UniProtKB/Swiss-Prot ID: P08571
Length: 375 aa, molecular weight: 40076 Da (of Precursor)
1. Basic Information from UniProtKB/Swiss-Prot Entry:

| FUNCTION | Cooperates with MD-2 and TLR4 to mediate the innate immune response to bacterial lipopolysaccharide (LPS). Acts via MyD88, TIRAP and TRAF6, leading to NF-kappa-B activation, cytokine secretion and the inflammatory response. Up-regulates cell surface molecules, including adhesion molecules. |
| --- | --- |
| SUBCELLULAR LOCATION | Cell membrane; Lipid-anchor, GPI-anchor. |

2. Sequence:

```
                                             (SEQ ID NO: 42)
MERASCLLLLLLPLVHVSATTPEPCELDDEDFRCVCNFSEPQPDWSEAFQ

CVSAVEVEIHAGGLNLEPFLKRVDADADPRQYADTVKALRVRRLTVGAAQ

VPAQLLVGALRVLAYSRLKELTLEDLKITGTMPPLPLEATGLALSSLRLR

NVSWATGRSWLAELQQWLKPGLKVLSIAQAHSPAFSCEQVRAFPALTSLD

LSDNPGLGERGLMAALCPHKFPAIQNLALRNTGMETPTGVCAALAAAGVQ

PHSLDLSHNSLRATVNPSAPRCMWSSALNSLNLSFAGLEQVPKGLPAKLR

VLDLSCNRLNRAPQPDELPEVDNLTLDGNPFLVPGTALPHEGSMNSGVVP

ACARSTLSVGVSGTLVLLQGARGFA
```

3. Alternative Name(s): Myeloid cell-specific leucine-rich glycoprotein; CD_antigen=CD14 Monocytes and T-cells play an important role in the development of atherosclerotic coronary artery disease. C14 is located on the monocytes and, therefore, changes to this protein can and have been linked to alterations to monocytes (including with coronary artery disease). However, this protein has not been measured in serum in context to myocardial ischemia or events leading up to a MI.

X. Peroxiredoxin-2
Name: Peroxiredoxin-2
IPI ID: IPI00027350
UniProtKB/Swiss-Prot ID: P32119; PRDX2_HUMAN; M.
Length: 198 aa, molecular weight: 21892 Da, CRC64 checksum: 1AC781D908B32B46

1. Basic Information from UniProtKB/Swiss-Prot Entry:

| | |
|---|---|
| Function | Involved in redox regulation of the cell. Reduces peroxides with reducing equivalents provided through the thioredoxin system. It is not able to receive electrons from glutaredoxin. May play an important role in eliminating peroxides generated during metabolism. Might participate in the signaling cascades of growth factors and tumor necrosis factor-alpha by regulating the intracellular concentrations of $H_2O_2$. |
| Catalytic activity | 2 R'—SH + ROOH = R'—S—S—R' + $H_2O$ + ROH. |
| Subunit structure | Homodimer; disulfide-linked, upon oxidation. May be found as a toroid-shaped decamer composed of 5 dimers, depending on pH and calcium concentration. Interacts with TIPIN. |
| Subcellular location | Cytoplasm. |
| Miscellaneous | The active site is the redox-active Cys-51 oxidized to Cys-SOH. Cys-SOH rapidly reacts with Cys-172-SH of the other subunit to form an intermolecular disulfide with a concomitant homodimer formation. The enzyme may be subsequently regenerated by reduction of the disulfide by thioredoxin. Inactivated upon oxidative stress by overoxidation of Cys-51 to Cys-$SO_2H$ and Cys-$SO_3H$. Cys-$SO_2H$ is retroreduced to Cys-SOH after removal of $H_2O_2$, while Cys-$SO_3H$ may be irreversibly oxidized. |
| Sequence similarities | Belongs to the ahpC/TSA family. Contains 1 thioredoxin domain. |

2. Sequence:

(SEQ ID NO: 43)
MASGNARIGKPAPDFKATAVVDGAFKEVKLSDYKGKYVVLFFYPLDFTFV

CPTEIIAFSNRAEDFRKLGCEVLGVSVDSQFTHLAWINTPRKEGGLGPLN

IPLLADVTRRLSEDYGVLKTDEGIAYRGLFIIDGKGVLRQITVNDLPVGR

SVDEALRLVQAFQYTDEHGEVCPAGWKPGSDTIKPNVDDSKEYFSKHN

3. Alternative Name(s): Thioredoxin peroxidase 1
  Thioredoxin-dependent peroxide reductase 1
  Thiol-specific antioxidant protein
    Short name=TSA
  PRP
  Natural killer cell-enhancing factor B
    Short name=NKEF-B This protein has been found to increase in the serum of a number diseases but none are cardiac related. This protein, to date, has not been shown to be increased in myocardial ischemia or events leading to MI.

Y. NCOR2 CTG26 Alternate Open Reading Frame
Name: CTG26 alternate open reading frame (Fragment)
IPI ID: IPI00006659.3

Basic information: Fragment
1. Sequence:

(SEQ ID NO: 44)
SFSSMEASSALCWGVMASSLLASLAIERVMRPLRLPWLLAVLRPLEATAS

FSSLSSPEVSSVFSLRRSSLSFSTSGFSSSFSASFSFSFSSFSSWLLRGM

GCCCCCCCCCCCCCCCCCWLLPRRR

This protein has not be linked to myocardial ischemia or events leading up to MI.

Example V

Validation Studies

Antibodies to two or more epitopes on each protein will be generated and used to develop a sandwich ELISA assay (as single or multiplex) that is specific and sensitive for the analyte. The analyte will either be peptide, protein fragment or protein and will be used to generate standard curve. Analysis will be carried out using conventional ELISA or on a Luminex or Mesoscale platform. Assays will be carried out at least in duplicate. For MRM assays, peptides (generated most likely by trypsin, chymotrypsin or Lys C) that are unique to the protein of interest and showing high MS signal response (prototypic peptides) which will help maximize the sensitivity of the assay. 2. Selection of predominant peptide fragments specific (MS/MS) for the parent peptide (useful MRM transition). 3. For each peptide-fragment pair, optimization of specific MS parameters (e.g. the collision energy) to maximize the signal response/sensitivity. 4. Validation of the MRM assay to confirm peptide identity, e.g. by acquiring a full MS2 spectrum of the peptide in the triple quadrupole MS instrument used for MRM. 5. Extraction of the final "coordinates" of the MRM assay, including the selected peptide and peptide fragments, the corresponding mass-to-charge ratios, the fragment intensity ratios, the associated collision energy, and the chromatographic elution time to be optionally used in time-constrained MRM analyses. We will add isotopically labeled internal peptide standards (with known concentrations determined by amino acid analysis) to facilitate absolute quantitation of selected peptides. Assays will be performed on a triple quadropole mass spectrometer at least in duplicate.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications (including provisional patent application 61/128,688, filed May 23, 2008) cited above and in the figures are hereby incorporated in their entirety by reference.

We claim:

1. A kit for detecting the presence of myocardial ischemia in a subject, comprising reagents for detecting the amount of at least three of the following proteins:
   i) Lumican, and/or
   ii) Extracellular matrix protein 1, and/or
   iii) Carboxypeptidase N, and/or
   iv) Angiogenin, and/or
   v) Semenogelin, and/or
   vi) Long palate, lung and nasal epithelium carcinoma-associated protein 1, and/or
   vii) Perioxiredoxin isoform 2, and/or
   viii) Syntaxin 3, and/or
   ix) S100 isoform A7, and/or
   x) S100 isoform A8, and/or
   xi) S100 isoform A9, and/or
   xii) Sortilin-related receptor, and/or
   xiii) Catalase, and/or
   xiv) Low density lipoprotein receptor related protein 1, and/or
   xv) Low density lipoprotein receptor related protein 2.

2. The kit of claim 1, further comprising reagents for detecting the amount of at least one of the following proteins:
   xvi) Hepatocyte growth factor activator, and/or
   xvii) Alpha-2-HS-glycoprotein, and/or
   xviii) Insulin like growth factor protein 6, and/or
   xix) Galectin-7, and/or
   xx) Hornerin, and/or
   xxi) Proteoglycan-4, and/or
   xxii) Profilaggrin (also referred to as Filaggrin), and/or
   xxiii) Vitamin D binding protein, and/or
   xxiv) C4b-binding protein alpha chain, and/or
   xxv) Thyroxine binding globulin, and/or
   xxvi) Alpha-2-glycoprotein 1, zinc, and/or
   xxvii) Serine 3 protease, and/or
   xxviii) Caspase 14, and/or
   xxix) Desmogelin, and/or
   xxx) Kininogen -1, and/or
   xxxi) Hepatocyte growth factor like protein.

* * * * *